US012653504B2

(12) United States Patent
Chiang et al.

(10) Patent No.: US 12,653,504 B2
(45) Date of Patent: Jun. 16, 2026

(54) TABLET ULTRASOUND SYSTEM

(71) Applicant: Teratech Corporation, Burlington, MA (US)

(72) Inventors: Alice M. Chiang, Wayland, MA (US); William M. Wong, Milton, MA (US); Noah Berger, Sudbury, MA (US)

(73) Assignee: Teratech Corporation, Burlington, MA (US)

( * ) Notice: Subject to any disclaimer, the term of this patent is extended or adjusted under 35 U.S.C. 154(b) by 0 days.

(21) Appl. No.: 17/834,771

(22) Filed: Jun. 7, 2022

(65) Prior Publication Data

US 2022/0304661 A1    Sep. 29, 2022

Related U.S. Application Data

(63) Continuation of application No. 16/806,118, filed on Mar. 2, 2020, which is a continuation of application
(Continued)

(51) Int. Cl.
*A61B 8/00* (2006.01)
*G01S 7/52* (2006.01)
(Continued)

(52) U.S. Cl.
CPC ............ *A61B 8/469* (2013.01); *A61B 8/4405* (2013.01); *A61B 8/4427* (2013.01);
(Continued)

(58) Field of Classification Search
CPC ..... A61B 8/469; A61B 8/4405; A61B 8/4427; A61B 8/4477; A61B 8/462; A61B 8/463;
(Continued)

(56) References Cited

U.S. PATENT DOCUMENTS 4,702,258 A    10/1987    Nicolas et al.
4,727,376 A    2/1988    Prenat
(Continued)

FOREIGN PATENT DOCUMENTS

CA    2902224 A1    9/2014
CN    1759327 A    4/2006
(Continued)

OTHER PUBLICATIONS

GE Healthcare, Technical Publications Direction 5265930-100 English, Rev. 10. Venue 40 Basic User Manual. Operating Documentation by General Electric Co. 303 pages (2008-2012).
(Continued)

*Primary Examiner* — Sanjay Cattungal
(74) *Attorney, Agent, or Firm* — McCarter & English, LLP

(57) ABSTRACT

Exemplary embodiments provide systems and methods for portable medical ultrasound imaging. Certain embodiments provide a multi-chip module for an ultrasound engine of a portable medical ultrasound imaging system, in which a transmit/receive chip, an amplifier chip and a beamformer chip are assembled in a vertically stacked configuration. Exemplary embodiments also provide an ultrasound engine circuit board including one or more multi-chip modules, and a portable medical ultrasound imaging system including an ultrasound engine circuit board with one or more multi-chip modules. Exemplary embodiments also provide methods for fabricating and assembling multi-chip modules as taught herein. A single circuit board of an ultrasound engine with one or more multi-chip modules may include 16 to 128 channels in some embodiments. Due to the vertical stacking arrangement of the multi-chip modules, a 128-channel ultrasound engine circuit board can be assembled within exemplary planar dimensions of about 10 cm×about 10 cm.

44 Claims, 82 Drawing Sheets

Related U.S. Application Data

No. 13/838,694, filed on Mar. 15, 2013, now Pat. No. 10,667,790.

(60) Provisional application No. 61/704,254, filed on Sep. 21, 2012, provisional application No. 61/615,627, filed on Mar. 26, 2012.

(51) Int. Cl.
| | |
|---|---|
| *G06F 3/0488* | (2022.01) |
| *A61B 8/06* | (2006.01) |
| *A61B 8/08* | (2006.01) |
| *G01S 15/89* | (2006.01) |

(52) U.S. Cl.
CPC ............ *A61B 8/4477* (2013.01); *A61B 8/462* (2013.01); *A61B 8/463* (2013.01); *A61B 8/465* (2013.01); *A61B 8/467* (2013.01); *A61B 8/468* (2013.01); *G01S 7/52074* (2013.01); *G01S 7/52082* (2013.01); *G01S 7/52084* (2013.01); *G06F 3/0488* (2013.01); *A61B 8/06* (2013.01); *A61B 8/08* (2013.01); *A61B 8/54* (2013.01); *G01S 15/8979* (2013.01); *H01L 2224/32145* (2013.01); *H01L 2224/32245* (2013.01); *H01L 2224/48091* (2013.01); *H01L 2224/48095* (2013.01); *H01L 2224/48247* (2013.01); *H01L 2224/48465* (2013.01); *H01L 2224/73265* (2013.01); *H01L 2924/181* (2013.01); *Y10T 29/49002* (2015.01)

(58) Field of Classification Search
CPC ......... A61B 8/465; A61B 8/467; A61B 8/468; A61B 8/06; A61B 8/08; A61B 8/54; G01S 7/52074; G01S 7/52082; G01S 7/52084; G01S 15/8979; G06F 3/0488; H01L 2224/32145; H01L 2224/32245; H01L 2224/48091; H01L 2224/48095; H01L 2224/48247; H01L 2224/48465; H01L 2224/73265; H01L 2924/181; Y10T 29/49002
See application file for complete search history.

(56) References Cited

U.S. PATENT DOCUMENTS

| | | | |
|---|---|---|---|
| 4,991,604 A | | 2/1991 | Wurster et al. |
| 5,170,791 A | | 12/1992 | Boos et al. |
| 5,311,095 A | | 5/1994 | Smith et al. |
| 5,381,794 A | | 1/1995 | Tei et al. |
| 5,465,095 A | | 11/1995 | Bryant |
| 5,487,388 A | | 1/1996 | Rello et al. |
| 5,598,845 A | | 2/1997 | Chandraratna et al. |
| 5,653,236 A | | 8/1997 | Miller |
| 5,690,114 A | | 11/1997 | Chiang et al. |
| 5,722,411 A | | 3/1998 | Suzuki et al. |
| 5,735,797 A | | 4/1998 | Muzilla et al. |
| 5,844,140 A | | 12/1998 | Seale |
| 5,904,652 A | | 5/1999 | Gilbert et al. |
| 5,957,846 A | | 9/1999 | Chiang et al. |
| 5,964,709 A | | 10/1999 | Chiang et al. |
| 6,059,727 A | | 5/2000 | Fowlkes et al. |
| 6,063,030 A | * | 5/2000 | Vara ...................... G16H 40/63 600/440 |
| 6,095,980 A | | 8/2000 | Burns et al. |
| 6,106,472 A | | 8/2000 | Chiang et al. |
| 6,111,816 A | | 8/2000 | Chiang et al. |
| 6,126,601 A | | 10/2000 | Gilling |
| 6,126,608 A | | 10/2000 | Kemme et al. |
| 6,131,459 A | | 10/2000 | Seale et al. |
| 6,139,501 A | | 10/2000 | Roundhill et al. |
| 6,146,331 A | | 11/2000 | Wong |

| | | | |
|---|---|---|---|
| 6,238,344 B1 | 5/2001 | Gamelsky et al. |
| 6,248,073 B1 | 6/2001 | Gilbert et al. |
| 6,261,234 B1 | 7/2001 | Lin |
| 6,371,918 B1 | 4/2002 | Bunce |
| 6,417,797 B1 | 7/2002 | Cousins et al. |
| 6,417,857 B2 | 7/2002 | Finger et al. |
| 6,425,865 B1 | 7/2002 | Salcudean et al. |
| 6,436,040 B1 | 8/2002 | Collamore et al. |
| 6,447,451 B1 | 9/2002 | Wing et al. |
| 6,450,958 B1 | 9/2002 | Linkhart et al. |
| 6,468,212 B1 | 10/2002 | Scott et al. |
| 6,500,122 B1 | 12/2002 | Washburn et al. |
| 6,500,126 B1 | 12/2002 | Brock-Fisher |
| 6,516,667 B1 | 2/2003 | Broad et al. |
| 6,519,632 B1 | 2/2003 | Brackett et al. |
| 6,520,912 B1 | 2/2003 | Brooks et al. |
| 6,530,887 B1 | 3/2003 | Gilbert et al. |
| 6,540,682 B1 | 4/2003 | Leavitt et al. |
| 6,558,326 B2 | 5/2003 | Pelissier |
| 6,569,102 B2 | 5/2003 | Imran et al. |
| 6,575,908 B2 | 6/2003 | Barnes et al. |
| 6,599,256 B1 | 7/2003 | Acker et al. |
| 6,603,494 B1 | 8/2003 | Banks et al. |
| 6,638,226 B2 | 10/2003 | He et al. |
| 6,648,825 B1 | 11/2003 | Mesaros et al. |
| 6,663,567 B2 | 12/2003 | Ji et al. |
| 6,669,633 B2 | 12/2003 | Brodsky et al. |
| 6,682,483 B1 | 1/2004 | Abend et al. |
| 6,689,055 B1 | 2/2004 | Mullen et al. |
| 6,709,391 B2 | 3/2004 | Mesaros et al. |
| 6,719,698 B2 | 4/2004 | Manor et al. |
| 6,760,755 B1 | 7/2004 | Brackett |
| 6,761,689 B2 | 7/2004 | Salgo et al. |
| 6,980,419 B2 | 12/2005 | Smith et al. |
| 7,022,075 B2 | 4/2006 | Grunwald et al. |
| 7,115,093 B2 | 10/2006 | Halmann et al. |
| 7,223,242 B2 | 5/2007 | He et al. |
| 7,338,450 B2 | 3/2008 | Kristoffersen et al. |
| 7,352,570 B2 | 4/2008 | Smith et al. |
| 7,457,672 B2 | 11/2008 | Katsman et al. |
| 7,604,601 B2 | 10/2009 | Altmann et al. |
| 7,736,313 B2 | 6/2010 | Luo et al. |
| 7,736,314 B2 | 6/2010 | Beach et al. |
| 7,794,398 B2 | 9/2010 | Salgo |
| 7,927,280 B2 | 4/2011 | Davidsen |
| 8,012,092 B2 | 9/2011 | Powers et al. |
| 8,128,563 B2 | 3/2012 | Kristoffersen |
| 8,172,753 B2 | 5/2012 | Halmann |
| 8,214,011 B2 | 7/2012 | Friedman et al. |
| 8,235,903 B2 | 8/2012 | Abraham |
| 8,241,220 B2 | 8/2012 | Wilser et al. |
| 8,319,770 B2 | 11/2012 | Friedman et al. |
| 8,357,094 B2 | 1/2013 | Mo et al. |
| 8,394,023 B2 | 3/2013 | Friedman et al. |
| 8,409,095 B1 | 4/2013 | Marquis |
| 8,435,183 B2 | 5/2013 | Barnes et al. |
| 8,659,507 B2 | 2/2014 | Roncalez et al. |
| 8,925,386 B2 | 1/2015 | Oshiki |
| 9,033,879 B2 | 5/2015 | Urness et al. |
| 9,072,471 B2 | 7/2015 | Kato et al. |
| 9,113,825 B2 | 8/2015 | Chaggares et al. |
| 9,163,980 B2 | 10/2015 | Herzog et al. |
| 9,173,639 B2 | 11/2015 | Ichioka et al. |
| 9,198,680 B2 | 12/2015 | Fraser et al. |
| 9,220,478 B2 | 12/2015 | Smith et al. |
| 9,301,730 B2 | 4/2016 | Poland |
| 9,314,225 B2 | 4/2016 | Steen et al. |
| 9,327,142 B2 | 5/2016 | Rothberg et al. |
| 9,386,964 B2 | 7/2016 | Bagge |
| 9,504,448 B2 | 11/2016 | Cheng et al. |
| 9,597,008 B2 | 3/2017 | Henkel et al. |
| 9,848,849 B2 | 12/2017 | Pfeiffer et al. |
| 9,877,699 B2 | 1/2018 | Chiang et al. |
| 9,962,143 B2 | 5/2018 | Funakubo |
| 9,983,905 B2 | 5/2018 | Tobias et al. |
| 9,986,972 B2 | 6/2018 | Halmann et al. |
| RE46,931 E | 7/2018 | McLaughlin et al. |
| 10,426,430 B2 | 10/2019 | Zagorchev et al. |
| 10,667,790 B2 | 6/2020 | Chiang et al. |

(56) References Cited

U.S. PATENT DOCUMENTS

| | | |
|---|---|---|
| 10,856,847 B2 | 12/2020 | Rothberg et al. |
| 11,179,138 B2 | 11/2021 | Chiang et al. |
| 11,287,309 B2 | 3/2022 | Schmid et al. |
| 11,660,003 B2 | 5/2023 | Schmid |
| 11,865,287 B2 | 1/2024 | Ignon et al. |
| 2002/0087061 A1 | 7/2002 | Lifshitz et al. |
| 2002/0120193 A1 | 8/2002 | Chiang et al. |
| 2002/0154727 A1 | 10/2002 | Ning |
| 2002/0173721 A1 | 11/2002 | Grunwald et al. |
| 2003/0013959 A1 | 1/2003 | Grunwald et al. |
| 2003/0078501 A1 | 4/2003 | Barnes et al. |
| 2003/0088182 A1 | 5/2003 | He et al. |
| 2003/0097071 A1 | 5/2003 | Halmann et al. |
| 2003/0139664 A1 | 7/2003 | Hunt et al. |
| 2003/0195418 A1 | 10/2003 | Barnes et al. |
| 2003/0212327 A1 | 11/2003 | Wang et al. |
| 2004/0015079 A1 | 1/2004 | Berger et al. |
| 2004/0059220 A1 | 3/2004 | Mourad et al. |
| 2004/0138569 A1 | 7/2004 | Grunwald et al. |
| 2004/0147840 A1 | 7/2004 | Duggirala et al. |
| 2004/0150963 A1 | 8/2004 | Holmberg et al. |
| 2004/0152982 A1 | 8/2004 | Hwang et al. |
| 2004/0152986 A1 | 8/2004 | Fidel et al. |
| 2004/0158154 A1 | 8/2004 | Hanafy et al. |
| 2004/0193042 A1 | 9/2004 | Scampini et al. |
| 2005/0085730 A1 | 4/2005 | Flesch et al. |
| 2005/0101864 A1 | 5/2005 | Zheng et al. |
| 2005/0113690 A1 | 5/2005 | Halmann et al. |
| 2005/0119574 A1 | 6/2005 | Maerfeld et al. |
| 2005/0281444 A1 | 12/2005 | Lundberg et al. |
| 2006/0020204 A1 | 1/2006 | Serra et al. |
| 2006/0020206 A1 | 1/2006 | Serra et al. |
| 2006/0058609 A1 | 3/2006 | Olstad |
| 2006/0173326 A1 | 8/2006 | Thiele |
| 2007/0139873 A1 | 6/2007 | Thomas et al. |
| 2007/0140424 A1 | 6/2007 | Serceki |
| 2007/0161905 A1 | 7/2007 | Munrow |
| 2007/0167709 A1 | 7/2007 | Slayton et al. |
| 2007/0211064 A1 | 9/2007 | Buck et al. |
| 2007/0265531 A1 | 11/2007 | He et al. |
| 2008/0055826 A1 | 3/2008 | Smith et al. |
| 2008/0108899 A1 | 5/2008 | Halmann et al. |
| 2008/0119731 A1 | 5/2008 | Becerra et al. |
| 2008/0146922 A1 | 6/2008 | Steins et al. |
| 2008/0161686 A1 | 7/2008 | Halmann |
| 2008/0161688 A1 | 7/2008 | Poland et al. |
| 2008/0172383 A1 | 7/2008 | Lea et al. |
| 2008/0208047 A1 | 8/2008 | Delso |
| 2008/0208061 A1 | 8/2008 | Halmann |
| 2008/0215982 A1 | 9/2008 | Washburn et al. |
| 2008/0249414 A1 | 10/2008 | Yang et al. |
| 2008/0253589 A1 | 10/2008 | Trahms |
| 2008/0319316 A1 | 12/2008 | Powers et al. |
| 2009/0012401 A1 | 1/2009 | Steinbacher |
| 2009/0043195 A1 | 2/2009 | Poland |
| 2009/0054781 A1 | 2/2009 | Stonefield et al. |
| 2009/0099453 A1 | 4/2009 | Kristoffersen |
| 2009/0125840 A1 | 5/2009 | Squilla et al. |
| 2009/0131793 A1 | 5/2009 | Stonefield et al. |
| 2009/0177086 A1 | 7/2009 | Steen |
| 2009/0198132 A1 | 8/2009 | Pelissier et al. |
| 2009/0275835 A1 | 11/2009 | Hwang et al. |
| 2010/0022890 A1 | 1/2010 | Fukukita et al. |
| 2010/0094132 A1 | 4/2010 | Hansen et al. |
| 2010/0145195 A1 | 6/2010 | Hyun |
| 2010/0160787 A1 | 6/2010 | Gorzitze |
| 2010/0174189 A1 | 7/2010 | Abraham |
| 2010/0179428 A1 | 7/2010 | Pedersen et al. |
| 2010/0217123 A1 | 8/2010 | Eran et al. |
| 2010/0217128 A1 | 8/2010 | Betts |
| 2010/0305444 A1 | 12/2010 | Fujii et al. |
| 2011/0050594 A1 | 3/2011 | Kim et al. |
| 2011/0099513 A1 | 4/2011 | Ameline |
| 2011/0112399 A1 | 5/2011 | Willems et al. |
| 2011/0125022 A1 | 5/2011 | Lazebnik |
| 2011/0218436 A1 | 9/2011 | Dewey et al. |
| 2011/0230764 A1 | 9/2011 | Baba et al. |
| 2011/0237948 A1 | 9/2011 | Corn |
| 2011/0313292 A1 | 12/2011 | Kwak et al. |
| 2012/0010508 A1 | 1/2012 | Sokulin et al. |
| 2012/0029303 A1 | 2/2012 | Shaya |
| 2012/0053463 A1 | 3/2012 | Yoo |
| 2012/0065513 A1 | 3/2012 | Lee |
| 2012/0078108 A1 | 3/2012 | Kim et al. |
| 2012/0089024 A1 | 4/2012 | Hong |
| 2012/0095342 A1 | 4/2012 | Lee |
| 2012/0101378 A1 | 4/2012 | Lee |
| 2012/0108962 A1 | 5/2012 | Yoon |
| 2012/0108964 A1 | 5/2012 | Lee et al. |
| 2012/0112605 A1 | 5/2012 | Kim |
| 2012/0130244 A1 | 5/2012 | Kim |
| 2012/0133601 A1 | 5/2012 | Marshall et al. |
| 2012/0136252 A1 | 5/2012 | Cho |
| 2012/0136254 A1 | 5/2012 | Kim |
| 2012/0157836 A1 | 6/2012 | Kim |
| 2012/0157844 A1 | 6/2012 | Halmann |
| 2012/0157847 A1 | 6/2012 | Kim |
| 2012/0157848 A1 | 6/2012 | Kim |
| 2012/0179037 A1 | 7/2012 | Halmann |
| 2012/0179038 A1 | 7/2012 | Meurer et al. |
| 2012/0184849 A1 | 7/2012 | Sandstrom et al. |
| 2012/0190984 A1 | 7/2012 | Kim et al. |
| 2012/0209107 A1 | 8/2012 | Guo et al. |
| 2012/0215108 A1 | 8/2012 | Park et al. |
| 2012/0220873 A1 | 8/2012 | Hyun |
| 2012/0232399 A1 | 9/2012 | Lee |
| 2012/0265027 A1 | 10/2012 | Lee et al. |
| 2012/0265074 A1 | 10/2012 | Na et al. |
| 2012/0283605 A1 | 11/2012 | Lewis, Jr. |
| 2012/0288172 A1 | 11/2012 | Perrey et al. |
| 2012/0289828 A1 | 11/2012 | Jensen et al. |
| 2012/0302883 A1 | 11/2012 | Kong et al. |
| 2012/0316444 A1 | 12/2012 | Shim et al. |
| 2013/0018265 A1 | 1/2013 | Kim et al. |
| 2013/0019193 A1 | 1/2013 | Rhee et al. |
| 2013/0072795 A1 | 3/2013 | Mo et al. |
| 2013/0072797 A1 | 3/2013 | Lee |
| 2013/0079627 A1 | 3/2013 | Lee |
| 2013/0144169 A1 | 6/2013 | Lee et al. |
| 2013/0144194 A1 | 6/2013 | Ahn et al. |
| 2013/0165783 A1 | 6/2013 | Kim et al. |
| 2013/0184578 A1 | 7/2013 | Lee et al. |
| 2013/0190624 A1 | 7/2013 | Beger et al. |
| 2013/0202169 A1 | 8/2013 | Lee et al. |
| 2013/0202174 A1 | 8/2013 | Lee |
| 2013/0218014 A1 | 8/2013 | Shim et al. |
| 2013/0218024 A1 | 8/2013 | Boctor et al. |
| 2013/0226001 A1 | 8/2013 | Steen et al. |
| 2013/0226004 A1 | 8/2013 | Lee |
| 2013/0237811 A1 | 9/2013 | Mihailescu et al. |
| 2013/0237824 A1 | 9/2013 | Kim |
| 2013/0237828 A1 | 9/2013 | Lee et al. |
| 2013/0239052 A1 | 9/2013 | Moody et al. |
| 2013/0245449 A1 | 9/2013 | Barnes et al. |
| 2013/0253316 A1 | 9/2013 | Choi |
| 2013/0253323 A1 | 9/2013 | Kim |
| 2013/0261434 A1 | 10/2013 | Kim et al. |
| 2013/0261448 A1 | 10/2013 | Hyun et al. |
| 2013/0261459 A1 | 10/2013 | Na et al. |
| 2013/0320485 A1 | 12/2013 | Ching Tee et al. |
| 2013/0324850 A1 | 12/2013 | Petruzzelli et al. |
| 2013/0328810 A1 | 12/2013 | Li et al. |
| 2013/0331694 A1 | 12/2013 | Barnes et al. |
| 2014/0005550 A1 | 1/2014 | Lu et al. |
| 2014/0009686 A1 | 1/2014 | Segal |
| 2014/0039277 A1 | 2/2014 | Abraham |
| 2014/0051984 A1 | 2/2014 | Berger et al. |
| 2014/0100440 A1 | 4/2014 | Cheline et al. |
| 2014/0107435 A1 | 4/2014 | Sharf et al. |
| 2014/0111451 A1 | 4/2014 | Park et al. |
| 2014/0114190 A1 | 4/2014 | Chiang et al. |
| 2014/0114194 A1 | 4/2014 | Kanayama et al. |
| 2014/0121524 A1 | 5/2014 | Chiang et al. |
| 2014/0164965 A1 | 6/2014 | Lee et al. |

(56) References Cited

U.S. PATENT DOCUMENTS

| | | | |
|---|---|---|---|
| 2014/0180111 A1 | 6/2014 | Gopinathan et al. |
| 2014/0187934 A1 | 7/2014 | Urness |
| 2014/0187946 A1 | 7/2014 | Miller et al. |
| 2014/0194742 A1 | 7/2014 | Sundaran Baby Sarojam et al. |
| 2014/0200452 A1 | 7/2014 | Chang et al. |
| 2014/0200456 A1 | 7/2014 | Owen |
| 2014/0237811 A1 | 8/2014 | Guercioni |
| 2014/0243614 A1 | 8/2014 | Rothberg et al. |
| 2014/0243669 A1 | 8/2014 | Halmann et al. |
| 2014/0257104 A1 | 9/2014 | Dunbar et al. |
| 2014/0296711 A1 | 10/2014 | Lee |
| 2014/0378835 A1 | 12/2014 | Satoh et al. |
| 2015/0087982 A1 | 3/2015 | Mullick et al. |
| 2015/0182197 A1 | 7/2015 | Willems et al. |
| 2015/0238168 A1 | 8/2015 | Poland |
| 2015/0313578 A1 | 11/2015 | Yu et al. |
| 2015/0366536 A1 | 12/2015 | Courtney et al. |
| 2016/0110875 A1 | 4/2016 | Sugiyama et al. |
| 2016/0135786 A1 | 5/2016 | Mullen et al. |
| 2016/0174937 A1 | 6/2016 | Bakshi et al. |
| 2016/0228091 A1 | 8/2016 | Chiang et al. |
| 2016/0278739 A1 | 9/2016 | Pelissier et al. |
| 2016/0287214 A1 | 10/2016 | Ralovich et al. |
| 2017/0000464 A1 | 1/2017 | Chang et al. |
| 2017/0020490 A1 | 1/2017 | Ryu et al. |
| 2017/0055951 A1 | 3/2017 | Messina et al. |
| 2017/0079551 A1 | 3/2017 | Henkel et al. |
| 2017/0095228 A1 | 4/2017 | Richard et al. |
| 2017/0095230 A1 | 4/2017 | Richard et al. |
| 2017/0095231 A1 | 4/2017 | Richard et al. |
| 2017/0143307 A1 | 5/2017 | Tahmasebi Maraghoosh |
| 2017/0249744 A1 | 8/2017 | Wang et al. |
| 2017/0360412 A1 | 12/2017 | Rothberg et al. |
| 2018/0182096 A1 | 6/2018 | Grady et al. |
| 2019/0046158 A1 | 2/2019 | Kroon et al. |
| 2019/0336101 A1 | 11/2019 | Chiang et al. |
| 2019/0365350 A1 | 12/2019 | Chiang |
| 2020/0268351 A1 | 8/2020 | Chiang et al. |
| 2021/0015456 A1 | 1/2021 | Chiang et al. |
| 2022/0015741 A1 | 1/2022 | Amador Carrascal et al. |
| 2022/0125407 A1 | 4/2022 | Chiang et al. |
| 2025/0213221 A1 | 7/2025 | Chiang et al. |

FOREIGN PATENT DOCUMENTS

| | | | |
|---|---|---|---|
| CN | 101390778 A | 3/2009 |
| CN | 101869484 A | 10/2010 |
| CN | 102178547 A | 9/2011 |
| CN | 102525556 A | 7/2012 |
| CN | 102626324 A | 8/2012 |
| CN | 102636787 A | 8/2012 |
| CN | 101742968 B | 1/2013 |
| CN | 102872542 A | 1/2013 |
| CN | 102930170 A | 2/2013 |
| CN | 102940507 A | 2/2013 |
| CN | 102988043 A | 3/2013 |
| CN | 101677805 B | 5/2013 |
| CN | 103140175 A | 6/2013 |
| CN | 103876781 A | 6/2014 |
| EP | 1016875 A2 | 7/2000 |
| EP | 1239396 A2 | 9/2002 |
| EP | 1589878 B1 | 10/2009 |
| EP | 2422705 A1 | 2/2012 |
| EP | 2425784 A1 | 3/2012 |
| EP | 2453256 A2 | 5/2012 |
| EP | 2455753 A2 | 5/2012 |
| EP | 2468191 A1 | 6/2012 |
| EP | 2575628 A2 | 4/2013 |
| EP | 2599442 A1 | 6/2013 |
| EP | 2605035 A2 | 6/2013 |
| EP | 2637166 A2 | 9/2013 |
| EP | 2023820 B1 | 3/2019 |
| EP | 2967486 B1 | 7/2020 |
| JP | 62-97539 A | 5/1987 |
| JP | 10-73658 A | 3/1998 |
| JP | H11-508461 A | 7/1999 |
| JP | 2003-190159 A | 7/2003 |
| JP | 2004-530463 A | 10/2004 |
| JP | 2005-137747 A | 6/2005 |
| JP | 2006-68524 A | 3/2006 |
| JP | 2008-18107 A | 1/2008 |
| JP | 2008-515583 A | 5/2008 |
| JP | 2008-536555 A | 9/2008 |
| JP | 2009-45081 A | 3/2009 |
| JP | 2009-119259 A | 6/2009 |
| JP | 2009-525538 A | 7/2009 |
| JP | 2009-183720 A | 8/2009 |
| JP | 2009-240779 A | 10/2009 |
| JP | 2010-131396 A | 6/2010 |
| JP | 2010-220218 A | 9/2010 |
| JP | 2011-72746 A | 4/2011 |
| JP | 2011-87949 A | 5/2011 |
| JP | 2011-104079 A | 6/2011 |
| JP | 2011-200482 A | 10/2011 |
| JP | 2012-24133 A | 2/2012 |
| JP | 2012-101075 A | 5/2012 |
| JP | 2013-043082 A | 3/2013 |
| JP | 2013-111203 A | 6/2013 |
| JP | 2013-172959 A | 9/2013 |
| JP | 2013-188328 A | 9/2013 |
| JP | 2015-515312 A | 5/2015 |
| JP | 2016-087020 A | 5/2016 |
| KR | 20120043642 A | 5/2012 |
| KR | 20120047785 A | 5/2012 |
| KR | 20120071319 A | 7/2012 |
| KR | 20120097324 A | 9/2012 |
| KR | 20120117714 A | 10/2012 |
| KR | 20120137206 A | 12/2012 |
| KR | 20120138478 A | 12/2012 |
| KR | 20130011793 A | 1/2013 |
| KR | 20130012501 A | 2/2013 |
| KR | 20130012844 A | 2/2013 |
| KR | 20130020035 A | 2/2013 |
| KR | 20130020054 A | 2/2013 |
| KR | 20130020371 A | 2/2013 |
| KR | 20130022249 A | 3/2013 |
| KR | 20130026041 A | 3/2013 |
| KR | 20130030663 A | 3/2013 |
| KR | 20130033717 A | 4/2013 |
| KR | 20130036327 A | 4/2013 |
| KR | 101269459 B1 | 5/2013 |
| KR | 20130043702 A | 5/2013 |
| KR | 20130054013 A | 5/2013 |
| KR | 20130056676 A | 5/2013 |
| KR | 101273585 B1 | 6/2013 |
| KR | 20130059307 A | 6/2013 |
| KR | 20130060007 A | 6/2013 |
| KR | 20130066821 A | 6/2013 |
| KR | 20130074398 A | 7/2013 |
| KR | 20130074399 A | 7/2013 |
| KR | 20130075458 A | 7/2013 |
| KR | 20130075465 A | 7/2013 |
| KR | 20130075472 A | 7/2013 |
| KR | 20130075477 A | 7/2013 |
| KR | 20130075481 A | 7/2013 |
| KR | 20130075486 A | 7/2013 |
| KR | 20130076031 A | 7/2013 |
| KR | 20130076042 A | 7/2013 |
| KR | 20130076054 A | 7/2013 |
| KR | 20130076064 A | 7/2013 |
| KR | 20130076071 A | 7/2013 |
| KR | 20130076404 A | 7/2013 |
| KR | 20130076428 A | 7/2013 |
| KR | 20130077118 A | 7/2013 |
| KR | 20130077121 A | 7/2013 |
| KR | 20130077406 A | 7/2013 |
| KR | 20130078935 A | 7/2013 |
| KR | 20130078972 A | 7/2013 |
| KR | 20130080640 A | 7/2013 |
| KR | 20130081067 A | 7/2013 |
| KR | 20130081626 A | 7/2013 |
| KR | 20130081684 A | 7/2013 |
| KR | 20130082267 A | 7/2013 |
| KR | 20130083725 A | 7/2013 |

(56)                References Cited

FOREIGN PATENT DOCUMENTS

| KR | 20130084049 A | 7/2013 |
| KR | 20130087291 A | 8/2013 |
| KR | 20130087478 | 8/2013 |
| KR | 20130088478 A | 8/2013 |
| KR | 20130089037 A | 8/2013 |
| KR | 20130090038 A | 8/2013 |
| KR | 20130094671 A | 8/2013 |
| KR | 20130095160 A | 8/2013 |
| KR | 20130095236 A | 8/2013 |
| KR | 20130095505 A | 8/2013 |
| TW | I378255 | 12/2012 |
| TW | I380014 | 12/2012 |
| TW | I406684 | 9/2013 |
| WO | 2000/31634 A1 | 6/2000 |
| WO | WO-2002/068992 A2 | 9/2002 |
| WO | 2003/027662 A2 | 7/2003 |
| WO | WO-2003/075769 A1 | 9/2003 |
| WO | WO-2005/053664 A2 | 6/2005 |
| WO | WO-2005/058168 A2 | 6/2005 |
| WO | WO-2006/030378 A1 | 3/2006 |
| WO | WO-2006/040697 A1 | 4/2006 |
| WO | 2006/111872 A2 | 10/2006 |
| WO | 2006/111874 A2 | 10/2006 |
| WO | WO-2006/111871 A1 | 10/2006 |
| WO | WO-2008/069021 A1 | 6/2008 |
| WO | WO-2008/115312 A2 | 9/2008 |
| WO | 2008/146208 A2 | 12/2008 |
| WO | WO-2009/129845 A1 | 10/2009 |
| WO | WO-2010/020939 A2 | 2/2010 |
| WO | 2010/032151 A1 | 3/2010 |
| WO | WO-2010/042282 A1 | 4/2010 |
| WO | WO-2010/051587 A1 | 5/2010 |
| WO | WO-2012/091518 A2 | 7/2012 |
| WO | 2012/101511 A2 | 8/2012 |
| WO | WO-2012/141550 A2 | 10/2012 |
| WO | WO-2013/030746 A1 | 3/2013 |
| WO | WO-2013/034175 A1 | 3/2013 |
| WO | WO-2013/055707 A1 | 4/2013 |
| WO | WO-2013/095032 A1 | 6/2013 |
| WO | WO-2013/122320 A1 | 8/2013 |
| WO | WO-2013/148730 A2 | 10/2013 |
| WO | WO-2013/162244 A1 | 10/2013 |
| WO | WO-2014/003404 A1 | 1/2014 |
| WO | WO-2014/014965 A1 | 1/2014 |
| WO | 2014/035567 A1 | 3/2014 |
| WO | WO-2014/134316 A1 | 9/2014 |
| WO | WO-2015/048327 A2 | 4/2015 |
| WO | WO-2015/114484 A1 | 8/2015 |
| WO | WO-2016/001865 A1 | 1/2016 |
| WO | WO-2016/083985 A1 | 6/2016 |
| WO | WO-2017/013511 A1 | 1/2017 |
| WO | WO-2017/222970 A1 | 12/2017 |

OTHER PUBLICATIONS

Ultrasound Diagnostic System, Model: SonoTouch 20, Operator's Manual, Direction: CHUM-001a, Rev. 1.0, 98 pages, Oct. 13, 2012.
U.S. Appl. No. 16/806,118, filed Mar. 2, 2020, 2020-0268351.
U.S. Appl. No. 17/520,150, filed Nov. 5, 2021, 2022-0125407.
alibaba.com, Chison SonoTouch 10 B&W Handled Ultrasound Tablet With CE FDA. Shaanxi Aipu Medical Instrument Co., Ltd. 6 pages, (2014).
Alrayashi et al., Hands-free continuous transthoracic echocardiography: A contemporary evolution of the precordial stethoscope. Paediatr Anaesth. May 2021;31(5):616-618.
AMD Case Study. AMD embedded G-Series APU boosts 3-D visualization for portable ultrasound device. 3 pages. (2014).
Basoglu et al., Applications of a next-generation programmable ultrasound machine. Proceedings SPIE Medical Imaging. 1 page, Abstract 3031, May 7, 1997.
Basoglu et al., Computing requirements of modern medical diagnostic ultrasound machines. Parallel Computing. Sep. 1998;24(9-10):1407-1431.

Brattain et al. Machine learning for medical ultrasound: status, methods, and future opportunities. Abdominal Radiology. Apr. 1, 2018;43(4):786-99.
Chison Medical Imaging Co., Ltd., Premarket Notification [510(k)] Summary. SonoTouch Series Diagnostic Ultrasound System. 11 pages, Aug. 2, 2012.
Dickson, Wireless communication options for a mobile ultrasound system. Thesis Submitted to the Faculty of Worcester Polytechnic Institute. 2008. 252 pages.
Esaote, MyLab Ultrasound Scanners, DICOM Conformance Statement, Document Version 6.3. May 21, 2010. 277 pages.
Esaote, MyLab Ultrasound Scanners, DICOM Conformance Statement, Document Version 6.5. Jul. 19, 2011. 278 pages.
Esaote, MyLab Ultrasound Scanners, DICOM Conformance Statement, Document Version 6.6. Mar. 1, 2012. 278 pages.
Felix et al., Biplane ultrasound arrays with integrated multiplexing solution for enhanced diagnostic accuracy in endorectal and transvaginal imaging. IEEE Ultrasonics Symposium, Sep. 18, 2005;4:2251-2254.
Gray et al., Ultrasound-guided Regional Anesthesia, Current State of the Art. Anesthesiology. Feb. 2006;104:368-73.
Kang et al., Stereoscopic augmented reality for laparoscopic surgery. Surg Endosc. 2014;28(7):2227-2235.
Karadayi et al., Software-based Ultrasound Beamforming on Multicore DSPs. IEEE International Ultrasonics. Oct. 18-21, 2011, 14 pages.
Khuri-Yakub et al., Capacitive micromachined ultrasonic transducers for medical imaging and therapy. J Micromech Microeng. May 2011;21(5):54004, 11 pages.
Lee et al., A new smart probe system for a tablet PC-based point-of-care ultrasound imaging system: feasibility study. IEEE International Ultrasonics Symposium Proceedings. 2014;1611-14.
Lewandowski et al., Modular and scalable ultrasound platform with GPU processing. Conference Paper, Warsaw, Poland. 5 pages. (Oct. 2012).
NanoMaxx Ultrasound System—Sonosite—User Guide. 100 pages (2010).
SOMA, Access Systems, Introducing AxoTrack™ Needle visualization as you've never seen it. Retrieved online at: SomaAccessSystems. com, 6 pages.
Song et al., Tailored Holder for Continuous Echocardiographic Monitoring. Anesth Analg. Feb. 2018;126(2):435-437.
SonoTouch, The Revolution is at Hand, catalog. Retrieved online at: www.sonatouch.com. 4 pages.
SonoTouch, The Revolution is at Hand, SonoTouch 20 Operation Manual. 68 pages.
Stolka et al., Needle guidance using handheld stereo vision and projection for ultrasound-based interventions. Med Image Comput Comput Assist Interv. 2014;17(Pt 2):684-91.
Wygant et al., Beamforming and hardware design for a multichannel front-end integrated circuit for real-time 3D catheter-based ultrasonic imaging. Proceedings of SPiE. 2006;6147:61470A-1.
York et al., Ultrasound Processing and Computing: Review and Future Directions. Annu Rev Biomed Eng. 1999;1:559-588.
York, Architecture and Algorithms for a Fully Programmable Ultrasound System. A dissertation in partial fulfillment of the requirements for the Degree of Doctor of Philosophy, University of Washington. 141 pages, (1999).
Zhang et al., A software package for portavle three-dimensional ultrasound imaging. 2nd IEEE International Symposium on Biomedical Imaging: Nano to Macro. 2004;1:539-42.
International Preliminary Report on Patentability for Application No. PCT/US2013/033941, dated Oct. 1, 2014. 24 pages.
International Search Report and Written Opinion for Application No. PCT/US2013/0333941, dated Oct. 8, 2013. 32 pages.
Invitation to Pay Additional Fees for Application No. PCT/US2014/057516, dated Jan. 13, 2015. 6 pages.
U.S. Appl. No. 13/838,694, filed Mar. 15, 2013, U.S. Pat. No. 10,667,790.
U.S. Appl. No. 14/037,106, filed Sep. 25, 2013, U.S. Pat. No. 9,877,699.
U.S. Appl. No. 15/025,058, filed Mar. 25, 2016, 2016/0228091.

(56) References Cited

OTHER PUBLICATIONS

U.S. Appl. No. 15/833,547, filed Dec. 6, 2017, U.S. Pat. No. 11,179,138.

U.S. Appl. No. 16/806,118, filed Mar. 2, 2020, U.S. Pat. No. 12,115,023.

U.S. Appl. No. 17/520,150, filed Nov. 5, 2021, U.S. Pat. No. 11,857,363.

U.S. Appl. No. 18/397,557, filed Dec. 27, 2023, U.S. Pat. No. 12,102,480.

U.S. Appl. No. 18/902,206, filed Sep. 30, 2024.

U.S. Appl. No. 18/914,810, filed Oct. 14, 2024.

U.S. Appl. No. 16/461,581, filed May 16, 2019, 2019-0365350.

U.S. Appl. No. 16/414,215, filed May 16, 2019, 2019-0336101.

U.S. Appl. No. 16/938,515, filed Jul. 24, 2020, 2021-0015456.

U.S. Appl. No. 18/090,316, filed Dec. 28, 2022, 2023-0181160.

U.S. Appl. No. 18/196,379, filed May 11, 2023, 2024-0057971.

Dewaraja et al., GPU engine enhances ultrasound-detected brain motion calculations. OpenSystems Media. Retrieved online at: https://embeddedcomputing.com/application/healthcare/gpu-engine-enhances-ultrasound-detected-brain-motion-calculations. 5 pages, May 1, 2009.

Kasai et al., Real-Time Two-Dimensional Blood Flow Imaging Using an Autocorrelation Technique. IEEE Transactions on Sonics and Ultrasonics. May 1985;32(3):458-464.

Shenzhen Mindray Bio-Medical Electronics Co., Ltd., Digital Ultrasonic Diagnostic Imaging System. installation Manual. 32 pages, (2007).

\* cited by examiner

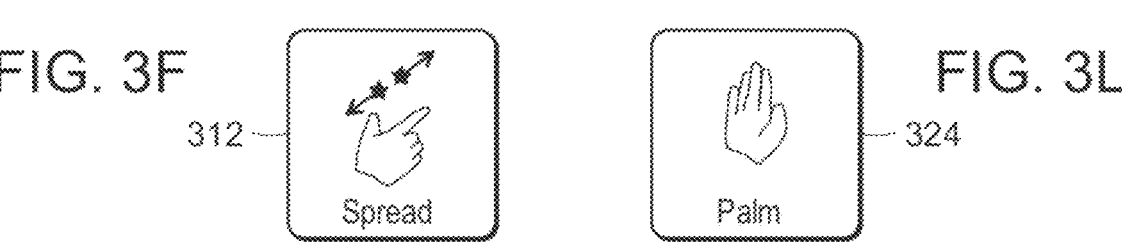
FIG. 3A   302 — Tap
FIG. 3B   304 — Pinch
FIG. 3C   306 — Flick
FIG. 3D   308 — Rotate
FIG. 3E   310 — Double Tap
FIG. 3F   312 — Spread
FIG. 3G   314 — Flick
FIG. 3H   316 — Rotate
FIG. 3I   318 — Drag
FIG. 3J   320 — Press
FIG. 3K   322 — Press & Drag
FIG. 3L   324 — Palm

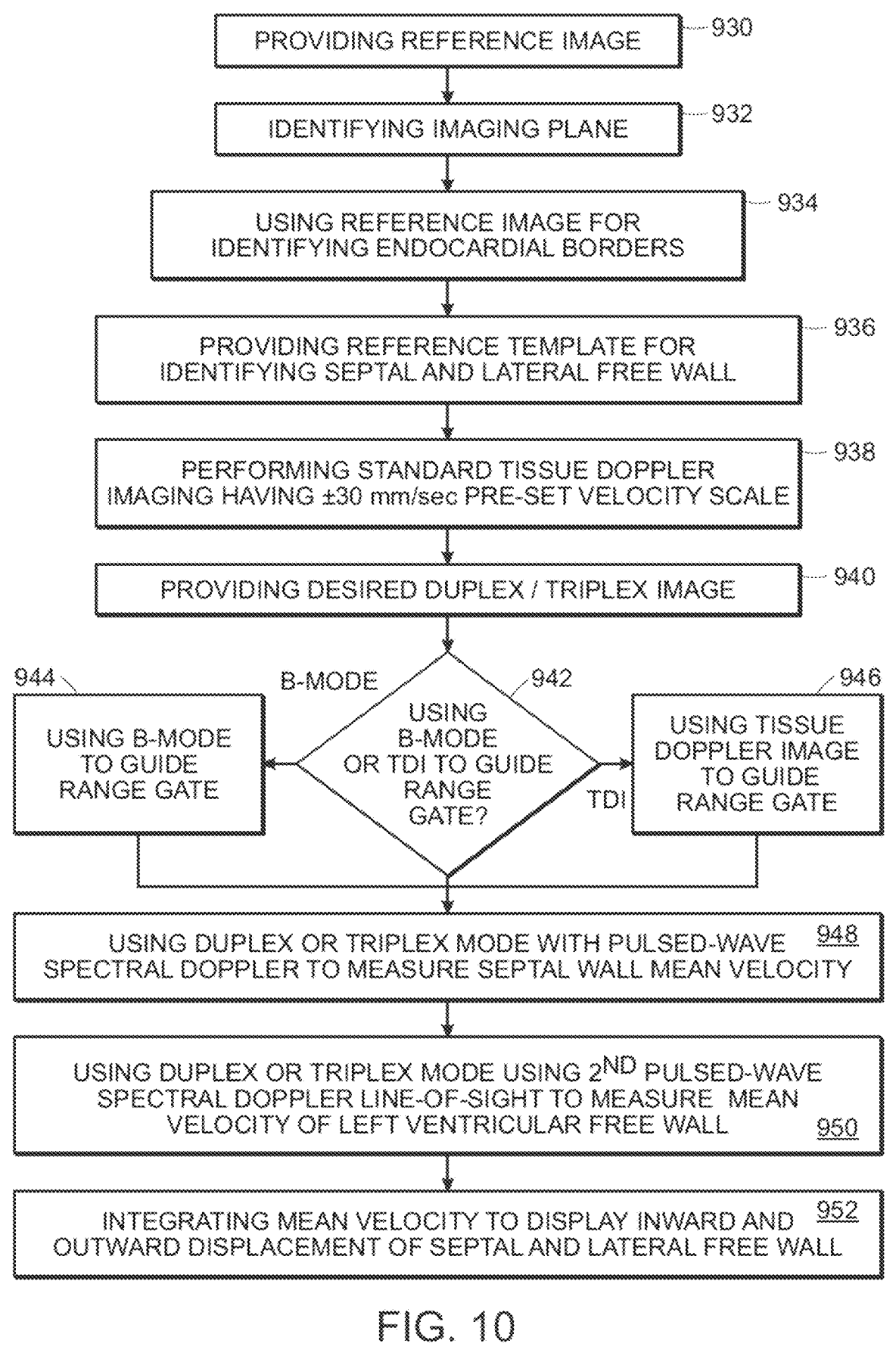

PROVIDING REFERENCE IMAGE —930

IDENTIFYING IMAGING PLANE —932

USING REFERENCE IMAGE FOR IDENTIFYING ENDOCARDIAL BORDERS —934

PROVIDING REFERENCE TEMPLATE FOR IDENTIFYING SEPTAL AND LATERAL FREE WALL —936

PERFORMING STANDARD TISSUE DOPPLER IMAGING HAVING ±30 mm/sec PRE-SET VELOCITY SCALE —938

PROVIDING DESIRED DUPLEX / TRIPLEX IMAGE —940

B-MODE ← USING B-MODE OR TDI TO GUIDE RANGE GATE? →942 TDI

944 — USING B-MODE TO GUIDE RANGE GATE

946 — USING TISSUE DOPPLER IMAGE TO GUIDE RANGE GATE

USING DUPLEX OR TRIPLEX MODE WITH PULSED-WAVE SPECTRAL DOPPLER TO MEASURE SEPTAL WALL MEAN VELOCITY 948

USING DUPLEX OR TRIPLEX MODE USING 2$^{ND}$ PULSED-WAVE SPECTRAL DOPPLER LINE-OF-SIGHT TO MEASURE MEAN VELOCITY OF LEFT VENTRICULAR FREE WALL 950

INTEGRATING MEAN VELOCITY TO DISPLAY INWARD AND OUTWARD DISPLACEMENT OF SEPTAL AND LATERAL FREE WALL 952

FIG. 10

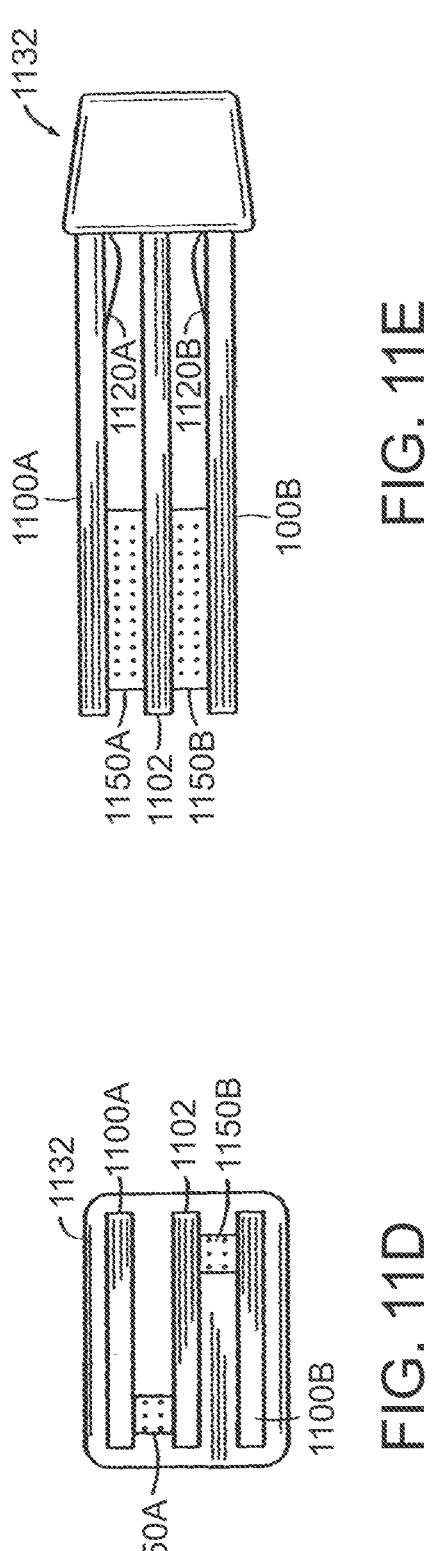
FIG. 11E
FIG. 11D
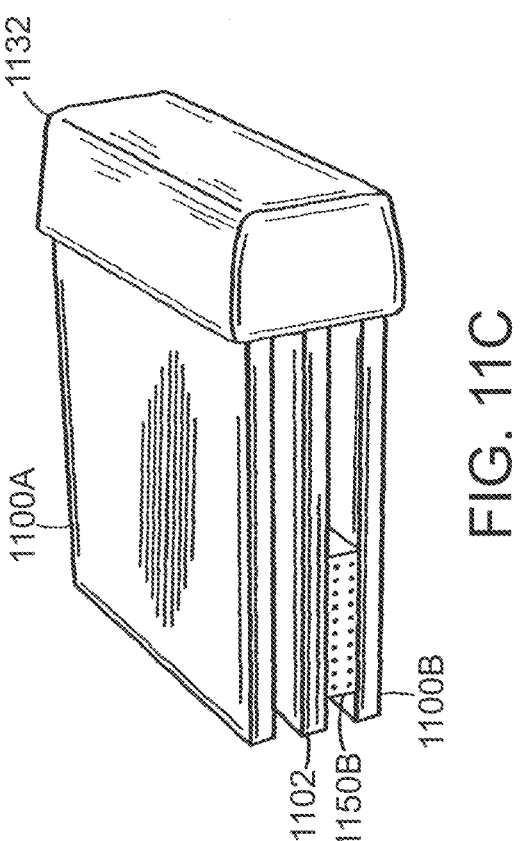
FIG. 11C

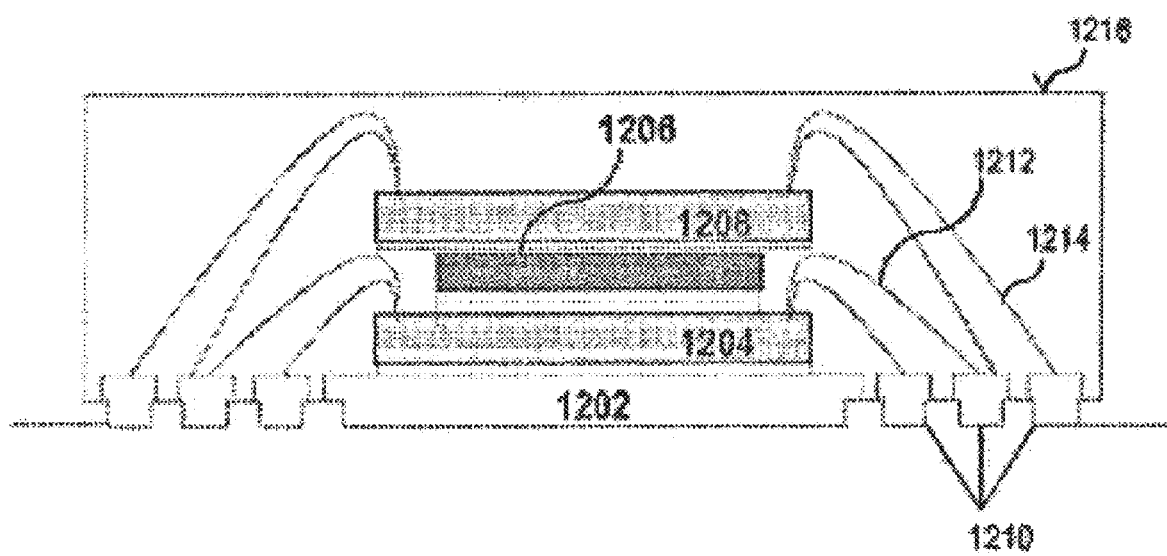
Fig. 12

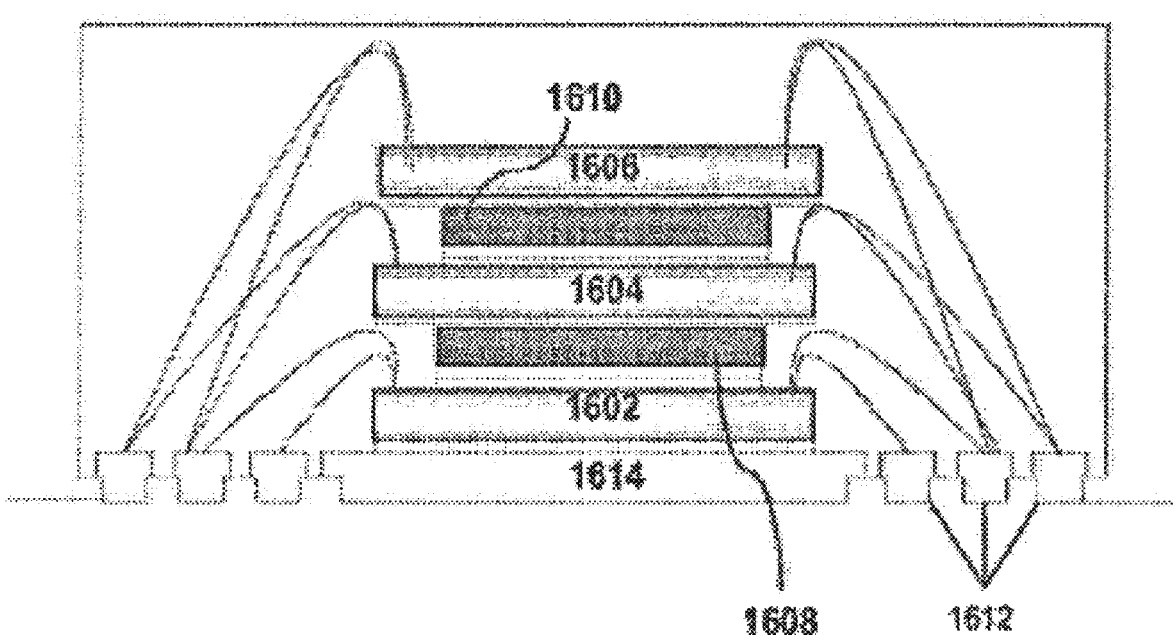
*Fig. 16*

Cart
System
2100

Probe Connector
2118

2102
Touch Screen
Display

Tablet 2104

2106
Adjustable
Height device

2122
Base
Assembly

Cart Stand 2108

2124
Operator
Console

2120
Hot Probe
Holder

2110
Gel Holder

2112
Keyboard

2114
Storage Bin

2126
Wheels

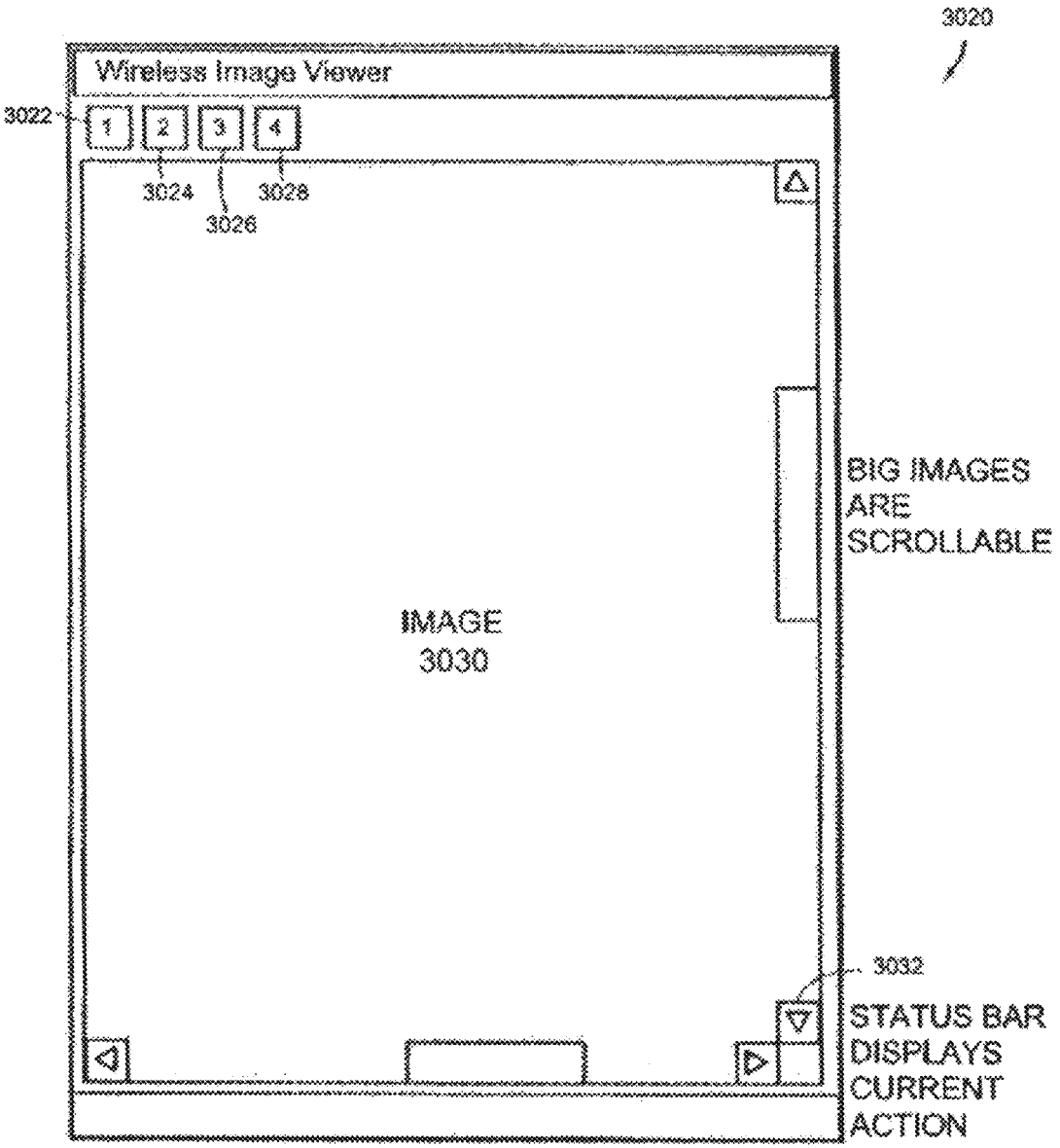

1    CONNECT BUTTON. INITIATES CONNECTION
      TO APPLICATION

2    DISCONNECT BUTTON. TERMINATES CONNECTION.

3    SELECT BUTTON. PROVIDES LIST OF PATIENTS AND
      IMAGES TO SELECT FROM. IMAGES CAN BE STORED
      LOCALLY OR REMOTELY. IF SELECTED IMAGE STORED
      REMOTELY INITIATES IMAGE TRANSMISSION. DISPLAYS
      SELECTED IMAGE.

4    OPTIONS BUTTON. ALLOWS TO CHANGE CONFIGURATION
      PARAMETERS SUCH AS IP ADDRESS.

Catheter
1.5mm
3412

3413

3432

3430

3506
Flexible Frequency
3502
2D Image Window 3504
2D Scan Image

Tablet
Display
3500

3600
Tablet Display

3602
Flexible Frequency
Controls
3604
2D Image Window
3606
2D Image

3608
Motion
Mode
Imaging

5170

Image control bar ~ 5176

Menu bar ~ 5172

Image display window ~ 5174

Image mode bar ~ 5184

Measurements toolbar
5180

Playback toolbar
5182

Freeze image button. When selected,
the Live button is then available.
5186

File toolbar
5178

5202

5200

Patient Folder

BODWIN, MARGE, M[RE4435K3]

Image Folder 06-22-2002

Browse

5210

5208

Image Control

Size

Depth    14

Focus    7.0

TABLET ULTRASOUND SYSTEM

CROSS REFERENCE TO RELATED APPLICATIONS

This application is a continuation of U.S. application Ser. No. 16/806,118, filed Mar. 2, 2020, which is a continuation of U.S. application Ser. No. 13/838,694, filed Mar. 15, 2013, now U.S. Pat. No. 10,667,790, which claims priority to U.S. Provisional Application No. 61/615,627 filed Mar. 26, 2012 and U.S. Provisional Application No. 61/704,254 filed Sep. 21, 2012. All of these applications are incorporated herein by reference in their entirety.

BACKGROUND

Medical ultrasound imaging has become an industry standard for many medical imaging applications. In recent years, there has been an increasing need for medical ultrasound imaging equipment that is portable to allow medical personnel to easily transport the equipment to and from hospital and/or field locations, and more user-friendly to accommodate medical personnel who may possess a range of skill levels.

Conventional medical ultrasound imaging equipment typically includes at least one ultrasound probe/transducer, a keyboard and/or a knob, a computer, and a display. In a typical mode of operation, the ultrasound probe/transducer generates ultrasound waves that can penetrate tissue to different depths based on frequency level, and receives ultrasound waves reflected back from the tissue. Further, medical personnel can enter system inputs to the computer via the keyboard and/or the knob, and view ultrasound images of tissue structures on the display.

However, conventional medical ultrasound imaging equipment that employ such keyboards and/or knobs can be bulky, and therefore may not be amenable to portable use in hospital and/or field locations. Moreover, because such keyboards and/or knobs typically have uneven surfaces, they can be difficult to keep clean in hospital and/or field environments, where maintenance of a sterile field can be crucial to patient health. Some conventional medical ultrasound imaging equipment have incorporated touch screen technology to provide a partial user input interface. However, conventional medical ultrasound imaging equipment that employ such touch screen technology generally provide only limited touch screen functionality in conjunction with a traditional keyboard and/or knob, and can therefore not only be difficult to keep clean, but also complicated to use.

SUMMARY

In accordance with the present application, systems and methods of medical ultrasound imaging are disclosed. The presently disclosed systems and methods of medical ultrasound imaging employ medical ultrasound imaging equipment that includes a handheld housing in a tablet form factor, and a touch screen display disposed on a front panel of the housing. The touch screen display includes a multitouch touch screen that can recognize and distinguish one or more single, multiple, and/or simultaneous touches on a surface of the touch screen display, thereby allowing the use of gestures, ranging from simple single point gestures to complex multipoint gestures, as user inputs to the medical ultrasound imaging equipment.

In accordance with one aspect, exemplary medical ultrasound imaging equipment includes a housing having a front panel and a rear panel, a touch screen display, a computer having at least one processor and at least one memory, an ultrasound beamforming system, and a battery. The housing of the medical ultrasound imaging equipment is implemented in a tablet form factor. The touch screen display is disposed on the front panel of the housing, and includes a multi-touch LCD touch screen that can recognize and distinguish one or more single, multiple, and/or simultaneous touches on a surface of the touch screen display. The computer, the ultrasound beamforming system or engine, and the battery are operatively disposed within the housing. The medical ultrasound imaging equipment can use a Firewire connection operatively connected between the computer and the ultrasound engine within the housing, and a probe connector having a probe attach/detach lever to facilitate the connection of at least one ultrasound probe/transducer. In addition, the exemplary medical ultrasound imaging equipment includes an I/O port connector and a DC power input.

In an exemplary mode of operation, medical personnel can employ simple single point gestures and/or more complex multipoint gestures as user inputs to the multi-touch LCD touch screen for controlling operational modes and/or functions of the exemplary medical ultrasound imaging equipment. Such single point/multipoint gestures can correspond to single and/or multipoint touch events that are mapped to one or more predetermined operations that can be performed by the computer and/or the ultrasound engine. Medical personnel can make such single point/multipoint gestures by various finger, palm, and/or stylus motions on the surface of the touch screen display. The multi-touch LCD touch screen receives the single point/multipoint gestures as user inputs, and provides the user inputs to the computer, which executes, using the processor, program instructions stored in the memory to carry out the predetermined operations associated with the single point/multipoint gestures, at least at some times, in conjunction with the ultrasound engine. Such single point/multipoint gestures on the surface of the touch screen display can include, but are not limited to, a tap gesture, a pinch gesture, a flick gesture, a rotate gesture, a double tap gesture, a spread gesture, a drag gesture, a press gesture, a press and drag gesture, and a palm gesture.

In accordance with an exemplary aspect, at least one flick gesture may be employed to control the depth of tissue penetration of ultrasound waves generated by the ultrasound probe/transducer. For example, a single flick gesture in the "up" direction on the touch screen display surface can increase the penetration depth by one (1) centimeter or any other suitable amount, and a single flick gesture in the "down" direction on the touch screen display surface can decrease the penetration depth by one (1) centimeter or any other suitable amount. Further, a drag gesture in the "up" or "down" direction on the touch screen display surface can increase or decrease the penetration depth in multiples of one (1) centimeter or any other suitable amount. Additional operational modes and/or functions controlled by specific single point/multipoint gestures on the touch screen display surface can include, but are not limited to, freeze/store operations, 2-dimensional mode operations, gain control, color control, split screen control, PW imaging control, cine/time-series image clip scrolling control, zoom and pan control, Doppler and 2-dimensional beam steering control, and/or body marking control. At least some of the operational modes and/or functions of the exemplary medical ultrasound imaging equipment can be controlled by one or more touch controls implemented on the touch screen display. Medical personnel can provide one or more specific single point/multipoint gestures as user inputs for specifying at least one selected subset of the touch controls to be implemented, as required and/or desired, on the touch screen display.

In accordance with another exemplary aspect, a press gesture can be employed inside a region of the touch screen display, and, in response to the press gesture, a virtual window can be provided on the touch screen display for displaying at least a magnified portion of an ultrasound image displayed on the touch screen display. In accordance with still another exemplary aspect, a press and drag gesture can be employed inside the region of the touch screen display, and, in response to the press and drag gesture, a predetermined feature of the ultrasound image can be traced. Further, a tap gesture can be employed inside the region of the touch screen display, substantially simultaneously with a portion of the press and drag gesture, and, in response to the tap gesture, the tracing of the predetermined feature of the ultrasound image can be completed.

By providing medical ultrasound imaging equipment with a multi-touch touch screen, medical personnel can control the equipment using simple single point gestures and/or more complex multipoint gestures, without the need of a traditional keyboard or knob. Because the multi-touch touch screen obviates the need for a traditional keyboard or knob, such medical ultrasound imaging equipment is easier to keep clean in hospital and/or field environments. Moreover, by providing such medical ultrasound imaging equipment in a tablet form factor, medical personnel can easily transport the equipment between hospital and/or field locations.

Certain exemplary embodiments provide a multi-chip module for an ultrasound engine of a portable medical ultrasound imaging system, in which a transmit/receive (TR) chip, a pre-amp/time gain compensation (TGC) chip and a beamformer chip are assembled in a vertically stacked configuration. The transmission circuit provides high voltage electrical driving pulses to the transducer elements to generate a transmit beam. As the transmit chip operates at voltages greater than 80V, a CMOS process utilizing a 1 micron design rule has been utilized for the transmit chip and a submicron design rule has been utilized for the low-voltage receiving circuits (less than 5V).

Preferred embodiments of the present invention utilize a submicron process to provide integrated circuits with sub-circuits operating at a plurality of voltages, for example, 2.5V, 5V and 60V or higher.

Thus, a single IC chip can be utilized that incorporates high voltage transmission, low voltage amplifier/TGC and low voltage beamforming circuits in a single chip. Using a 0.25 micron design rule, this mixed signal circuit can accommodate beamforming of 32 transducer channels in a chip area less than $0.7 \times 0.7$ (0.49) cm$^2$. Thus, 128 channels can be processed using four 32 channel chips in a total circuit board area of less than $1.5 \times 1.5$ (2.25) cm$^2$.

The term "multi-chip module," as used herein, refers to an electronic package in which multiple integrated circuits (IC) are packaged with a unifying substrate, facilitating their use as a single component, i.e., as a higher processing capacity IC packaged in a much smaller volume. Each IC can comprise a circuit fabricated in a thinned semiconductor wafer. Exemplary embodiments also provide an ultrasound engine including one or more such multi-chip modules, and a portable medical ultrasound imaging system including an ultrasound engine circuit board with one or more multi-chip modules. Exemplary embodiments also provide methods for fabricating and assembling multi-chip modules as taught herein. Vertically stacking the TR chip, the pre-amp/TGC chip, and the beamformer chip on a circuit board minimizes the packaging size (e.g., the length and width) and the footprint occupied by the chips on the circuit board.

The TR chip, the pre-amp/TGC chip, and the beamformer chip in a multi-chip module may each include multiple channels (for example, 8 channels per chip to 64 channels per chip). In certain embodiments, the high-voltage TR chip, the pre-amp/TGC chip, and the sample-interpolate receive beamformer chip may each include 8, 16, 32, 64 channels. In a preferred embodiment, each circuit in a two layer beamformer module has 32 beamformer receive channels to provide a 64 channel receiving beamformer. A second 64 channel two layer module can be used to form a 128 channel handheld tablet ultrasound device having an overall thickness of less than 2 cm. A transmit multi-chip beamformer can also be used having the same or similar channel density in each layer.

Exemplary numbers of chips vertically integrated in a multi-chip module may include, but are not limited to, two, three, four, five, six, seven, eight, and the like. In one embodiment of an ultrasound device, a single multi-chip module is provided on a circuit board of an ultrasound engine that performs ultrasound-specific operations. In other embodiments, a plurality of multi-chip modules are provided on a circuit board of an ultrasound engine. The plurality of multi-chip modules may be stacked vertically on top of one another on the circuit board of the ultrasound engine to further minimize the packaging size and the footprint of the circuit board.

Providing one or more multi-chip modules on a circuit board of an ultrasound engine achieves a high channel count while minimizing the overall packaging size and footprint. For example, a 128-channel ultrasound engine circuit board can be assembled, using multi-chip modules, within exemplary planar dimensions of about 10 cm×about 10 cm, which is a significant improvement over the much larger space requirements of conventional ultrasound circuits. A single circuit board of an ultrasound engine including one or more multi-chip modules may have 16 to 128 channels in some embodiments. In certain embodiments, a single circuit board of an ultrasound engine including one or more multi-chip modules may have 16, 32, 64, 128 channels, and the like.

The ultrasonic imaging system in accordance with preferred embodiments may be used for patient monitoring systems such as bedside monitoring system, pacemaker monitoring, for providing image guided implants, and pacemaker implantation. Further, preferred embodiments of the systems of the present invention may be used for cardiac rhythm management, for radiation therapy systems and for image guided surgery, such as, but not limited to, image guided neurosurgery, breast biopsy and computer enabled surgery.

The ultrasonic imaging operations which may be invoked include scanning operations, to be applied to live, real time ultrasonic image gathering, and processing operations, which may be applied to live or frozen ultrasonic images. Typical scanning ultrasonic imaging operations which are known to those skilled in the art and which may be applied by the ultrasonic imaging system include size, depth, focus, gain, Time Gain Compensation (TGC) and TGC lock. Typical processing ultrasonic imaging operations include view, inversion, palette, smoothing, persistence, map, and contrast.

Preferred embodiments of the present invention include control and data transfer methods that allow a third party Windows® based application to control, for example, a portable Windows® based ultrasound system by running the ultrasound application as a background task, sending control commands to the ultrasound application server and receiving images (data) in return. Further, the embodiment configures a portable ultrasound Windows® based application as a server of live ultrasound image frames supplying another Windows® based application that acts as a client. This client application receives these ultrasound image frames and processes them further. In addition, an alternate embodiment configures the portable ultrasound Windows® based application as a server, interacting with a third party client application via two communication mechanisms, for example, a component object model (COM) automation interface used by third party, hereinafter referred to as an external application or a client to startup and control the portable ultrasound Windows® based application and a high-speed shared memory interface to deliver live ultrasound images.

A preferred embodiment includes and configures a shared memory interface to act as a streaming video interface between a portable Windows® based Ultrasound application and another third party Windows® based application. This streaming video interface is designed to provide ultrasound images to a third party client in real-time.

A preferred embodiment allows the third party Windows® based application to control the flow rate of images from the portable ultrasound Windows® based application through the shared memory interface within the same PC platform and the amount of memory required to implement this interface. These controls consist of a way to set the number of image buffers, the size of each buffer and the rate of image transfer. This flow rate control can be set for zero data loss thus ensuring that every frame is delivered to the third party Windows® based application from the ultrasound system, or minimum latency thus delivering the latest frame generated by the ultrasound system to the third party Windows® based application first.

A preferred embodiment formats the ultrasound image frame such that probe, spatial, and temporal information can be interpreted by the third party Windows® based application as it retrieves the images (generated by the portable ultrasound Windows® based application) from the shared memory interface. The actual image data passed between the server (i.e. portable ultrasound application) and the client application (third party Windows® based application) is a Microsoft" device independent bitmap (DIB) with 8 bit pixels and a 256 entry color table. The image frame also contains a header that provides the following additional information, for example, but not limited to, Probe Type, Probe Serial Number, Frame Sequence Number, Frame Rate, Frame Timestamp, Frame Trigger Timestamp, Image Width (in pixels), Image Height (in pixels), Pixel Size (in X and Y), Pixel Origin (x,y location of the first pixel in image relative to the Transducer Head, and Direction (spatial direction along or across each line of the image).

Further, the preferred embodiment controls the shared memory interface used to transfer ultrasound images between a Windows® based portable ultrasound system and a third party Windows® based system through the use of ActiveX controls. The Windows® based portable ultrasound application contains an ActiveX control that transfers a frame into the shared memory and sends out a Windows® Event (that includes a pointer to the frame just written) to the third party Windows® based application. This third party application has a similar ActiveX control that receives this Event and pulls the image frame out of shared memory.

In accordance with a preferred embodiment the present invention includes a method for providing streaming video in an ultrasonic imaging system including providing an ultrasonic application server having at least one ultrasonic operation and corresponding ultrasonic data. The method further includes sending, from an external application, a command indicative of one of the ultrasonic operations, executing in the ultrasonic application server, a result corresponding to the commands and sending data from the ultrasonic server to the external application. A shared memory is in communication with the ultrasonic application server and the external application. The method further includes an integrated interface program having a plurality of entry points into the application server, transmitting via the integrated interface program a command to the ultrasonic application server, receiving over a predetermined communication interface, ultrasonic data indicative of ultrasonic image formation and transmitting the result to the external application via the integrated interface program.

The integrated interface program is adapted to transmit real-time imaging data including ultrasonic imaging for radiation therapy planning and treatment, minimally invasive and robotic surgery methods including biopsy procedures, invasive procedures such as catheter introduction for diagnostic and therapeutic angiography, fetal imaging, cardiac imaging, vascular imaging, imaging during endoscopic procedures, imaging for telemedicine applications, imaging for veterinary applications, cryotherapy and ultrasound elastography.

In preferred embodiments, the streaming video includes radio frequency data, real-time image data and transformation parameters. The external application can reside on the same computing device as the ultrasonic application server or be resident on a different computing device. The external application communicates with the ultrasonic application server using a control program using a component object model automation interface and a shared memory interface.

The command in the method for providing streaming video includes operations selected from the group consisting of an ultrasound application initialization/shutdown functions such as, for example, start ultrasound application, load preset files, exit application; ultrasound setup functions such as, for example, set shared memory parameters, initialize communication to shared memory, set image frame size, set shared memory size, set transfer priority (for low latency, high throughput, or first in, first out), set image resolution and format; and ultrasound image capture functions such as, for example, freeze live data, fetch live data, and resume live imaging.

The ultrasonic application server includes a graphical user interface having image control presets which are operable to store image settings. The image settings include application controls such as, for example, image mode, patient name, patient ID; B-mode controls, for example, size, depth, focus, TGC, change examination type; M-mode controls, for example, sweep speed, scan line position; image quality controls, for example, brightness, contrast, invert, palette, smoothing persistence; and Doppler controls, for example, color region of interest, pulse repetition rate, wall filter, steering angle, color gain, color invert, color priority, color baseline and line density control.

In a preferred embodiment, in certain applications such as angiographic monitoring, it is desirable for the system user to remain visually focussed on the patient and not be distracted by the need to view a display outside the user's field of view. For such applications, a display can be integrated into the probe housing and/or the interface housing.

BRIEF DESCRIPTION OF THE DRAWINGS

The foregoing and other objects, aspects, features, and advantages of exemplary embodiments will become more apparent and may be better understood by referring to the following description taken in conjunction with the accompanying drawings, in which:

FIGS. 3A-3L illustrates exemplary single point and multipoint gestures that can be employed as user inputs to the medical ultrasound imaging equipment of FIG. 1;

FIG. 10 shows a method of measuring heart wall motion;

FIGS. 11C-11E illustrate a particular embodiment of packaging integrated probe electronics;

FIG. 12 depicts a schematic side view of a circuit board including a multi-chip module assembled in a vertically stacked configuration;

FIG. 16 is a schematic side view of a multi-chip module including an ultrasound transmit/receive IC chip, an amplifier IC chip and an ultrasound beamformer IC chip vertically integrated in a vertically stacked configuration;

FIG. 30 is a diagram of a wireless viewer graphical user interface in accordance with a preferred embodiment of the present invention;

FIGS. 52A-52C are views of a graphical user interface showing the icons used to control the size of windows, and creation of floating windows in accordance with a preferred embodiment of the present invention;

DETAILED DESCRIPTION

Systems and methods of medical ultrasound imaging are disclosed. The presently disclosed systems and methods of medical ultrasound imaging employ medical ultrasound imaging equipment that includes a housing in a tablet form factor, and a touch screen display disposed on a front panel of the housing. The touch screen display includes a multi-touch touch screen that can recognize and distinguish one or more single, multiple, and/or simultaneous touches on a surface of the touch screen display, thereby allowing the use of gestures, ranging from simple single point gestures to complex multipoint gestures, as user inputs to the medical ultrasound imaging equipment. Further details regarding tablet ultrasound systems and operations are described in U.S. application Ser. No. 10/997,062 filed on Nov. 11, 2004, Ser. No. 10/386,360 filed Mar. 11, 2003 and U.S. Pat. No. 6,969,352, the entire contents of these patents and applications are incorporated herein by reference.

Figure 1:
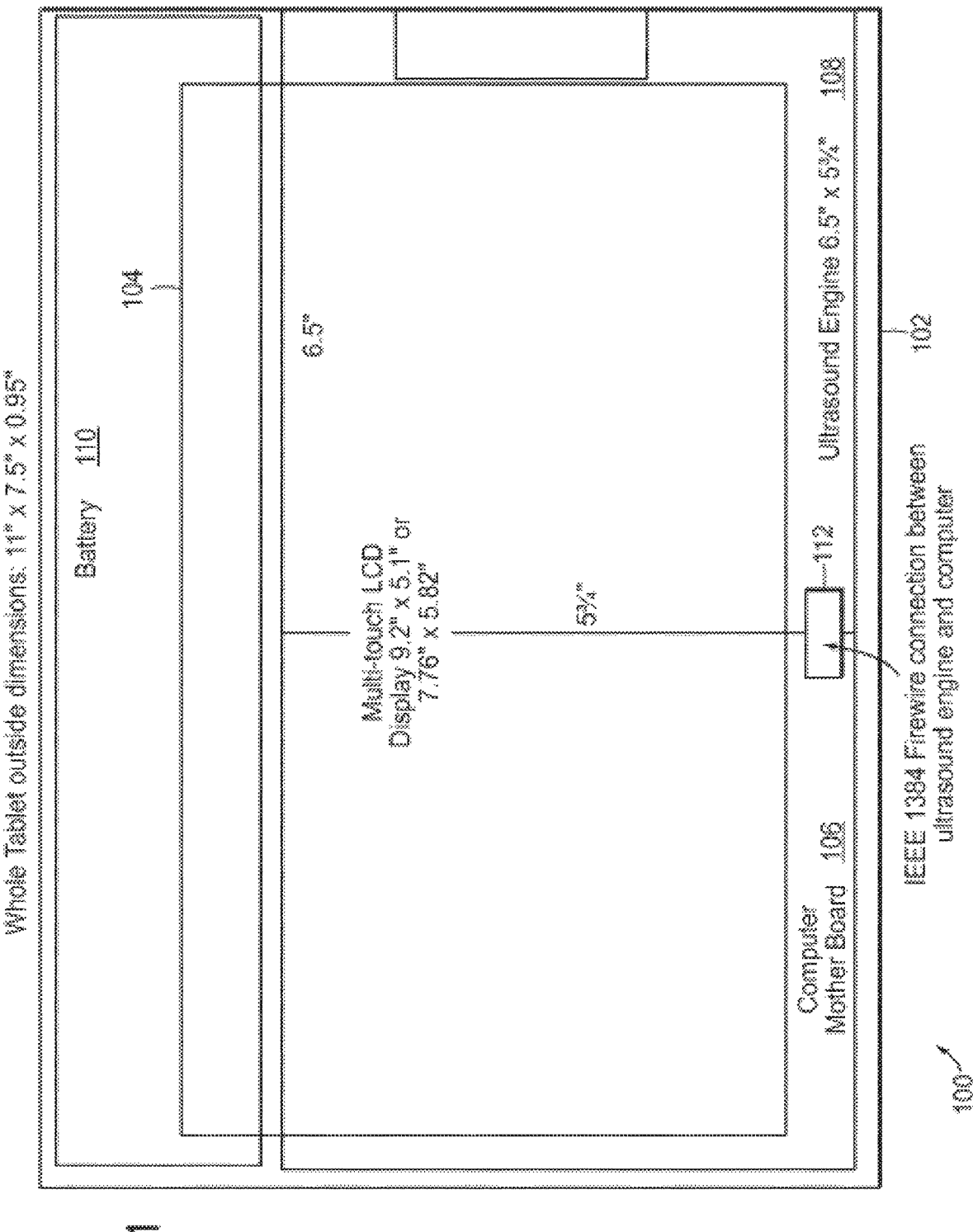
FIG. 1 is a plan view of exemplary medical ultrasound imaging equipment, in accordance with an exemplary embodiment of the present application.
Figures 2A, 2B:
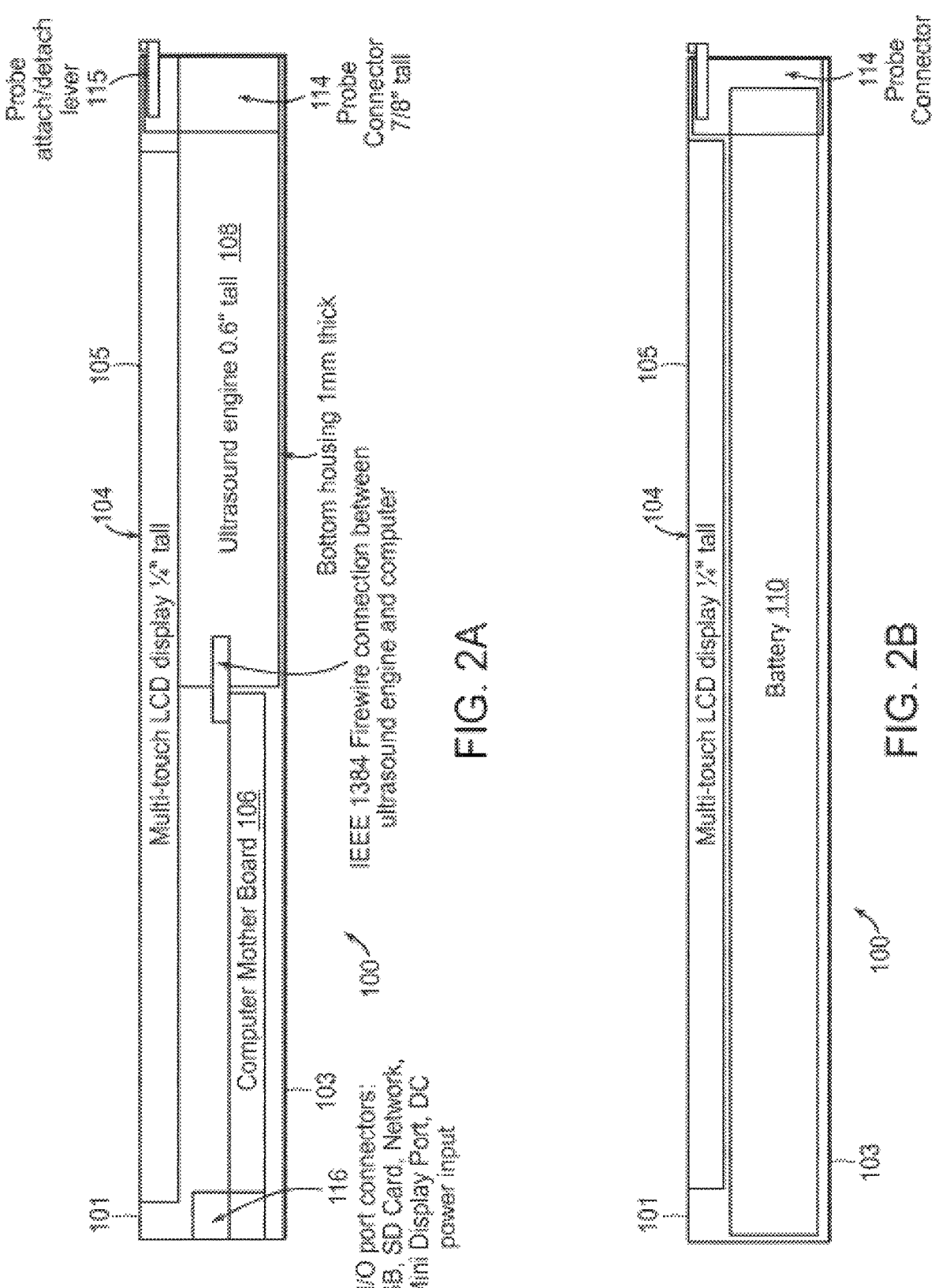
FIGS. 2A and 2B are side views of the medical ultrasound imaging equipment of FIG. 1.

FIG. 1 depicts an illustrative embodiment of exemplary medical ultrasound imaging equipment 100, in accordance with the present application. As shown in FIG. 1, the medical ultrasound imaging equipment 100 includes a housing 102, a touch screen display 104, a computer having at least one processor and at least one memory implemented on a computer motherboard 106, an ultrasound engine 108, and a battery 110. For example, the housing 102 can be implemented in a tablet form factor, or any other suitable form factor. As shown in FIG. 2A, the housing 102 has a front panel 101 and a rear panel 103. The touch screen display 104 is disposed on the front panel 101 of the housing 102, and includes a multi-touch LCD touch screen that can recognize and distinguish one or more multiple and/or simultaneous touches on a surface 105 of the touch screen display 104. The computer motherboard 106, the ultrasound engine 108, and the battery 110 are operatively disposed within the housing 102. The medical ultrasound imaging equipment 100 further includes a Firewire connection 112 (see also FIG. 2A) operatively connected between the computer motherboard 106 and the ultrasound engine 108 within the housing 102, and a probe connector 114 having a probe attach/detach lever 115 (see FIGS. 2A and 2B) to facilitate the connection of at least one ultrasound probe/transducer. In addition, the medical ultrasound imaging equipment 100 has one or more I/O port connectors 116 (see FIG. 2A), which can include, but are not limited to, one or more USB connectors, one or more SD cards, one or more network ports, one or more mini display ports, and a DC power input.

In an exemplary mode of operation, medical personnel (also referred to herein as the "user" or "users") can employ simple single point gestures and/or more complex multipoint gestures as user inputs to the multi-touch LCD touch screen of the touch screen display 104 for controlling one or more operational modes and/or functions of the medical ultrasound imaging equipment 100. Such a gesture is defined herein as a movement, a stroke, or a position of at least one finger, a stylus, and/or a palm on the surface 105 of the touch screen display 104. For example, such single point/multipoint gestures can include static or dynamic gestures, continuous or segmented gestures, and/or any other suitable gestures. A single point gesture is defined herein as a gesture that can be performed with a single touch contact point on the touch screen display 104 by a single finger, a stylus, or a palm. A multipoint gesture is defined herein as a gesture that can be performed with multiple touch contact points on the touch screen display 104 by multiple fingers, or any suitable combination of at least one finger, a stylus, and a palm. A static gesture is defined herein as a gesture that does not involve the movement of at least one finger, a stylus, or a palm on the surface 105 of the touch screen display 104. A dynamic gesture is defined herein as a gesture that involves the movement of at least one finger, a stylus, or a palm, such as the movement caused by dragging one or more fingers across the surface 105 of the touch screen display 104. A continuous gesture is defined herein as a gesture that can be performed in a single movement or stroke of at least one finger, a stylus, or a palm on the surface 105 of the touch screen display 104. A segmented gesture is defined herein as a gesture that can be performed in multiple movements or stokes of at least one finger, a stylus, or a palm on the surface 105 of the touch screen display 104.

Such single point/multipoint gestures performed on the surface 105 of the touch screen display 104 can correspond to single or multipoint touch events, which are mapped to one or more predetermined operations that can be performed by the computer and/or the ultrasound engine 108. Users can make such single point/multipoint gestures by various single finger, multi-finger, stylus, and/or palm motions on the surface 105 of the touch screen display 104. The multi-touch LCD touch screen receives the single point/multipoint gestures as user inputs, and provides the user inputs to the processor, which executes program instructions stored in the memory to carry out the predetermined operations associated with the single point/multipoint gestures, at least at some times, in conjunction with the ultrasound engine 108. As shown in FIGS. 3A-3L, such single point/multipoint gestures on the surface 105 of the touch screen display 104 can include, but are not limited to, a tap gesture 302, a pinch gesture 304, a flick gesture 306, 314, a rotate gesture 308, 316, a double tap gesture 310, a spread gesture 312, a drag gesture 318, a press gesture 320, a press and drag gesture 322, and/or a palm gesture 324. For example, such single point/multipoint gestures can be stored in at least one gesture library in the memory implemented on the computer motherboard 106.

In accordance with the illustrative embodiment of FIG. 1, at least one flick gesture 306 or 314 may be employed by a user of the medical ultrasound imaging equipment 100 to control the depth of tissue penetration of ultrasound waves generated by the ultrasound probe/transducer. For example, a dynamic, continuous, flick gesture 306 or 314 in the "up" direction, or any other suitable direction, on the surface 105 of the touch screen display 104 can increase the penetration depth by one (1) centimeter, or any other suitable amount. Further, a dynamic, continuous, flick gesture 306 or 314 in the "down" direction, or any other suitable direction, on the surface 105 of the touch screen display 104 can decrease the penetration depth by one (1) centimeter, or any other suitable amount. Moreover, a dynamic, continuous, drag gesture 318 in the "up" or "down" direction, or any other suitable direction, on the surface 105 of the touch screen display 104 can increase or decrease the penetration depth in multiple centimeters, or any other suitable amounts.

Additional operational modes and/or functions controlled by specific single point/multipoint gestures on the surface 105 of the touch screen display 104 can include, but are not limited to, freeze/store operations, 2-dimensional mode operations, gain control, color control, split screen control, PW imaging control, cine/time-series image clip scrolling control, zoom and pan control, Doppler and 2-dimensional beam steering control, and/or body marking control. At least some of the operational modes and/or functions of the medical ultrasound imaging equipment 100 can be controlled by one or more touch controls implemented on the touch screen display 104. Further, users can provide one or more specific single point/multipoint gestures as user inputs for specifying at least one selected subset of the touch controls to be implemented, as required and/or desired, on the touch screen display 104.

Figure 4A:
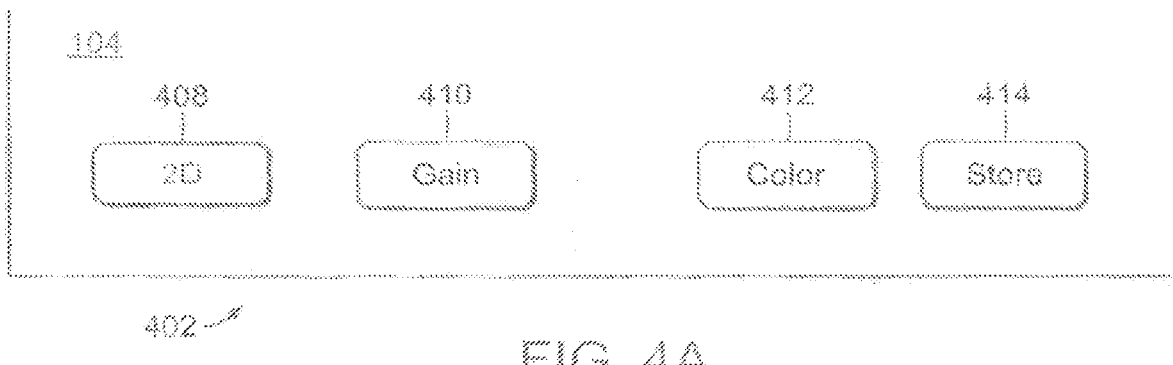
FIGS. 4A-4C illustrate exemplary subsets of touch controls that can be implemented on the medical ultrasound imaging equipment of FIG. 1.
Figure 4B:
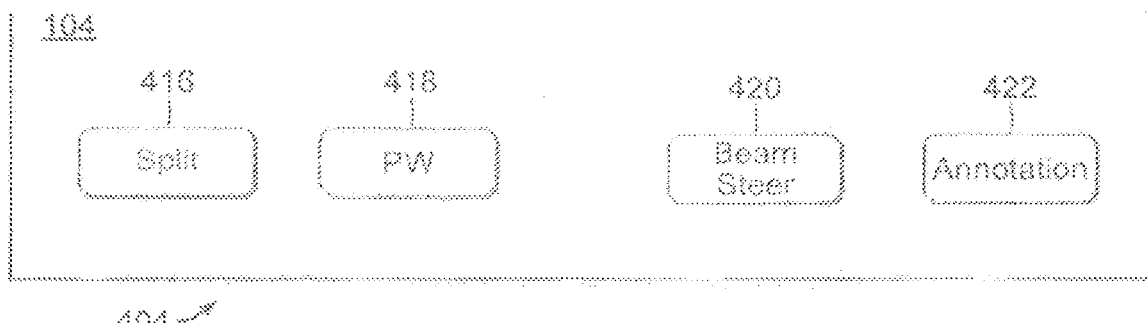
Figure 4C:
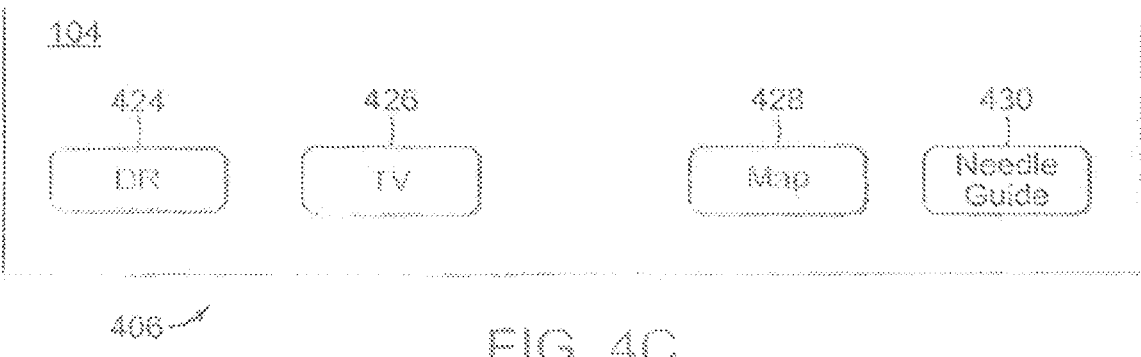

FIGS. 4A-4C depict exemplary subsets 402, 404, 406 of touch controls that can be implemented by users of the medical ultrasound imaging equipment 100 on the touch screen display 104. It is noted that any other suitable subset(s) of touch controls can be implemented, as required and/or desired, on the touch screen display 104. As shown in FIG. 4A, the subset 402 includes a touch control 408 for performing 2-dimensional (2D) mode operations, a touch control 410 for performing gain control operations, a touch control 412 for performing color control operations, and a touch control 414 for performing image/clip freeze/store operations. For example, a user can employ the press gesture 320 to actuate the touch control 408, returning the medical ultrasound imaging equipment 100 to 2D mode. Further, the user can employ the press gesture 320 against one side of the touch control 410 to decrease a gain level, and employ the press gesture 320 against another side of the touch control 410 to increase the gain level. Moreover, the user can employ the drag gesture 318 on the touch control 412 to identify ranges of densities on a 2D image, using a predetermined color code. In addition, the user can employ the press gesture 320 to actuate the touch control 414 to freeze/store a still image or to acquire a cine image clip.

As shown in FIG. 4B, the subset 404 includes a touch control 416 for performing split screen control operations, a touch control 418 for performing PW imaging control operations, a touch control 420 for performing Doppler and 2-dimensional beam steering control operations, and a touch control 422 for performing annotation operations. For example, a user can employ the press gesture 320 against the touch control 416, allowing the user to toggle between opposing sides of the split touch screen display 104 by alternately employing the tap gesture 302 on each side of the split screen. Further, the user can employ the press gesture 320 to actuate the touch control 418 and enter the PW mode, which allows (1) user control of the angle correction, (2) movement (e.g., "up" or "down") of a baseline that can be displayed on the touch screen display 104 by employing the press and drag gesture 322, and/or (3) an increase or a decrease of scale by employing the tap gesture 302 on a scale bar that can be displayed on the touch screen display 104. Moreover, the user can employ the press gesture 320 against one side of the touch control 420 to perform 2D beam steering to the "left" or any other suitable direction in increments of five (5) or any other suitable increment, and employ the press gesture 320 against another side of the touch control 420 to perform 2D beam steering to the "right" or any other suitable direction in increments of five (5) or any other suitable increment. In addition, the user can employ the tap gesture 302 on the touch control 422, allowing the user to enter annotation information via a pop-up keyboard that can be displayed on the touch screen display 104.

As shown in FIG. 4C, the subset 406 includes a touch control 424 for performing dynamic range operations, a touch control 426 for performing Teravision™ software operations, a touch control 428 for performing map operations, and a touch control 430 for performing needle guide operations. For example, a user can employ the press gesture 320 and/or the press and drag gesture 322 against the touch control 424 to control or set the dynamic range. Further, the user can employ the tap gesture 302 on the touch control 426 to choose a desired level of the Teravision™ software to be executed from the memory by the processor on the computer motherboard 106. Moreover, the user can employ the tap gesture 302 on the touch control 428 to perform a desired map operation. In addition, the user can employ the press gesture 320 against the touch control 430 to perform a desired needle guide operation.

In accordance with the present application, various measurements and/or tracings of objects (such as organs, tissues, etc.) displayed as ultrasound images on the touch screen display 104 of the medical ultrasound imaging equipment 100 (see FIG. 1) can be performed, using single point/multipoint gestures on the surface 105 of the touch screen display 104. The user can perform such measurements and/or tracings of objects directly on an original ultrasound image of the displayed object, on a magnified version of the ultrasound image of the displayed object, and/or on a magnified portion of the ultrasound image within a virtual window 506 (see FIGS. 5C and 5D) on the touch screen display 104.

Figure 5A:
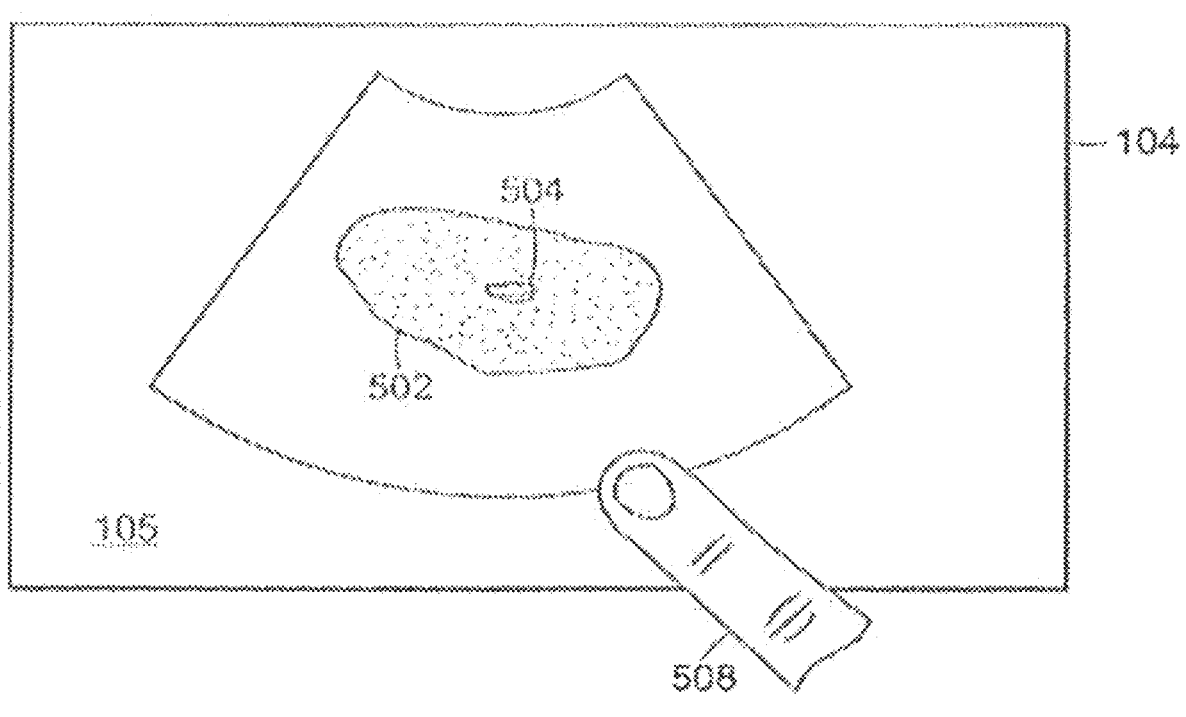
FIGS. 5A and 5B are exemplary representations of a liver with a cystic lesion on a touch screen display of the medical ultrasound imaging equipment of FIG. 1.
Figure 5B:
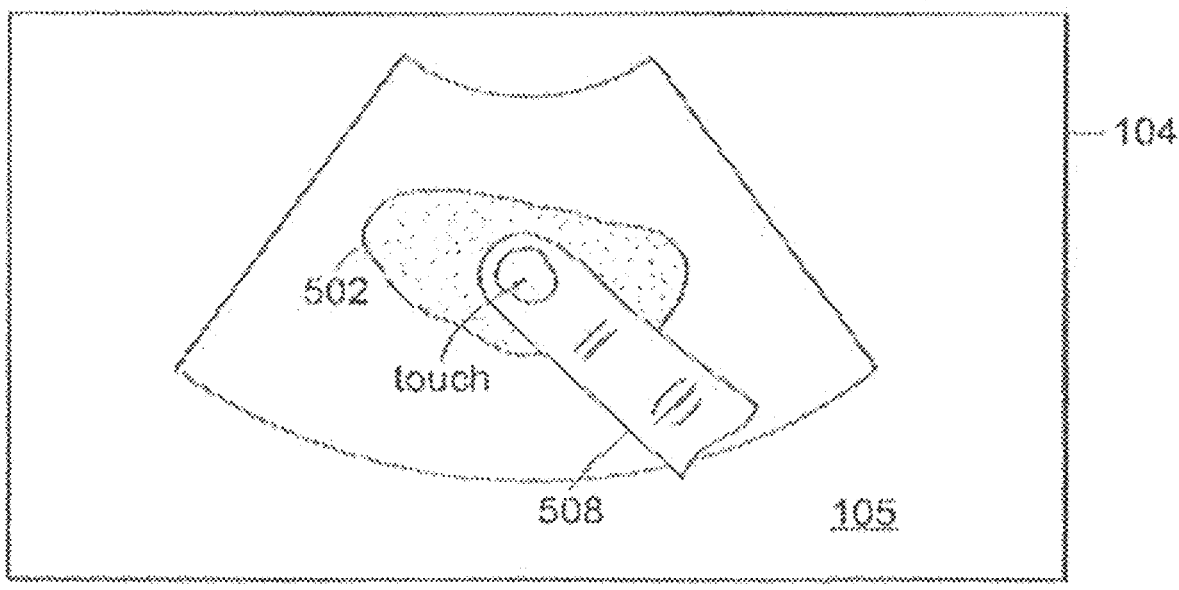
Figure 5C:
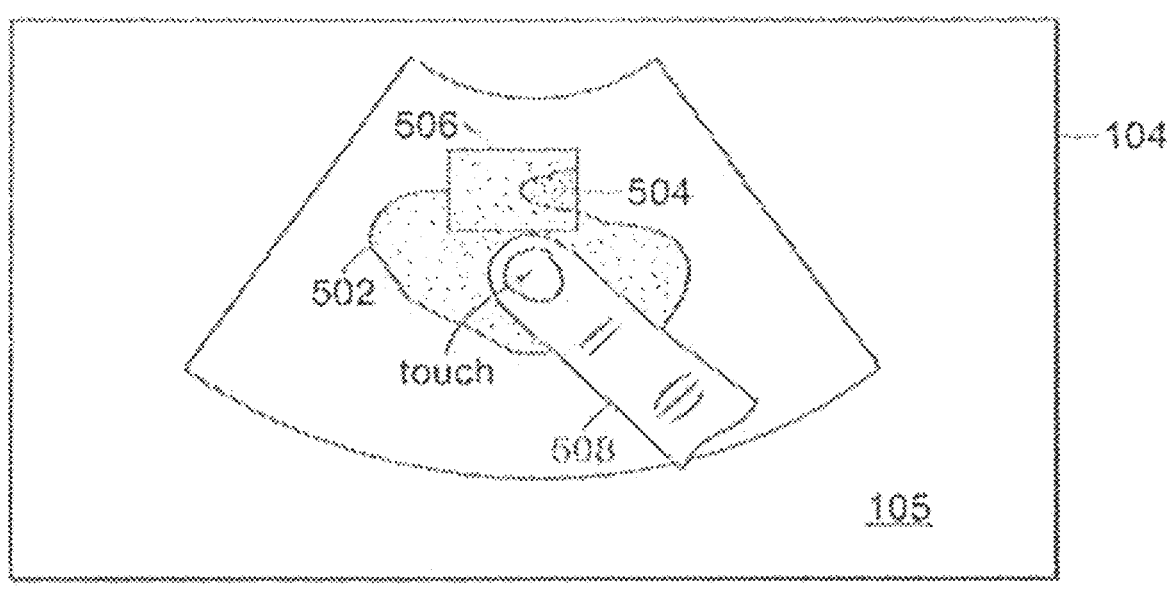
FIGS. 5C and 5D are exemplary representations of the liver and cystic lesion on the touch screen display of FIGS. 5A and 5B, including a virtual window that corresponds to a magnified portion of the liver.
Figure 5D:
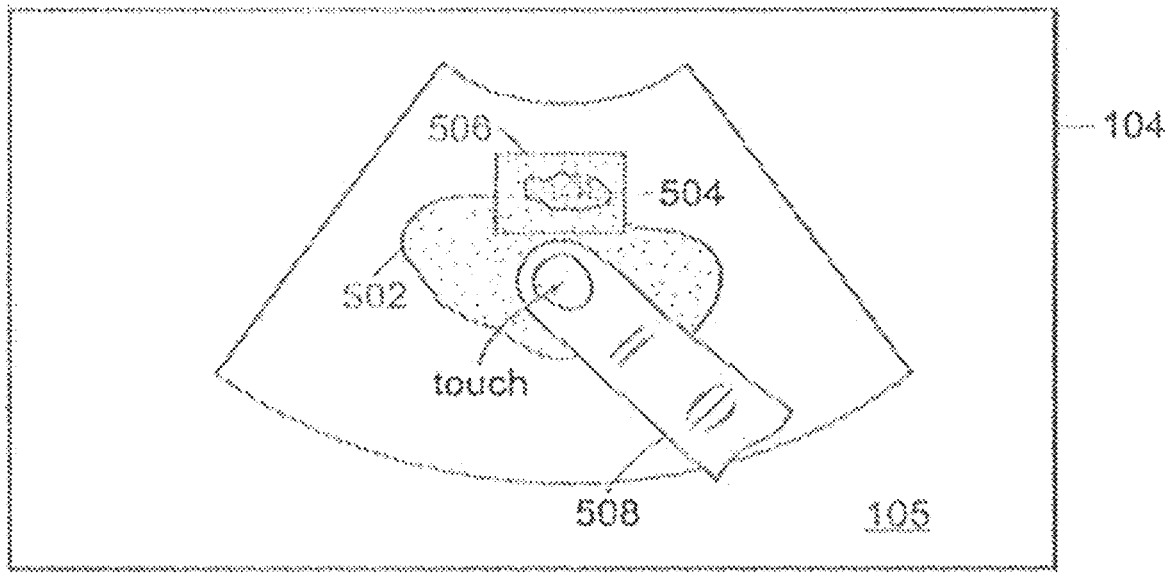

FIGS. 5A and 5B depict an original ultrasound image of an exemplary object, namely, a liver 502 with a cystic lesion 504, displayed on the touch screen display 104 of the medical ultrasound imaging equipment 100 (see FIG. 1). It is noted that such an ultrasound image can be generated by the medical ultrasound imaging equipment 100 in response to penetration of the liver tissue by ultrasound waves generated by an ultrasound probe/transducer operatively connected to the equipment 100. Measurements and/or tracings of the liver 502 with the cystic lesion 504 can be performed directly on the original ultrasound image displayed on the touch screen display 104 (see FIGS. 5A and 5B), or on a magnified version of the ultrasound image. For example, the user can obtain such a magnified version of the ultrasound image using a spread gesture (see, e.g., the spread gesture 312; FIG. 3F) by placing two (2) fingers on the surface 105 of the touch screen display 104, and spreading them apart to magnify the original ultrasound image. Such measurements and/or tracings of the liver 502 and cystic lesion 504 can also be performed on a magnified portion of the ultrasound image within the virtual window 506 (see FIGS. 5C and 5D) on the touch screen display 104.

For example, using his or her finger (see, e.g., a finger 508; FIGS. 5A-5D), the user can obtain the virtual window 506 by employing a press gesture (see, e.g., the press gesture 320; FIG. 3J) against the surface 105 of the touch screen display 104 (see FIG. 5B) in the vicinity of a region of interest, such as the region corresponding to the cystic lesion 504. In response to the press gesture, the virtual window 506 (see FIGS. 5C and 5D) is displayed on the touch screen display 104, possibly at least partially superimposed on the original ultrasound image, thereby providing the user with a view of a magnified portion of the liver 502 in the vicinity of the cystic lesion 504. For example, the virtual window 506 of FIG. 5C can provide a view of a magnified portion of the ultrasound image of the cystic lesion 504, which is covered by the finger 508 pressed against the surface 105 of the touch screen display 104. To re-position the magnified cystic lesion 504 within the virtual window 506, the user can employ a press and drag gesture (see, e.g., the press and drag gesture 322; FIG. 3K) against the surface 105 of the touch screen display 104 (see FIG. 5D), thereby moving the image of the cystic lesion 504 to a desired position within the virtual window 506. In one embodiment, the medical ultrasound imaging equipment 100 can be configured to allow the user to select a level of magnification within the virtual window 506 to be 2 times larger, 4 times larger, or any other suitable number of times larger than the original ultrasound image. The user can remove the virtual window 506 from the touch screen display 104 by lifting his or her finger (see, e.g., the finger 508; FIGS. 5A-5D) from the surface 105 of the touch screen display 104.

Figure 6A:
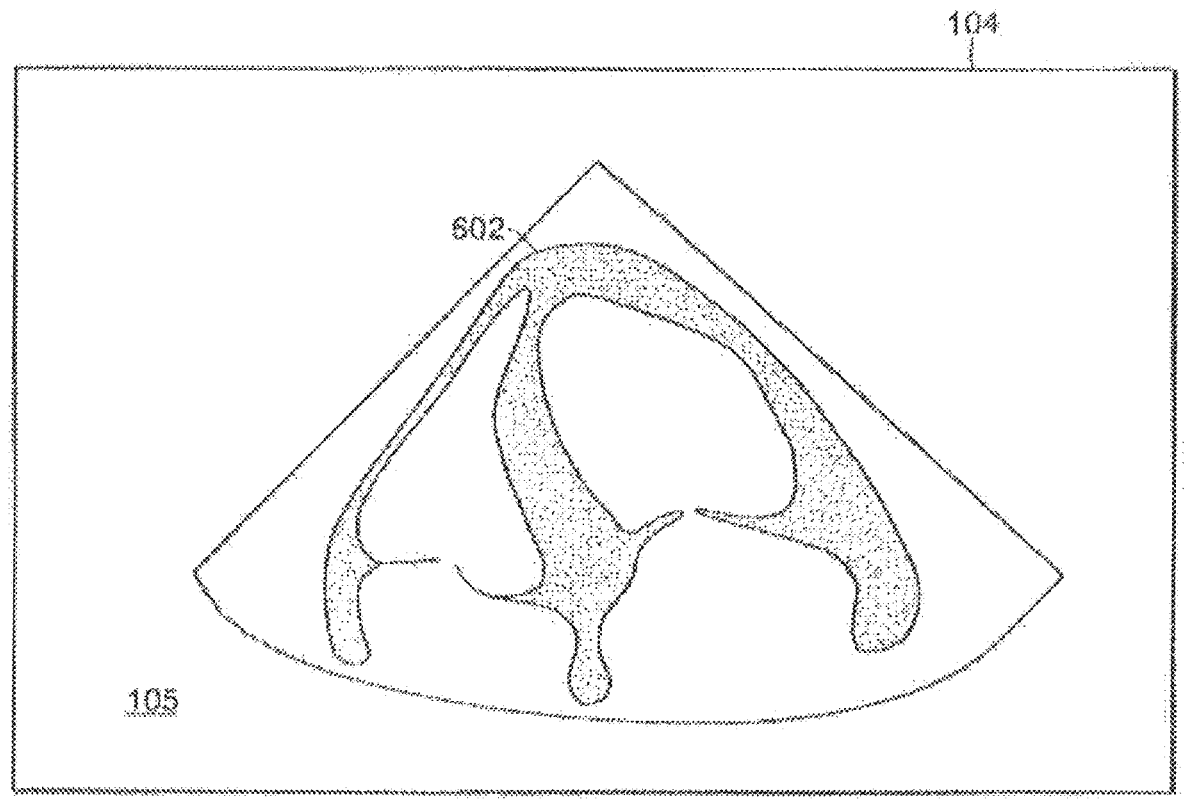
FIG. 6A is an exemplary representation of an apical four (4) chamber view of a heart on the touch screen display of the medical ultrasound imaging equipment of FIG. 1.
Figure 6B:
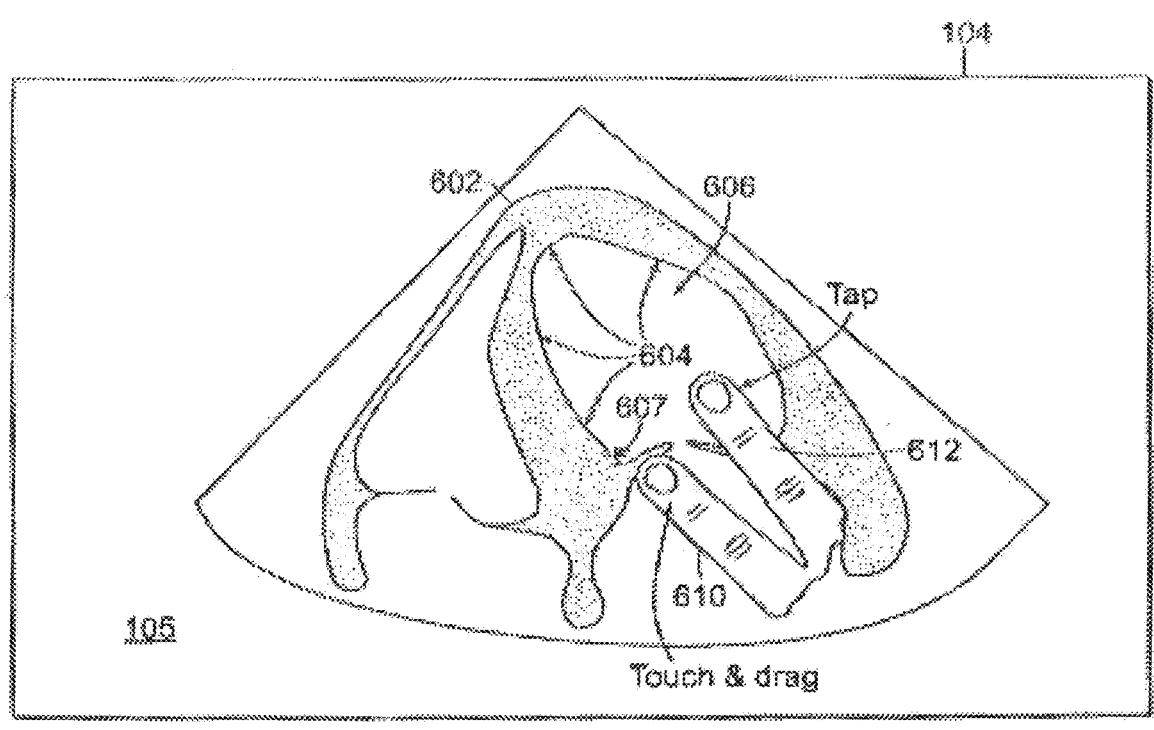
FIGS. 6B-6E6E illustrate an exemplary manual tracing of an endocardial border of a left ventricle of the heart on the touch screen display of FIG. 6A.
Figure 6C:
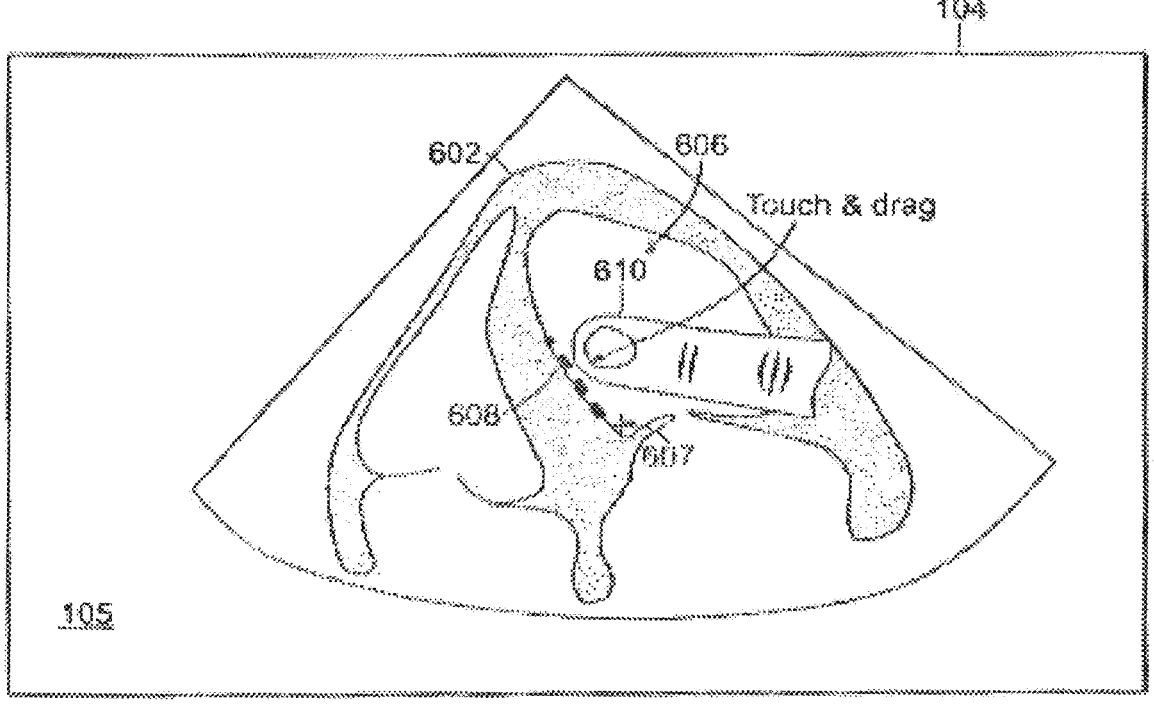
Figure 6D:
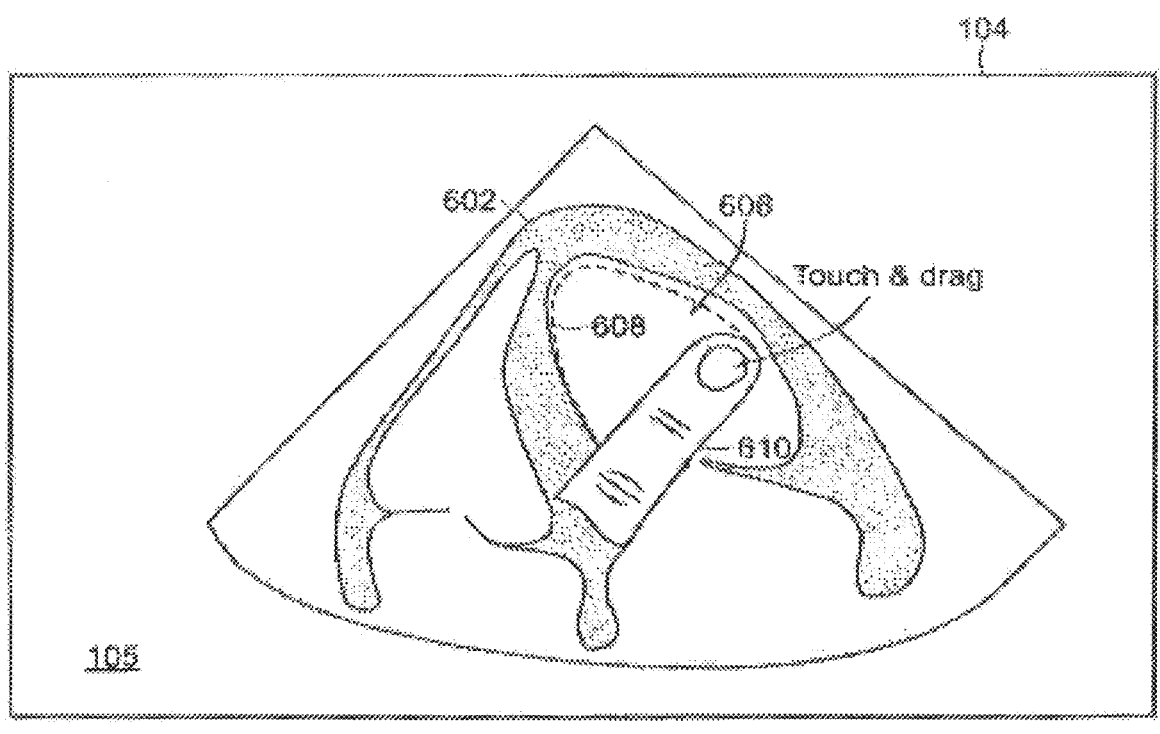
Figure 6E:
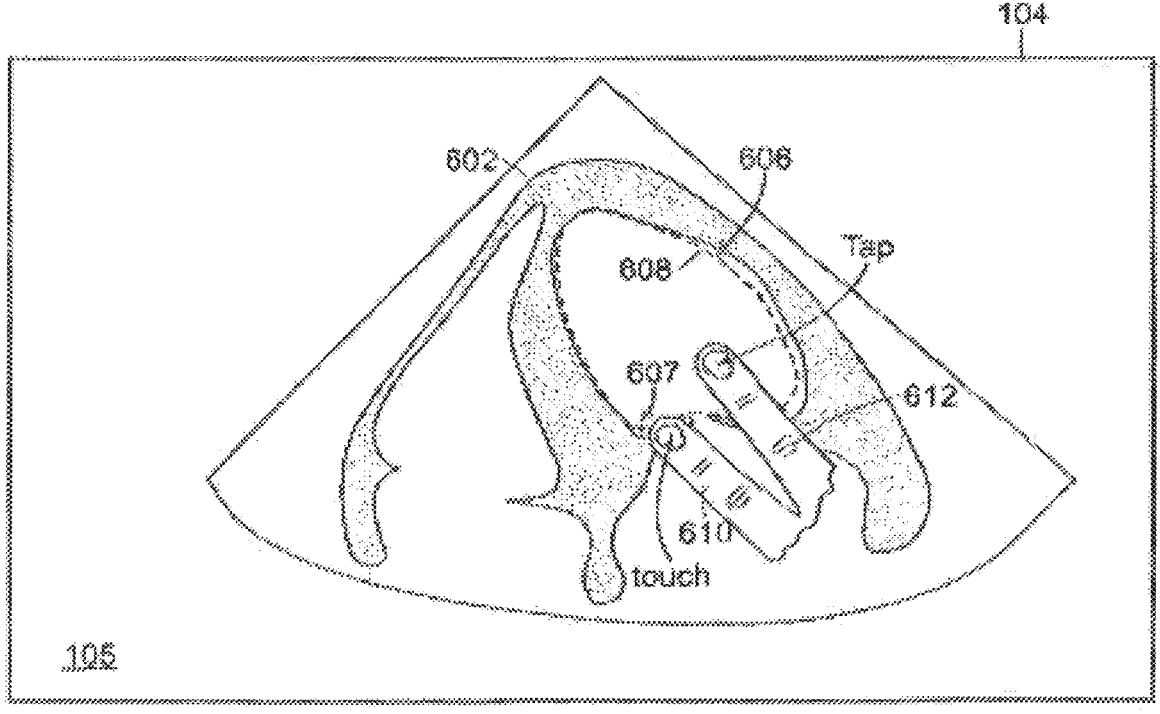

FIG. 6A depicts an ultrasound image of another exemplary object, namely, an apical four (4) chamber view of a heart 602, displayed on the touch screen display 104 of the medical ultrasound imaging equipment 100 (see FIG. 1). It is noted that such an ultrasound image can be generated by the medical ultrasound imaging equipment 100 in response to penetration of the heart tissue by ultrasound waves generated by an ultrasound probe/transducer operatively connected to the equipment 100. Measurements and/or tracings of the heart 602 can be performed directly on the original ultrasound image displayed on the touch screen display 104 (see FIGS. 6A-6E), or on a magnified version of the ultrasound image. For example, using his or her fingers (see, e.g., fingers 610, 612; FIGS. 6B-6E), the user can perform a manual tracing of an endocardial border 604 (see FIG. 6B) of a left ventricle 606 (see FIGS. 6B-6E) of the heart 602 by employing one or more multi-finger gestures on the surface 105 of the touch screen display 104. In one embodiment, using his or her fingers (see, e.g., the fingers 610, 612; FIGS. 6B-6E), the user can obtain a cursor 607 (see FIG. 6B) by employing a double tap gesture (see, e.g., the double tap gesture 310; FIG. 3E) on the surface 105 of the touch screen display 104, and can move the cursor 607 by employing a drag gesture (see, e.g., the drag gesture 318; FIG. 3I) using one finger, such as the finger 610, thereby moving the cursor 607 to a desired location on the touch screen display 104. The systems and methods described herein can be used for the quantitative measurement of heart wall motion and specifically for the measurement of ventricular dysynchrony as described in detail in U.S. application Ser. No. 10/817,316 filed on Apr. 2, 2004, the entire contents of which is incorporated herein by reference. Once the cursor 607 is at the desired location on the touch screen display 104, as determined by the location of the finger 610, the user can fix the cursor 607 at that location by employing a tap gesture (see, e.g., the tap gesture 302; see FIG. 3A) using another finger, such as the finger 612. To perform a manual tracing of the endocardial border 604 (see FIG. 6B), the user can employ a press and drag gesture (see, e.g., the press and drag gesture 322; FIG. 3K) using the finger 610, as illustrated in FIGS. 6C and 6D. Such a manual tracing of the endocardial border 604 can be highlighted on the touch screen display 104 in any suitable fashion, such as by a dashed line 608 (see FIGS. 6C-6E). The manual tracing of the endocardial border 604 can continue until the finger 610 arrives at any suitable location on the touch screen display 104, or until the finger 610 returns to the location of the cursor 607, as illustrated in FIG. 6E. Once the finger 610 is at the location of the cursor 607, or at any other suitable location, the user can complete the manual tracing operation by employing a tap gesture (see, e.g., the tap gesture 302; see FIG. 3A) using the finger 612. It is noted that such a manual tracing operation can be employed to trace any other suitable feature(s) and/or waveform(s), such as a pulsed wave Doppler (PWD) waveform. In one embodiment, the medical ultrasound imaging equipment 100 can be configured to perform any suitable calculation(s) and/or measurement(s) relating to such feature(s) and/or waveform(s), based at least in part on a manual tracing(s) of the respective feature(s)/waveform(s).

Figures 7A, 7B, 7C:
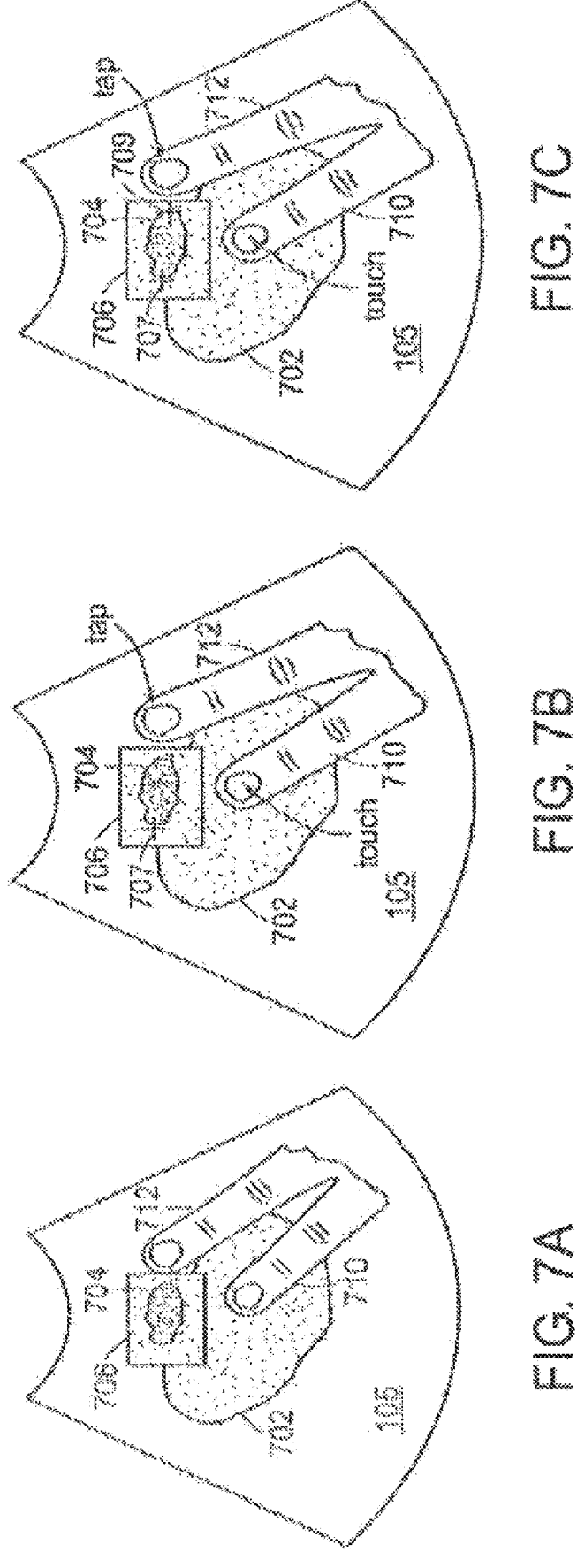
FIGS. 7A-7C illustrate an exemplary measurement of the size of the cystic lesion on the liver within the virtual window of FIGS. 5C and 5D.

As described above, the user can perform measurements and/or tracings of objects on a magnified portion of an original ultrasound image of a displayed object within a virtual window on the touch screen display 104. FIGS. 7A-7C depict an original ultrasound image of an exemplary object, namely, a liver 702 with a cystic lesion 704, displayed on the touch screen display 104 of the medical ultrasound imaging equipment 100 (see FIG. 1). FIGS. 7A-7C further depict a virtual window 706 that provides a view of a magnified portion of the ultrasound image of the cystic lesion 704, which is covered by one of the user's fingers, such as a finger 710, pressed against the surface 105 of the touch screen display 104. Using his or her fingers (see, e.g., fingers 710, 712; FIGS. 7A-7C), the user can perform a size measurement of the cystic lesion 704 within the virtual window 706 by employing one or more multi-finger gestures on the surface 105 of the touch screen display 104. For example, using his or her fingers (see, e.g., the fingers 710, 712; FIGS. 7A-7C), the user can obtain a first cursor 707 (see FIGS. 7B, 7C) by employing a double tap gesture (see, e.g., the double tap gesture 310; FIG. 3E) on the surface 105, and can move the first cursor 707 by employing a drag gesture (see, e.g., the drag gesture 318; FIG. 3I) using one finger, such as the finger 710, thereby moving the first cursor 707 to a desired location. Once the first cursor 707 is at the desired location, as determined by the location of the finger 710, the user can fix the first cursor 707 at that location by employing a tap gesture (see, e.g., the tap gesture 302; see FIG. 3A) using another finger, such as the finger 712. Similarly, the user can obtain a second cursor 709 (see FIG. 7C) by employing a double tap gesture (see, e.g., the double tap gesture 310; FIG. 3E) on the surface 105, and can move the second cursor 709 by employing a drag gesture (see, e.g., the drag gesture 318; FIG. 3I) using the finger 710, thereby moving the second cursor 709 to a desired location. Once the second cursor 709 is at the desired location, as determined by the location of the finger 710, the user can fix the second cursor 709 at that location by employing a tap gesture (see, e.g., the tap gesture 302; see FIG. 3A) using the finger 712. In one embodiment, the medical ultrasound imaging equipment 100 can be configured to perform any suitable size calculation(s) and/or measurement(s) relating to the cystic lesion 704, based at least in part on the locations of the first and second cursors 707, 709.

Figures 8A, 8B, 8C:
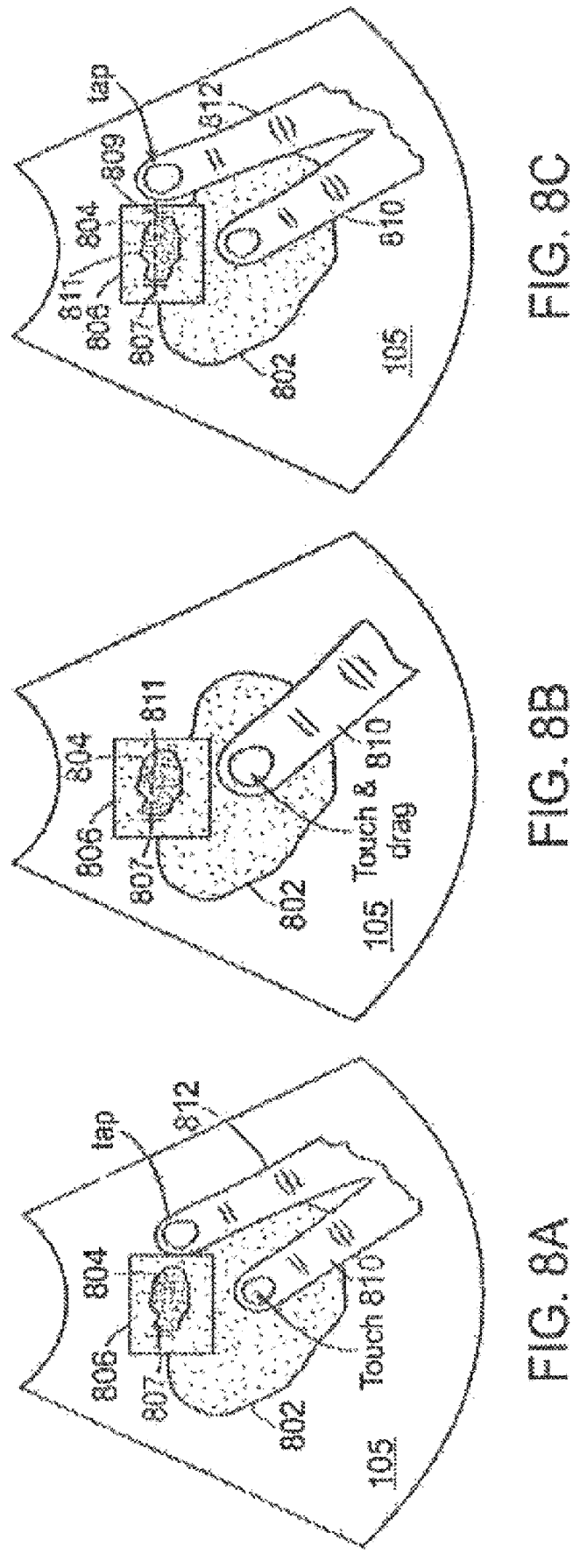
FIGS. 8A-8C illustrate an exemplary caliper measurement of the cystic lesion on the liver within the virtual window of FIGS. 5C and 5D.

FIGS. 8A-8C depict an original ultrasound image of an exemplary object, namely, a liver 802 with a cystic lesion 804, displayed on the touch screen display 104 of the medical ultrasound imaging equipment 100 (see FIG. 1). FIGS. 8A-8C further depict a virtual window 806 that provides a view of a magnified portion of the ultrasound image of the cystic lesion 804, which is covered by one of the user's fingers, such as a finger 810, pressed against the surface 105 of the touch screen display 104. Using his or her fingers (see, e.g., fingers 810, 812; FIGS. 8A-8C), the user can perform a caliper measurement of the cystic lesion 804 within the virtual window 806 by employing one or more multi-finger gestures on the surface 105 of the touch screen display 104.

Figure 31:
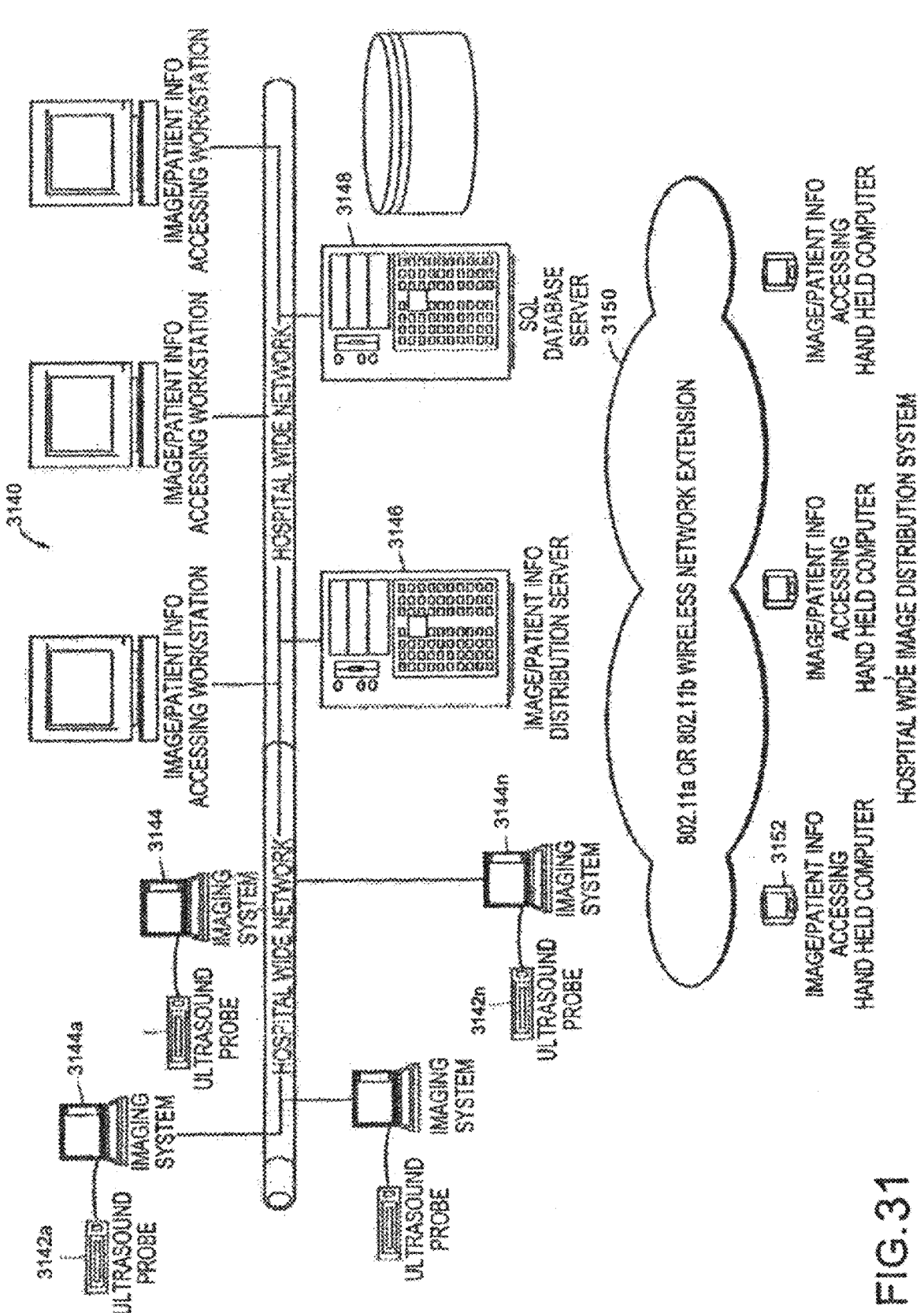
FIG. 31 is a diagram of a facility wide ultrasound image distribution system in accordance with a preferred embodiment of the present invention.

For example, using his or her fingers (see, e.g., the fingers 810, 812; FIGS. 8A-8C), the user can obtain a first cursor 807 (see FIGS. 8B, 8C) by employing a double tap gesture (see, e.g., the double tap gesture 310; FIG. 3E) on the surface 105, and can move the cursor 807 by employing a drag gesture (see, e.g., the drag gesture 318; FIG. 31) using one finger, such as the finger 810, thereby moving the cursor 807 to a desired location. Once the cursor 807 is at the desired location, as determined by the location of the finger 810, the user can fix the cursor 807 at that location by employing a tap gesture (see, e.g., the tap gesture 302; see FIG. 3A) using another finger, such as the finger 812. The user can then employ a press and drag gesture (see, e.g., the press and drag gesture 322; FIG. 3K) to obtain a connecting line 811 (see FIGS. 8B, 8C), and to extend the connecting line 811 from the first cursor 807 across the cystic lesion 804 to a desired location on another side of the cystic lesion 804. Once the connecting line 811 is extended across the cystic lesion 804 to the desired location on the other side of the cystic lesion 804, the user can employ a tap gesture (see, e.g., the tap gesture 302; see FIG. 3A) using the finger 812 to obtain and fix a second cursor 809 (see FIG. 8C) at that desired location. In one embodiment, the medical ultrasound imaging equipment 100 can be configured to perform any suitable caliper calculation(s) and/or measurement(s) relating to the cystic lesion 804, based at least in part on the connecting line 811 extending between the locations of the first and second cursors 807, 809.

Figure 9A:
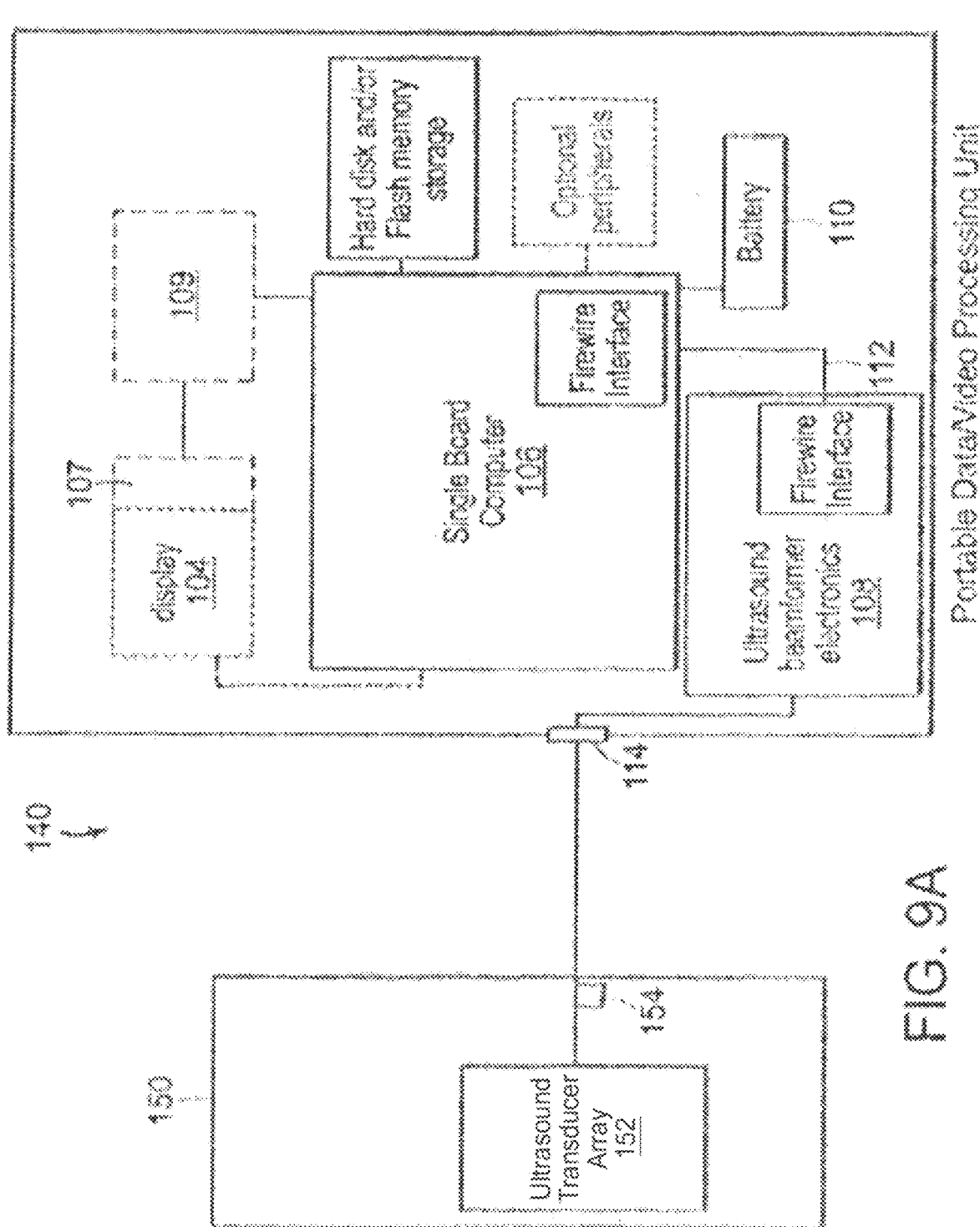
FIG. 9A illustrates one of a plurality of transducer arrays attached to the processor housing.

FIG. 9A shows a system 140 in which a transducer housing 150 with an array of transducer elements 1151 can be attached at connector 114 to housing 102. Each probe 150 can have a probe identification circuit 154 that uniquely identifies the probe that is attached. When the user inserts a different probe with a different array, the system identifies the probe operating parameters.

Figure 9B:
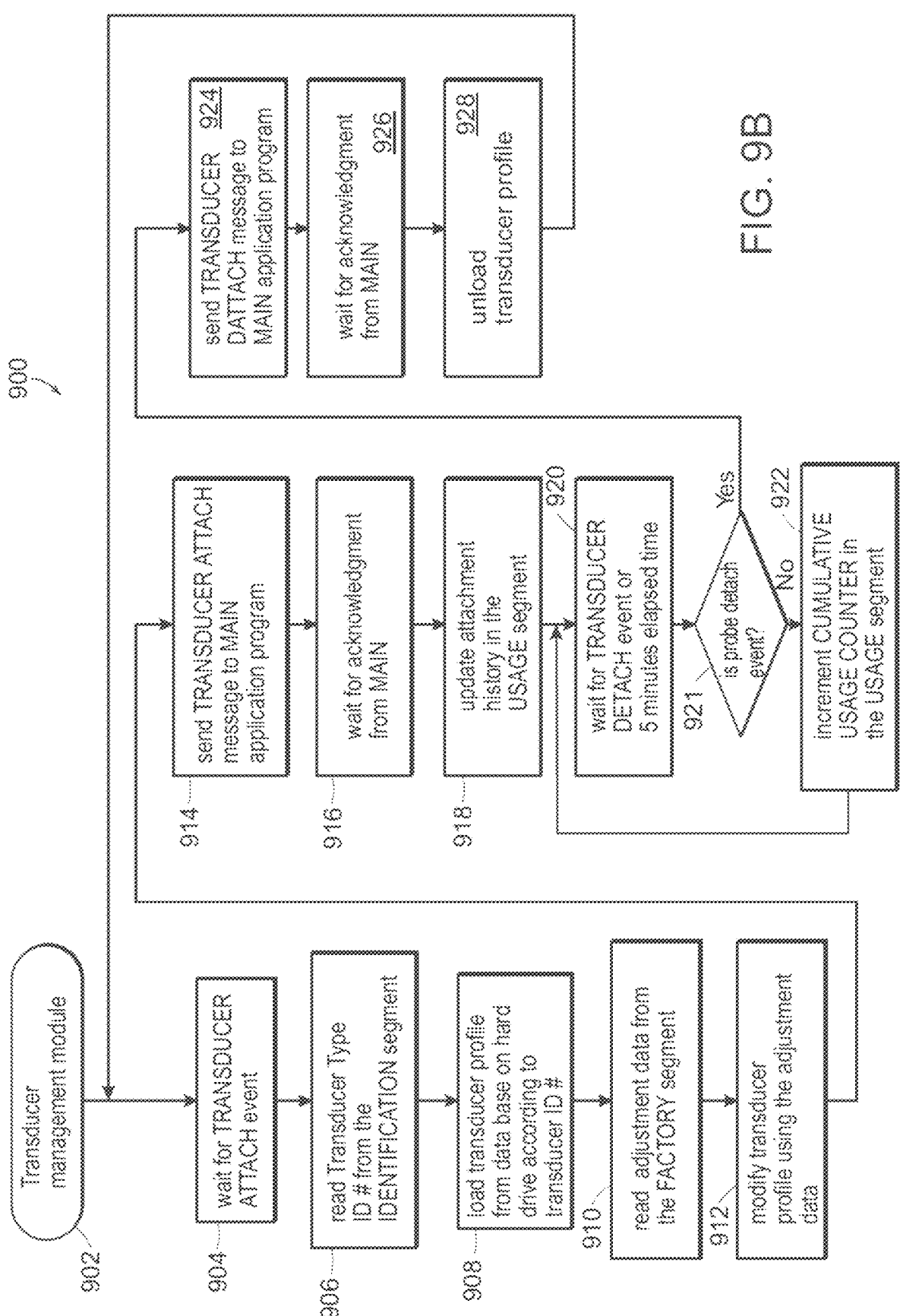
FIG. 9B shows a transducer attach sequence in accordance with exemplary embodiments.

FIG. 9B shows a software flowchart 900 of a typical transducer management module 902 within the ultrasound application program.

When a TRANSDUCER ATTACH 904 event is detected, the Transducer Management Software Module 902 first reads the Transducer type ID and hardware revision information from the IDENTIFICATION Segment 906. The information is used to fetch the particular set of transducer profile data from the hard disk and load it into the memory of the application program 908. The software then reads the adjustment data from the FACTORY Segment 910 and applies the adjustments to the profile data just loaded into memory 912. The software module then sends a TRANSDUCER ATTACH Message to the main ultrasound application program 914, which uses the transducer profile already loaded. After acknowledgment 916, an ultrasound imaging sequence is performed and the USAGE segment is updated 918. The Transducer Management Software Module then waits for either a TRANSDUCER DETACH event, or the elapse of 5 minutes 920. If a TRANSDUCER DETACH event is detected 921, a message 924 is sent and acknowledged 926, the transducer profile data set is removed 928 from memory and the module goes back to wait for another TRANSDUCER ATTACH event. If a 5 minutes time period expires without detecting a TRANSDUCER DETACH event, the software module increments a Cumulative Usage Counter in the USAGE Segment 922, and waits for another 5 minutes period or a TRANSDUCER DETACH event. The cumulative usage is recorded in memory for maintenance and replacement records.

There are many types of ultrasound transducers. They differ by geometry, number of elements, and frequency response. For example, a linear array with center frequency of 10 to 15 MHz is better suited for breast imaging, and a curved array with center frequency of 3 to 5 MHz is better suited for abdominal imaging.

It is often necessary to use different types of transducers for the same or different ultrasound scanning sessions. For ultrasound systems with only one transducer connection, the operator will change the transducer prior to the start of a new scanning session.

In some applications, it is necessary to switch among different types of transducers during one ultrasound scanning session. In this case, it is more convenient to have multiple transducers connected to the same ultrasound system, and the operator can quickly switch among these connected transducers by hitting a button on the operator console, without having to physically detach and re-attach the transducers, which takes a longer time.

FIG. 10 illustrates an exemplary method for monitoring the synchrony of a heart in accordance with exemplary embodiments. In the method, a reference template is loaded into memory and used to guide a user in identifying an imaging plane (per step 930). Next a user identifies a desired imaging plane (per step 932). Typically an apical 4-chamber view of the heart is used; however, other views may be used without departing from the spirit of the invention.

At times, identification of endocardial borders may be difficult, and when such difficulties are encountered tissue Doppler imaging of the same view may be employed (per step 934). A reference template for identifying the septal and lateral free wall is provided (per step 936). Next, standard tissue Doppler imaging (TDI) with pre-set velocity scales of, say, ±30 cm/sec may be used (per step 938).

Then, a reference of the desired triplex image may be provided (per step 940). Either B-mode or TDI may be used to guide the range gate (per step 942). B-mode can be used for guiding the range gate (per step 944) or TDI for guiding the range gate (per step 946). Using TDI or B-mode for guiding the range gate also allows the use of a direction correction angle for allowing the Spectral Doppler to display the radial mean velocity of the septal wall. A first pulsed-wave spectral Doppler is then used to measure the septal wall mean velocity using duplex or triplex mode (per step 948).

A second range-gate position is also guided using a duplex image or a TDI (per step 950), and a directional correction angle may be used if desired. After step 950, the mean velocity of the septal wall and lateral free wall are being tracked by the system. Time integration of the Spectral Doppler mean velocities at regions of interest (e.g., the septum wall and the left ventricular free wall) then provides the displacement of the septal and left free wall, respectively (per step 952).

The above method steps may be utilized in conjunction with a high pass filtering means, analog or digital, known in the relevant arts for removing any baseline disturbance present in collected signals. In addition, the disclosed method employs multiple simultaneous PW Spectral Doppler lines for tracking movement of the interventricular septum and the left ventricular fee wall. In additional, a multiple gate structure may be employed along each spectral line, thus allowing quantitative measurement of regional wall motion. Averaging over multiple gates may allow measurement of global wall movement.

Figure 11A:
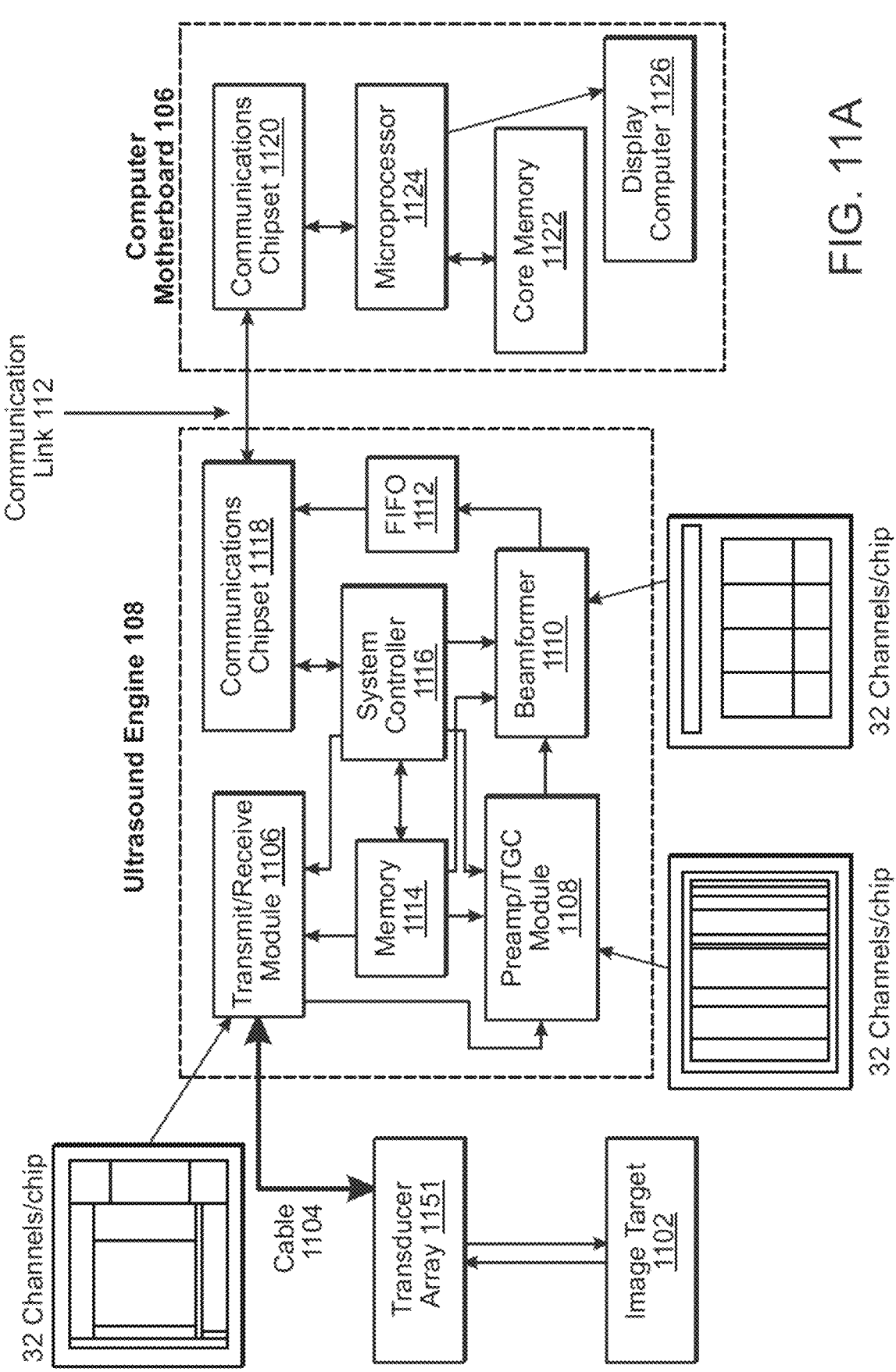
FIG. 11A is a detailed schematic block diagram of an exemplary embodiment of an ultrasound engine (i.e., the front-end ultrasound specific circuitry) and an exemplary embodiment of a computer motherboard (i.e., the host computer) of the exemplary ultrasound device illustrated in FIGS. 1 and 2A.

FIG. 11A is a detailed schematic block diagram of an exemplary embodiment of the ultrasound engine 108 (i.e., the front-end ultrasound specific circuitry) and an exemplary embodiment of the computer motherboard 106 (i.e., the host computer) of the ultrasound device illustrated in FIGS. 1 and 2A. The components of the ultrasound engine 108 and/or the computer motherboard 106 may be implemented in application-specific integrated circuits (ASICs). Exemplary ASICs have a high channel count and can pack 32 or more channels per chip in some exemplary embodiments. One of ordinary skill in the art will recognize that the ultrasound engine 108 and the computer motherboard 106 may include more or fewer modules than those shown. For example, the ultrasound engine 108 and the computer motherboard 106 may include the modules shown in FIG. 17.

A transducer array 1151 is configured to transmit ultrasound waves to and receive reflected ultrasound waves from one or more image targets 1102. The transducer array 1151 is coupled to the ultrasound engine 108 using one or more cables 1104.

The ultrasound engine 108 includes a high-voltage transmit/receive (TR) module 1106 for applying drive signals to the transducer array 1151 and for receiving return echo signals from the transducer array 1151. The ultrasound engine 108 includes a pre-amp/time gain compensation (TGC) module 1108 for amplifying the return echo signals and applying suitable TGC functions to the signals. The ultrasound engine 108 includes a sampled-data beamformer 1110 that the delay coefficients used in each channel after the return echo signals have been amplified and processed by the pre-amp/TGC module 1108.

In some exemplary embodiments, the high-voltage TR module 1106, the pre-amp/TGC module 1108, and the sample-interpolate receive beamformer 1110 may each be a silicon chip having 8 to 64 channels per chip, but exemplary embodiments are not limited to this range. In certain embodiments, the high-voltage TR module 1106, the pre-amp/TGC module 1108, and the sample-interpolate receive beamformer 1110 may each be a silicon chip having 8, 16, 32, 64 channels, and the like. As illustrated in FIG. 11A, an exemplary TR module 1106, an exemplary pre-amp/TGC module 1108 and an exemplary beamformer 1110 may each take the form of a silicon chip including 32 channels.

The ultrasound engine 108 includes a first-in first-out (FIFO) buffer module 1112 which is used for buffering the processed data output by the beamformer 1110. The ultrasound engine 108 also includes a memory 1114 for storing program instructions and data, and a system controller 1116 for controlling the operations of the ultrasound engine modules.

The ultrasound engine 108 interfaces with the computer motherboard 106 over a communications link 112 which can follow a standard high-speed communications protocol, such as the Fire Wire (IEEE 1394 Standards Serial Interface) or fast (e.g., 200-400 Mbits/second or faster) Universal Serial Bus (USB 2.0 USB 3.0), protocol. The standard communication link to the computer motherboard operates at least at 400 Mbits/second or higher, preferably at 800 Mbits/second or higher. Alternatively, the link 112 can be a wireless connection such as an infrared (IR) link. The ultrasound engine 108 includes a communications chipset 1118 (e.g., a Fire Wire chipset) to establish and maintain the communications link 112.

Similarly, the computer motherboard 106 also includes a communications chipset 1120 (e.g., a Fire Wire chipset) to establish and maintain the communications link 112. The computer motherboard 106 includes a core computer-readable memory 1122 for storing data and/or computer-executable instructions for performing ultrasound imaging operations. The memory 1122 forms the main memory for the computer and, in an exemplary embodiment, may store about 4 Gb of DDR3 memory. The computer motherboard 106 also includes a microprocessor 1124 for executing computer-executable instructions stored on the core computer-readable memory 1122 for performing ultrasound imaging processing operations. An exemplary microprocessor 1124 may be an off-the-shelf commercial computer processor, such as an Intel Core-i5 processor. Another exemplary microprocessor 1124 may be a digital signal processor (DSP) based processor, such as one or more DaVinci™ processors from Texas Instruments. The computer motherboard 106 also includes a display controller 1126 for controlling a display device that may be used to display ultrasound data, scans and maps.

Exemplary operations performed by the microprocessor 1124 include, but are not limited to, down conversion (for generating I, Q samples from received ultrasound data), scan conversion (for converting ultrasound data into a display format of a display device), Doppler processing (for determining and/or imaging movement and/or flow information from the ultrasound data), Color Flow processing (for generating, using autocorrelation in one embodiment, a color-coded map of Doppler shifts superimposed on a B-mode ultrasound image), Power Doppler processing (for determining power Doppler data and/or generating a power Doppler map), Spectral Doppler processing (for determining spectral Doppler data and/or generating a spectral Doppler map), and post signal processing. These operations are described in further detail in WO 03/079038 A2, filed Mar. 11, 2003, titled "Ultrasound Probe with Integrated Electronics," the entire contents of which are expressly incorporated herein by reference.

To achieve a smaller and lighter portable ultrasound devices, the ultrasound engine 108 includes reduction in overall packaging size and footprint of a circuit board providing the ultrasound engine 108. To this end, exemplary embodiments provide a small and light portable ultrasound device that minimizes overall packaging size and footprint while providing a high channel count. In some embodiments, a high channel count circuit board of an exemplary ultrasound engine may include one or more multi-chip modules in which each chip provides multiple channels, for example, 32 channels. The term "multi-chip module," as used herein, refers to an electronic package in which multiple integrated circuits (IC) are packaged into a unifying substrate, facilitating their use as a single component, i.e., as a larger IC. A multi-chip module may be used in an exemplary circuit board to enable two or more active IC components integrated on a High Density Interconnection (HDI) substrate to reduce the overall packaging size. In an exemplary embodiment, a multi-chip module may be assembled by vertically stacking a transmit/receive (TR) silicon chip, an amplifier silicon chip and a beamformer silicon chip of an ultrasound engine. A single circuit board of the ultrasound engine may include one or more of these multi-chip modules to provide a high channel count, while minimizing the overall packaging size and footprint of the circuit board.

Figure 11B:
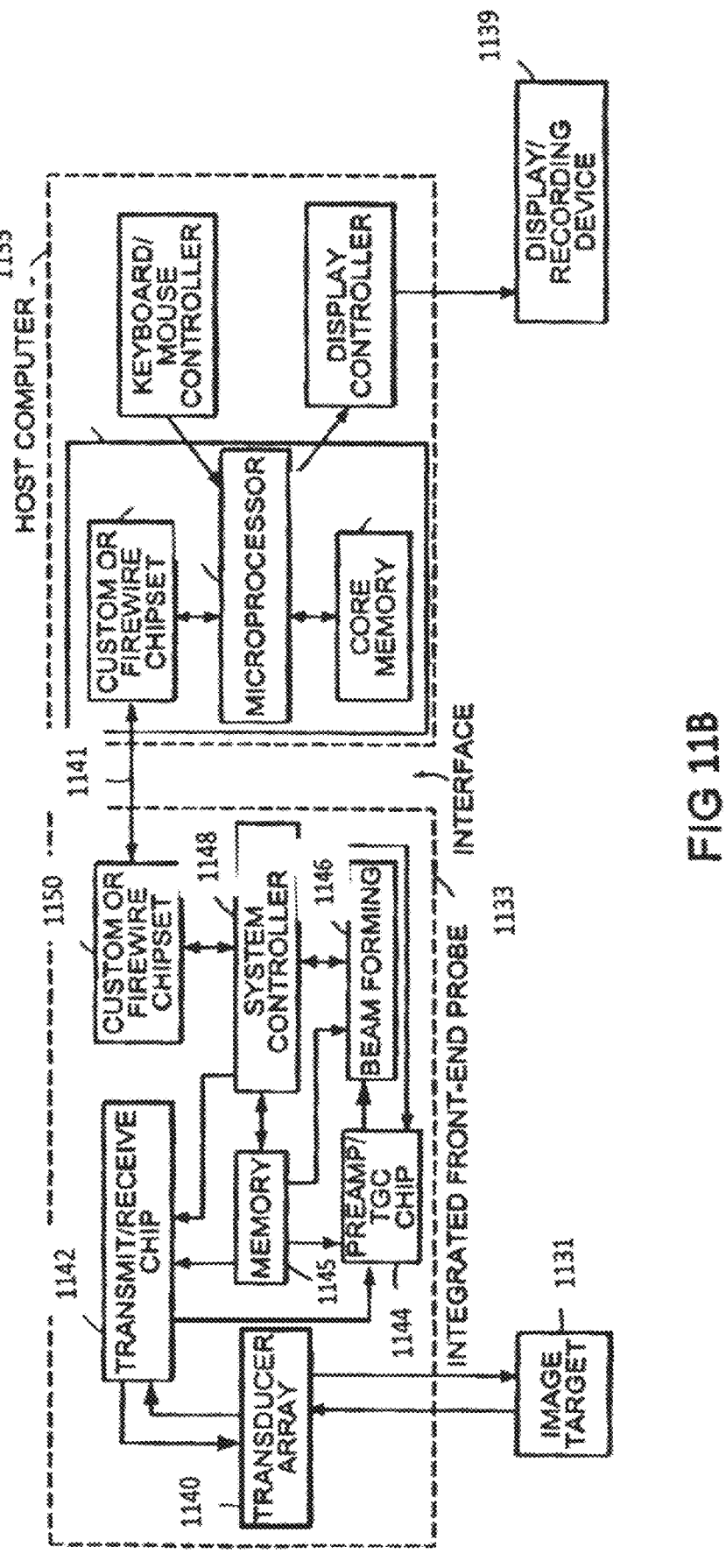
FIG. 11B is a schematic block diagram of an integrated probe system.

FIG. 11B is a schematic block diagram of an integrated probe system. Illustrated are a target object 1131, a front-end probe 1133, and a host computer 1135, and a supplemental display/recording device 1139. The front-end probe 1133 integrates a transducer array 1140 and control circuitry into a single hand-held housing. The control circuitry includes a transmit/receive module 1142, a pre-amp/time-gain compensation (TGC) module 1144, a charge domain processor (CDP) beamforming module 1146, and a system controller 1148. Memory 1145 stores program instructions and data. The CDP beamformer integrated circuit 1146 includes a computational capacity that can be used to calculate the delay coefficients used in each channel. The probe 1133 interfaces with the host computer 1135 over a communications link 1141, which can follow a standard high-speed communications protocol, such as the FireWire (IEEE P1394 Standards Serial Interface) or fast (e.g., 200 Mbits/second or faster) Universal Serial Bus (USB 2.0) protocol. The standard communication link to the personal computer operates at least at 100 Mbits/second or higher, preferably at 200 Mbits/second, 400 Mbits/second or higher. Alternatively, the link 1141 can be a wireless connection such as an infrared (IR) link. The probe 1133 thus includes a communications chipset 1150.

The components in the portable ultrasound system require a continuous source of data for correct operation. For instance, the beamformer 1146 requires steering data, the transmit circuitry 1142 requires data to instruct it where to focus the next pulse and when to fire, and the TGC 1144 needs to know what gain level is appropriate at the given time. Additionally, further information may be required synchronous to the scanning operation to control how the beamformed data is sent back to the host. For instance, a DATAVALID signal can be helpful to reduce the amount of data that the host 1135 actually has to process. Along with data, the various parts of the ultrasound system relies on common synchronization for the system to work in harmony. For example, the transmitter must be fired at an exact time with respect to when the beamformer is looking at a particular position.

Engineering goals of the ultrasonic probe include small size, thermal management, low-power consumption, and the capability and flexibility to allow efficient high resolution imaging as well as calibration and experimentation. The small size and low-power operation implies dense storage. The capability and flexibility entails the ability to use irregular firing sequences, concurrent reprogramming and use for seamless adaptive beamforming modes, as well as full flexibility to perform debugging and complete-set imaging. Ergonomic, economic portable design also requires a cost-effective, non-encumbering connection between the scan head 1133 and the PC host 1135. A general description of the probe system can be found in International Application PCT/US96/11166, filed on Jun. 28, 1996, in U.S. application Ser. No. 08/981,427 filed on Dec. 29, 1997 now U.S. Pat. No. 5,964,709 issued on Oct. 12, 1999, in U.S. application Ser. No. 08/599,816 filed on Feb. 12, 1996 now U.S. Pat. No. 5,690,114 issued on Nov. 25, 1997, in U.S. application Ser. Nos. 08/496,804 and 08/496,805 both filed on Jun. 29, 1995, now U.S. Pat. Nos. 5,590,658 and 5,839,442, respectively, issued Jan. 7, 1997 and Nov. 24, 1998, respectively, and further embodiments are described in U.S. application Ser. No. 09/364,699 filed Jul. 30, 1999, now U.S. Pat. No. 6,292,433 issued on Sep. 18, 2001, in International Application No. PCT/US98/02291 filed on Feb. 3, 1998, and in U.S. application Ser. No. 09/447,144 filed on Nov. 23, 1999 now U.S. Pat. No. 6,379,304 issued on Apr. 30, 2002, in International Application No. PCT/US97/24291 filed on Dec. 23, 1997 the above patents and applications being incorporated herein by reference in their entirety.

Additional factors of interest include ease, speed, and low-cost of design and manufacturing. These factors motivate the use of a Field Programmable Gate Array (FPGA) architecture. Additionally, they involve the use of a design that can be extended easily to diverse applications.

FIGS. 11C-11E illustrate a particular embodiment of integrated probe electronics.

FIG. 11C is a perspective view showing a transducer array housing 1132, an upper circuit board 1100A, a lower circuit board 1100B, and a central circuit board 1102. Also shown is a lower Molex connector 1150B carrying data and signal lines between a central circuit board 1102 and the lower circuit board 1100B. The transducer array housing 1132 can be a commercially available unit having a pair of flexible cable connectors 1120A, 1120B (See FIG. 11E) connected to the upper board 1150A and lower board 1150B, respectively, with strain relief. FIG. 11D is a back-end view of the probe, which also shows an upper Molex connector 1150A. FIG. 11E is a side-view of the probe. Using 8 mm high Molex connectors 1150A, 1150B, the entire stack has a thickness of approximately 30 or less, with this particular embodiment being about 21 mm.

Small size is achieved through the use of modern fabrication and packaging techniques. For example, by exploiting modern semiconductor fabrication techniques, numerous circuit functions can be integrated onto single chips. Furthermore, the chips can be mounted using space-saving packaging, such as chip on-board technology. As technology improves, it is expected that the size of the electronic components will decrease further.

More functionality can be included within the hand-held probe such as a wireless IEEE 1394 connection to the personal computer. A display can be mounted directly on the hand-held probe, for example, to provide a more usable and user-friendly instrument.

Figure 11F:
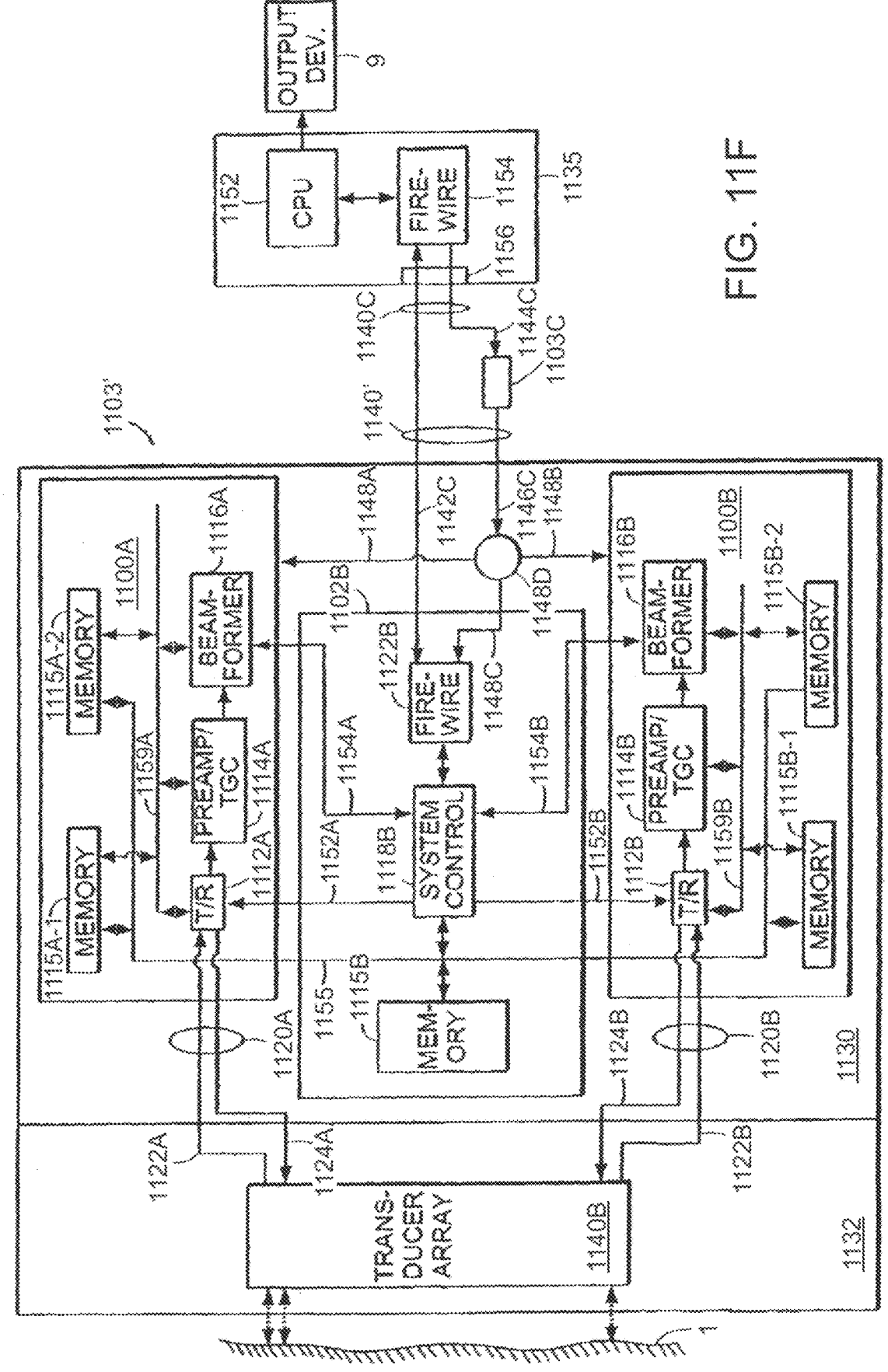
FIG. 11F is a schematic block diagram of a particular embodiment of an integrated probe system.

FIG. 11F is a schematic block diagram of a particular embodiment of an integrated probe system. The host computer 1135 can be a commercially available personal computer having a microprocessor CPU 1152 and a communications chipset 1154. A communications cable 1140C is connected through a communications port 1156 to the communications chipset 1154.

The front-end probe 1103' includes a transducer head 1132, which can be an off-the-shelf commercial product, and an ergonomic hand-held housing 1130. The transducer head 1132 houses the transducer array 1140B. The housing 1130 provides a thermally and electrically insulated molded plastic handle that houses the beamforming and control circuitry.

The, beamforming circuitry, as shown, can be embodied in a pair of analog circuit boards 1100A, 1100B. Each analog circuit board 1100A, 1100B includes a respective transmit/receive chip 1112A, 1112B; a preamp/TGC chip 1114A, 1114B; a beamformer chip 1116A, 1116B; all of which are interconnected with a pair of the memory chips 1115A-1, 1115B-1, 1115A-2, 1115B-2 via an operational bus 1159A, 1159B. In a particular embodiment of the invention, the memory chips are Video Random Access Memory (VRAM) chips and the operational bus is 32 bits wide. Furthermore, preamp/TGC chips 1114A, 1114B and beamformer chips 1116A, 1116B operate on 32 channels simultaneously. The transmit/receive chips 1112A, 1112B include a 64 channel driver and a 64-to-32 demultiplexer.

Figure 11H:
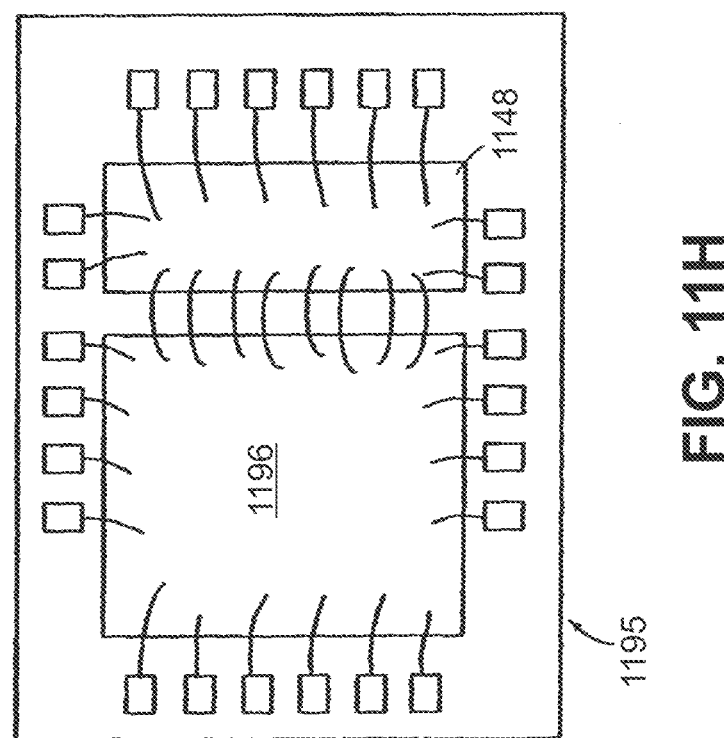
FIGS. 11G and 11H illustrate embodiments of the transmit/receive circuit.
Figure 11G:
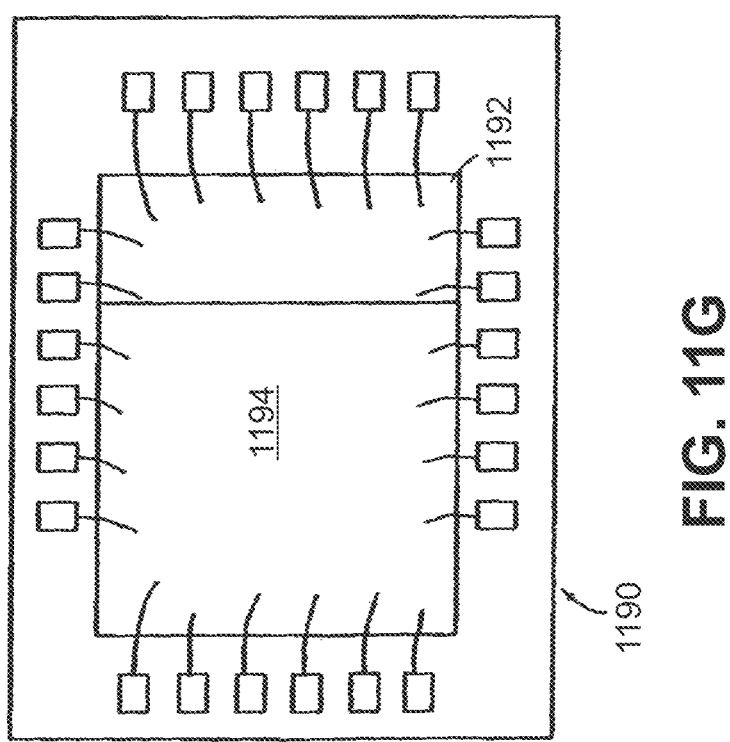
Figure 11I:
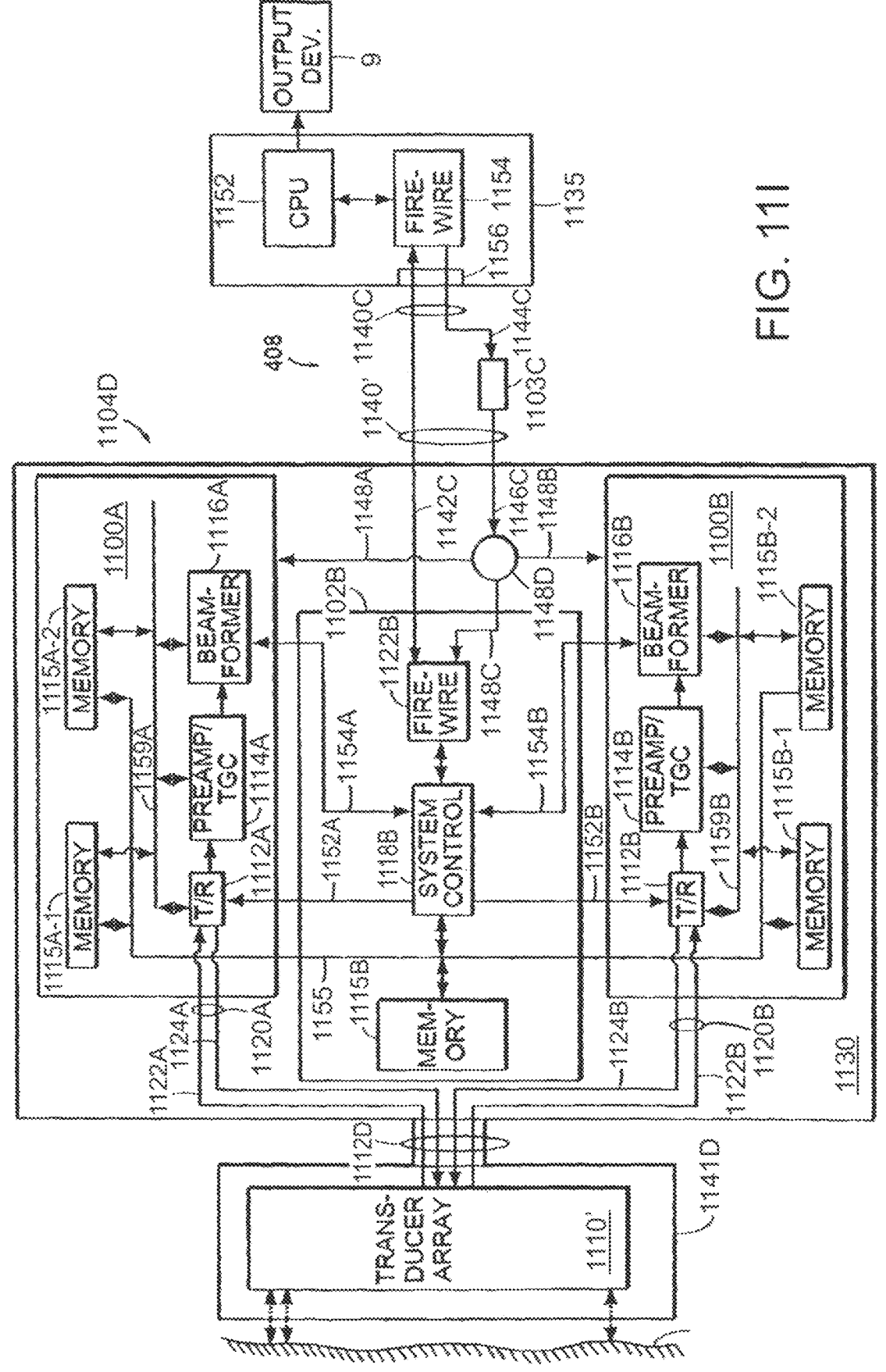
FIG. 11I illustrates an alternate embodiment in which the probe housing is separated from the interface housing by a cable.
Figure 11J:
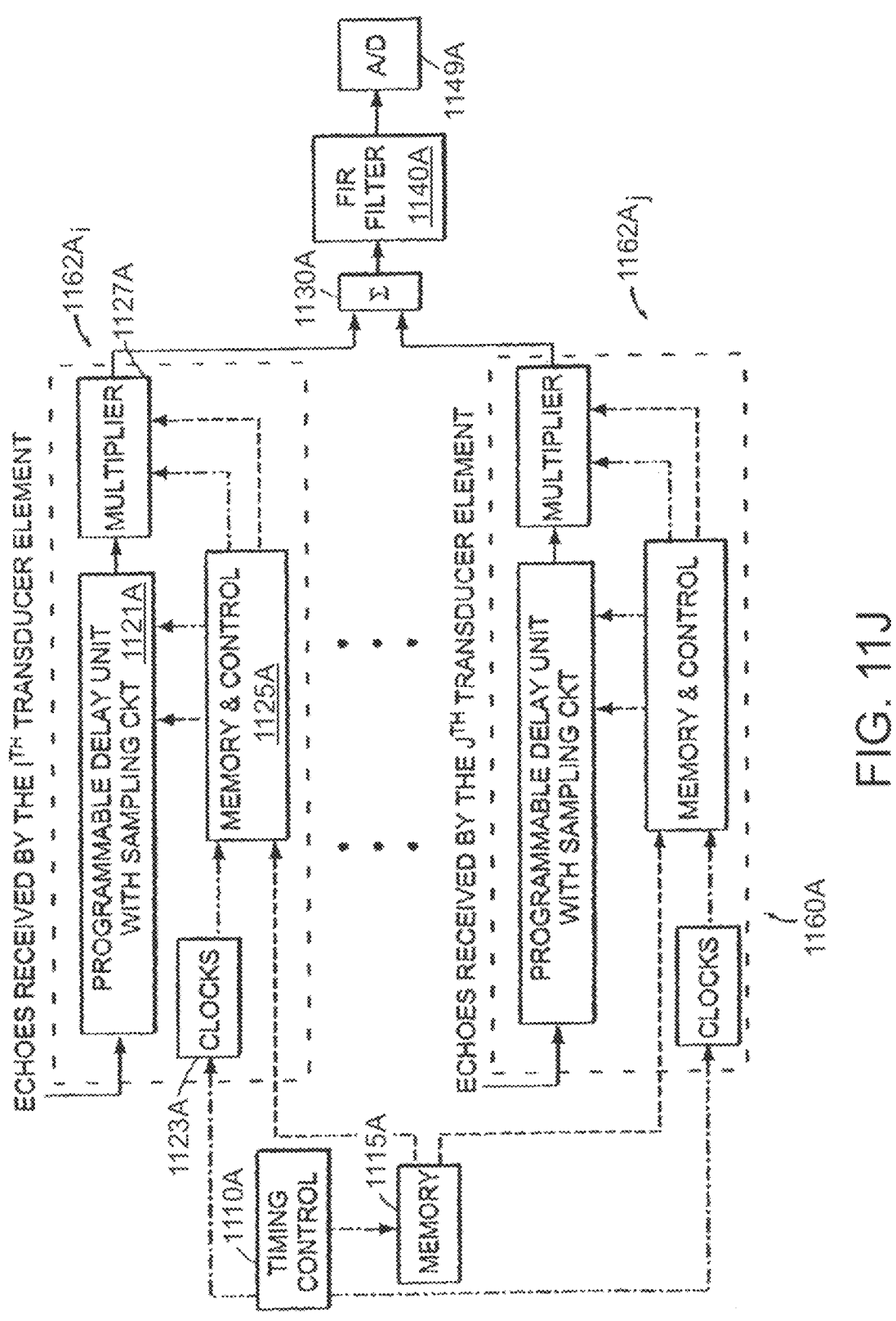
FIG. 11J is a block diagram of a particular 1-dimensional time-domain beamformer.

FIG. 11J is a block diagram of a particular 1-dimensional time-domain beamformer. The beamformer 1160A features 32-channel programmable apodized delay lines. In addition, the beamformer 1160A can include an on-chip output band-pass filtering and analog-to-digital conversion.

As illustrated in FIG. 11J, the beamformer 1160A includes a plurality of single channel beamforming processors 1162A subscript I, . . . , 1162A subscript J. imaging signals are represented by solid leader lines, digital data is represented by dashed leader lines, and clock and control signals are illustrated by alternating dot and dash leader lines. A timing controller 1110A and memory 1115A interface with the single channel beamforming processors 1162A. Each single channel beamforming processor includes clock circuitry 1123A, memory and control circuitry 1125A, a programmable delay unit with sampling circuitry 1121A, in a multiplier circuit 1127A.

Each programmable delay unit 1121A receives an imaging signal echo E from a respective transducer element. The outputs from the single channel beamforming processors 1162A are added in a summer 1130A. A frequency impulse response (FIR) filter 1140A processes the resulting imaging signal, which is digitized by the analog-to-digital (A/D) converter 1149A. In a particular embodiment of the invention, both the FIR filter 1130A and the A/D converter 1149A are fabricated on chip with the beamforming processors 1162A.

The choice of a Field Programmable Gate Array (FPGA) implementation as well as extensibility for ease of modification, points to the use of VRAMs for the memory modules. VRAM is a standard Dynamic RAM (DRAM) with an additional higher-speed serial access port. While DRAM has two basic operations, for example, read and write memory location, VRAM adds a third operation: transfer block to serial readout register. This transfers a block (typically 128 or 256 words) of data to the serial readout register which can then be clocked out at a constant rate without further tying up the DRAM core. Thus refresh, random access data read/write, and sequential readout can operate concurrently. Alternate embodiments may include a synchronous Dynamic Ram (synchDRAM) memory.

In the probe 1103', dual-ported operation is beneficial so the data loading performed by the host 1135 can be decoupled from data sent to memory modules. A modular architecture which allows additional VRAMs to be added in order to obtain additional bandwidth is useful, particularly when the exact data rate requirements may change. Using wide memories, the data does not have to be buffered before going to the various destination modules in the system. A particular embodiment uses five 256 Kword by 16 bit VRAMs which yields a total of 80 output lines. If fewer output lines are required, fewer VRAMs can be used. If more output lines are required, only very minor modifications to the controller have to be made.

The downside is that VRAM is lower density than other varieties of DRAM. Currently only 512 Kbyte VRAM chips are available. Synchronous DRAM (SDRAM) is 2 Mbyte/chip, but expects buffering of all data from the memory to the various destination modules because it is not continuous. The use of SDRAM implies that the modules accept data bursts instead of continuous data. Additionally, more buffering of host data can be used or else concurrent readout and loading may not be possible. Using a multiple data rate feature in the controller can reduce the storage requirements making VRAM a first embodiment. However, a further preferred embodiment uses SDRAM to provide further improvements in the speed and capacity of the system.

The control circuitry, as shown in FIG. 11F, is embodied in a digital circuit board 1102B. The digital circuit board 1102B includes a FireWire chipset 1122B, a system control chip 1118B to control the scan head, and a memory chip 1115B. In a particular embodiment of the invention, the memory chip 1115B is a VRAM chip and the system control chip 1118B is interconnected to the various memory chips 1115A-1, 1115A-2 over a control bus 1155, which in this particular application is 16 bits wide.

As illustrated, the system control chip 1118B provides scan head control signals to transmit/receive chips 1112A, 1112B over respective signal lines 1152A, 1152B. The transmit/receive chips 1112A, 1112B energize the transducer array 1140B over transmit lines 1124A, 1124B. Received energy from the transducer array 1140B is provided to the transmit/receive chips 1112A, 1112B over receive lines 1122A, 1122B. The received signals are provided to the pre-amp/TGC chips 1114A, 1114B. After being amplified, the signals are provided to the beamformer chips 1116A, 1116B. Control signals are exchanged between the beamformer and the system controller over signal lines 1154A, 1154B to adjust the scan beam.

The five VRAM chips 1115A-1, 1115A-2, 1115B-1, 1115B-2, 1115B serve to supply the real-time control data needed by the various operating modules. The term "operating modules" refers to the different parts of the system that require control data—namely the beamformers 1116A, 1116B, transmit/receive chips 1112A, 1112B, and preamp/TGC chips 1114A, 1114B. The system controller 1118B maintains proper clocking and operation of the VRAM to assure continuous data output. Additionally, it generates clocks and control signals for the various operating modules of the system so that they know when the data present at the DRAM serial port output is for them. Finally, it also interfaces with the host (PC) 1135 via a PC communications protocol (e.g., FireWire or high speed bus) to allow the host to write data into the VRAM.

Some of the VRAMs are shared by multiple modules. The 64-bit output of four VRAMs 1115A-1, 1115A-2, 1115B-1, 1115B-2 is used by the transmit module as well as the beamformer. This is not a problem, because typically only one requires data at any given time. Additionally, the transmit module chip uses relatively less data and thus it is wasteful to have to dedicate entire VRAMs for transmit operations. In order to allow the VRAM data to be shared by multiple modules, codes are embedded in the VRAM data that the controller deciphers and asserts the appropriate MODCLOCK line.

The fifth VRAM 1115B is used to generate data that is not shared by multiple modules. For example, it is convenient to put the control for the TGC here because that data is required concurrently with beamformer data. It can also be useful to have one dedicated control bit which indicates when valid data is available from the beamformer and another bit indicating frame boundaries. Thus, because the location of the data in the VRAM corresponds to the position in the frame scanning sequence, additional bits are synchronized with the operation of the system. CCD clock enable signals can also be generated to gate the CCD clock to conserve power. Lastly, the VRAM can be used to generate test data for a D/A converter to test the analog circuitry with known waveforms.

As the system is reduced in size, the number of VRAMs may be reduced. In a SDRAM system clocked twice as fast, the four shared VRAM chips may be merged into two SDRAM chips in a 128 line system, for example.

The data sent to the beamformer and transmit modules are bit-serial within a channel, with all channels being available in parallel. For the transmit module, two transmit channels share each bit line with alternating clocks strobing in data for the two channels. All per channel transmit module coefficients (such as start time) are presented bit-serially.

The data in the VRAM is organized into runs. A run consists of a one word header, which is interpreted by the VRAM controller, followed by zero or more actual data words which are used by the various modules. The headers (see Table 1) specify where the data in the run is destined, how fast it should be clocked out, and how many values there are in the run. (Note that the run destination is only for the data coming out of the 4 VRAMs. The bits coming out of the controller VRAM always have the same destinations.) The headers are also used to encode the special instructions for Jump, Pause, and End described below.

TABLE 1

| | | | | | | | | | | | | | | | | |
|---|---|---|---|---|---|---|---|---|---|---|---|---|---|---|---|---|
| VRAM Instruction Data Format (Only top VRAM matters) | | | | | | | | | | | | | | | | |

| | | | | | | | | Bit Position | | | | | | | | |
|---|---|---|---|---|---|---|---|---|---|---|---|---|---|---|---|---|
| Command | 15 | 14 | 13 | 12 | 11 | 10 | 9 | 8 | 7 | 6 | 5 | 4 | 3 | 2 | 1 | 0 |
| Data | Mod | Sel (2-7) | | Rate | | | | | | Length | | | | | | |
| Pause | 0 | 0 | 1 | Rate (not 0 1) | | | | | | Pause Count | | | | | | |
| Wait | 0 | 0 | 1 | 0 | 1 | 0 | 0 | 0 | 0 | 0 | 0 | 0 | 0 | 0 | 0 | 1 |
| Jump | 0 | 0 | 0 | 0 | 0 | 0 | | | | Jump Addr/0x100 | | | | | | |
| End | 0 | 0 | 0 | 0 | 0 | 1 | X | X | X | X | X | X | X | X | X | X |

The data in the VRAM are read out basically sequentially but some variations are allowed to reduce the memory requirements and facilitate system operation based on several observations about how the ultrasound system operates.

The first observation is that the peak control data rate requirements are far higher than the average rates needed. This is because, during close zone imaging, the focus may be updated at every clock to maintain maximal sharpness. However, for deep zones approaching the far field, the focusing parameters need not vary very quickly. Thus the data may be supplied at a lower rate. This is accomplished by the use of a 2-bit RATE field associated with each run (see Table 2). The RATE field allows the specified run to be clocked out at either the full system clock rate (which can be 8-32 MHZ), one-half, one-quarter, or one-eighth of that rate.

TABLE 2

| | | | |
|---|---|---|---|
| Rate Field Definitions | | | |

| Rate | | | |
|---|---|---|---|
| Bit 12 | Bit 11 | Data Meaning | Pause Length |
| 0 | 0 | New Data Every Clock | PauseCount Clock |
| 0 | 1 | New Data Every Other Clock | PauseCount*2 Clocks |
| 1 | 0 | New Data Every 4 Clocks | PauseCount* Clocks |
| 1 | 1 | New Data Every 8 Clocks | PauseCount*8 Clocks |

The next observation is that there are often large gaps during which time data is not required. After a transmit pulse is fired into a deep zone, a relatively large amount of time can pass before its echo is received and the beamformer is activated. Thus it is advantageous to not have to waste VRAM space for work time periods. For this reason, explicit pause commands are allowed. When the system controller 218 receives a pause command, it waits the specified number of clock cycles before reading the next word in the VRAM memory. The PAUSECOUNT is an 11 bit number which can take on the range 1-2047. This is additionally scaled by the RATE field to allow pauses of up to 16376 (2047*8) system clock cycles. Note that the RATE field can only take on the values 0, 2 and 3 because a pause of RATE 1 is interpreted as a wait command, described next. This is not a problem, however, because typically only RATE 0 is used for maximum wait accuracy (to within one clock) and RATE 3 is used for maximum wait time (up to 16376 clock cycles).

Because the data from the beamformer 1116A, 1116B has to be sent back to the host 1135 over a bandwidth-constrained link, buffering and flow-control are required to prevent data loss. The buffering is achieved by a 16 K by 18 FIFO while the flow control is achieved by feeding the FIFO fullness indication back to the system controller 1148. In this way, if the FIFO becomes too full, the scanning stops until the FIFO has been emptied. However, the scanning should not stop arbitrarily because it is timed with the propagation of the sound waves. Thus explicit synchronization points can be inserted into the code, and at these points the controller waits until the FIFO is empty enough to proceed safely. The wait command is used to indicate these synchronization points. The wait command causes the controller to wait until the WAITPROCEED line is high. In one embodiment, this is connected (via the aux FPGA) to the "not half-full" indicator on the FIFO. Thus the wait commands can be placed at least every 8 K data-generating cycles to assure that data overflow cannot occur. Because this is greater than one ultrasound line, it still allows multi-line interleaving to be used.

The next command is the jump command. This allows non-sequential traversal through the VRAM memory. This is employed so that the VRAM memory can be modified concurrently with the readout operation and also to make it easier to add and remove variable size control sequences. To understand why this is useful, consider the following example: Imagine that one wants to change the data in VRAM locations 512-1023 while continuing operation of the scanning using the other locations. If the host were to just modify locations 512-1023, there is no guarantee that they will not be used exactly when they are in the middle of being modified. Thus the data would be in an indeterminate state and can lead to an erroneous sequence. However, if location 512 is first modified to be a jump to location 1024, and locations to 513-1023 are then modified to their new values, and location 512 is then finally modified to its new value, this race condition cannot occur. (Assuming that it is not reading locations 513-1023 at the start of the modifications but blank regions can be left to get around this.) Additionally "subroutines" (which can only be used once per scan due to the fact that the return is coded as an absolute jump) can be used to allow easy change of the scan sequence.

A jump always takes 128 cycles to execute because the system controller has to load this new start address into the VRAMs and transfer the new row of data to the serial shift register. This typically takes only about 25 cycles, but because other parts of the system controller may have access to the VRAM (such as the refresh or host controller), a safe upper bound is used to maintain a fixed delay.

The last command is the end command. This is used at the end of the sequence for a frame to tell the system controller that the frame has completed. The controller then stops fetching instructions until it is restarted (from location 0) by host if it is in single-frame mode. If it is in continuous mode then it will start immediately on the next frame. (After 128 cycles required for the implied jump 0).

Figure 11K:
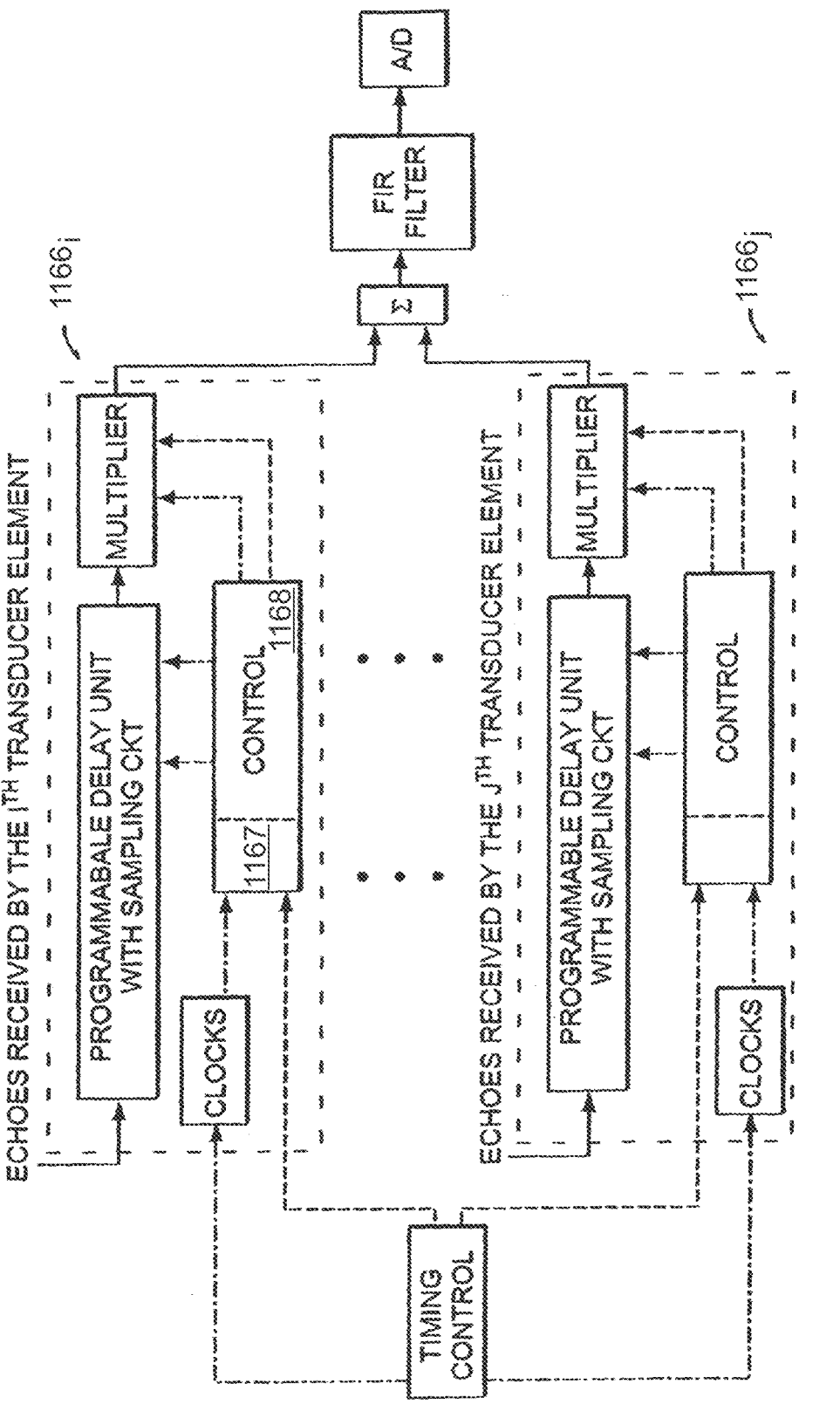
FIG. 11K illustrates another preferred embodiment of a beamformer in accordance with the invention.
Figure 11L:
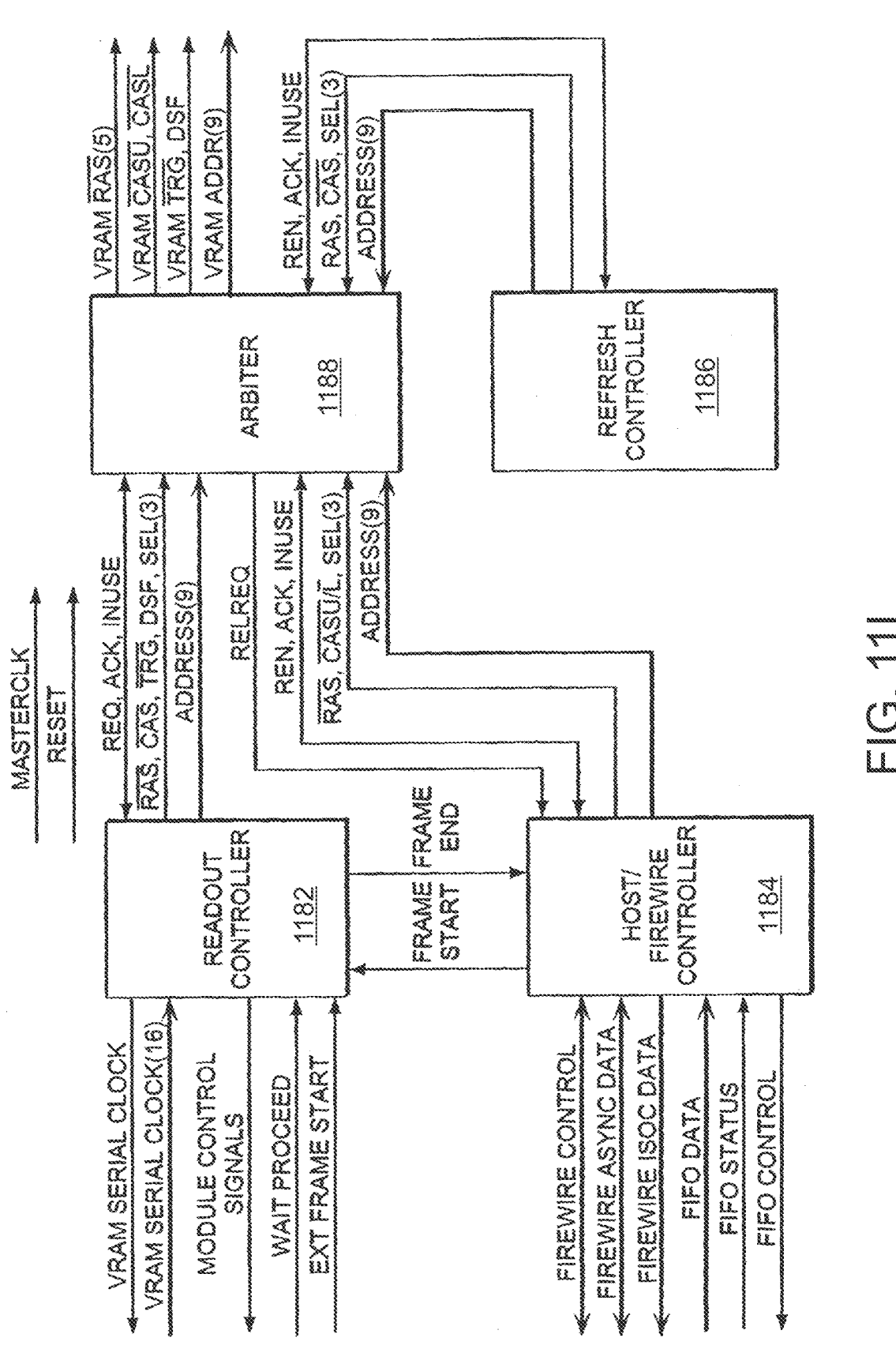
FIG. 11L is a functional block diagram of the system controller.

FIG. 11L is a functional block diagram of the architecture of the system controller of FIG. 11F. The system controller 1118B has four basic parts: a readout controller 1182, a host controller 1184, the refresh controller 1186, and the Arbiter 1188. The first three support the three basic operations on the VRAM: reading out data, writing in of data at host's request, and refreshing the DRAM core. The arbiter 1188 is responsible for merging the requests of the first three sections into one connection to the VRAM's DRAM core. Only one of the first three sections can have control at a given time, so they explicitly request control and wait until this request is acknowledged by the arbiter 1188. They also must tell the arbiter 1188 when they are still using the DRAM so that the arbiter knows not to grant it to one of the other sections. This is done via the INUSE lines.

Additionally the arbiter 1188 sends the host controller 1184 a RELREQ or relinquish request signal to ask the host controller 1184 to give up ownership of the DRAM core because some other section wants it. Note that only the host 1184 controller needs to be asked to relinquish the bus because the readout controller 1182 and refresh controller 1186 both only use the DRAM core for fixed short intervals. The host controller 1184, however, can hold on to the DRAM as long as there is data coming over the FireWire to be written into the DRAM, so it needs to be told when to temporarily stop transferring data.

Note that the serial section of the VRAMs is not multiplexed—it is always controlled by the readout controller 1182. The VRAM serial data also only goes to the readout controller 1182.

The readout controller 1182 controls the sequencing of the data out the VRAMs' serial access ports. This involves parsing the data headers to determine what locations should be read, clocking the VRAM Serial Clock at the correct time, driving the module control lines, and also arranging for the proper data from the VRAM's DRAM core to be transferred into the serial access memory.

The host controller 1184 is the part of the VRAM Controller that interfaces to the host 1135 via FireWire to allow the host to write into the VRAM. When the host wants to write into the VRAM, it sends asynchronous packets specifying which VRAM and which addresses to modify as well as the new data to write. The host controller 1184 then asks the arbiter 1188 for access to the VRAM. When the DRAM core is not in use by either the readout 1182 or refresh controller 1186, the arbiter 1188 grants control to the host controller 1184. The host controller 1184 then takes care of address and control signal generation. When the whole packet has been decoded, the host controller 1184 releases its request line giving up the DRAM control, allowing the other two sections to use it.

The refresh controller 1186 is responsible for periodically generating refresh cycles to keep the DRAM core of the VRAM from losing its data. The refresh controller 1186 has its own counter to keep track of when it needs to request a refresh. Once it gains access to the VRAMs via the arbiter 1188, it generates one refresh cycle for each of the VRAMs sequentially. This reduces the amount of spikes on the DRAM power supply lines as compared to refreshing all five VRAMs in parallel.

The REFRATE inputs control how many system clock cycles occur between refresh cycles. (See Table 3.) This compensates for different system clock rates. Additionally, refresh may be disabled for debugging purposes.

TABLE 3

| | Refresh Rate Definitions | | |
| --- | --- | --- | --- |
| RefRate1 | RefRate0 | System clock cycles between refresh cycles | Minimum System Clock to achieve 16 us refresh rate |
| 0 | 0 | 128 | 8 MHZ |
| 0 | 1 | 256 | 16 MHZ |
| 1 | 0 | 512 | 32 MHZ |
| 1 | 1 | No Refresh | .infin. |

The arbiter 1188 controls the access to the VRAM by the Readout, Host, and Refresh Controller 1182, 1184, 1186 sections. Only one section may have access to the DRAM port of the VRAM at any given time. The arbiter 1188 does not reassign control of the VRAM to another section until the section with control relinquishes it by de-asserting its IN USE line. The sections are prioritized with the Readout Controller 1182 getting the highest priority and the host controller 1184 getting the lowest priority. The reasoning is that if the readout controller 1182 needs access to the VRAM, but does not get it, then the system may break down as the serial output data will be incorrect. The refresh controller 1186 can tolerate occasional delay, although it should not happen much. Finally, the host controller 1184 can potentially tolerate very long delays because the host can be kept waiting without too many consequences except that the writing of the VRAM may take longer.

A highly capable, yet cost-effective and physically nonencumbering connection between the scan head and host computer is possible using the FireWire standard (also known as IEEE 1394). The FireWire standard is used for multimedia equipment and allows 100-200 Mbps and preferably in the range of 400-800 Mbps operation over an inexpensive 6 wire cable. Power is also provided on two of the six wires so that the FireWire cable is the only necessary electrical connection to the probe head. A power source such as a battery or EEE1394 hub can be used. The FireWire protocol provides both isochronous communication for transferring high-rate, low-latency video data as well as asynchronous, reliable communication that can be used for configuration and control of the peripherals as well as obtaining status information from them. Several chipsets are available to interface custom systems to the FireWire bus. Additionally, PCI-to-FireWire chipsets and boards are currently available to complete the other end of the head-to-host connection. CardBus-to-FireWire boards can also be used.

Although the VRAM controller directly controls the ultrasound scan head, higher level control, initialization, and data processing and display comes from a general purpose host such as a desktop PC, laptop, or palmtop computer. The display can include a touchscreen capability. The host writes the VRAM data via the VRAM Controller. This is performed both at initialization as well as whenever any parameters change (such as number or positions of zones, or types of scan head) requiring a different scanning pattern. During routine operation when data is just being continually read from the scan head with the same scanning parameters, the host need not write to the VRAM. Because the VRAM controller also tracks where in the scan pattern it is, it can perform the packetization to mark frame boundaries in the data that goes back to the host. The control of additional functions such as power-down modes and querying of buttons, or dial on the head can also be performed via the FireWire connection.

Although FireWire chipsets manage electrical and low-level protocol interface to the FireWire interface, the system controller has to manage the interface to the FireWire chipset as well as handling higher level FireWire protocol issues such as decoding asynchronous packets and keeping frames from spanning isochronous packet boundaries.

Asynchronous data transfer occurs at any time and is asynchronous with respect to the image data. Asynchronous data transfers take the form of a write or read request from one node to another. The writes and reads are to a specific range of locations in the target node's address space. The address space can be 48 bits. The individual asynchronous packet lengths are limited to 1024 bytes for 200 Mbps operation. Both reads and writes are supported by the system controller. Asynchronous writes are used to allow the host to modify the VRAM data as well as a control word in the controller which can alter the operation mode. Asynchronous reads are used to query a configuration ROM (in the system controller FPGA) and can also be used to query external registers or I/O such as a "pause" button. The configuration ROMs contain a querible "unique ID" which can be used to differentiate the probe heads as well as allow node-lockings of certain software features based on a key.

Using isochronous transfers, a node reserves a specified amount of bandwidth, and it gets guaranteed low-overhead bursts of link access every {fraction ($\frac{1}{8000}$)} second. All image data from the head to the host is sent via isochronous packets. The FireWire protocol allows for some packet-level synchronization and additional synchronization is built into the system controller.

The asynchronous write request packets are sent from the host to the probehead in order to:

a) Configure the Link Layer controller chip (TI GPLynx or TI GP2 Lynx)

b) Control the system controller FPGA c) Write sequencing data into the VRAM

Both the "Asynchronous Write Request with Block Payload" or the "Asynchronous Write Request with Quadlet Payload" forms can be used. The later simply restricts the payload to one quadlet (4 bytes). The formats of the two packets are shown in Table 4 and Table 5. Note that these are how the packets are passed on by the TI LINK controller chip. The difference between this and the format over the wire is that the CRCs are stripped and the speed code (spd) and acknowledgment code (ackSent) are appended to the end. The Adaptec API and device driver take care of assembling the packets.

TABLE 4

Asynchronous Write Request with Quadlet Payload as Delivered by TI LINK chip

| Word | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 |
|---|---|---|---|---|---|---|---|---|---|---|---|---|---|---|---|---|---|---|---|---|---|---|---|---|---|---|---|
| 1 | | | | | | | | | | | | destinationOffsetHi | | | | | | | | | | | | | | | |
| 2 | | | | | | | | | | | | | | | | | | | | | | | | | | | |
| 3 | | Data 1 | | | | | | | | Data 2 | | | | | | | | | Data 3 | | | | | | | | |
| 4 | | | | | | | spd | | | | | | | | | | | | | | ackSent | | | | | | |

Bit (bit 0 is MSB)

TABLE 5

Asynchronous Write Request with Block Payload as Delivered by TI LINK chip

Bit (bit 0 is MSB)

| Word | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 |
|---|---|---|---|---|---|---|---|---|---|---|---|---|---|---|---|---|---|---|---|---|---|---|---|---|---|---|---|
| 0 | | | | | | | | | | | | tLabel | | | | | rt | | tCode = 1 | | | | priority | | | | |
| 1 | | | | | | | | | | | | destinationOffsetHi | | | | | | | | | | | | | | | |
| 2 | | | | | | | | | | | | | | | | | | | | | | | | | | | |
| 3 | | | | | | | | | | | | extendedTcode | | | | | | | | | | | | | | | |
| 4 | | Data 1 | | | | | | | | Data 2 | | | | | | | | | Data 3 | | | | | | | | |
| 5 | | Data 5 | | | | | | | | Data 6 | | | | | | | | | Data 7 | | | | | | | | |
| 6 | | . . . | | | | | | | | . . . | | | | | | | | | . . . | | | | | | | | |
| 3 + N/4 | | Data N − 3 | | | | | | | | Data N − 2 | | | | | | | | | Data N − 1 | | | | | | | | |
| 4 | | | | | | | spd | | | | | | | | | | | | | | ackSent | | | | | | |

The destinationID field holds the node ED of the destination which is the probe head FireWire controller. The physical layer chip can use this to determine if the packet is for it. The system controller can ignore this field. The tLabel field is used to match requests and responses. For write requests, this does not matter and can be ignored. The rt is the retry code used at link and/or phy level. It is not used by the system controller. The tCode field is the transaction code which determines what type of packet it is. In particular 0 is for quadlet write requests and 1 is for block write requests. The system controller parses this field to determine what type of packet it is. Currently only tCode values of 0 and 1 are recognized. The priority field is used by the PHY chip only and is ignored by the system controller. It is used in, i.e. in selecting which unit on the interface is to receive a particular packet of data.

Next, the destinationOffsetHi and destinationOffsetLo fields form the 48 but destination start address. This indicates within the node what the data should be used for. The system controller used the destinationOffsetHi to determine the function as shown in table 6. Note that only the 3 least FireWire. An explicit counter in the system controller is used due to the fact that the TI GPLynx chip does not assert the end-of-packet indication until one word too late. Note that the ISO Packet length also has to be set in the LINK chip. The value written is the number of 16-bit words in the ISO Packet length which also has to be set in the LINK chip. The value written is the number of 16-bit words in the ISO packet (i.e. bytes/2) and it is written in little endian order because it is only interpreted by system controller and not the LINK chip.

Specifying a destinationOffsetHi value of 6 signifies that the system controller mode word is to be modified. Currently only the least significant 16 bits are used out of each quadlet and all quadlets go to the same place so writing multiple values just causes the system controller mode word to be rewritten. Please note that the payload data is again little endian. (Putting these two facts together yields that the first two out of every four bytes are used and the second two are ignored.) The definition of the system controller Mode Word is given in Table 7.

TABLE 7

| System Controller Mode Word Bit (bit 31 is MSB) | | | | | | | | | |
|---|---|---|---|---|---|---|---|---|---|
| 31-36 | 15-8 | 7 | 6 | 5 | 4 | 3 | 2 | 1 | 0 |
| unused | BOF Word | unused | unused | Abort-Frame | Single Frame | Run | Extra 2 | Extra 1 | Data Loop-back | significant bits of the destinationOffsetHi field are currently examined. The spd field indicates the speed at which the data was sent while the ackSent field is used to indicate status by saying how the LINK chip acknowledged the packet.

TABLE 6

| destinationOffsetHi values | |
|---|---|
| destinationOffsetHi | Meaning |
| 0 | Write VRAM 0 |
| 1 | Write VRAM 1 |
| 2 | Write VRAM 2 |
| 3 | Write VRAM 3 |
| 4 | Write VRAM 4 |
| 5 | Write ISO packet Length Register |
| 6 | Write System Controller Mode Word |
| 7 | Wrote to LINK chip |

As can be seen, destinationOffsetHi values of 0-4 correspond to writing the VRAMs. In this case the destination-OffsetLow is set to the byte address to start writing. This is twice the standard VRAM address which is typically formed in 16-bit words. Note also that the start address (destinationOffsetLow) and the length (dataLength) can both be multiples of 4 such that all operations are quadlet aligned. The payload data is little endian and thus need not be converted if written by an Intel PC host. The length (dataLength) must additionally be between 4 and 128 bytes due to the size of the GPLynx FIFO. The total FIFO size is 200 bytes, but 72 bytes are dedicated to the asynchronous transmit FIFO required for read responses.

A destinationOffsetHi value of 5 signifies that the system controller ISO Packet Length register is to be written. The ISO Packet Length has to be set in the controller to allow it to correctly format the ISO packets back to the host via The BOF Word field is used to set the value that the system controller will put in the high byte of the first word of an isochronous packet to indicate the beginning of frame. The BOF word field can be set to some value that is not likely to occur in typical data. This not crucial, however, because choosing a BOF word that occurs in the data will make it more likely to miss incorrect frame synchronization but will never cause false alarms where it thinks it is mis-synchronized but is really correctly synchronized. The initial value upon reset is 80 hex.

The AbortFrame, SingleFrame, and Run bits are used to control the system operation. Their use is shown in Table 8. The data FIFO is never allowed to fully empty so an entire frame cannot be read out until part of the next one is the queue.

TABLE 8

| Use of AbortFrame, SingleFrame, and Run bits in System Controller Mode Word | | | |
|---|---|---|---|
| Abort Frame | Single Frame | Run | Meaning |
| 1 | 0 | 0 | Abort any current frame and wait |
| 0 | 1 | 0 | Start a single new frame |
| 0 | 0 | 1 | Keep scanning new frames |
| 0 | 0 | 0 | Let any current frame complete |

The DataLoopback bit is used to control whether the data that is read back from the host comes from A/D or from one of the VRAMs. (Currently this is VRAM 1.) This second option can used for test purposes to test the digital data generation and collection without testing the beamformer and A/D conversion. A 0 in the DataLoopback bit indicates normal operation of reading from A/D while a 1 means that it should get data from the VRAM.

The Extra1 and Extra2 bits are available for general use. They are latched by the system controller and currently brought out on pins called EXTRACLOCK0 and EXTRACLOCK1 but can be used for any purpose.

Finally setting destinationOffsetHi to 7 indicates that the data in the asynchronous packet be written back to the FireWire Link chip. This allows any of the TI TSB12LV31's (or 32's) registers to be modified by the host. This can be used to configure and enable the Isochronous data transmit. The destinationOffsetLow specifies the first register to write. Because the registers are all 4-bytes in size and must be written in their entirety, destinationOffsetLow and dataLength must both be multiples of 4. Multiple consecutive registers can be written with a single packet. Note that the data is big-endian because the TSB12LV31 is designed as big-endian. This byte-swapping must be performed by the Intel PC host.

Read request packets are used to asynchronously read data from the probehead. This currently only consists of configuration ROM data (see below) but can be easily used for other types of data such as status information or button indications.

The Adaptec device drivers send Asynchronous Read Requests in response to explicit application requests as well as to interrogate the node's FireWire configuration ROM in response to a SendPAPICommand of P GET DEV INFO or after a bus reset or when an application tries to obtain a handle to a node.

Asynchronous read requests can either be of the quadlet or block variety as with the asynchronous write requests. The formants are shown in Table 9 and Table 10. They are similar to the write request formats.

TABLE 9

| Asynchronous Read Request with Quadlet Payload as Delivered by TI LINK chip | | | | | | | | | | | | | | | | | | | | | | | | | | |
| --- | --- | --- | --- | --- | --- | --- | --- | --- | --- | --- | --- | --- | --- | --- | --- | --- | --- | --- | --- | --- | --- | --- | --- | --- | --- | --- |
| Bit (bit 0 is MSB) | | | | | | | | | | | | | | | | | | | | | | | | | | |
| Word | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 |
| 0 | | | | | | | | | | | | | | tLabel | | | | | rt | | tCode = 4 | | | | priority | | |
| 1 | | | | | | | | | | | | | | | | destinationOffsetHi | | | | | | | | | | | |
| 2 | | | | | | | | | | | | | | | | | | | | | | | | | | | |
| 4 | | | | | spd | | | | | | | | | | | | | | | | | | | | ackSent | | |

TABLE 10

| Asynchronous Read Request with Quadlet Payload as Delivered by TI LINK chip | | | | | | | | | | | | | | | | | | | | | | | | | | |
| --- | --- | --- | --- | --- | --- | --- | --- | --- | --- | --- | --- | --- | --- | --- | --- | --- | --- | --- | --- | --- | --- | --- | --- | --- | --- | --- |
| Bit (bit 0 is MSB) | | | | | | | | | | | | | | | | | | | | | | | | | | |
| Word | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 |
| 0 | | | | | | | | | | | | | | tLabel | | | | | rt | | tCode = 5 | | | | priority | | |
| 1 | | | | | | | | | | | | | | | | destinationOffsetHi | | | | | | | | | | | |
| 2 | | | | | | | | | | | | | | | | | | | | | | | | | | | |
| 3 | | | | | | | | | | | | | | | | | | | extendedTcode | | | | | | | | |
| 4 | | | | | spd | | | | | | | | | | | | | | | | | | | | ackSent | | |

As with the asynchronous write packets, the destinationOffsetHi and destinationOffsetLow determine what is being requested. The high addresses are defined for use as Control and Status Registers and the configuration ROM while the lower address are for more general purpose use. In particular, the FireWire configuration ROM starts at destinationOffsetHi=0.times.ffff, and destinationOffsetLow=0.times.f00004-00, for example.

When the system controller receives a Quadlet or Block Read Request packet from the TI LINK chip's General Receive FIFO, it formulates a Quadlet or Block Read Response packet and places it in the LINK chip's Asynchronous Transmit FIFO. The format of these packets (as placed in the Asynchronous Transmit FIFO) is shown in Table 11 and Table 12.

TABLE 11

| Asynchronous Read Response with Quadlet Payload as Expected by TI LINK chip | | | | | | | | | | | | | | | | | | | | | | | | | | |
| --- | --- | --- | --- | --- | --- | --- | --- | --- | --- | --- | --- | --- | --- | --- | --- | --- | --- | --- | --- | --- | --- | --- | --- | --- | --- | --- |
| Bit (bit 0 is MSB) | | | | | | | | | | | | | | | | | | | | | | | | | | |
| Word | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 |
| 0 | | | | | | | | spd | | | | tLabel | | | | | rt | | tCode = 6 | | | | priority | | | | |
| 1d | | | | | | | | | | | rCode | | | | | | | reserved = 0 | | | | | | | | | |

TABLE 11-continued

| | | | | | | | | | | | | | | | | | | | | | | | | | | |
|---|---|---|---|---|---|---|---|---|---|---|---|---|---|---|---|---|---|---|---|---|---|---|---|---|---|---|
| Asynchronous Read Response with Quadlet Payload as Expected by TI LINK chip | | | | | | | | | | | | | | | | | | | | | | | | | | |

| | | | | | | | | | | | | | | | | | | | | | | | | | | |
|---|---|---|---|---|---|---|---|---|---|---|---|---|---|---|---|---|---|---|---|---|---|---|---|---|---|---|
| Bit (bit 0 is MSB) | | | | | | | | | | | | | | | | | | | | | | | | | | |

| Word | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 |
|---|---|---|---|---|---|---|---|---|---|---|---|---|---|---|---|---|---|---|---|---|---|---|---|---|---|---|---|---|
| 2 | | | | | | | | | | | | | | | | | | | | | | | | | | | |
| 3 | | | | | | | Data 1 | | | | | | | | | Data 2 | | | | | | | Data 3 | | | | |

TABLE 12

| | | | | | | | | | | | | | | | | | | | | | | | | | | |
|---|---|---|---|---|---|---|---|---|---|---|---|---|---|---|---|---|---|---|---|---|---|---|---|---|---|---|
| Asynchronous Read Response with Block Payload as Expected by TI LINK chip | | | | | | | | | | | | | | | | | | | | | | | | | | |

| | | | | | | | | | | | | | | | | | | | | | | | | | | |
|---|---|---|---|---|---|---|---|---|---|---|---|---|---|---|---|---|---|---|---|---|---|---|---|---|---|---|---|
| Bit (bit 0 is MSB) | | | | | | | | | | | | | | | | | | | | | | | | | | |

| Word | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 |
|---|---|---|---|---|---|---|---|---|---|---|---|---|---|---|---|---|---|---|---|---|---|---|---|---|---|---|---|---|
| 0 | | | | | | | | | | | spd | | | | tLabel | | | rt | | | tCode = 7 | | | | priority | | |
| 1 | | | | | | | | | | | | | | | rCode | | | | | | reserved = 0 | | | | | | |
| 2 | | | | | | | | | | | | | | | | | | | | | | | | | | | |
| 3 | | | | | | | | | | | | | | | | | | | extendedTcode | | | | | | | | |
| 4 | | | | | | | Data 1 | | | | | | | | | Data 2 | | | | | | | Data 3 | | | | |
| 5 | | | | | | | Data 5 | | | | | | | | | Data 6 | | | | | | | Data 7 | | | | |
| . . . | | | | | | | . . . | | | | | | | | | . . . | | | | | | | . . . | | | | |
| 3 + N/4 | | | | | | | Data N − 3 | | | | | | | | | Data N − 2 | | | | | | | Data N − 1 | | | | |

The spd, tLabel, rt, and priority values are copied from the request packet. The destinationID is taken from the sourceID of the request packet. Note that all packet CRCs are generated by the TI LINK chip and are thus note included data that the system controller must generate. (The ROM CRCs do have to be computed explicitly off-line).

The rCode field is used to indicate the status of the reply. In particular, 0 means resp complete indicating all is well. A value of 6 means resp type error indicating that some field of the packet was invalid or unsupported. In this case, if the request was a block request then the dataLength of the response packet must be 0 and no data should be included. A resp type error is returned if the dataLength or destinationOffsetLow of the request packet were not multiples of 4 or if the dataLength was not between 4 and 32 (for block packets). This is because the TI chip's asynchronous transmit FIFO is configured to be 12 quadlets (for 8 payload quadlets+4 quadlet header) so that the receive FIFO can be 36 quadlets in order to allow 128 byte payload write packets. The longest request the Adaptec device drivers should request is 8 quadlets because that is the length of the configuration ROM. In any case, it is assumed that if a long transfer failed, it falls back toga smaller request.

The FireWire specification expects each FireWire node to have a configuration ROM that contains various details about the device, its requirements, and its capabilities. This ROM is to be queried via Read Request packets. There are two types of ROM implementations: a minimal ROM and a general ROM. The former has only one quadlet (4-byte) piece of data indicating a 24-bit vendor DD. The general ROM has many other fields, and many which are optional ranging from the ASCII name of the vendor and device to its power consumption and how to access its capabilities.

One of the required fields in a general ROM is a node unique ID. This consists of the 24-bit vendor ID and a 40-bit chip ID. The 40-bit chip-ID is up to the vendor to assign such that all nodes have unique values. The node unique ID's are required to keep a consistent handle on the device if the FireWire bus is reset or reconfigured during operation. When a device is first opened, the application reads its configuration ROM and determines if it wants to work with it. If so it records its node unique ID and opens a connection to the device via that node unique ID. This is then at any given time mapped to its FireWire ID (16-bit) by the host adapter and its device driver. If the topology changes or a FireWire bus reset occurs, the node's FireWire ID can change, however the node unique ID will not. Thus, in such an event, the adapter automatically determines the new FireWire ID and continues. Thus for smooth operation, particularly with multiple heads attached to the system, implementing node unique IDs and the configuration ROM is required.

The configuration ROM is divided into several sections. The sections of particular interest are the first word, which defines the length and CRC of the ROM, the next 4 words comprising the Bus Info Block, which gives some fixed 1394-specific information (such as Node Unique ID), and the last 3 words representing the Root Directory which is a set of key-value tagged entries. Only the two required key-value pairs are included the ROM built into the FPGA. An 8-word ROM that can be used is shown in Table 13.

TABLE 13

| | | | | | | | | | | | | | | | | | | | | | | | | | | |
|---|---|---|---|---|---|---|---|---|---|---|---|---|---|---|---|---|---|---|---|---|---|---|---|---|---|---|
| FireWire Configuration ROM built into FPGA | | | | | | | | | | | | | | | | | | | | | | | | | | |

| | | | | | | | | | | | | | | | | | | | | | | | | | | |
|---|---|---|---|---|---|---|---|---|---|---|---|---|---|---|---|---|---|---|---|---|---|---|---|---|---|---|---|
| Bit (bit 0 is MSB) | | | | | | | | | | | | | | | | | | | | | | | | | | |

| Word | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 |
|---|---|---|---|---|---|---|---|---|---|---|---|---|---|---|---|---|---|---|---|---|---|---|---|---|---|---|---|---|
| 0 | | | | | crc_length = 0x07 | | | | | | | | | | | | | rom_crc_value = 0xfbc8 | | | | | | | | | | |
| 1 | | | | | 0x33 ("3") | | | | | | | | | 0x39 ("9") | | | | | | | | | 0x34 ('4") | | | | |

TABLE 13-continued

| FireWire Configuration ROM built into FPGA |
| --- |

| | Bit (bit 0 is MSB) |
| --- | --- |

| Word | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 |
| --- | --- | --- | --- | --- | --- | --- | --- | --- | --- | --- | --- | --- | --- | --- | --- | --- | --- | --- | --- | --- | --- | --- | --- | --- | --- | --- | --- |
| 2 | | | | | | cyc_clk_acc = 0xff | | | | | | max_rec = 6 | | | | | | | | reserve = 0x000 | | | | | | | |
| 3 | | | | | | | | | | | | | | | | | | | | | | chip_is_hi = 0 | | | | | |
| 4 | | | | | | | | | | | | | | | | | | | | | | | | | | | |
| 5 | | | | | | | | | | | | | | | | | | | | Root_Dir_CRC = 0xbc8e | | | | | | | |
| 6 | | | | | | | | | | | | module_vendor_id = 1234567 (0x12d687) | | | | | | | | | | | | | | | |
| 7 | | | | | | | | | | | | node_capabilities0x000000 | | | | | | | | | | | | | | | |

Isochronous packets are used for the probehead-to-host communication of beamformed data. This is conceptually a stream of 16-bit numbers punctuated by frame markers. The frame markers are important to keep in sync with where in the frame the data corresponds. While some ultrasound systems use elaborate frame and line markers embedded in the data, the integrated system can use a single auxiliary bit, which is not sent as part of the data, to mark frame boundaries. Line boundaries can be derived by knowing the VRAM sequencing program.

While asynchronous packets can be sent at will and do not have any guarantee of bandwidth availability, isochronous packets can be used as low-overhead way to send a guaranteed rate of data. Once a peripheral reserves a specified amount of bandwidth, it gets guaranteed bursts of link access every {fraction (1/8000)} second. All data from the head to the host is sent via isochronous packets. Because isochronous packets are limited to {fraction (1/8000)} second, this is a frame of data. The FireWire specification describes the use of synchronization bits which can be used to tag each isochronous packet with a 4 bit SYNC code. The Adaptec FireWire-to-PCI bridge can then use the Sync field to assure proper frame alignment. However, the TI GPLynx Controller chip only supports frame-level granularity of when to send packets and not packet level so when the System. Controller tells the FireWire link chip it has data, it must be prepared to send a whole frame of data. Because the FIFO is much smaller than a frame, a sage option is to reduce the effective FireWire frame size to one packet. Then a specific Beginning of Frame (BOF) code in the high byte of the first word of every ultrasound frame and force the start of ultrasound frames to occur at the beginning of FireWire frames (and packets) and do frame-level synchronization in the Ultrasound application software. For efficiency, a full ultrasound frame of data can still be read in one FireWire call (and hence one interrupt).

There are three steps in setting up for Isochronous head-to-host data transfers. These initialization steps need only be performed once per probe initialization.

The first step is to reserve isochronous bandwidth. This reservation causes a central record of the request (in the FireWire isochronous cycle manager node) to be kept to assure that the total bandwidth allocated does not exceed the total bandwidth of the link. For example, this reservation is achieved using the Adaptec API BusConfig 0 command with Cmd field set to P ALLOCATE RESOURCE. A requested payload in bytes is passed in. This can be the amount of data desired in every {fraction (1/8000)} second. Setting this value too high simply wastes reserved bandwidth on the FireWire interface which is not a problem if there is only one device. Setting this value too low may constrain the head-to-host data rate. No overflows or data loss are likely to occur, the scanning may simply proceed slower. The resource allocation call will return both an isochronous channel number as well as the payload size granted. This payload size granted may be less than that requested if part of the link has already been reserved.

The next step is to set the system controller ISO packet length word to tell how long of an ISO packet to expect.

The final step is to initialize the probehead LINK chip. This is done via the writeback to LINK chip asynchronous packets described above. In particular, initializing registers 54h, 58h, and 5ch is necessary. The probehead can then be told to start sequencing and the data will flow back.

If multiple probes are connected to the system then the isochronous bandwidth reservation can take place once but at any given time, only one probe's isochronous transmission (as well as its sequencing) is enabled.

As previously described, isochronous data transfers are used to deliver the probe head data to the host. Maintaining frame synchronization is necessary. The FireWire will support sub-frame packetization of about 3000 bytes but it is up to the system controller to implement frame synchronization on top of this. Synchronization is achieved via two methods:

1. The high byte of the first word in the first packet of a frame is set to the Beginning of Frame (BOF) code. (This can be set in the system controller Mode word).
2. All frames are padded to consume a whole number of packets.

When these two are combined, they guarantee that frame synchronization will be maintained if the correct number of packets are read at a time and the resynchronization can be effected by just scanning the high-byte of the first word of each packet in the data stream.

An example packetization is shown in Table 14. This depicts 4 packets of 4 words (8 bytes) apiece showing one complete ultrasound frame and the first packet of the next frame. The ultrasound frame size is 10 words. As can be seen, the Hi byte of the first word is set to the BOF code. This can be examined to assure that proper synchronization has been maintained. The data is then split into the three packets 1-3. Because the frame ends in the middle of packet 3, the end of packet 3 is padded with the BOF code in the high word. Importantly, this means that the first word of the fourth packet will be the first word of the second frame even though the ultrasound frame size is not a multiple of the packet size.

TABLE 14

| Example Packetization of Isochronous Head-to-Host Data | | | |
| --- | --- | --- | --- |
| Packet | Word | Lo Byte | Hi Byte |
| 1 | 1 | Data 1 Lo | BOF |
| (Frame 1) | 2 | Data 2 Lo | Data 2 Hi |

TABLE 14-continued

| Example Packetization of Isochronous Head-to-Host Data | | | |
|---|---|---|---|
| Packet | Word | Lo Byte | Hi Byte |
| | 3 | Data 3 Lo | Data 3 Hi |
| | 4 | Data 4 Lo | Data 4 Hi |
| 2 | 1 | Data 5 Lo | Data 5 Hi |
| (Frame 1) | 2 | Data 6 Lo | Data 6 Hi |
| | 3 | Data 7 Lo | Data 7 Hi |
| | 4 | Data 8 Lo | Data 8 Hi |
| 3 | 1 | Data 9 Lo | Data 9 Hi |
| (Frame 1) | 2 | Data 10 Lo | Data 10 Hi |
| | 3 | Data 1 Lo | BOF |
| | 4 | Data 1 Lo | BOF |
| 4 | 1 | Data 1 Lo | BOF |
| (Frame 2) | 2 | Data 3 Lo | Data 2 Hi |
| | 3 | Data 3 Lo | Data 3 Hi |
| | 4 | | |

The TSB12LV31 (or 32) performs packetization of the isochronous data but informs the system controller of packet boundaries via the ISORST signal. The system controller then uses this to reset its internal word-to-byte multiplexer as well as packetization circuitry. If it receives a frame marker from the FIFO then stops clocking data out of the FIFO until it receive a ISORST pulse.

The module interface defines how the various modules in the system are controlled by the VRAM controller. There are two types of modules, those that receive data from the four VRAMs which are shared (two on each analog board), and those that receive data from the VRAM on the digital board, (via the VRAM controller) which is dedicated. The two types of modules use different control signals to synchronize their operation.

Figure 11M:
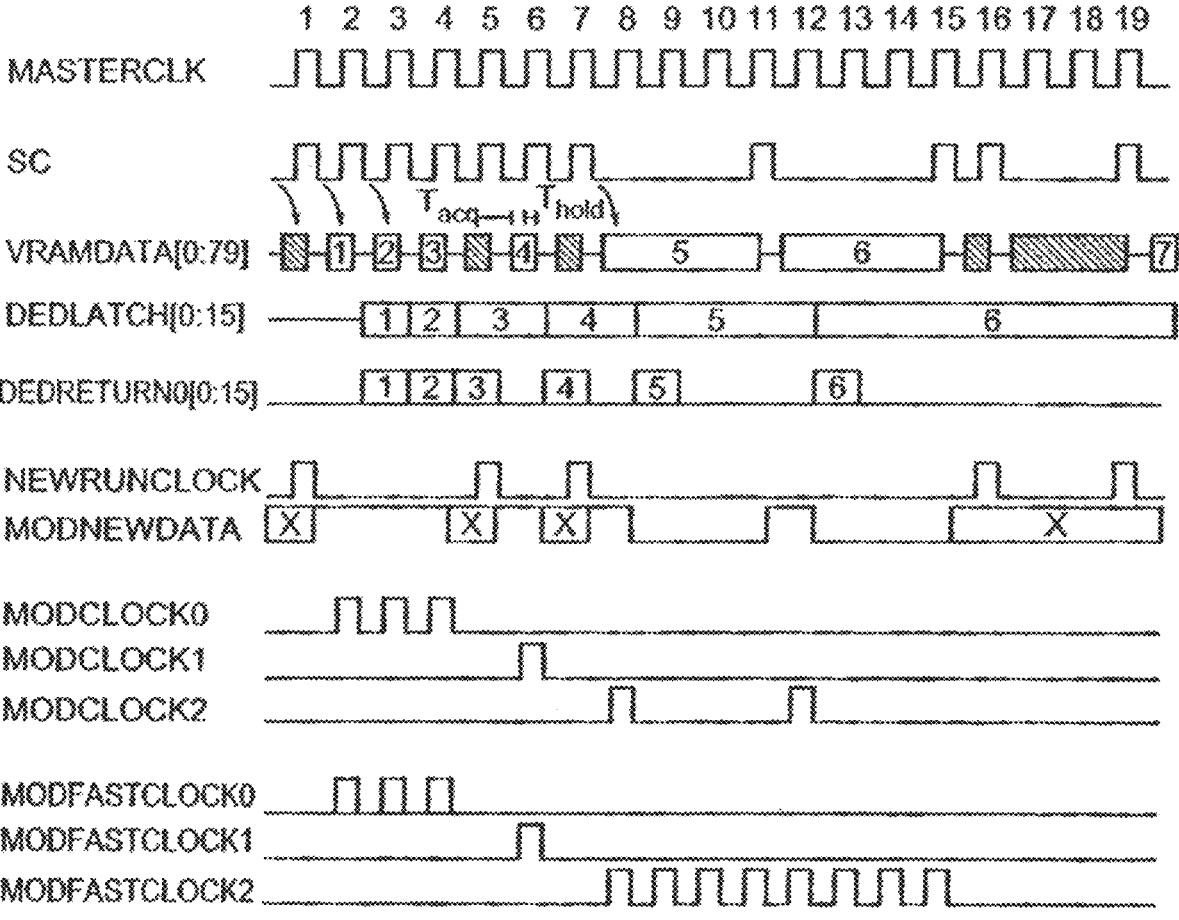
FIG. 11M schematically illustrates a timing diagram for the control of modules in the system.

Much of the timing depends on the speed of the runs of the module (shared/dedicated VRAM usage.) FIG. 11M shows typical timing for the different module interfacing modes for a typical program sequence.

As previously stated, VRAMDATA, the data from the loopback VRAM, control the execution. The diagonal shaded boxes denote header data used by the VRAM controller while the shaded boxes denote module data in FIG. 11M. The data in the four other VRAMs go to the modules. The data from the first VRAM is looped back into the system controller and then used for dedicated data supply for things like the TGC, feedback control, etc.

In clocks 1-4 in FIG. 11M a run of data at a rate 1/1 destined for module 0. The header is clocked out at clock 1. The pulse of NEWRUNCLOCK at clock 1 lets the modules know that the next clock will be the first in a run. They thus reset their internal run-related state if necessary. The data is clocked out during clocks 2, 3, and 4. Since the data is destined for module 0, the MODCLOCK0 is pulsed once per new data word. Module 0 should latch the data at VRAM-DATA on the rising edge of MODCLOCK0.

Note that the access and hold times of the VRAM (T.sub.acc and T.sub.hold in FIG. 11M) must be observed carefully. Since the access time of the VRAM is 15 ns-25 ns depending on the speed grade the hold time can be as low as 4 ns, this does not leave a lot of margin when operating at data no earlier than T.sub.clk-T.sub.acc before the rising edge of their module clock. (Any skew between SC and the MODCLOCK tightens this bound accordingly but due to the way the VRAM controller was designed to generate both signals as gated clocks from the same MASTER CLK the skew is minimal assuming that the loading conditions are not too dissimilar.) given a master clock frequency of 33

MHz and the fast VRAM, this gives 15 ns slack. Using the slower VRAMs gives 5 ns slack.

The modules accepting data at the full rate must additionally make sure that they do not latch the data more than T.sub.hold after the rising clock. This is because the same clock is used to retrieve the next words from the VRAM. Thus in general modules should make sure to delay the data inputs at least as much as they delay the clock inputs to effectively clock at or before the rising edge of their module clock. This second constraint does not exist when 1/2, 1/4, or 1/8 rate data is used.

Since the first example is of 1/1 rate data, the MODULE-FASTCLOCK0 signal follows the MODULECLOCK0 line. They will only differ when 1/2, 1/4, or 1/8 rate data is used.

Clocks 7-15 show a run of length 2 at rate 1/4 destined for Module 2. Thus new data will be clocked out of the VRAMs only once every 4.sup.th master clock. Here MODULE-FASTCLOCK2 will exhibit different behavior than MOD-ULECLOCK2. Again the NEWRUNCLOCK at clock 7 signals that a new run is beginning on the next clock cycle. During clock 7, the VRAM controller has latched the header data indicating that the next run is for module 2 at a rate of 1/4. Also during clock 7, the VRAM generates the module data that the module will use. At clock 8, a MODCLOCK2 occurs, telling module 2 to latch in and use the VRAM's data. Note that the data will present until the master clock before the next MODCLOCK2.

Although MODCLOCK2 is only clocked once per new data word, MODULEFASTCLOCK2 is clocked once per master clock for the duration of the run. This is useful for modules, such as the beamformer which may only need data at a lower rate but need to perform computation at the full rate. The MODNEWDATA signal can also be used by modules using the MODFASTCLOCK lines to determine on which of the fast clocks new data has been presented.

Clocks 16-18 show the result of a pause command. Here the NEWRUNCLOCK is sequenced as usual but no MOD-CLOCK or MODFASTCLOCK is generated.

As noted above, the particular embodiment was chosen based on a number of criteria, including simplicity of implementation using an FPGA. This motivated the use of VRAMs. An ASIC interface using more dense SDRAM requires at least some buffering, but this can be built into the controller, or alternatively, with the beamformer, T/R circuit or amplifier modules. In this way they receive bursts of data as opposed to the simple synchronous, continuous data that the above system supplies. The benefit is that SDRAMs are more dense and can provide data at higher rates, which reduces the parts count. Such a configuration is shown in FIG. 11K, for example, in which the 64 or 128 channel (1166.sub.I-1166.sub.J) system is configured on one or two printed circuit boards. In this two board system, the T/R circuit and the preamplifier/TGC circuit are fabricated in a single integrated circuit and are placed on one board with a CDP beamformer that is formed as a second integrated circuit. The beamformer control circuits can include the calculation of weighted inputs with processor 1167. The memory for this system is either a SDRAM or VRAM located on the second board along with the system controller and the digital communication control circuit.

Returning to FIG. 11F, the standard FireWire cable 1140C includes a plurality of FireWire signal lines 1142C and a FireWire power line 1144C. In order to provide the necessary voltages, the FireWire power line 1144C is fed to an inline DC-DC converter 1103C. The DC-DC converter 1103C generates the necessary voltages and provides them over a plurality of power lines 1146C. These new power lines 1146C are repackaged with the FireWire signal lines 1142C in a custom cable 1140'. In the probe housing 1103', the FireWire signal lines 1142C are connected to the FireWire chipset 1122B and the custom power lines 1146C are connected to a power distributor 1148D, which filters and distributes the various voltages over respective internal voltage lines 1148A, 1148B, 1148C. In addition, the power distributor 1148D may perform additional DC-DC conversions, as described in more detail below.

The transmit/receive control chip is needed to interface with the transducer array. In a transmit mode, the chip can provide delays to the high-voltage driving pulses applied to each of the selected transducer elements such that the transmitted pulses will be coherently summed on the image place at the required transmit focus point. In a receive mode, it provides connection of the reflected sound waves received by a selected element to its corresponding amplifier. The functions of a multi-channel transmit/receive chip can be separated into two parts: a core function which provide low-voltage transmit/receive control and a buffer function which level shifts the low-voltage transmit/receive control into high voltage and directly interfaces with the transducer array. The core function of the transmit/receive chip includes a global counter which broadcasts a master clock and bit values to each channel processor; a global memory which controls transmit frequency, pulse number, pulse sequence and transmit/receive select; a local comparator which provides delay selection for each channel. For example, for a 60 MHZ clock and a 10 bit global counter, it can provide each channel with up to 17.mu.s delay; a local frequency counter which provides programmable transmit frequency; a local pulse counter which provides different pulse sequences. For example, a 7-bit counter can provide programmable transmitted pulse lengths from one pulse up to 128 pulses; a locally programmable phase selector which provides sub-clock delay resolution. For example, for a 60 MHz master clock and a two-to-one phase selector provides 8 ns delay resolution.

While typically the period of the transmit-chip clock determines the delay resolution, a technique called programmable sub-clock delay resolution allows the delay resolution to be more precise than the clock period. With programmable sub-clock delay resolution, the output of the frequency counter is gated with a phase of the clock that is programmable on a per-channel basis. In the simplest form, a two-phase clock is used and the output of the frequency counter is either gated with the asserted or de-asserted clock. Alternatively, multiple skewed clocks can be used. One per channel can be selected and used to gate the coarse timing signal from the frequency counter.

As can be seen in FIG. 11G, a semiconductor process that can support both high-voltage and low-voltage operations is ideally matched for a single-chip solution to the transmit/receive chip described above. The core function of the transmit/receive chip can be implemented on low-voltage transistors to reduce power consumption. The level-shifting function can be implemented on high-voltage transistors to provide the necessary driving pulses to the transducer array. However, only selected semiconductor processes can make the integration of both high-voltage (buffer 1192) and low-voltage transistors (1194) on one chip 1190 possible. As a result, the high/low voltage process has been so far offered only with 0.8-to-lum-design rules. With these design rules, a 64-channel transmit/receive chip can easily be integrated on a single chip in less than 1 cm.sup.2 chip area.

As shown in FIG. 11H, the multi-chip set can be mounted in a single package to realize the transmit/receive control function. With multi-chip module approach, a 128-channel transmit/receive controller can easily be integrated on one package. In order to save power and silicon area, a multi-chip module 1195 can be used to implement a transmit/receive chip. For example, a deep-sub-micron process can be used to implement the core function 1196 of the module, and a separate process can be used to implement the buffer 1198 function.

FIG. 11I illustrates an alternate embodiment in which the transducer array 1110' is located in a separate probe housing 1141D connected to the interface housing 1104D by a cable 1112D. Such a system is also illustrated in connection with FIG. 12. Note that another embodiment involves a probe housing in which certain circuit elements such as the transmit/receive circuitry and/or the preamp/TGC circuitry is included with the transducer array while the beamformer, system control and memory circuits remain in the interface. The system in FIG. 11I provides for the use of standard probes and a beamformer interface that weighs less than 10 lbs and which can be connected to a standard personal computer. The interface 1104D has a volume of less than 1500 cm.sup.3 and a weight that is preferably less than 5 lbs.

Figure 11N:
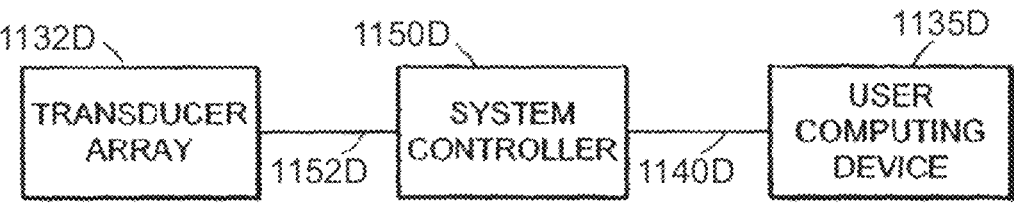
FIG. 11N shows a block diagram of an ultrasonic imaging system adapted for external application integration.

FIG. 11N shows a block diagram of another particular embodiment of an ultrasonic imaging system adapted for external application integration. Referring to FIG. 11N, the transducer array housing 1132D and associated circuitry are connected to a system controller 1150D via an ultrasound (US) interface 1152D. The system controller 1150D is connected to a host user computing device 1135D such as a PC via a standard interface 1140D which is a predetermined communication link, such as an IEEE 1394 interface, also known as FireWire. The US data therefore, is transmitted to a user computing device 1135D via the standard interface 1140D, relieving the need for specialized components to be employed in the user computing device. The user computing device 1135D therefore provides an ultrasonic application server which may be integrated with an external application, as will be described further below.

The ultrasonic application server running on the user computer device 1135D, therefore, receives the US data, and makes it available to be invoked by an external application for further processing. The external application may be either local, and therefore running on the user computer device 1135D, or remote, and accessing the ultrasonic application server remotely.

Figure 11O:
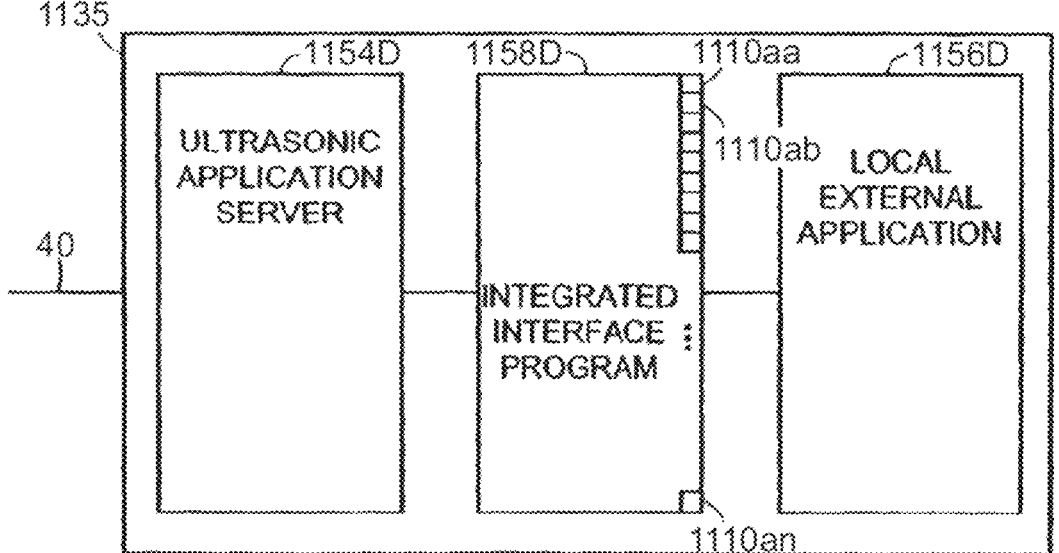
FIG. 11O shows an integrated interface program operable for use with a local external application.

FIG. 11O shows an integrated interface program operable for use with a local external application. Referring to FIG. 11O the ultrasonic server application 1154D is running on the user computing device 1135. A local external application 1156D is also running on the user computing device 1135, and transmits to and from the ultrasonic server application 1154D via an integrated interface program 1158D. The integrated interface program 1158D contains a series of predetermined entry points 1110aa . . . 1110an corresponding to operations which the ultrasonic application server 1154D may perform on behalf of the local external application 1156D. The local external application 1156D sends a command, which includes an instruction and optional parameters as defined by the predetermined entry points 1110aa-1110an. The local external application 1156D transmits the command to the ultrasonic server application 1154D by invoking the entry point 1110an in the integrated interface program which corresponds to intended operation. The entry point may be invoked by procedure or function call via a stack call, message transmission, object passing, or other suitable interprocess communication mechanism. In a particular embodiment, Windows® messages may be used.

The command is received by the ultrasonic server application 1154D via the desired entry point 1110an from the integrated interface program 1158D, and is processed. The ultrasonic server application 1154D executes a result corresponding to the desired function, and transmits the result back to the local external application 1156D via the integrated interface program 1158D, typically by similar inter-process communication mechanisms employed in transmitting the corresponding command. The operations performed by the ultrasonic application server may include the following as referenced in Table 15:

TABLE 15

| OPERATION | DESCRIPTION |
|---|---|
| Freeze Image | Freeze active ultrasound data image; used to capture still frames |
| Resume Live | Obtain realtime ultrasound image |
| Export Frame | Export a frame of ultrasound image data in a format as determined by the parameters |
| Application Status | Return a status code of a previous operation |
| Initialize | Initialize Ultrasonic Application Server to begin receiving commands from an external application |
| Exit Application | Disconnect external application from the Ultrasonic Application Server |

The result received by the local external application 1156D, therefore, may be employed and analyzed by any functions provided by the local external application. The local external application 1156D may be extended and modified to provide desired functions without modifying the ultrasonic application server 1154D or the integrated interface program 1158D. Further, additional entry points 1110aa . . . 1110n to other operations provided by the ultrasonic server application 1154D may require only modification of the integrated interface program 1158D. Further, multiple external applications may access the integrated interface program 1158D by computing the proper instructions and parameters of the commands as defined by the integrated interface program.

In particular embodiments, the local external application 1156D is operable to process 2 dimensional and 3 dimensional radiation therapy data, fetal image data, cardiac image data, and image guided surgery data. Such applications are employed in the medical field by operators such as surgeons to provide visual feedback about medical information. For example, fetal image data is used to view a fetus in utero. By employing multidimensional data to provide a visual image, conditions such as birth defects, treatable ailments, gender, size, and others can be determined. Similarly, radiation therapy data may be employed to simultaneously display information about the direction and intensity of radiation treatment, and a visual image of the treatment area. Such visual image data may also be employed in image guided surgery, to indicate the location of a surgical instrument. Such information is particularly useful in contexts such as brain surgery, where it may not be possible to expose the afflicted area.

Figure 11P:
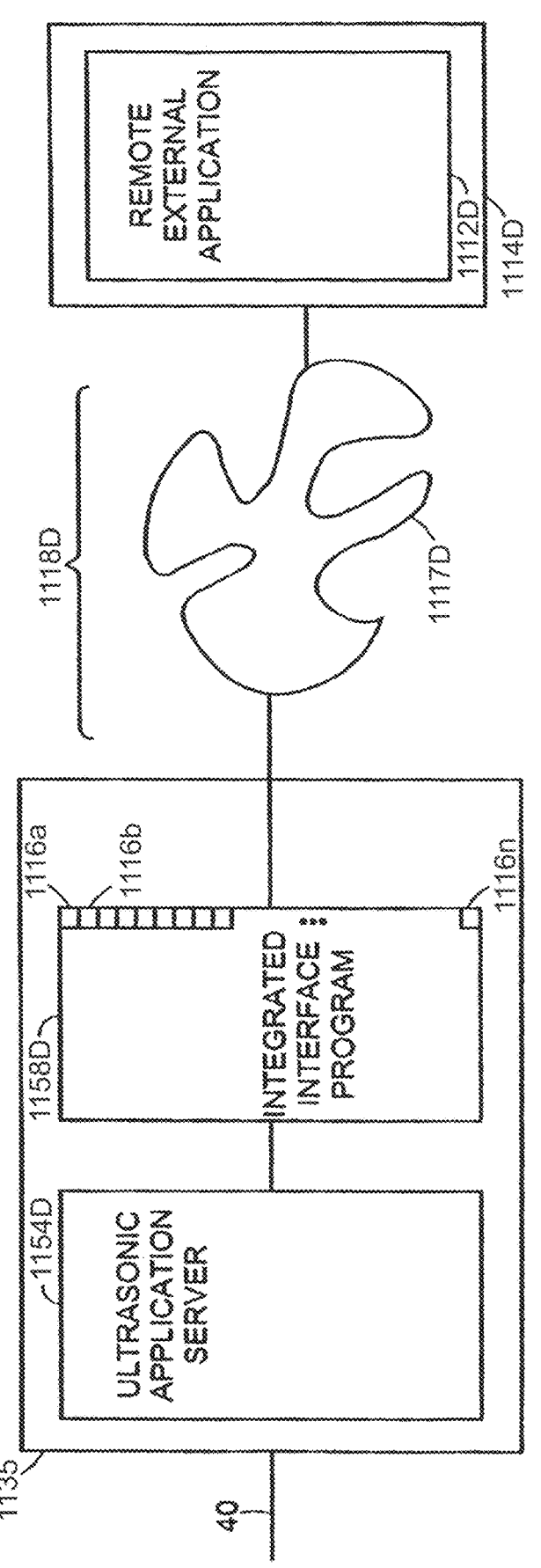
FIG. 11P show an integrated interface program operable for use with a remote external application.

FIG. 11P shows an integrated interface program 1158D operable for use with a remote external application 1112D. In such an embodiment, a remote external application 1112D is running on a remote computing device 1114D such as a PC, and is connected to the user computing device 1135 via a public access network 1117D such as the Internet via a communication link 1118D. The integrated interface program 1158D includes connection points 1116a . . . 1116n such as remote procedure call (RPC) points or other inter-node communication mechanism. In a particular embodiment the connection points are sockets in accordance with the TCP/IP protocol.

Similar to the local external application 1156D, the remote external application 1112D is operable to compute a command corresponding to an intended operation in the ultrasonic application server 1154D. The connection points 1116a . . . 1116n are generally operable to receive a command transmitted from the remote external application 1112D. The ultrasonic application server 1154D sends a result corresponding to the command, and transmits the result back to the remote external application 1112D via the integrated interface program 1158D by an inter-node communication mechanism such as that used to transmit the command. Further, the same integrated interface program 1158D could have both entry points 1110aa . . . 1110an, generally to be accessed by the local external application 1156D, and connection points 1116a . . . 1116n, generally accessible by the remote external application 1112D.

FIG. 12 depicts a schematic side view of a portion of a circuit board 1200 including a multi-chip module assembled in a vertically stacked configuration. Two or more layers of active electronic integrated circuit components are integrated vertically into a single circuit. The IC layers are oriented in spaced planes that extend substantially parallel to one another in a vertically stacked configuration. In FIG. 12, the circuit board includes an HDI substrate 1202 for supporting the multi-chip module. A first integrated circuit chip 1204 including, for example, a first beamformer device is coupled to the substrate 1202 using any suitable coupling mechanism, for example, epoxy application and curing. A first spacer layer 1206 is coupled to the surface of the first integrated circuit chip 1204 opposite to the substrate 1202 using, for example, epoxy application and curing. A second integrated circuit chip 1208 having, for example, a second beamforer device is coupled to the surface of the first spacer layer 1206 opposite to the first integrated circuit chip 1204 using, for example, epoxy application and curing. A metal frame 1210 is provided for mechanical and/or electrical connection among the integrated circuit chips. An exemplary metal frame 1210 may take the form of a leadframe. The first integrated circuit chip 1204 may be coupled to the metal frame 1210 using wiring 1212. The second integrated circuit chip 1208 may be coupled to the same metal frame 1210 using wiring 1214. A packaging 1216 is provided to encapsulate the multi-chip module assembly and to maintain the multiple integrated circuit chips in substantially parallel arrangement with respect to one another.

As illustrated in FIG. 12, the vertical three-dimensional stacking of the first integrated circuit chip 1204, the first spacer layer 1206 and the second integrated circuit chip 1208 provides high-density functionality on the circuit board while minimizing overall packaging size and footprint (as compared to an ultrasound engine circuit board that does not employ a vertically stacked multi-chip module). One of ordinary skill in the art will recognize that an exemplary multi-chip module is not limited to two stacked integrated circuit chips. Exemplary numbers of chips vertically integrated in a multi-chip module may include, but are not limited to, two, three, four, five, six, seven, eight, and the like.

In one embodiment of an ultrasound engine circuit board, a single multi-chip module as illustrated in FIG. 12 is provided. In other embodiments, a plurality of multi-chip modules is provided. In an exemplary embodiment, a plurality of multi-chip modules (for example, two multi-chip modules) may be stacked vertically on top of one another on a circuit board of an ultrasound engine to further minimize the packaging size and footprint of the circuit board.

In addition to the need for reducing the footprint, there is also a need for decreasing the overall package height in multi-chip modules. Exemplary embodiments may employ wafer thinning to sub-hundreds micron to reduce the package height in multi-chip modules.

Any suitable technique can be used to assemble a multi-chip module on a substrate. Exemplary assembly techniques include, but are not limited to, laminated MCM (MCM-L) in which the substrate is a multi-layer laminated printed circuit board, deposited MCM (MCM-D) in which the multi-chip modules are deposited on the base substrate using thin film technology, and ceramic substrate MCM (MCM-C) in which several conductive layers are deposited on a ceramic substrate and embedded in glass layers that layers are co-fired at high temperatures (HTCC) or low temperatures (LTCC).

Figure 13:
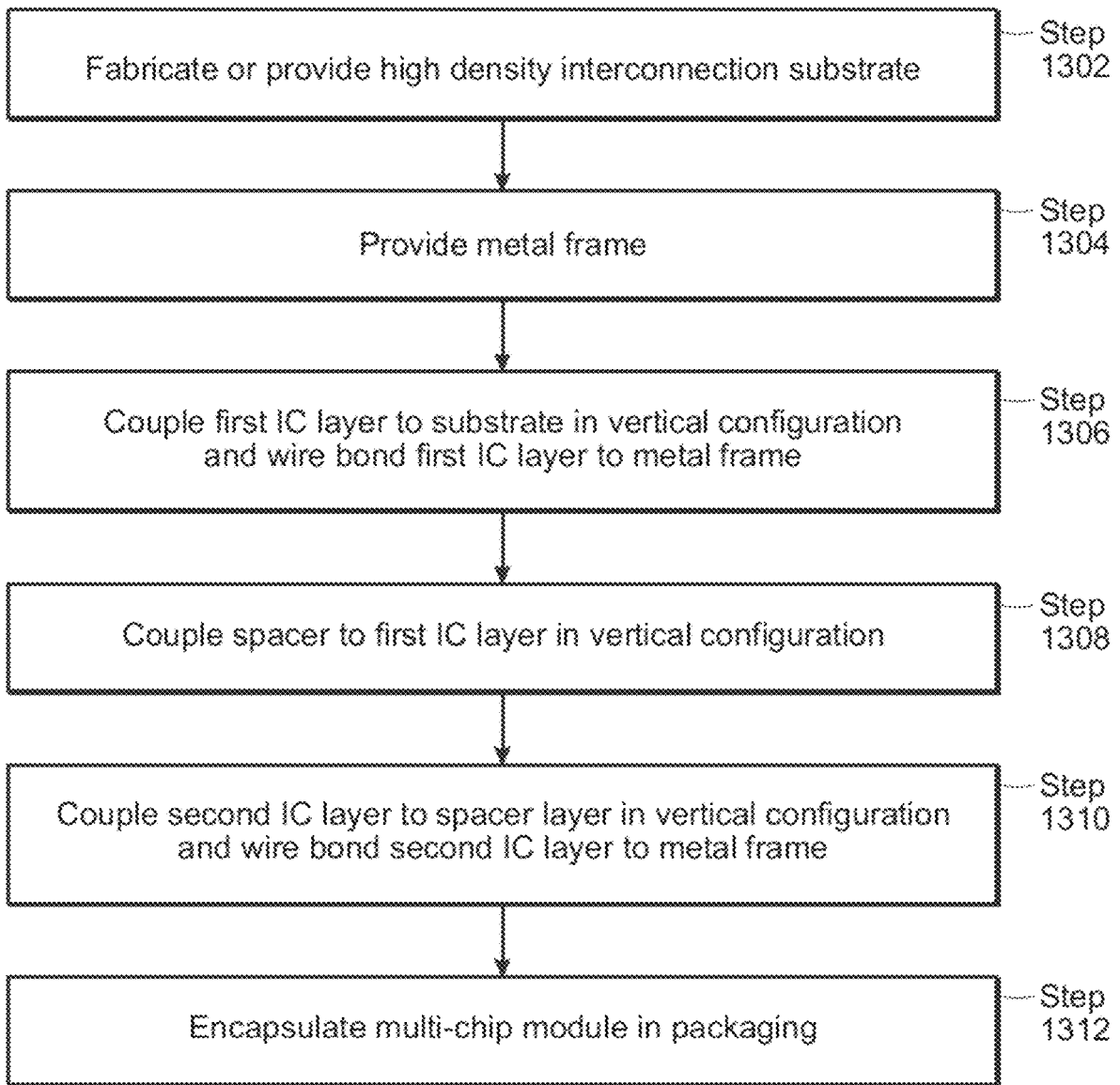
FIG. 13 is a flowchart of an exemplary method for fabricating a circuit board including a multi-chip module assembled in a vertically stacked configuration.

FIG. 13 is a flowchart of an exemplary method for fabricating a circuit board including a multi-chip module assembled in a vertically stacked configuration. In step 1302, a HDI substrate is fabricated or provided. In step 1304, a metal frame (e.g., leadframe) is provided. In step 1306, a first IC layer is coupled or bonded to the substrate using, for example, epoxy application and curing. The first IC layer is wire bonded to the metal frame. In step 1308, a spacer layer is coupled to the first IC layer using, for example, epoxy application and curing, so that the layers are stacked vertically and extend substantially parallel to each other. In step 1310, a second IC layer is coupled to the spacer layer using, for example, epoxy application and curing, so that all of the layers are stacked vertically and extend substantially parallel to one another. The second IC layer is wire bonded to the metal frame. In step 1312, a packaging is used to encapsulate the multi-chip module assembly.

Exemplary chip layers in a multi-chip module may be coupled to each other using any suitable technique. For example, in the embodiment illustrated in FIG. 12, spacer layers may be provided between chip layers to spacedly separate the chip layers. Passive silicon layers, die attach paste layers and/or die attach film layers may be used as the spacer layers. Exemplary spacer techniques that may be used in fabricating a multi-chip module is further described in Toh C H et al., "Die Attach Adhesives for 3D Same-Sized Dies Stacked Packages," the 58th Electronic Components and Technology Conference (ECTC2008), pp. 1538-43, Florida, US (27-30 May 2008), the entire contents of which are expressly incorporated herein by reference.

Important requirements for the die attach (DA) paste or film is excellent adhesion to the passivation materials of adjacent dies. Also, a uniform bond-link thickness (BLT) is required for a large die application. In addition, high cohesive strength at high temperatures and low moisture absorption are preferred for reliability.

Figure 14A:
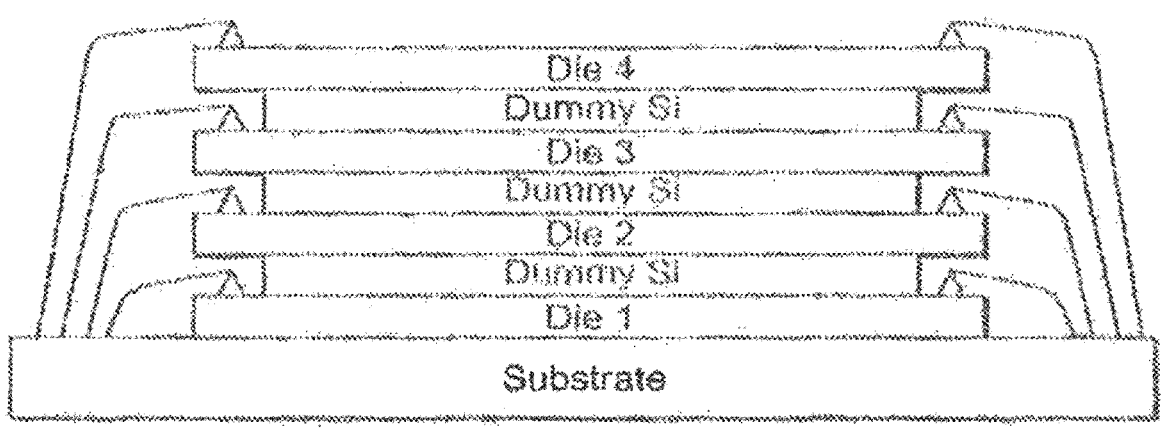
FIG. 14A is a schematic side view of a multi-chip module including four vertically stacked dies in which the dies are spacedly separated from one another by passive silicon layers with a 2-in-1 dicing die attach film (D-DAF)
Figure 14B:
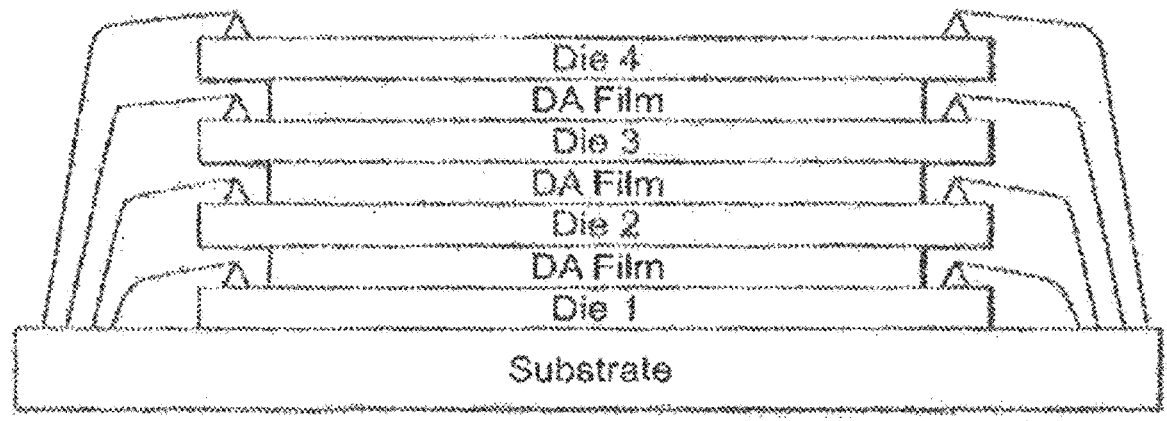
FIG. 14B is a schematic side view of a multi-chip module including four vertically stacked dies in which the dies are spacedly separated from one another by DA film-based adhesives acting as die-to-die spacers.
Figure 14C:
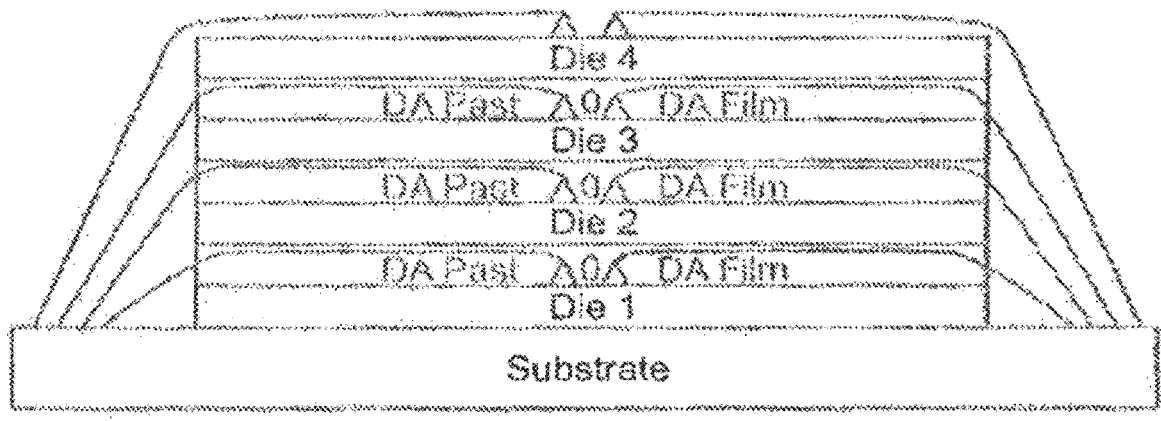
FIG. 14C is a schematic side view of a multi-chip module including four vertically stacked dies in which the dies are spacedly separated from one another by DA paste or film-based adhesives acting as die-to-die spacers.

FIGS. 14A-14C are schematic side views of exemplary multi-chip modules, including vertically stacked dies, that may be used in accordance with exemplary embodiments. Both peripheral and center pads wire bond (WB) packages are illustrated and may be used in wire bonding exemplary chip layers in a multi-chip module. FIG. 14A is a schematic side view of a multi-chip module including four vertically stacked dies in which the dies are spacedly separated from one another by passive silicon layers with a 2-in-1 dicing die attach film (D-DAF). FIG. 14B is a schematic side view of a multi-chip module including four vertically stacked dies in which the dies are spacedly separated from one another by DA film-based adhesives acting as die-to-die spacers. FIG. 14C is a schematic side view of a multi-chip module including four vertically stacked dies in which the dies are spacedly separated from one another by DA paste or film-based adhesives acting as die-to-die spacers. The DA paste or film-based adhesives may have wire penetrating capability in some exemplary embodiments. In the exemplary multi-chip module of FIG. 14C, film-over wire (FOW) is used to allow long wire bonding and center bond pads stacked die packages. FOW employs a die-attach film with wire penetrating capability that allows the same or similar-sized wire-bonded dies to be stacked directly on top of one another without passive silicon spacers. This solves the problem of stacking same or similar-sized dies directly on top of each other, which otherwise poses a challenge as there is no or insufficient clearance for the bond wires of the lower dies.

The DA material illustrated in FIGS. 14B and 14C preferably maintain a bond-line thickness (BLT) with little to no voiding and bleed out through the assembly process. Upon assembly, the DA materials sandwiched between the dies maintain an excellent adhesion to the dies. The material properties of the DA materials are tailored to maintain high cohesive strength for high temperature reliability stressing without bulk fracture. The material properties of the DA materials are tailored to also minimize or preferably eliminate moisture accumulation that may cause package reliability failures (e.g., popcorning whereby interfacial or bulk fractures occur as a result of pressure build-up from moisture in the package).

Figure 15:
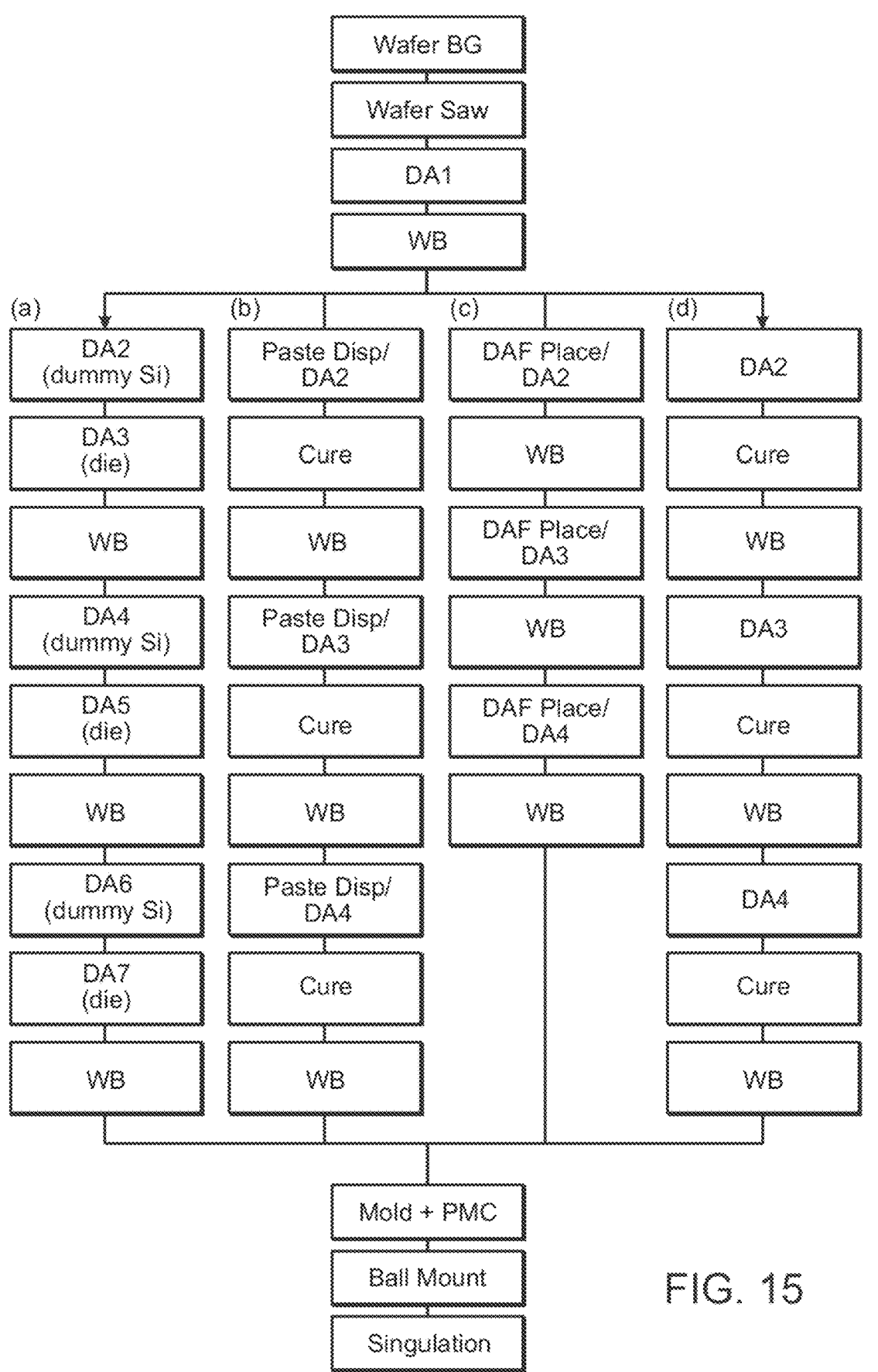
FIG. 15 is a flowchart of another exemplary method of die-to-die stacking using (a) passive silicon layers with a 2-in-1 dicing die attach film (D-DAF), (b) DA paste, (c) thick DA-film, and (d) film-over wire (FOW) including a 2-in-1 D-DAF.

FIG. 15 is a flowchart of certain exemplary methods of die-to-die stacking using (a) passive silicon layers with a 2-in-1 dicing die attach film (D-DAF), (b) DA paste, (c) thick DA-film, and (d) film-over wire (FOW) that employs a die-attach film with wire penetrating capability that allows the same or similar-sized wire-bonded dies to be stacked directly on top of one another without passive silicon spacers. Each method performs backgrinding of wafers to reduce the wafer thickness to enable stacking and high density packaging of integrated circuits. The wafers are sawed to separate the individual dies. A first die is bonded to a substrate of a multi-chip module using, for example, epoxy application and curing in an oven. Wire bonding is used to couple the first die to a metal frame.

In method (a), a first passive silicon layer is bonded to the first die in a stacked manner using a dicing die-attach film (D-DAF). A second die is bonded to the first passive layer in a stacked manner using D-DAF. Wire bonding is used to couple the second die to the metal frame. A second passive silicon layer is bonded to the second die in a stacked manner using D-DAF. A third die is bonded to the second passive layer in a stacked manner using D-DAF. Wire bonding is used to couple the third die to the metal frame. A third passive silicon layer is bonded to the third die in a stacked manner using D-DAF. A fourth die is bonded to the third passive layer in a stacked manner using D-DAF. Wire bonding is used to couple the fourth die to the metal frame.

In method (b), die attach (DA) paste dispensing and curing is repeated for multi-thin die stack application. DA paste is dispensed onto a first die, and a second die is provided on the DA paste and cured to the first die. Wire bonding is used to couple the second die to the metal frame. DA paste is dispensed onto the second die, and a third die is provided on the DA paste and cured to the second die. Wire bonding is used to couple the third die to the metal frame. DA paste is dispensed onto the third die, and a fourth die is provided on the DA paste and cured to the third die. Wire bonding is used to couple the fourth die to the metal frame.

In method (c), die attach films (DAF) are cut and pressed to a bottom die and a top die is then placed and thermal compressed onto the DAF. For example, a DAF is pressed to the first die and a second die is thermal compressed onto the DAF. Wire bonding is used to couple the second die to the metal frame. Similarly, a DAF is pressed to the second die and a third die is thermal compressed onto the DAF. Wire bonding is used to couple the third die to the metal frame. A DAF is pressed to the third die and a fourth die is thermal compressed onto the DAF. Wire bonding is used to couple the fourth die to the metal frame.

In method (d), film-over wire (FOW) employs a die-attach film with wire penetrating capability that allows the same or similar-sized wire-bonded dies to be stacked directly on top of one another without passive silicon spacers. A second die is bonded and cured to the first die in a stacked manner. Film-over wire bonding is used to couple the second die to the metal frame. A third die is bonded and cured to the first die in a stacked manner. Film-over wire bonding is used to couple the third die to the metal frame. A fourth die is bonded and cured to the first die in a stacked manner. Film-over wire bonding is used to couple the fourth die to the metal frame.

After the above-described steps are completed, in each method (a)-(d), wafer molding and post-mold curing (PMC) are performed. Subsequently, ball mount and singulation are performed.

Further details on the above-described die attachment techniques are provided in Toh C H et al., "Die Attach Adhesives for 3D Same-Sized Dies Stacked Packages," the 58th Electronic Components and Technology Conference (ECTC2008), pp. 1538-43, Florida, US (27-30 May 2008), the entire contents of which are expressly incorporated herein by reference.

FIG. 16 is a schematic side view of a multi-chip module 1600 including a TR chip 1602, an amplifier chip 1604 and a beamformer chip 1606 vertically integrated in a vertically stacked configuration on a substrate 1614. Any suitable technique illustrated in FIGS. 12-15 may be used to fabricate the multi-chip module. One of ordinary skill in the art will recognize that the particular order in which the chips are stacked may be different in other embodiments. First and second spacer layers 1608, 1610 are provided to spacedly separate the chips 1602, 1604, 1606. Each chip is coupled to a metal frame (e.g., a leadframe) 1612. In certain exemplary embodiments, heat transfer and heat sink mechanisms may be provided in the multi-chip module to sustain high temperature reliability stressing without bulk failure. Other components of FIG. 16 are described with reference to FIGS. 12 and 14.

In this exemplary embodiment, each multi-chip module may handle the complete transmit, receive, TGC amplification and beam forming operations for a large number of channels, for example, 32 channels. By vertically integrating the three silicon chips into a single multi-chip module, the space and footprint required for the printed circuit board is further reduced. A plurality of multi-chip modules may be provided on a single ultrasound engine circuit board to further increase the number of channels while minimizing the packaging size and footprint. For example, a 128 channel ultrasound engine circuit board 108 can be fabricated within exemplary planar dimensions of about 10 cm×about 10 cm, which is a significant improvement of the space requirements of conventional ultrasound circuits. A single circuit board of an ultrasound engine including one or more multi-chip modules may have 16 to 128 channels in preferred embodiments. In certain embodiments, a single circuit board of an ultrasound engine including one or more multi-chip modules may have 16, 32, 64, 128 channels, and the like.

Figure 17:
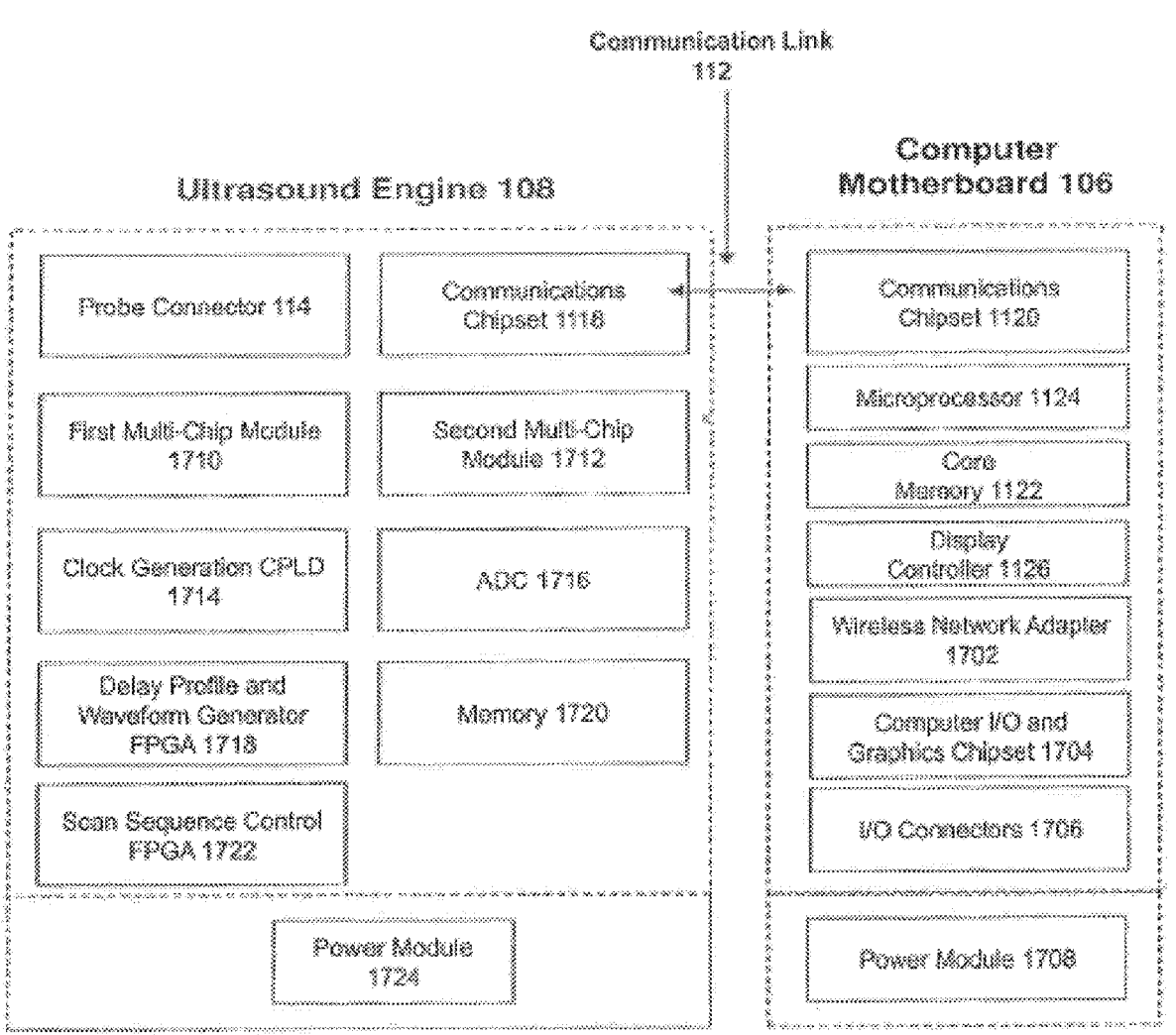
FIG. 17 is a detailed schematic block diagram of an exemplary embodiment of an ultrasound engine (i.e., the front-end ultrasound specific circuitry) and an exemplary embodiment of a computer motherboard (i.e., the host computer) provided as a single board complete ultrasound system.

FIG. 17 is a detailed schematic block diagram of an exemplary embodiment of the ultrasound engine 108 (i.e., the front-end ultrasound specific circuitry) and an exemplary embodiment of the computer motherboard 106 (i.e., the host computer) provided as a single board complete ultrasound system. An exemplary single board ultrasound system as illustrated in FIG. 17 may have exemplary planar dimensions of about 25 cm×about 18 cm, although other dimensions are possible. The single board complete ultrasound system of FIG. 17 may be implemented in the ultrasound device illustrated in FIGS. 1, 2A, 2B, and 9A, and may be used to perform the operations depicted in FIGS. 3A-8C, 9B, and 10.

The ultrasound engine 108 includes a probe connector 114 to facilitate the connection of at least one ultrasound probe/transducer. In the ultrasound engine 108, a TR module, an amplifier module and a beamformer module may be vertically stacked to form a multi-chip module as shown in FIG. 16, thereby minimizing the overall packaging size and footprint of the ultrasound engine 108. The ultrasound engine 108 may include a first multi-chip module 1710 and a second multi-chip module 1712, each including a TR chip, an ultrasound pulser and receiver, an amplifier chip including a time-gain control amplifier, and a sample-data beamformer chip vertically integrated in a stacked configuration as shown in FIG. 16. The first and second multi-chip modules 1710, 1712 may be stacked vertically on top of each other to further minimize the area required on the circuit board. Alternatively, the first and second multi-chip modules 1710, 1712 may be disposed horizontally on the circuit board. In an exemplary embodiment, the TR chip, the amplifier chip and the beamformer chip is each a 32-channel chip, and each multi-chip module 1710, 1712 has 32 channels. One of ordinary skill in the art will recognize that exemplary ultrasound engines 108 may include, but are not limited to, one, two, three, four, five, six, seven, eight multi-chip modules.

The ASICs and the multi-chip module configuration enable a 128-channel complete ultrasound system to be implemented on a small single board in a size of a tablet computer format. An exemplary 128-channel ultrasound engine 108, for example, can be accommodated within exemplary planar dimensions of about 10 cm×about 10 cm, which is a significant improvement of the space requirements of conventional ultrasound circuits. An exemplary 128-channel ultrasound engine 108 can also be accommodated within an exemplary area of about 100 cm².

The ultrasound engine 108 also includes a clock generation complex programmable logic device (CPLD) 1714 for generating timing clocks for performing an ultrasound scan using the transducer array. The ultrasound engine 108 includes an analog-to-digital converter (ADC) 1716 for converting analog ultrasound signals received from the transducer array to digital RF formed beams. The ultrasound engine 108 also includes one or more delay profile and waveform generator field programmable gate arrays (FPGA) 1718 for managing the receive delay profiles and generating the transmit waveforms. The ultrasound engine 108 includes a memory 1720 for storing the delay profiles for ultrasound scanning. An exemplary memory 1720 may be a single DDR3 memory chip. The ultrasound engine 108 includes a scan sequence control field programmable gate array (FPGA) 1722 configured to manage the ultrasound scan sequence, transmit/receiving timing, storing and fetching of profiles to/from the memory 1720, and buffering and moving of digital RF data streams to the computer motherboard 106 via a high-speed serial interface 112. The high-speed serial interface 112 may include Fire Wire or other serial or parallel bus interface between the computer motherboard 106 and the ultrasound engine 108. The ultrasound engine 108 includes a communications chipset 1118 (e.g., a Fire Wire chipset) to establish and maintain the communications link 112.

A power module 1724 is provided to supply power to the ultrasound engine 108, manage a battery charging environment and perform power management operations. The power module 1724 may generate regulated, low noise power for the ultrasound circuitry and may generate high voltages for the ultrasound transmit pulser in the TR module.

The computer motherboard 106 includes a core computer-readable memory 1122 for storing data and/or computer-executable instructions for performing ultrasound imaging operations. The memory 1122 forms the main memory for the computer and, in an exemplary embodiment, may store about 4 Gb of DDR3 memory. The memory 1122 may include a solid state hard drive (SSD) for storing an operating system, computer-executable instructions, programs and image data. An exemplary SSD may have a capacity of about 128 Gb.

The computer motherboard 106 also includes a microprocessor 1124 for executing computer-executable instructions stored on the core computer-readable memory 1122 for performing ultrasound imaging processing operations. Exemplary operations include, but are not limited to, down conversion, scan conversion, Doppler processing, Color Flow processing, Power Doppler processing, Spectral Doppler processing, and post signal processing. An exemplary microprocessor 1124 may be an off-the-shelf commercial computer processor, such as an Intel Core-i5 processor. Another exemplary microprocessor 1124 may be a digital signal processor (DSP) based processor, such as DaVinci™ processors from Texas Instruments.

The computer motherboard 106 includes an input/output (I/O) and graphics chipset 1704 which includes a co-processor configured to control I/O and graphic peripherals such as USB ports, video display ports and the like. The computer motherboard 106 includes a wireless network adapter 1702 configured to provide a wireless network connection. An exemplary adapter 1702 supports 802.11g and 802.11n standards. The computer motherboard 106 includes a display controller 1126 configured to interface the computer motherboard 106 to the display 104. The computer motherboard 106 includes a communications chipset 1120 (e.g., a Fire Wire chipset or interface) configured to provide a fast data communication between the computer motherboard 106 and the ultrasound engine 108. An exemplary communications chipset 1120 may be an IEEE 1394b 800 Mbit/sec interface. Other serial or parallel interfaces 1706 may alternatively be provided, such as USB3, Thunder-Bolt, PCIe, and the like. A power module 1708 is provided to supply power to the computer motherboard 106, manage a battery charging environment and perform power management operations.

An exemplary computer motherboard 106 may be accommodated within exemplary planar dimensions of about 12 cm×about 10 cm. An exemplary computer motherboard 106 can be accommodated within an exemplary area of about 120 cm².

Figure 18:
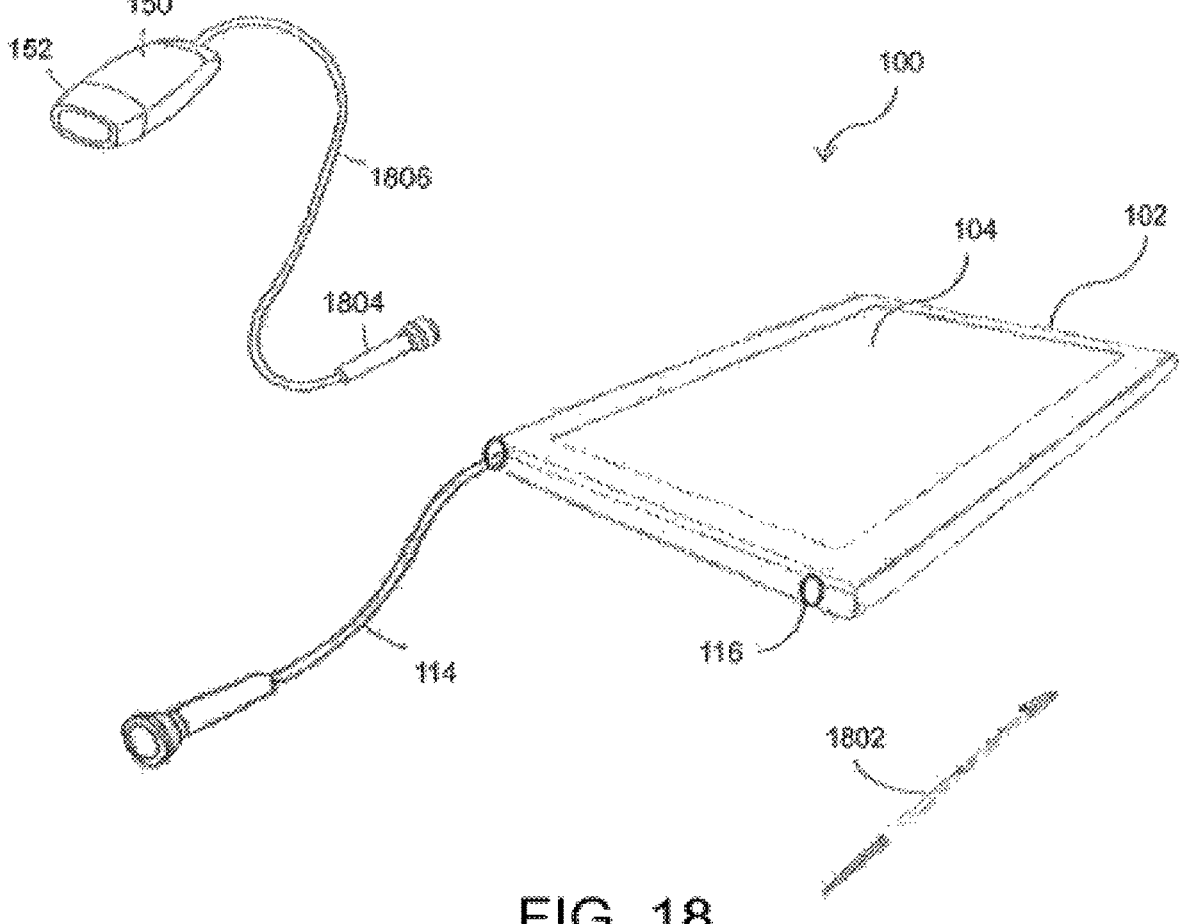
FIG. 18 is a perspective view of an exemplary portable ultrasound system provided in accordance with exemplary embodiments.

FIG. 18 is a perspective view of an exemplary portable ultrasound system 100 provided in accordance with exemplary embodiments. The system 100 includes a housing 102 that is in a tablet form factor as illustrated in FIG. 18, but that may be in any other suitable form factor. An exemplary housing 102 may have a thickness below 2 cm and preferably between 0.5 and 1.5 cm. A front panel of the housing 102 includes a multi-touch LCD touch screen display 104 that is configured to recognize and distinguish one or more multiple and/or simultaneous touches on a surface of the touch screen display 104. The surface of the display 104 may be touched using one or more of a user's fingers, a user's hand or an optional stylus 1802. The housing 102 includes one or more I/O port connectors 116 which may include, but are not limited to, one or more USB connectors, one or more SD cards, one or more network mini display ports, and a DC power input.

The housing 102 includes or is coupled to a probe connector 114 to facilitate connection of at least one ultrasound probe/transducer 150. The ultrasound probe 150 includes a transducer housing including one or more transducer arrays 152. The ultrasound probe 150 is couplable to the probe connector 114 using a housing connector 1804 provided along a flexible cable 1806. One of ordinary skill in the art will recognize that the ultrasound probe 150 may be coupled to the housing 102 using any other suitable mechanism, for example, an interface housing that includes circuitry for performing ultrasound-specific operations like beamforming. Other exemplary embodiments of ultrasound systems are described in further detail in WO 03/079038 A2, filed Mar. 11, 2003, titled "Ultrasound Probe with Integrated Electronics," the entire contents of which is expressly incorporated herein by reference.

Figure 19:
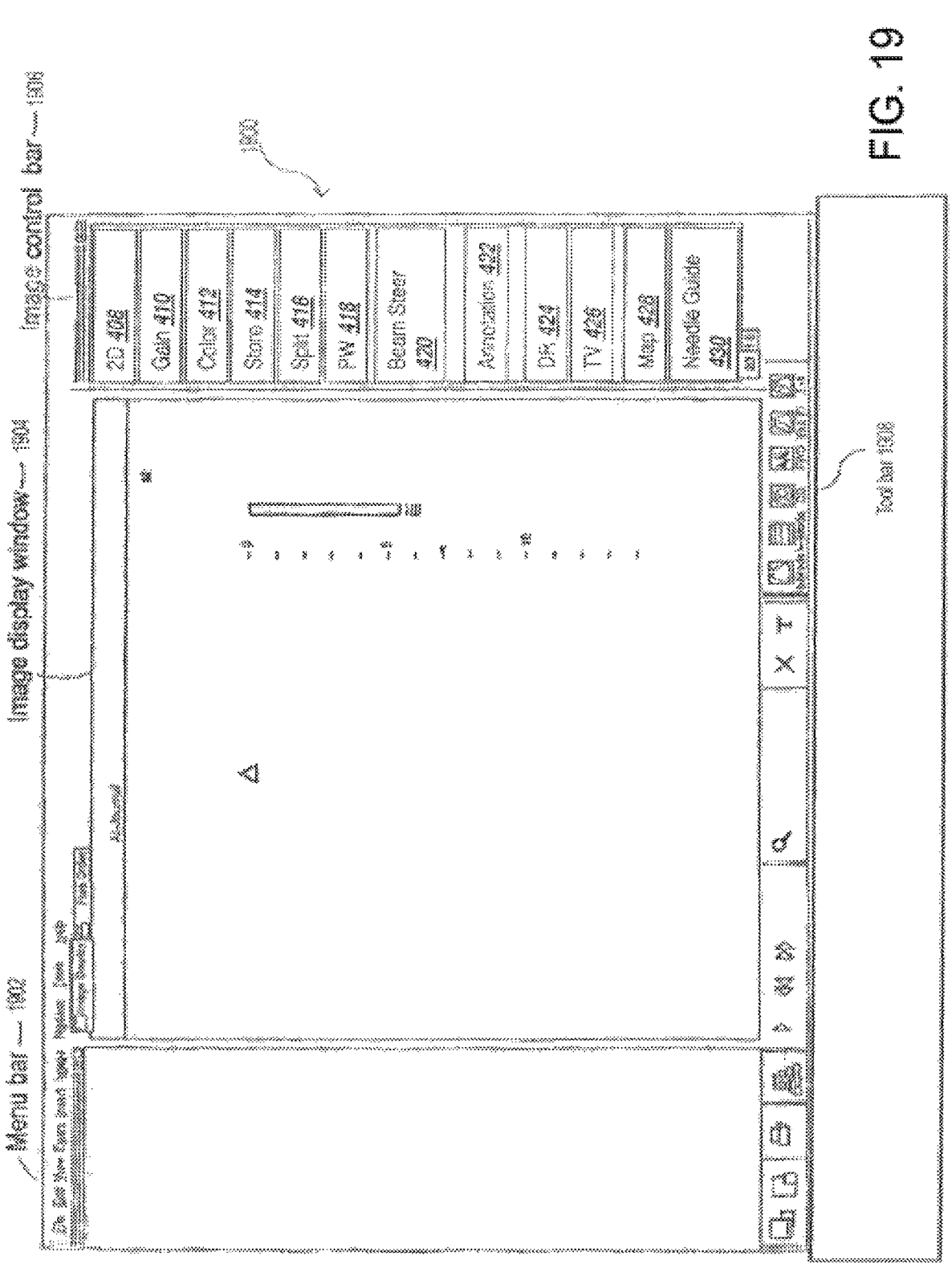
FIG. 19 illustrates an exemplary view of a main graphical user interface (GUI) rendered on a touch screen display of the exemplary portable ultrasound system of FIG. 18.

FIG. 19 illustrates an exemplary view of a main graphical user interface (GUI) 1900 rendered on the touch screen display 104 of the portable ultrasound system 100 of FIG. 18. The main GUI 1900 may be displayed when the ultrasound system 100 is started. To assist a user in navigating the main GUI 1900, the GUI may be considered as including four exemplary work areas: a menu bar 1902, an image display window 1904, an image control bar 1906, and a tool bar 1908. Additional GUI components may be provided on the main GUI 1900 to, for example, enable a user to close, resize and exit the GUI and/or windows in the GUI.

The menu bar 1902 enables a user to select ultrasound data, images and/or videos for display in the image display window 1904. The menu bar 1902 may include, for example, GUI components for selecting one or more files in a patient folder directory and an image folder directory. The image display window 1904 displays ultrasound data, images and/or videos and may, optionally, provide patient information. The tool bar 1908 provides functionalities associated with an image or video display including, but not limited to, a save button for saving the current image and/or video to a file, a save Loop button that saves a maximum allowed number of previous frames as a Cine loop, a print button for printing the current image, a freeze image button for freezing an image, a playback toolbar for controlling aspects of playback of a Cine loop, and the like. Exemplary GUI functionalities that may be provided in the main GUI 1900 are described in further detail in WO 03/079038 A2, filed Mar. 11, 2003, titled "Ultrasound Probe with Integrated Electronics," the entire contents of which are expressly incorporated herein by reference.

The image control bar 1906 includes touch controls that may be operated by touch and touch gestures applied by a user directly to the surface of the display 104. Exemplary touch controls may include, but are not limited to, a 2D touch control 408, a gain touch control 410, a color touch control 412, a storage touch control 414, a split touch control 416, a PW imaging touch control 418, a beamsteering touch control 20, an annotation touch control 422, a dynamic range operations touch control 424, a Teravision™ touch control 426, a map operations touch control 428, and a needle guide touch control 428. These exemplary touch controls are described in further detail in connection with FIGS. 4A-4C.

Figure 20:
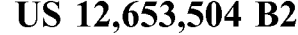
FIG. 20 is a top view of the medical ultrasound imaging equipment.

FIG. 20 depicts an illustrative embodiment of exemplary medical ultrasound imaging equipment 2000, implemented in the form factor of a tablet in accordance with the invention. The table may have the dimensions of 12.5"× 1.25"×8.75" or 31.7 cm×3.175 cm×22.22 cm but it may also be in any other suitable form factor having a volume of less than 2500 cm$^3$ and a weight of less than 8 lbs. As shown in FIG. 20, the medical ultrasound imaging equipment 2000, includes a housing 2030, a touch screen display 2010, wherein ultrasound images 2010, and ultra sound data 2040, can be displayed and ultrasound controls 2020, are configured to be controlled by a touchscreen display 2010. The housing 2030, may have a front panel 2060 and a rear panel 2070. The touchscreen display 2010, forms the front panel 2060, and includes a multi-touch LCD touch screen that can recognize and distinguish one or more multiple and or simultaneous touches of the user on the touchscreen display 2010. The touchscreen display 2010, may have a capacitive multi-touch and AVAH LCD screen. For example, the capacitive multi-touch and AVAH LCD screen may enable a user to view the image from multi angles without losing resolution. In another embodiment, the user may utilize a stylus for data input on the touch screen.

Capacitive touchscreen module comprises an insulator for example glass, coated with a transparent conductor, such as indium tin oxide. The manufacturing process may include a bonding process among glass, x-sensor film, y-sensor film and a liquid crystal material. The tablet is configured to allow a user to preform multi-touch gestures such as pinching and stretching while wearing dry or a wet glove. The surface of the screen registers the electrical conductor making contact with the screen. The contact distorts the screens electrostatic field resulting in measureable changes in capacitance. A processor then interprets the change in the electrostatic field. Increasing levels of responsiveness are enabled by reducing the layers and by producing touch screens with "in-cell" technology. "In-cell" technology eliminates layers by placing the capacitors inside the display. Applying "in-cell" technology reduces the visible distance between the user's finger and the touchscreen target, thereby creating a more directive contact with the content displayed and enabling taps and gestures to have an increase in responsiveness.

Figure 21:
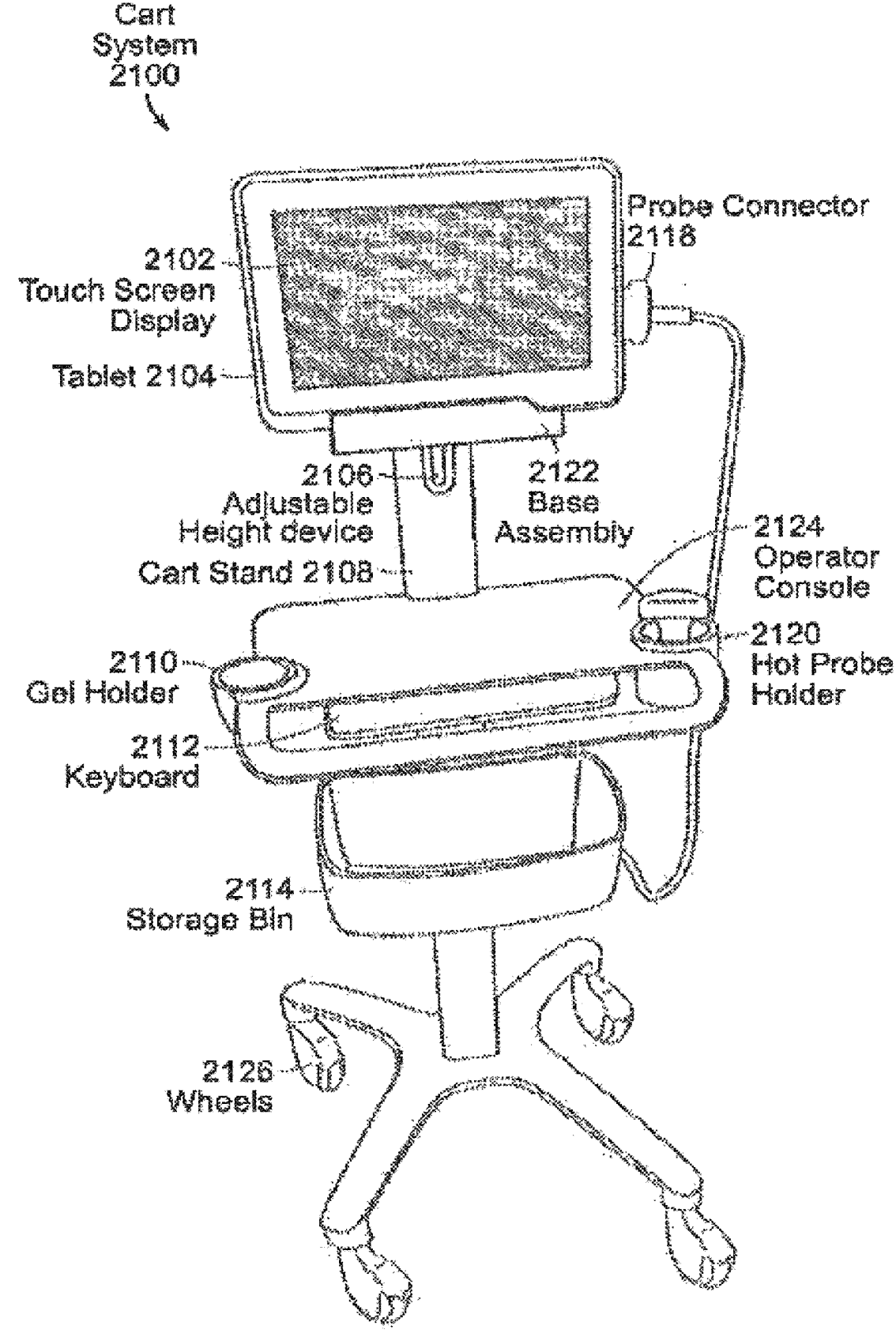
FIG. 21 illustrates a preferred cart system for a tablet ultrasound system in accordance with preferred embodiment of the invention.

FIG. 21 illustrates a preferred cart system for a modular ultrasound imaging system in accordance with the invention. The cart system 2100, uses a base assembly 2122 including a docking bay that receives the tablet. The cart configuration 2100, is configured to dock tablet 2104, including a touch screen display 2102, to a cart 2108, which can include a full operator console 2124. After the tablet 2104, is docked to the cart stand 2108, the system forms a full feature roll about system. The full feature roll about system may include, an adjustable height device 2106, a gel holder 2110, a storage bin 2114, a plurality of wheels 2116, a hot probe holder 2120, and the operator console 2124. The control devices may include a keyboard 2112 on the operator console 2124, that may also have other peripherals added such as a printer or a video interface or other control devices.

Figure 22:
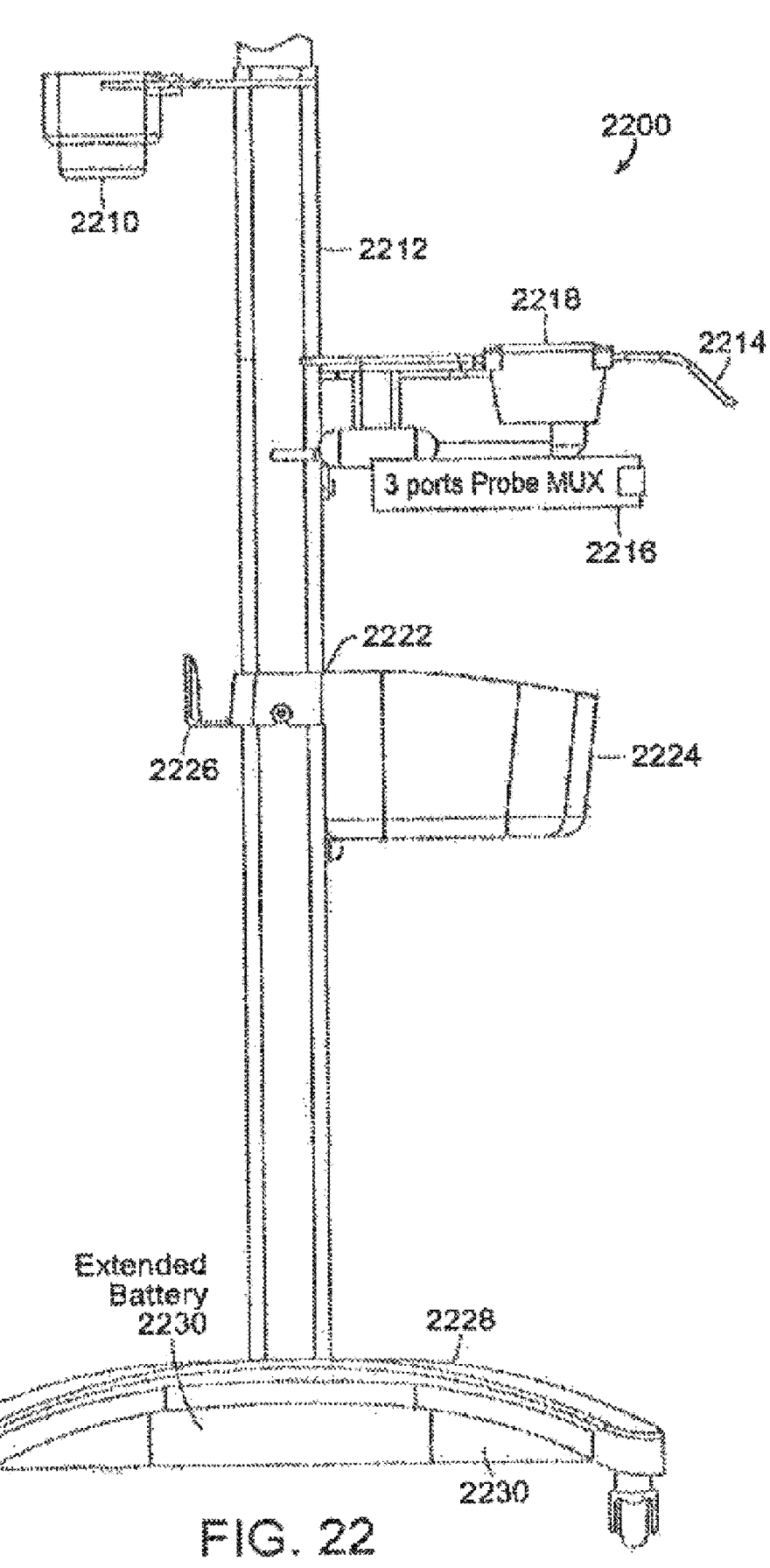
FIG. 22 illustrates a preferred cart system for a modular ultrasound imaging system in accordance with preferred embodiments of the invention.

FIG. 22 illustrates a preferred cart system 2200, for use in embodiments with a modular ultrasound imaging system in accordance with the invention. The cart system 2200, may be configured with a vertical support member 2212, coupled to a horizontal support member 2028. An auxiliary device connector 2218, having a position for auxiliary device attachment 2214, may be configured to connect to the vertical support member 2212. A 3 port Probe MUX connection device 2216, may also be configured to connect to the tablet. A storage bin 2224 can be configured to attach by a storage bin attachment mechanism 2222, to vertical support member 2212. The cart system 2200 may also include a cord management system 2226, configured to attach to the vertical support member. The cart system 2200 includes the vertical support member 2212 mounted on a base 2228 having wheels 2232 and a battery 2230 that provides power for extended operation of the tablet. The assembly can also include an accessory holder 2224 mounted with height adjustment device 2226. Holders 2210, 2218 can be mounted on beam 2212 or on console panel 2214. The 3 port Probe MUX connection device 2216 connects to the tablet to provide simultaneous connection of several transducer probes which the user can select in sequence with the displayed virtual switch.

Figure 23:
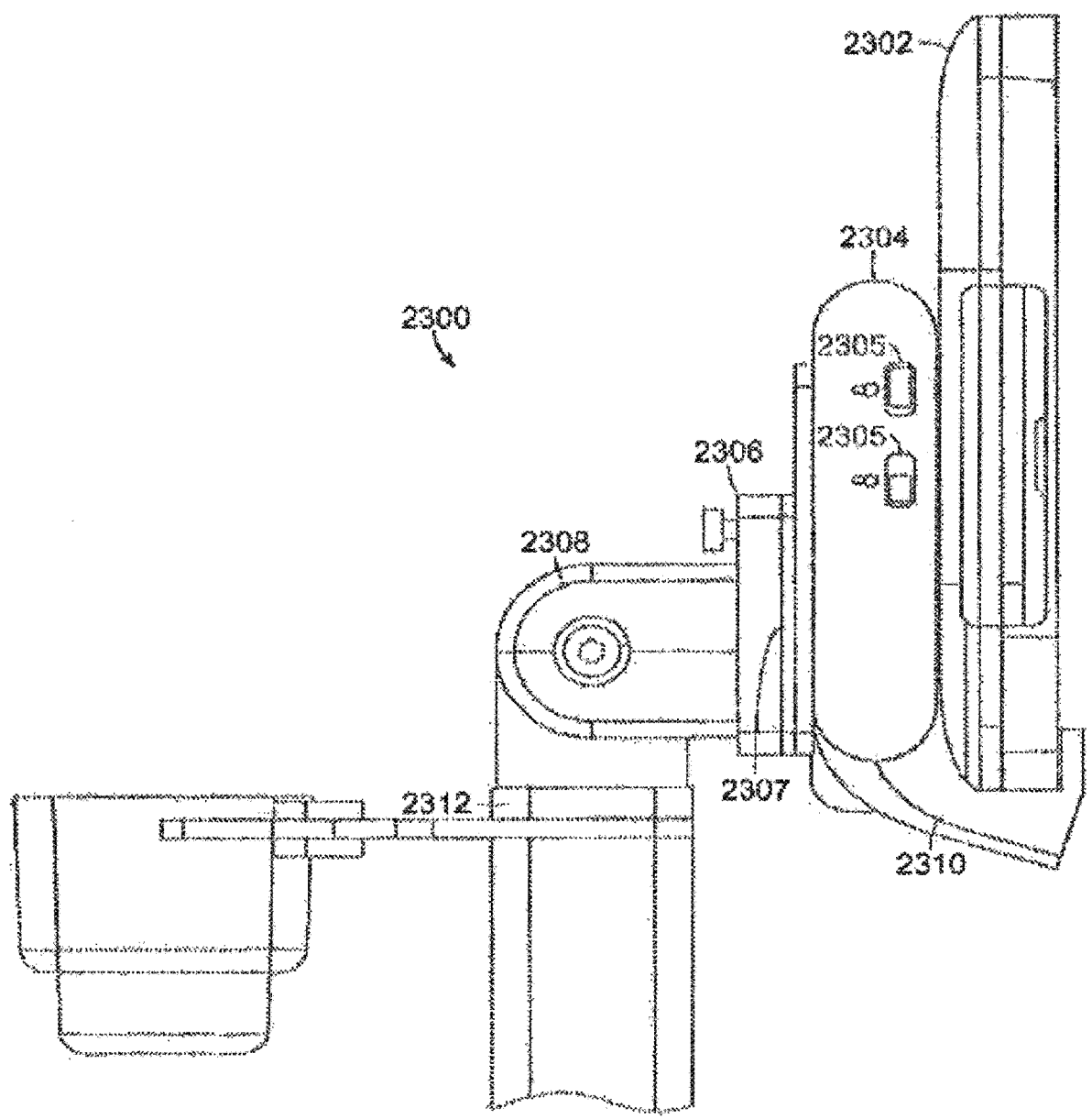
FIG. 23 illustrates a preferred cart system for a modular ultrasound imaging system in accordance with preferred embodiments of the invention.

FIG. 23 illustrates preferred cart mount system 2300 for a modular ultrasound imaging system in accordance with the invention. Cart mount system 2300, depicts the tablet 2302, coupled to the docking station 2304. The docking station 2304 is affixed to the attachment mechanism 2306. The attachment mechanism 2306 may include a hinged member 2308, allowing for the user display to tilted into a user desired position. The attachment mechanism 2306, is attached to the vertical member 2312. A tablet 2302 as described herein can be mounted on the base docking unit 2304 which is mounted to a mount assembly 2306 on top of beam 2212. The base unit 2304 includes cradle 2310, electrical connectors 2305 and a port 2307 to connect to the system 2302 to battery 2230 and multiplexor device 2216.

Figure 24:
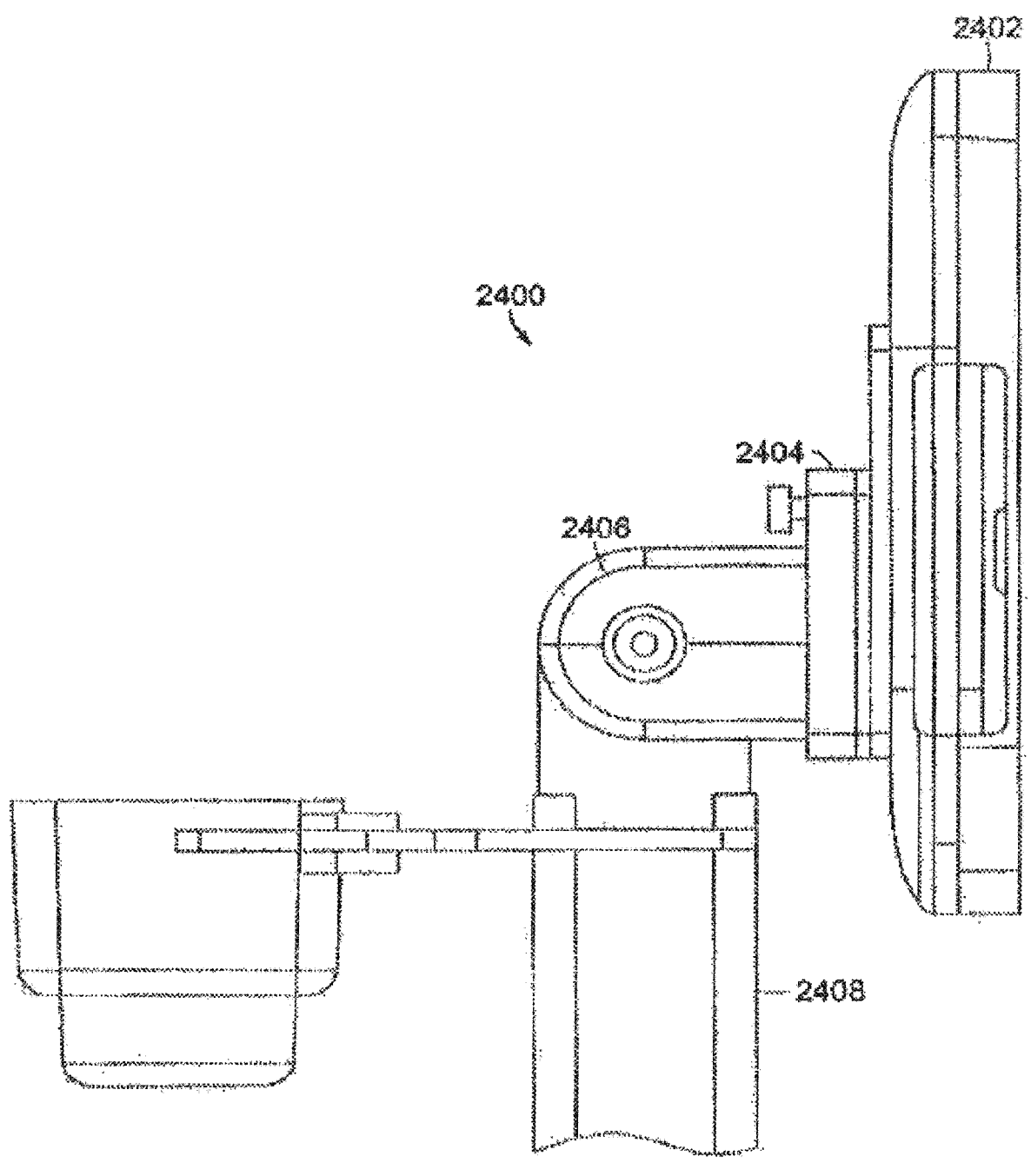
FIG. 24 illustrates a preferred cart system for a modular ultrasound imaging system in accordance with preferred embodiments of the invention.

FIG. 24 illustrates preferred cart system 2400 modular ultrasound imaging system in accordance with the invention in which tablet 2402 is connected on mounting assembly 2406 with connector 2404. Cart mount system 2400, depicts the tablet 2402, coupled to the vertical support member 2408, via attachment mechanism 2404 without the docking element 2304. Attachment mechanism 2404 may include a hinged member 2406 for display adjustment.

Figures 25A, 25B:
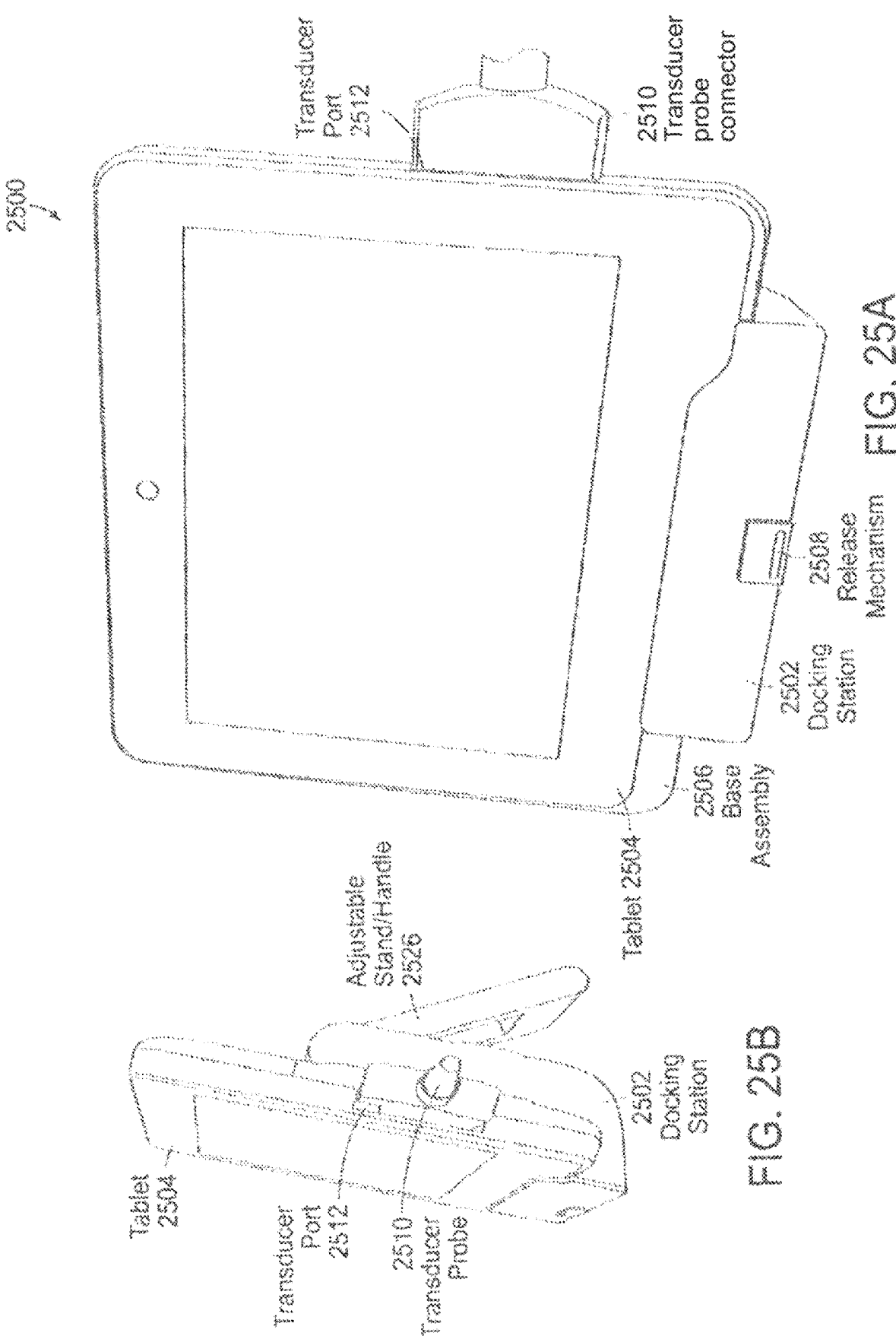
FIGS. 25A-25B illustrate a multifunction docking base for tablet ultrasound device.

FIGS. 25A and 25B illustrate a multi-function docking station. FIG. 25 a illustrates docking station 2502, and tablet 2504, having a base assembly 2506, that mates to the docking station 2502. The tablet 2504, and the docking station 2502, may be electrically connected. The tablet 2504, may be released from docking station 2502, by engaging the release mechanism 2508. The docking station 2502, may contain a transducer port 2512, for connection of a transducer probe 2510. The docking station 2502, can contain 3 USB 3.0 ports, a LAN port, a headphone jack and a power connector for charging. FIG. 25B illustrates a side view of the tablet 2504, and docking station 2502, having a stand in accordance with the preferred embodiments of the present invention. The docking station may include an adjustable stand/handle 2526. The adjustable stand/handle 2526, may be tilted for multiple viewing angles. The adjustable stand/handle 2526, may be flipped up for transport purposes. The side view also illustrates a transducer port 2512, and a transducer probe connector 2510.

The quantitative parameters may be in a range of discrete values, or may span a continuum. A control key 2520, employed in conjunction with the up arrow key or down arrow key allows an operator to toggle between two control tabs depicted in FIGS. 25C and 25D, as will be described further below. Since all keys employed in controlling and selecting the ultrasonic imaging operations are accessible from a common operating position, an operator may focus on the ultrasonic image of the subject and on the hand-held probe, and need not be distracted by unwieldy controls. Traditional directional keypads allow only directional control to be applied by the directional keypads, and do not allow both qualitative and quantitative selection of operations from a common, unitary operating position accessible by a single hand.

Figure 25C:
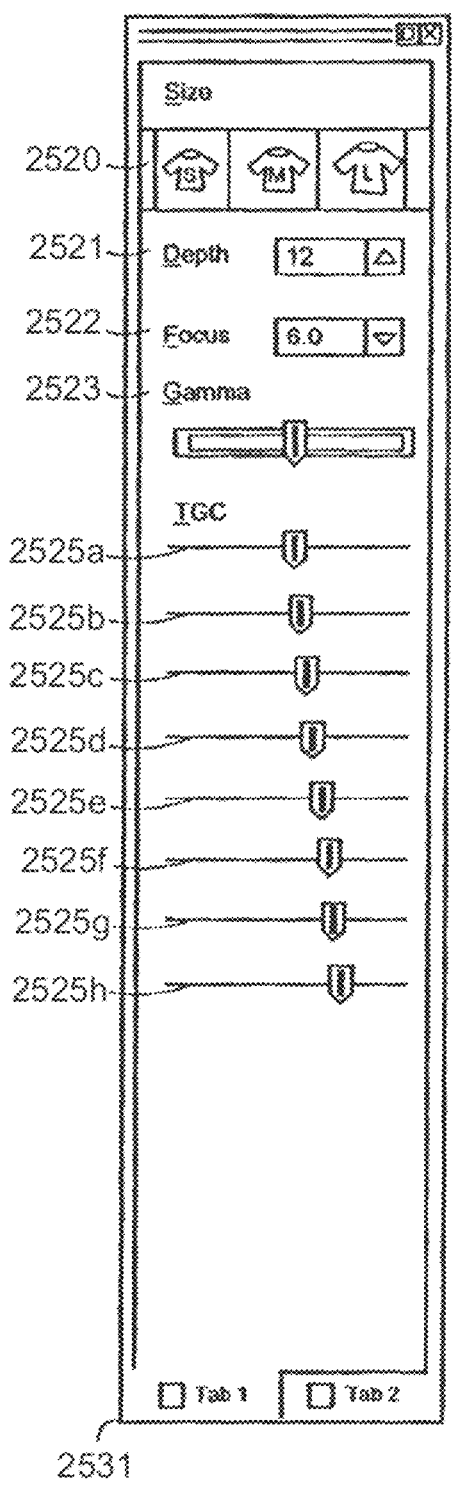
FIG. 25C shows a graphical user interface (GUI) for controlling the scanning operations of the ultrasonic imaging system.
Figure 25D:
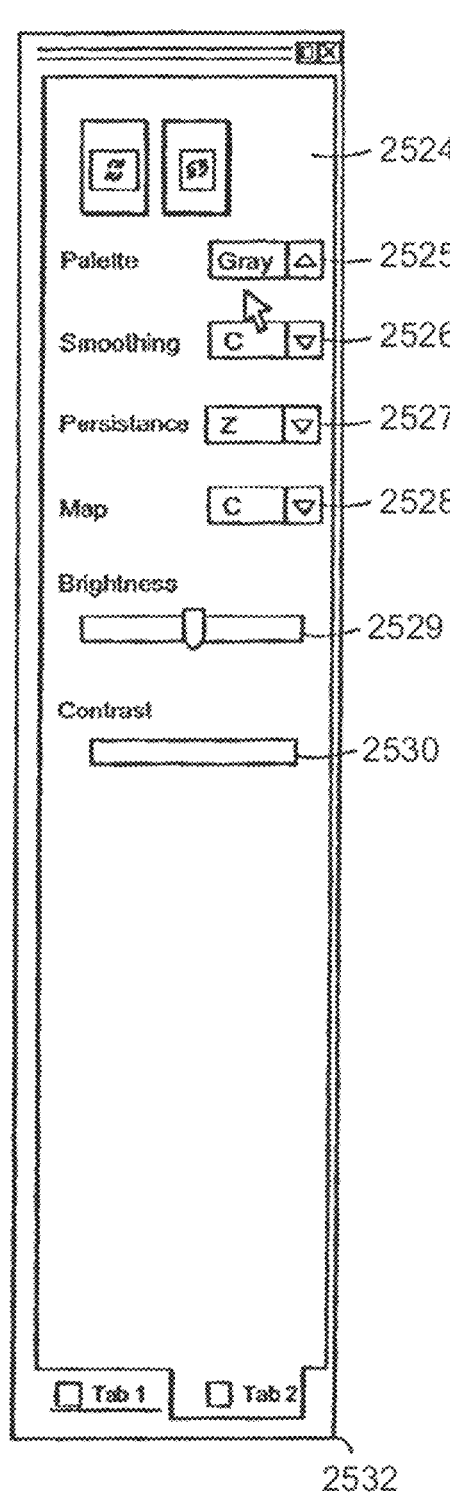
FIG. 25D shows a graphical user interface (GUI) for controlling the processing operations of the ultrasonic imaging system.

FIGS. 25C and 25D show qualitative and quantitative selection of ultrasonic imaging operations via invoking the unitary directional keypad. Referring to FIG. 25C, ultrasonic imaging operations applicable to scanning are shown. The scanning operations are directed to active acquisition of real-time, dynamic ultrasonic image data, and are typically applied as the hand-held probe is manipulated over the subject imaging area. A size operation 2520 sets a series of predetermined defaults for other ultrasonic imaging operations. A small, medium, or large subject may be selected via the left and right arrow keys. A depth operation 2521 allows selection of a depth parameter via the arrow keys. Focus is controlled by a focus 2522 operation. Gain 2523 control adjusts the TGC for all TGC settings 2525a-2525h. TGC operations 2525a-2525f adjusts amplification of return signals at varying depth, ranging from the least depth 2525a to greatest depth 2525h, via the arrow keys.

Referring to FIG. 25D, ultrasonic imaging operations applicable to processing are shown. The processing operations may be applied to static real-time or frozen images. An inversion operation is controlled by the inversion 2524 selection, and rotates the image via the arrow keys. Palate, smoothing, persistence, and mapping 2525, 2526, 2527 and 2528, respectively are selected via the up and down arrow keys, and parameters selected via the arrow keys. Brightness and contrast scales are selected via sliders 2529 and 2530, respectively, and are changed using arrow keys.

Figure 25E:
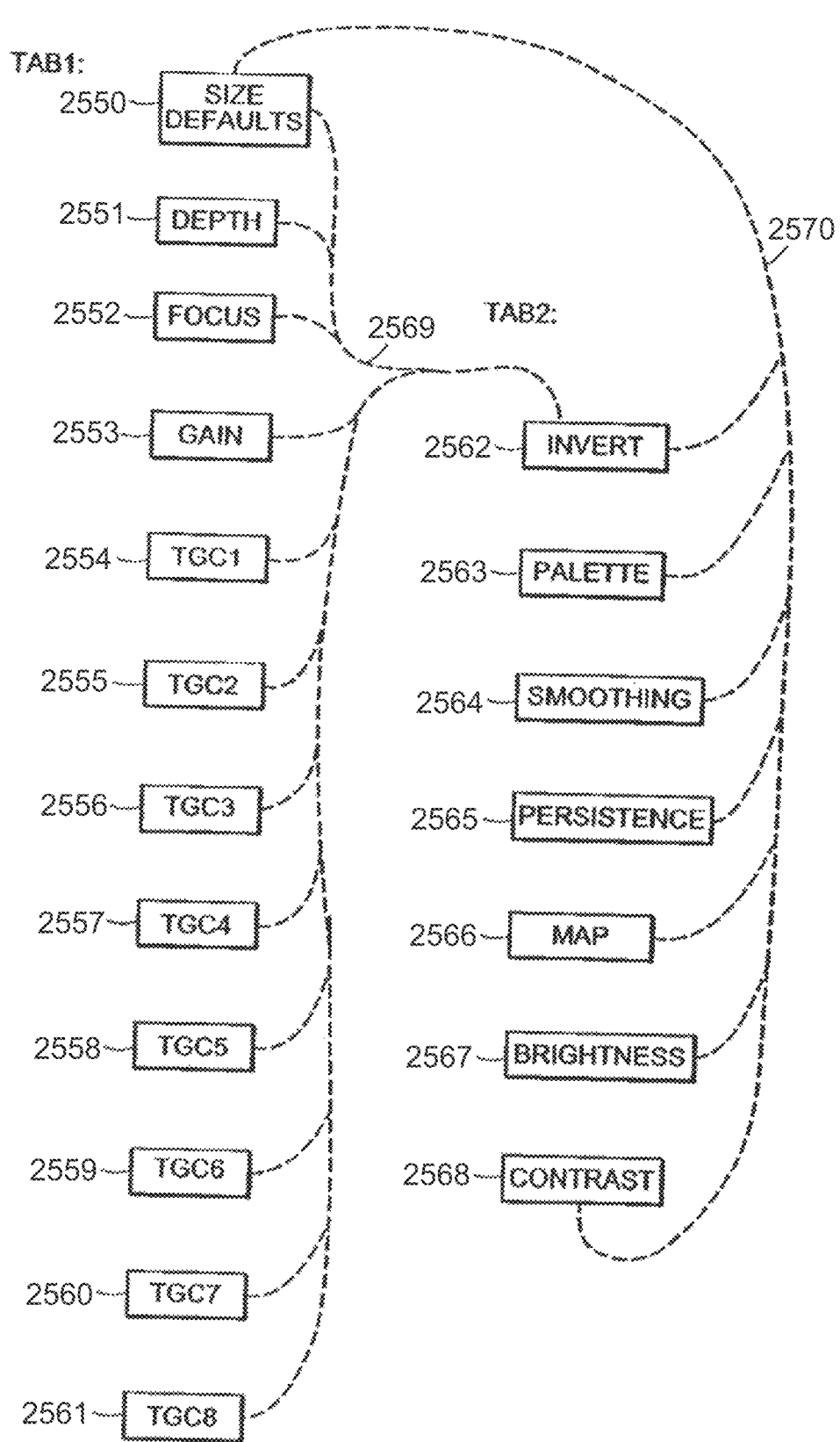
FIG. 25E shows a state diagram corresponding to the GUI of FIGS. 25C-25D.

FIG. 25E shows a state diagram depicting transition between the ultrasonic imaging operations depicted in FIGS. 25C and 25D. Tab 1 operations are selected via the up and down arrow keys and transition according to the following state sequence: size 2550, depth 2551, focus 2552, Gain 2553 and TGC degrees 2554, 2555, 2556, 2557, 2558, 2559, 2560 and 2561. Similarly, the Tab 2 operations are selected according to the following sequence: invert 2562, palette 2563, smoothing 2564, persistence 2565, map 2566, brightness 2566, and contrast 2567. As indicated above, selection of operations may be toggled between Tab 1 and Tab 2 using control key and arrow keys.

The scanning operations shown in FIG. 25C are displayed on Tab 1. The processing operations are displayed and selected on Tab 2. Control is toggled between Tab 1 and Tab 2 using a combination of the control key and either the up or down arrow keys as shown by dotted lines 2569 and 2570.

In general the use of medical ultrasound systems requires the user to have significant training and regular practice to keep skills at a high level. Another embodiment of the invention involves providing the user with an intuitive and simple way to use the interface, and with the ability to quickly and automatically set imaging parameters based on a software module. This enables general medical personnel with limited ultrasound experience to obtain diagnostic-quality images without having to adjust the controls. The "Quick Look" feature provides the user with a very simple mechanism of image optimization. It allows the user to simply adjust the image so as to obtain appropriate diagnostic image quality with one push of one button.

The benefits of programmed image parameters are many. The user no longer is required to adjust multiple controls in order to obtain a good image. Exams may be performed in a shorter period of time as a result. The use of this feature also results in more uniform images, regardless of the skills and expertise of the user. This approach is advantageous when performing exams under adverse circumstances such as emergency medical procedures performed in ambulances or remote locations.

The procedure involves the use of predefined histograms. Separate histograms are provided for different anatomical structures that are to be examined. The user chooses a structure, similar to the existing method of choosing a preset. Once the structure is chosen, the user places the transducer on the area of interest in the scanning window. At that time, pressing the selected control button triggers the system to adjust the system contrast and brightness control values so that a histogram of the gray levels in the image closely matches the corresponding pre-defined histogram for that structure. The result is an image of diagnostic image quality that is easily recreated.

The procedure is highly dependent upon the brightness and contrast controls. As a result, a preferred embodiment provides an independent control which allows the user to adjust for ambient lighting changes. In many applications the programmed parameters gets the user very close, but they may choose to fine tune the contrast and brightness.

Figure 26A:
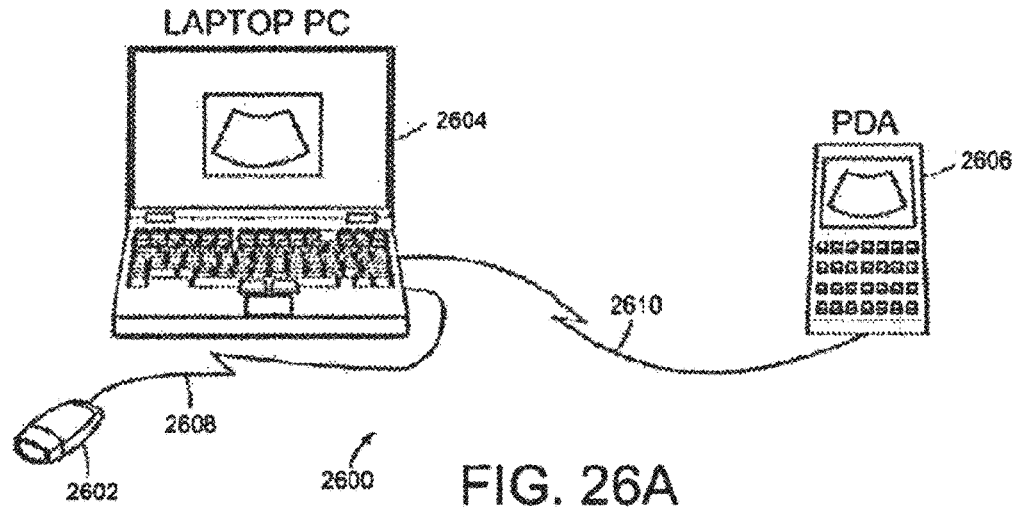
FIG. 26A is a block diagram illustrating an ultrasound imaging system with wired and wireless communication.

Referring to FIG. 26A, the integrated probe system 2600 includes the front end probe 2602, the host computer 2604, and a portable information device such as a personal digital assistant (PDA) 2606. The PDA 2606, such as a Palm Pilot device, or other hand-held computing device is a remote display and/or recording device. In the embodiment shown, the front end probe 2602 is connected to the host computer 2604 by the communication link 2608 that is a wired link. The host computer 2604, a computing device, is connected to the PDA 2606 by a communication link or interface that is wireless link 2610.

In that the integrated ultrasound probe system 2600 in the embodiment described has a Windows®-based host computer 2604, the system can leverage the extensive selection of software available for the Windows® operating system. One potentially useful application is electronically connecting ultrasound systems allowing physicians to send and receive messages, diagnostic images, instructions, reports or even remotely controlling the front-end probe 2602 using the system.

The connections through the communication links or interfaces 2608 and 2610 can be either wired through an Ethernet or wireless through a wireless communication link such as, but not limited to, IEEE 802.11a, IEEE 802.11b, Hyperlink or HomeRF. FIG. 26A shows a wired link for the communication link 2608 and a wireless link for the communication link 2610. It is recognized that other wired embodiments or protocols can be used.

The wireless communication link 2610 can use various different protocols, such as, an RF link which may be implemented using all or parts of a specialized protocol, such as the IEEE 1394 protocol stack or Bluetooth system protocol stack. IEEE 1394 is a preferred interface for high bandwidth applications such as high quality digital video editing of ultrasonic imaging data. The Bluetooth protocol uses a combination of circuit and packet switching. Slots can be reserved for synchronous packets. Bluetooth can support an asynchronous data channel, up to three simultaneous synchronous channels, or a channel which simultaneously supports asynchronous data and synchronous voice. Each synchronous channel support a 64 kb/s synchronous (voice) channel in each direction. The asynchronous channel can support maximal 723.2 kb/s asymmetric, or 433.9 kb/s symmetric.

The Bluetooth system consists of a radio unit, a link control unit, and a support unit for link management and host terminal interface functions. The link controller carries out the baseband protocols and other low-level link routines.

The Bluetooth system provides a point-to-point connection (only two Bluetooth units involved), or a point-to-multipoint connection. In the point-to-multipoint connection, the channel is shared among several Bluetooth units. Two or more units sharing the same channel form a piconet. One Bluetooth unit acts as the master of the piconet, whereas the other units act as slaves. Up to seven slaves can be active in a piconet.

The Bluetooth link controller has two major states: STANDBY and CONNECTION, in addition, there are seven sub states, page, page scan, inquiry, inquiry scan, master response, slave response, and inquiry response. The sub-states are interim states that are used to add new slaves to a piconet.

The link may also be implemented using, but not limited to, Home RF, or the IEEE 802.11 wireless LAN specification. For more information on the IEEE 802.11 Wireless LAN specification, see the IEEE standard for Wireless LAN incorporated herein by reference. IEEE standards can be found on the World Wide Web at the Universal Resource Locator (URL) www.ieee.org. For example, hardware supporting IEEE standard 802.11b provides a communications link between two personal computers at 2 and 11 Mbps. The frequency bands allocated for transmission and reception of the signals is approximately 2.4 GHz. In comparison, IEEE standard 802.11a provides 54 Mbps communications. The frequency allocation for this standard is around 5 GHz. Recently, vendors, such as Proxim, have manufactured PC Cards and access points (basestations) that use a proprietary data-doubling, chipset, technology to achieve 108 Mbps communications. The chip that provides the data doubling (the AR5000) is manufactured by Atheros Communications. As with any radio system, the actual data rate maintained between two computers is related to the physical distance between the transmitter and receiver.

The wireless link 2610 can also take on other forms, such as, an infrared communications link as defined by the Infrared Data Association (IrDA). Depending on the type of communication desired (i.e., Bluetooth, Infrared, etc.) the host computer 2604 and the remote display and/or recording device 2606 each has the desired communication port.

Figure 26B:
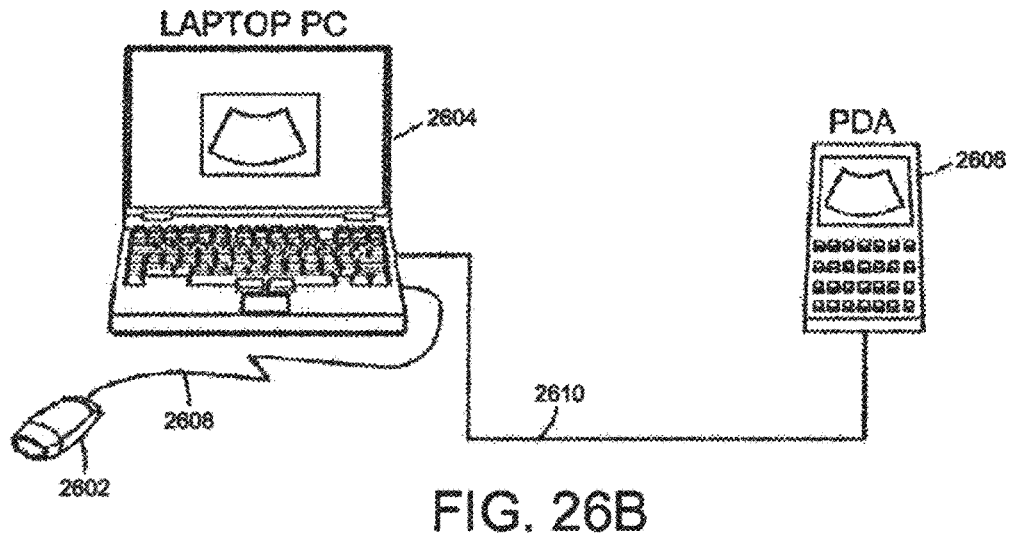
FIG. 26B is a block diagram illustrating an ultrasound imaging system with wireless and wired communication.

FIG. 26B shows the communication link 2608 between the probe 2602 and the host computer 2604 as a wireless link. The communication link 2610 between the host computer 2604 and the PDA 2606 is shown as a wired link.

Figure 26C:
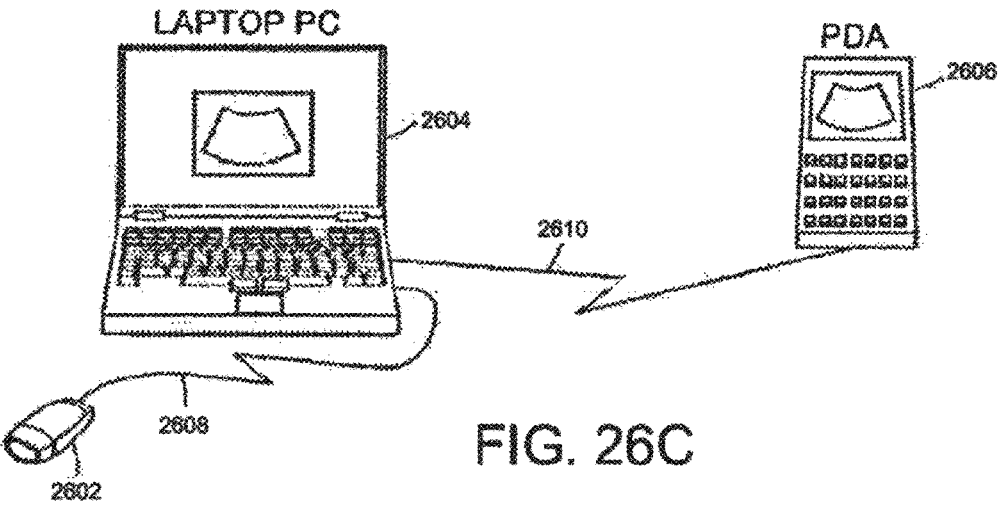
FIG. 26C is a block diagram illustrating an ultrasound imaging system with wireless communication.

The integrated probe system 2600 of FIG. 26C has wireless links for both the communication link 2608 between the probe 2602 and the host computer 2604 and the communication link 2610 between the host computer 2604 and the PDA 2606. It is recognized that wired and wireless links can both be used together or in the alternative, can be exclusively wired links or wireless links in a system 2600.

Figure 27:
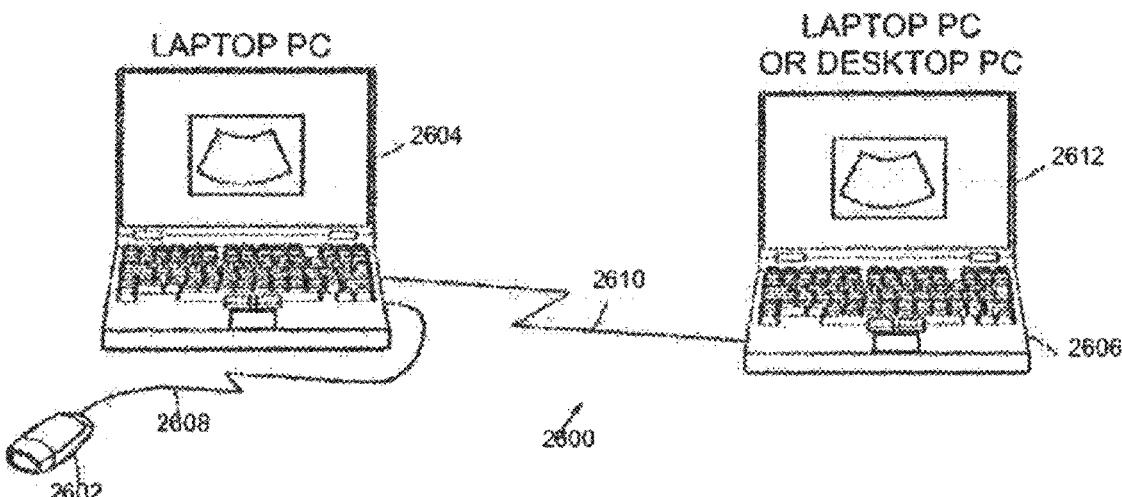
FIG. 27 is a block diagram illustrating an ultrasound imaging system with a remote or secondary controller/viewer and wireless communication.

The remote display and/or recording device 2606 of the integrated probe system 2600 of FIG. 27 is a remote computing system 2612. The remote computing system 2612 in addition to having remote display and/or recording capability can also remotely control the probe 2602. The communication link 2610 is shown as a wireless link. The communication link 2608 between the probe 2602 and the host computer 2604 is shown as a wired link.

An example of a remote control system includes using a wearable computer (such as the one manufactured by Xybernaut Corporation), a pair of high-speed, wireless PC Cards (such as those provided by Proxim) and the ultrasound program and the probe 2602. A portable-networked ultrasound system can be configured weighing less than 2.5 pounds. Using a program similar to Microsoft® NetMeeting, a real-time connection between a remote PC and the wearable computer can be established. The remote host can monitor all interactions with the wearable computer, including real-time ultrasound imaging (at display rates up to approximately 4 frames per second). NetMeeting can also be used to "take control" of the wearable computer and manage the ultrasound session from the remote personal computer in real time. In addition, images and iterative executable software instructions that are archived to the hard disk on the wearable computer can be transferred at 108 Mbps to the host computer. With this technology, real time ultrasound diagnoses can be performed and relayed to a remote sight at speeds that rival a hardwired 100 million bits per second (Mbps) local area network (LAN).

Figure 28:
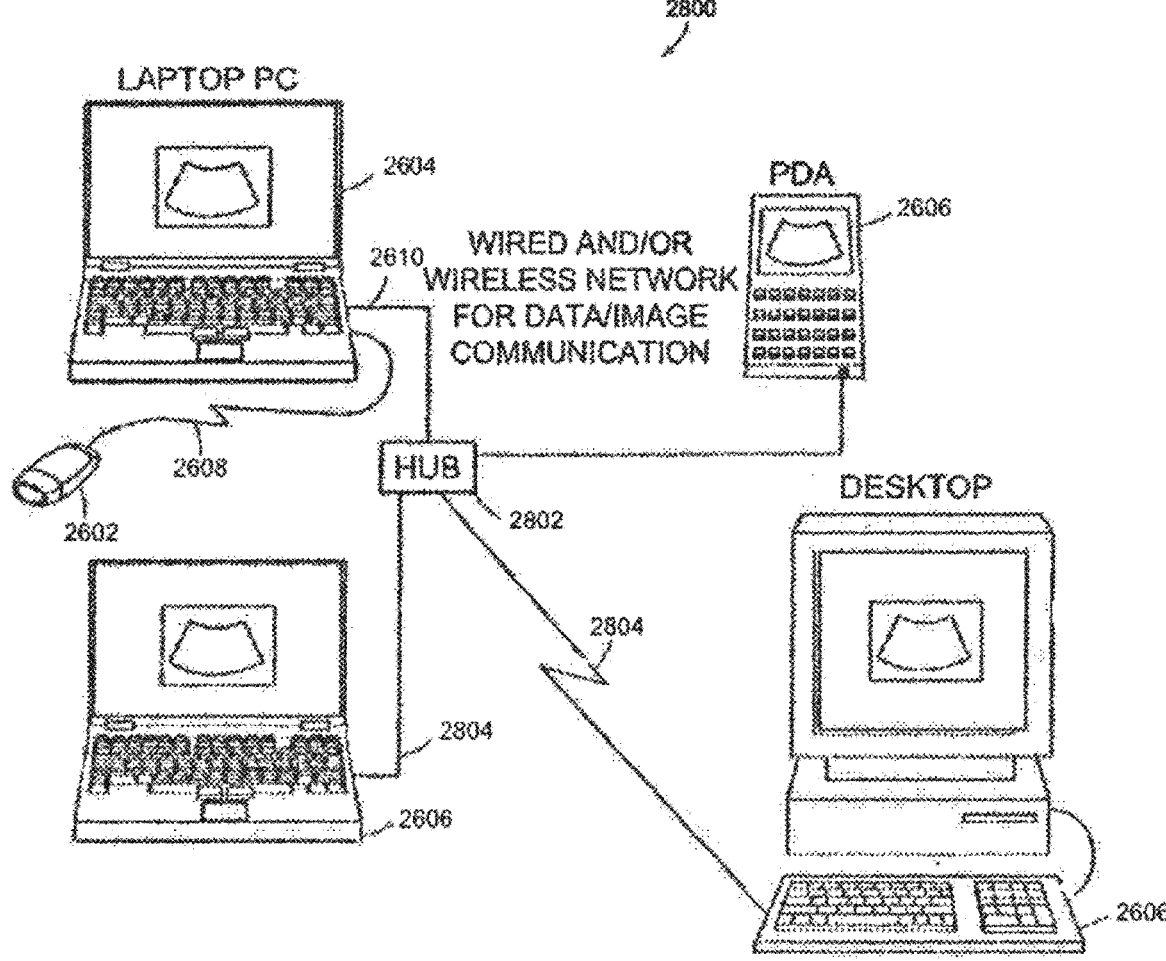
FIG. 28 is a block diagram illustrating an ultrasound imaging system with wired and wireless network communication capability.

FIG. 28 illustrates an integrated probe system 2800 that has a hub 2802 for connecting a plurality of remote devices 2606 to the host computer 2604. The communication link 2804 from the hub 2802 to the remote devices are shown both as wireless and wired links. It is recognized that a completely wired network such as a LAN or Ethernet can be used. In the alternative, with a wireless transceiver and port in each of the computers (remote device) 2606, a wireless Network/Communication system can readily be established. With the recent advent of high-speed wireless standards, such as IEEE 802.11a, the communications between the remote and local machines can rival that of a wired, 100 Mbps local area network (LAN). Another alternative is using a Bluetooth system to form a piconet.

The increasing use of combined audio-visual and computer data is leading to greater need for multimedia networking capabilities and solutions are beginning to emerge that are included in preferred embodiments of the present invention. Standardization of multimedia networking is underway, and IEEE 1394 is emerging as the leading contender, capable of interfacing with a number of audio-visual (AV), computer and other digital consumer electronics and providing transmission bandwidth of up to 400 Mbps.

Preferred embodiments use IEEE 1394 technology which uses a wireless solution for the transmission of 1394 protocols over IEEE 802.11, the emerging standard for wireless data transmission in the corporate environment and increasingly in the home as well. In a preferred embodiment IEEE 1394 is implemented as a Protocol Adaptation Layer (PAL) on top of the 802.11 radio hardware and Ethernet protocols, bringing together a convergence of these important technologies. This protocol adaptation layer enables the PC to function as a wireless 1394 device. The engineering goal is for real delivered IEEE 1394 bandwidth sufficient for the transmission of a single high-definition MPEG2 video stream (or multiple standard-definition MPEG2 video streams) from one room in a facility to another.

Preferred embodiments of the present invention include the use of wireless transmission of IEEE 1394 at 2.4 GHz using Wi-LAN's Wideband Orthogonal Frequency Division Multiplexing (W-OFDM) technology. This development establishes W-OFDM, the most bandwidth-efficient wireless transmission technology, as one of the technologies capable of providing data rates necessary for in-home multimedia networking.

The Wireless IEEE 1394 system includes an MPEG-2 data stream generator, which feeds a multiple transport stream into a Set Top Box (STB) such as provided by Philips Semiconductors. The STB converts this signal to an IEEE 1394 data stream and applies it to the W-OFDM radio system such as provided by Wi-LAN™. The radio transmitter then sends the IEEE 1394 data stream over the air to the corresponding W-OFDM receiver in the host computer, for example. On the receive side, the IEEE 1394 signal is demodulated and sent to two STBs, which display the content of the different MPEG-2 data streams on two separate TV monitors. Using IEEE 1394 as the interface for the wired part of the network optimizes the entire system for transmission of isochronous information (voice, live video) and provides an ideal interface to multimedia devices in the facility. W-OFDM technology is inherently immune to the effects of multipath. Like all modulation schemes, OFDM encodes data inside a radio frequency (RF) signal. Radio communications are often obstructed by occurring noise, stray and reflected signals. By sending high-speed signals concurrently on different frequencies, OFDM technology offers robust communications. OFDM-enabled systems are highly tolerant to noise and multipath, making wide-area and in-home multi-point coverage possible. Additionally, as these systems are very efficient in use of bandwidth, many more high-speed channels are possible within a frequency band. W-OFDM is a cost-effective variation of OFDM that allows much larger throughputs than conventional OFDM by using a broad frequency band. W-OFDM further processes the signal to maximize the range. These improvements to conventional OFDM result in the dramatically increased transmission speeds.

OFDM technology is becoming increasingly more visible as American and European standardization committees are choosing it as the only technology capable of providing reliable wireless high data rate connections. European terrestrial digital video broadcasting uses OFDM and the IEEE 802.11 working group recently selected OFDM in its proposed 6 to 54 Mbps wireless LAN standard. The European Telecommunications Standards Institute is considering W-OFDM for the ETSI BRAN standard. Detailed information on Wi-LAN™ can be found on the Web at http://www.wi-lan.com/Philips Semiconductors, a division of Royal Philips Electronics, headquartered in Eindhoven, The Netherlands. Additional information on Philips Semiconductors can be obtained by accessing its home page at http://www.semiconductors.philips.com/.

Further, NEC Corporation's wireless transmission technology based on the IEEE 1394 high-speed serial bus capable of 400 megabits (Mbps), at transmission ranges of up to 7 meters through interior walls and up to 12 meters by line-of-sight may also be used in preferred embodiments. This embodiment uses 60 GHz millimeter wavelength transmissions, which does not require any kind of license, with the amplitude shift keying (ASK) modulation scheme and the development of a low cost transceiver. This embodiment incorporates an echo detection function in NEC's PD72880 400 Mbps long-distance transmission physical layer device, to prevent the influence of signal reflections, a significant obstacle to stable operation of IEEE 1394 over a wireless connection.

Wireless IEEE 1394 can play an important role in bridging the PC to clusters of interconnected IEEE 1394 devices, which can be in another room in the facility. Three example applications are sourcing video or audio stream from a PC, providing internet content and connectivity to a IEEE 1394 cluster, and provide command, control and configuration capabilities to the cluster. In the first embodiment, the PC may provide data to someone in another room in a facility. In the second embodiment, the PC may provide an avenue for 1394 enabled devices to access the Internet. In the third embodiment, the PC plays the role of orchestrating activities in the 1394 clusters and routing data within the clusters and over bridges—though the actual data does not flow through the PC.

Figure 29:
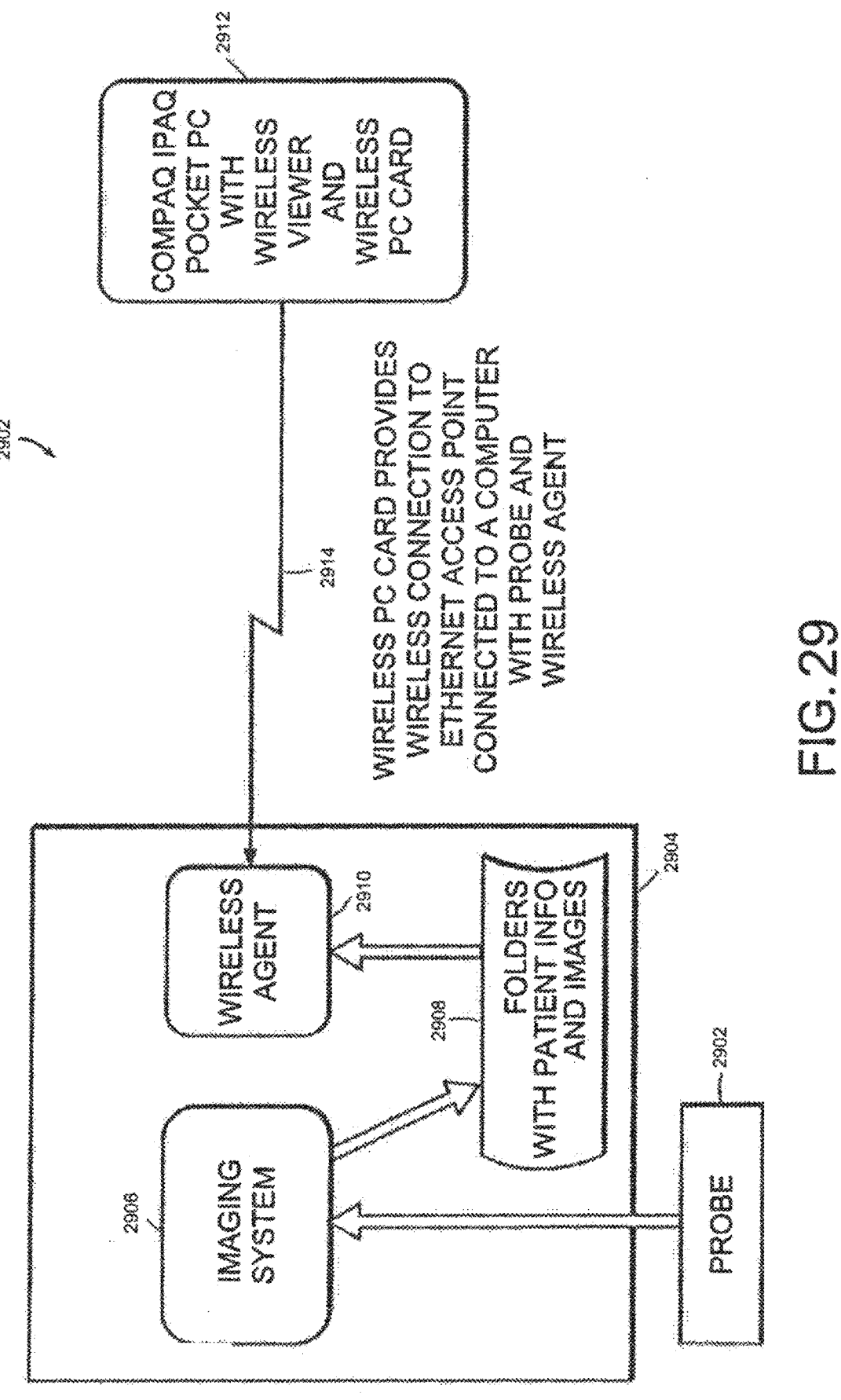
FIG. 29 is a diagram illustrating further details of the architecture of the ultrasound imaging system in accordance with a preferred embodiment of the present invention.

FIG. 29 is a diagram showing the provision of wireless access to the images created by a preferred embodiment ultrasound imaging system and the associated architecture. The imaging system 2906 exports patient information and images (from data gathered by probe 2902) to files in corresponding folders 2908. Executable software instructions have all functionality required to implement the ultrasonic imaging methods described hereinbefore.

The wireless agent 2910 serves to detect patient directories and image files and opens a port for wireless clients to get connection thereto. Upon establishing a connection it sends back to the client list of patients and corresponding images. For example, the wireless agent 2910 may include data interface circuitry which may include a first port such as a RF interface port.

The wireless viewer 2912 residing on a handheld side can establish connection to the wireless agent 2910 and retrieve patient and image information. Upon user selection of the patient and image it initiates file transmission from the wireless agent 2910. Upon receiving an image the viewer 2912 displays this image along with patient information. The image gets stored on the handheld for future use. The handheld user can view images retrieved in previous sessions or can request new image transmission.

Figure 33:
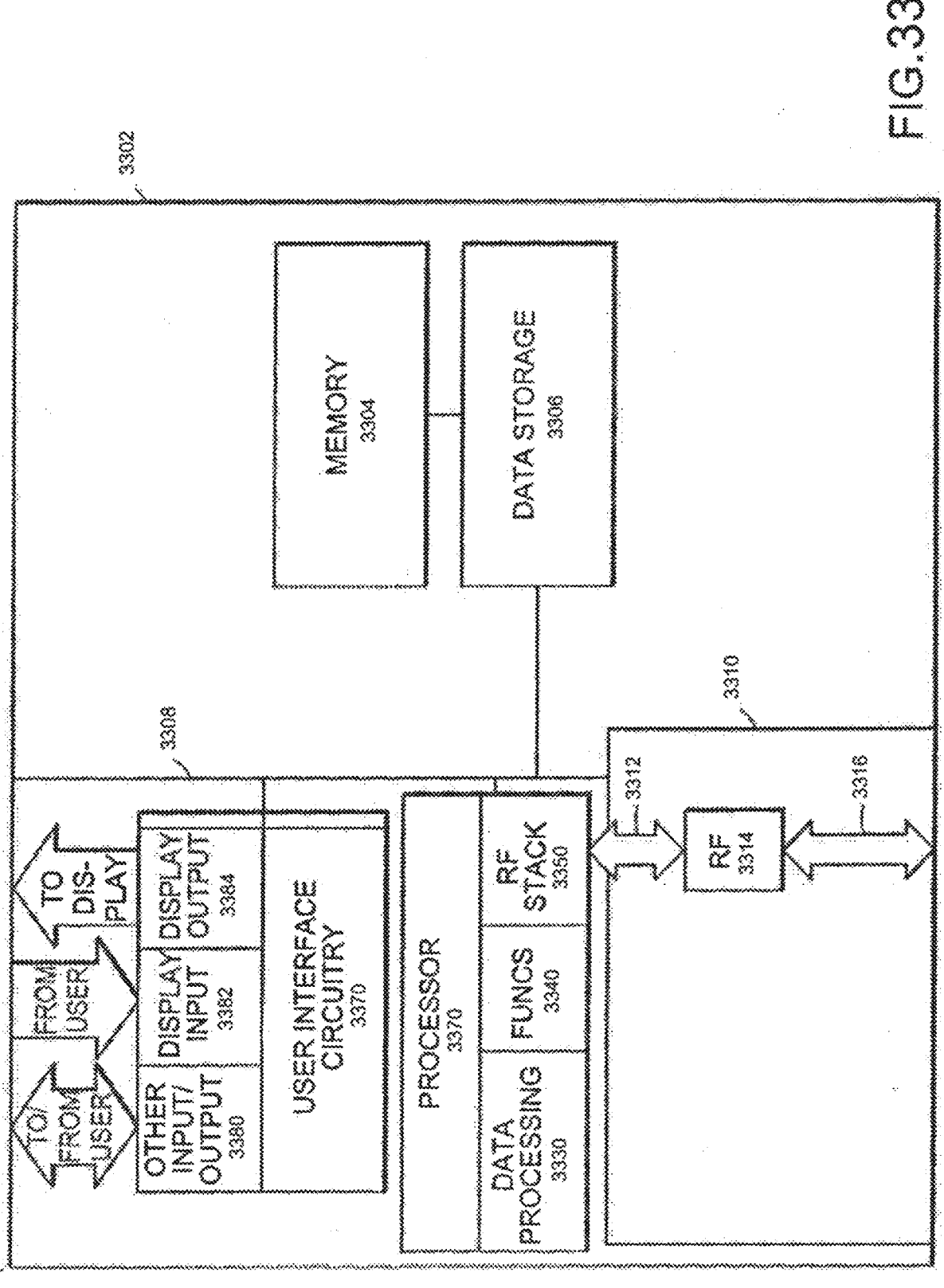
FIG. 33 is a block diagram illustrating a personal digital assistant (PDA) in communication with the host computer or probe system in accordance with preferred embodiment of the present invention.

FIG. 33 is a block diagram illustrating a portable information device 3302 such as a personal digital assistant (PDA) or any computing device according to an exemplary embodiment of the present invention. The link interface or data interface circuitry 3310 illustrates, but is not limited to, one link interface for establishing a wireless link to another device. The wireless link is preferably an RF link, defined by IEEE 1394 communications specifications. However, the wireless link can take on other forms, such as the infrared communications link as defined by the Infrared Data Association (IrDA). The PDA 3302 includes a processor 3370 that is capable of executing an RF stack 3350 that communicates with a data interface circuitry 3310 through bus 3312. The processor 3370 is also connected through bus 3312 to user interface circuitry 3370, data storage 3306 and memory 3304.

The data interface circuitry 3310 includes a port such as the RF interface port. The RF link interface may include a first connection 3312 which includes radio-frequency (RF) circuitry 3314 for converting signals into radio-frequency output and for accepting radio-frequency input. The RF circuitry 3314 can send and receive RF data communications via a transceiver that establishes communication port 3316. RF communication signals received by the RF circuitry 3314 are converted into electrical signals and relayed to the RF stack 3350 in processor 3370 via bus 3312. The radio interface 3314, 3316 and the link between the laptop PC (host computer) and the PDA may be implemented by, without limitation, IEEE 1394 specifications.

Similarly, the PC host computer has a RF stack and circuitry to be able to communicate to the remotely located image viewer. In a preferred embodiment, the remote image viewer may be used to monitor and/or control the ultrasonic imaging operations not just display the resultant imaging data.

The current market offers a lot of different options related to wireless connectivity. In a preferred embodiment, spread-spectrum technology Wireless LAN is used. Among wireless LAN solutions the most advanced is the 802.11b standard. Many manufacturers offer 802.11b compliant equipment. Compatibility with the selected handheld is the major criteria in a specified class of wireless connectivity options.

The handheld market offers various handheld devices as well. For imaging purposes it is very important to have high quality screen and enough processing power to display an image. Considering these factors, in a preferred embodiment, a Compaq iPAQ is used, in particular a Compaq iPAQ 3870 is used. A wireless PC card compatible with the handheld is used such as Compaq's Wireless PC Card WL110 and corresponding Wireless Access Point.

FIG. 30 illustrates the image viewer 3020 in communication with the personal computer in a preferred embodiment or the probe in an alternate embodiment. The image viewer has user interface buttons 3022, 3024, 3026, 3028 that allow the user to interface with the ultrasonic imaging system computer or probe in accordance with preferred embodiments of the present invention. In a preferred embodiment, a communicating interface such as button 3022 allows the user to initiate a connection with the ultrasonic imaging application. Similarly, button 3024 is used to terminate an established connection with the ultrasonic imaging application. A button 3026 functions as a selection button that is used to provide a list of patients and corresponding images that are selectable. These images are either stored locally or remotely. If selected, the image that may be stored remotely is transmitted to the viewer 3030. The selected image is displayed on the viewer 3030.

Additional communication interface buttons such as button 3028 functions as an options button which may, but is not limited to, allow changing configuration parameters such as an internet protocol (IP) address.

FIG. 31 is a diagram illustrating a preferred embodiment ultrasound image collection and distribution system 3140 including four major software components. The main hardware element of the system is ultrasound probe 3142a . . . n. The probe in communication with the laptop computer 3144a . . . n allows generation of the ultrasound images and related patient information and submits images and information to an image/patient information distribution server 3146. The distribution server utilizes an SQL database server 3148 to store and retrieve images and related patient information. The SQL server provides distributed database management. Multiple workstations can manipulate data stored on the server, and the server coordinates operations and performs resource-intensive calculations.

Image viewing software or executable instructions may be implemented in two different embodiments. In a first embodiment, a full stationary version of the Image Viewer as described in FIG. 30 may reside on a workstation or laptop computer equipped with high bandwidth network connection. In a second embodiment, a lightweight version of the Image Viewer may reside on a small PocketPC handheld 3152 equipped with IEEE 802.11b and/or IEEE 802.11a compliant network card. The PocketPC image viewer implements only limited functionality allowing basic image viewing operations. The wireless network protocols 3150 such as IEEE 802.11 may be used to transmit information to a handheld or other computing devices 3152 in communication with a hospital network.

This preferred embodiment describes the ultrasound imaging system to cover hospital wide image collecting and retrieving needs. It also provides instant access to non-image patient related information. In order to provide inter-hospital information exchange, image distribution servers have the ability to maintain connectivity with each other across wide area networks.

Figure 32:
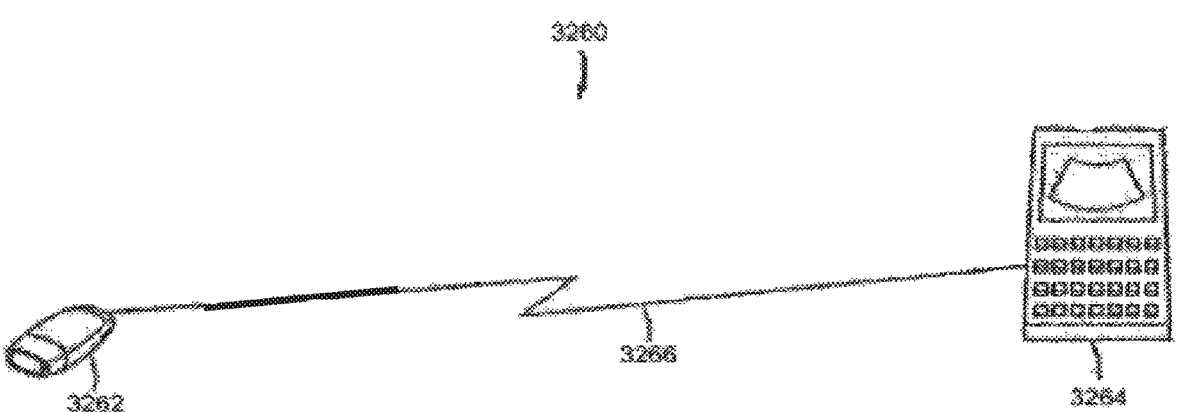
FIG. 32 is a diagram illustrating an ultrasound imaging system in accordance with a preferred embodiment of the present invention.

In another preferred embodiment, the probe may directly communicate with a remote computing device such as a PDA 3264 using a wireless communication link 3266, as shown in FIG. 32. The communication link may use the IEEE 1394 protocol. The probe and the PDA both have an RF stack and circuitry described with respect to FIG. 33 to communicate using wireless protocols. The probe includes a transducer array, beamforming circuitry, transmit/receive module, a system controller and digital communication control circuitry. Post processing of the ultrasonic image data including scan conversion is provided in the PDA.

Figure 34A:
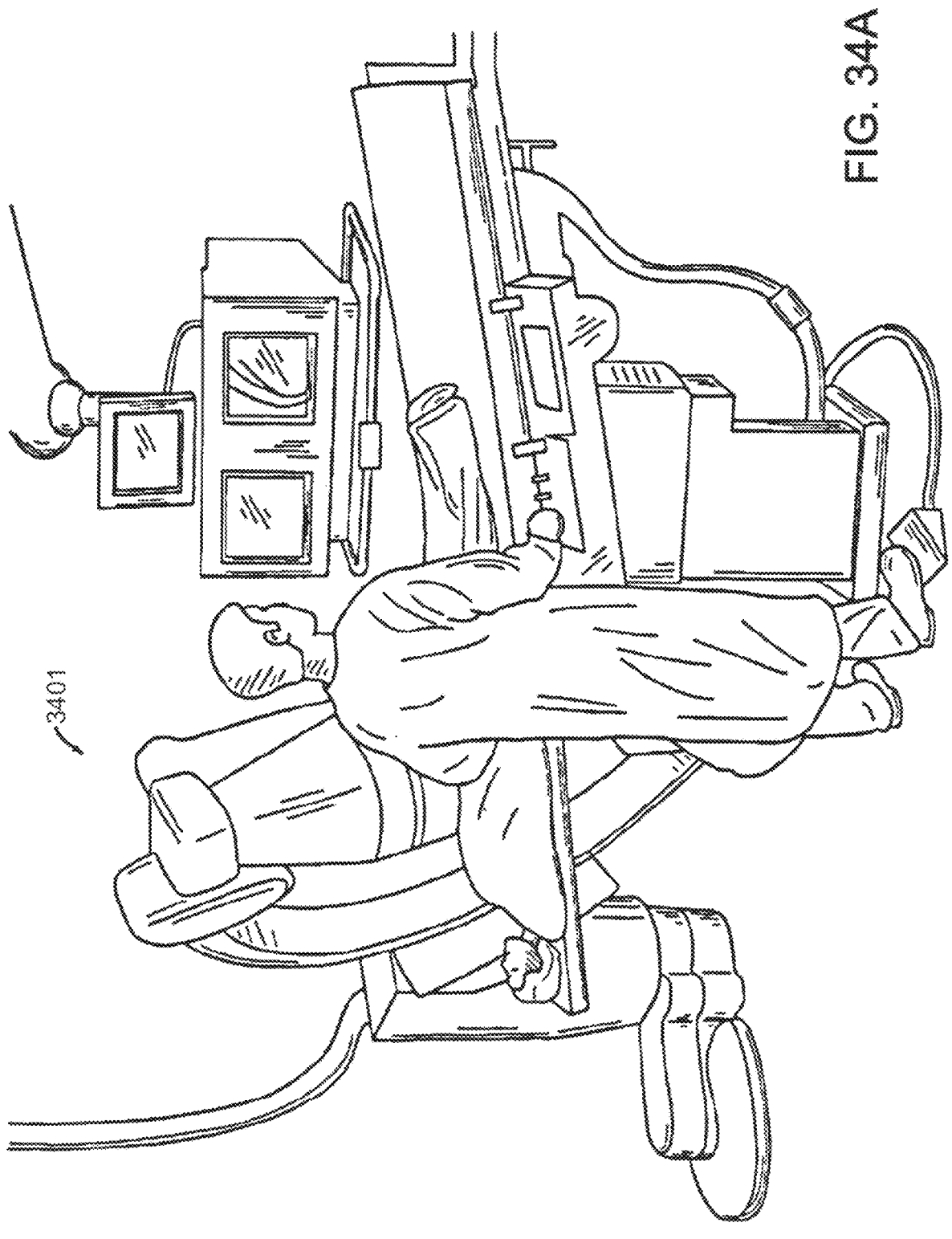
FIGS. 34A-34C illustrate an ultrasound system in accordance with a preferred embodiment of the present invention integrated with an angiography system, a high frequency image of the carotid artery with directional power doppler and an image of the carotid artery with simultaneous quantitative spectral doppler, respectively.
Figure 34B:
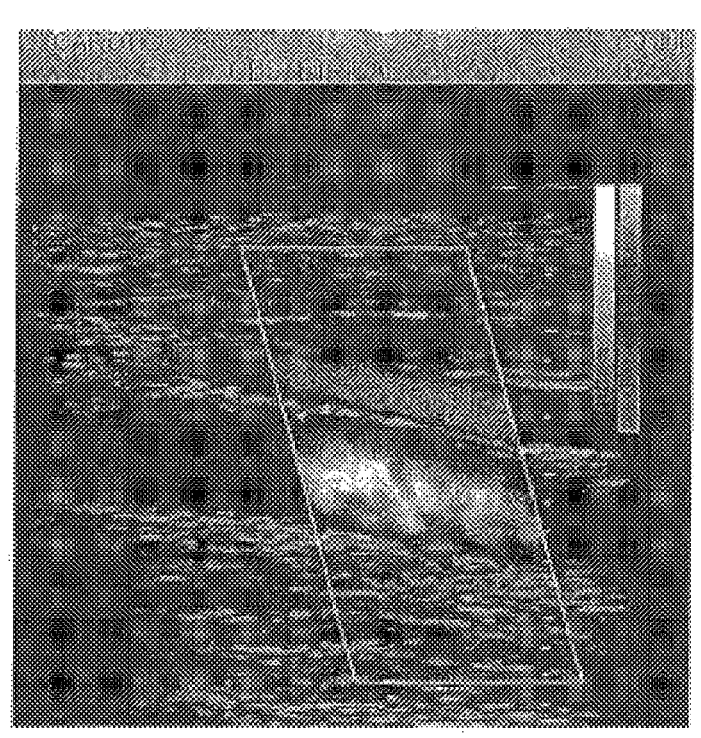
Figure 34C:
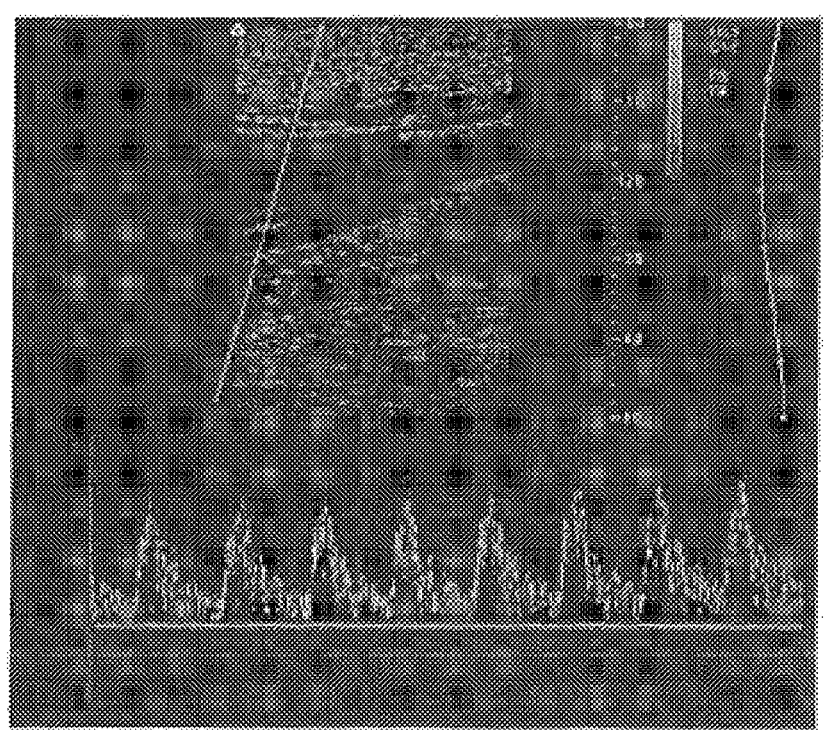

FIGS. 34A-34C illustrate an ultrasound system 3401 in accordance with a preferred embodiment of the present invention integrated with an angiography system, a high frequency image 3402 of the carotid artery with directional power doppler and an image 3404 of the carotid artery with simultaneous quantitative spectral doppler, respectively. During an acute coronary syndrome, multiple atherosclerotic plaques typically rupture, suggesting that the syndrome is associated with overall coronary instability. Intravascular ultrasound with the system of the present invention can evaluate the entire coronary circulation. Ultrasonographic screening reduces mortality from abdominal aortic aneurysms. The ultrasound system of a present invention provides easy guidance and confirmation of aortic arch placement, helps the rapid delivery of cold perfusate into the aortic arch, hypothermic preservation of the brain, heart, and spinal cord. Further, sensor monitoring for critical flow/temperature/physiological data can be provided. Automatic computer controlled flow-temperature adjustments can be facilitated along with exsanguination control and blood pressure management using the embodiment of the present invention. Preferred embodiments use a touch screen display.

Figure 34D:
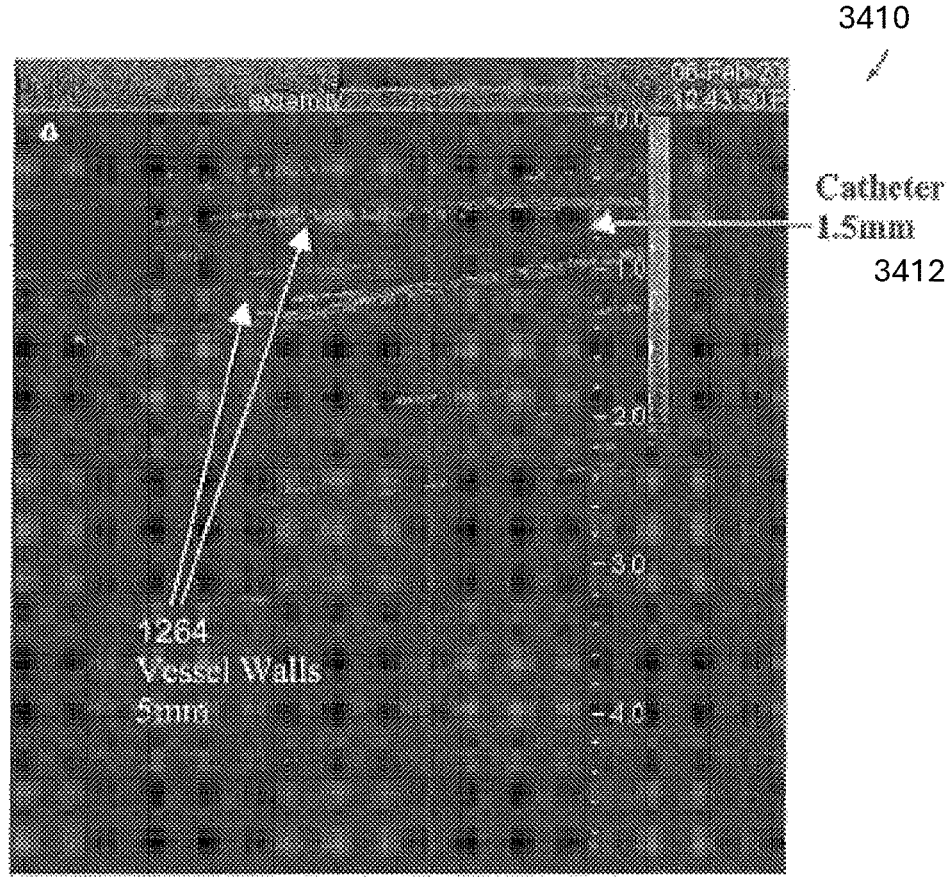
FIGS. 34D and 34E illustrate an ultrasound image of vessel walls in accordance with a preferred embodiment of the system of the present invention and a catheter used with the system, respectively.
Figure 34E:
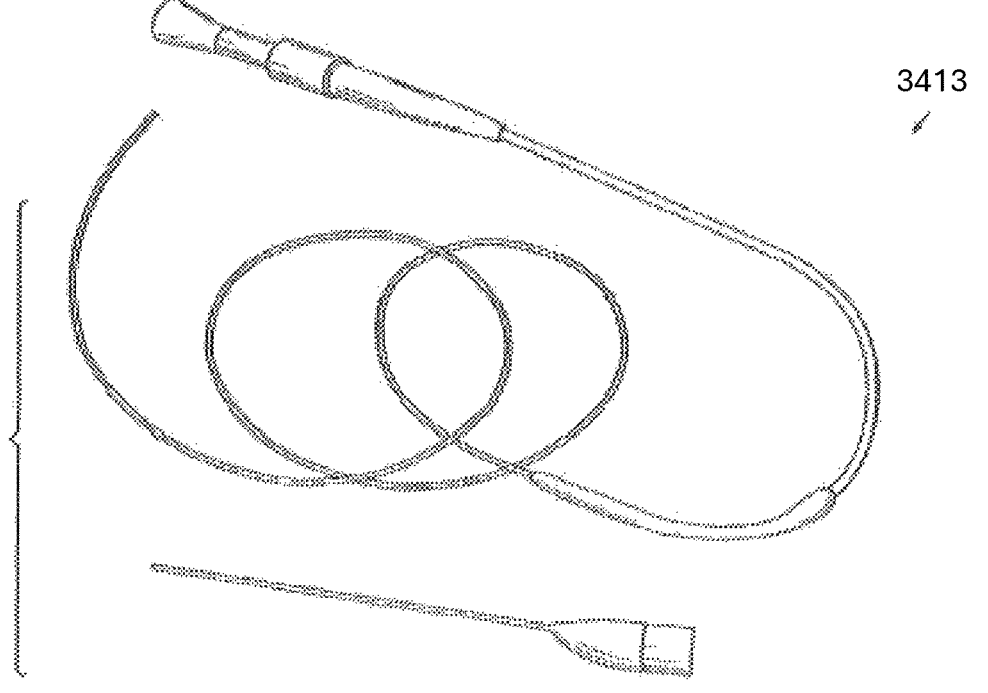

In an alternate preferred embodiment, the ultrasound system ensures accurate vessel localization. FIGS. 34D and 34E illustrate an ultrasound image of vessel walls 3410 in accordance with a preferred embodiment of the system of the present invention and a catheter placement 3412 used with the system. Surgeons can use the ultrasonic system for catheter or line placements for both guidance and confirmation of placement. In preferred embodiments, the image file or raw RF data is directly accessed using a direct digital memory access. Thus, the ultrasound system provides real-time RF data output.

In an alternate embodiment, the ultrasound system of the present invention contributes to accurate surgical planning and imaging by providing neuro-navigation during neurosurgery.

Figures 34F, 34G:
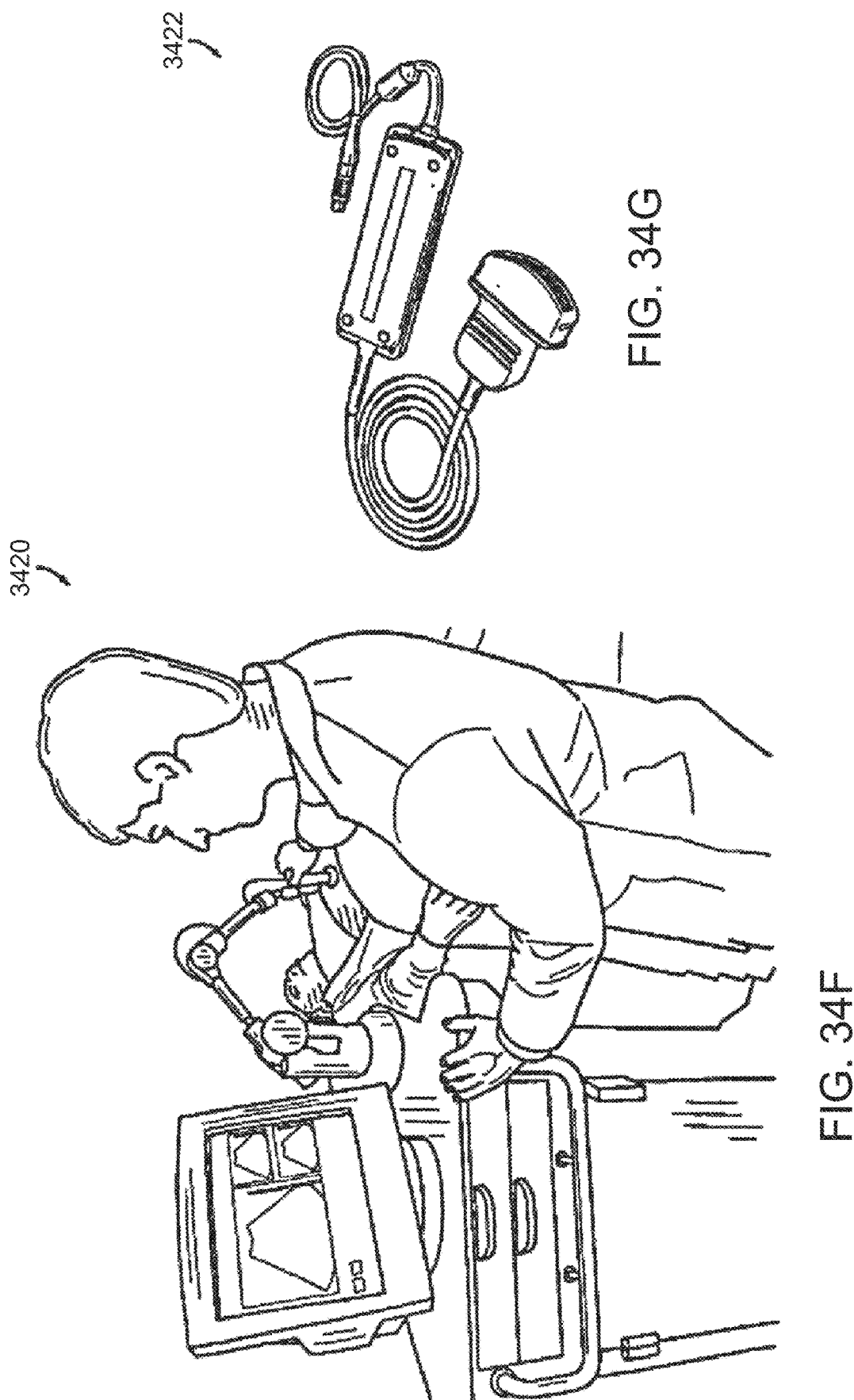
FIGS. 34F and 34G illustrate a radiation planning system integrating the ultrasound system in accordance with preferred embodiments of the present invention and the probe of the ultrasound system, respectively.

In an alternate embodiment, the ultrasound system of the present invention assists in radiation therapy by helping in planning and treatment phases. FIGS. 34F and 34G illustrate a radiation planning system 3420 integrating the ultrasound system in accordance with a preferred embodiment of the present invention and the probe 3422 of the ultrasound system, respectively. The ultrasound image can be integrated in the display.

Figures 34H, 34I:
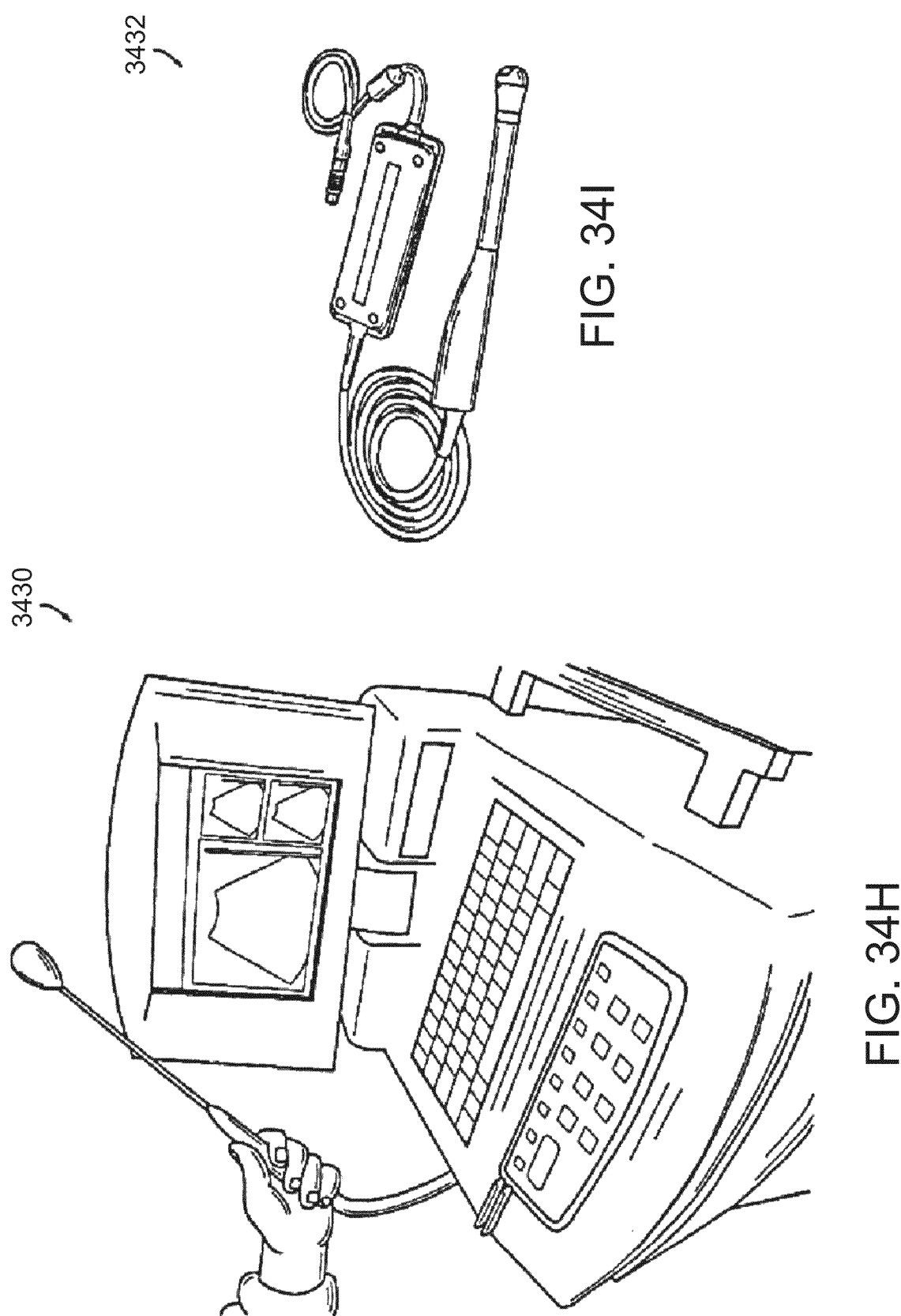
FIGS. 34H and 34I illustrate an ultrasonic imaging system for cryotherapy in accordance with a preferred embodiment of the present invention and a probe used in the system, respectively.

FIGS. 34H and 34I illustrate an ultrasonic imaging system 3430 for cryotherapy in accordance with a preferred embodiment of the present invention and a probe 3432 used in the system, respectively. In prostate cancer patients with limited disease, percutaneous ultrasound-guided cryosurgery applied focally can spare one neurovascular bundle and thus preserve potency without compromising cancer control. The cryotherapy can be used for urological surgery also. Preferred embodiments of the present invention provide multi-plane images with processing instructions that easily switch between planes in real time. At least two orthogonal transducer arrays having 64 or 128 elements can be used.

Figure 34J:
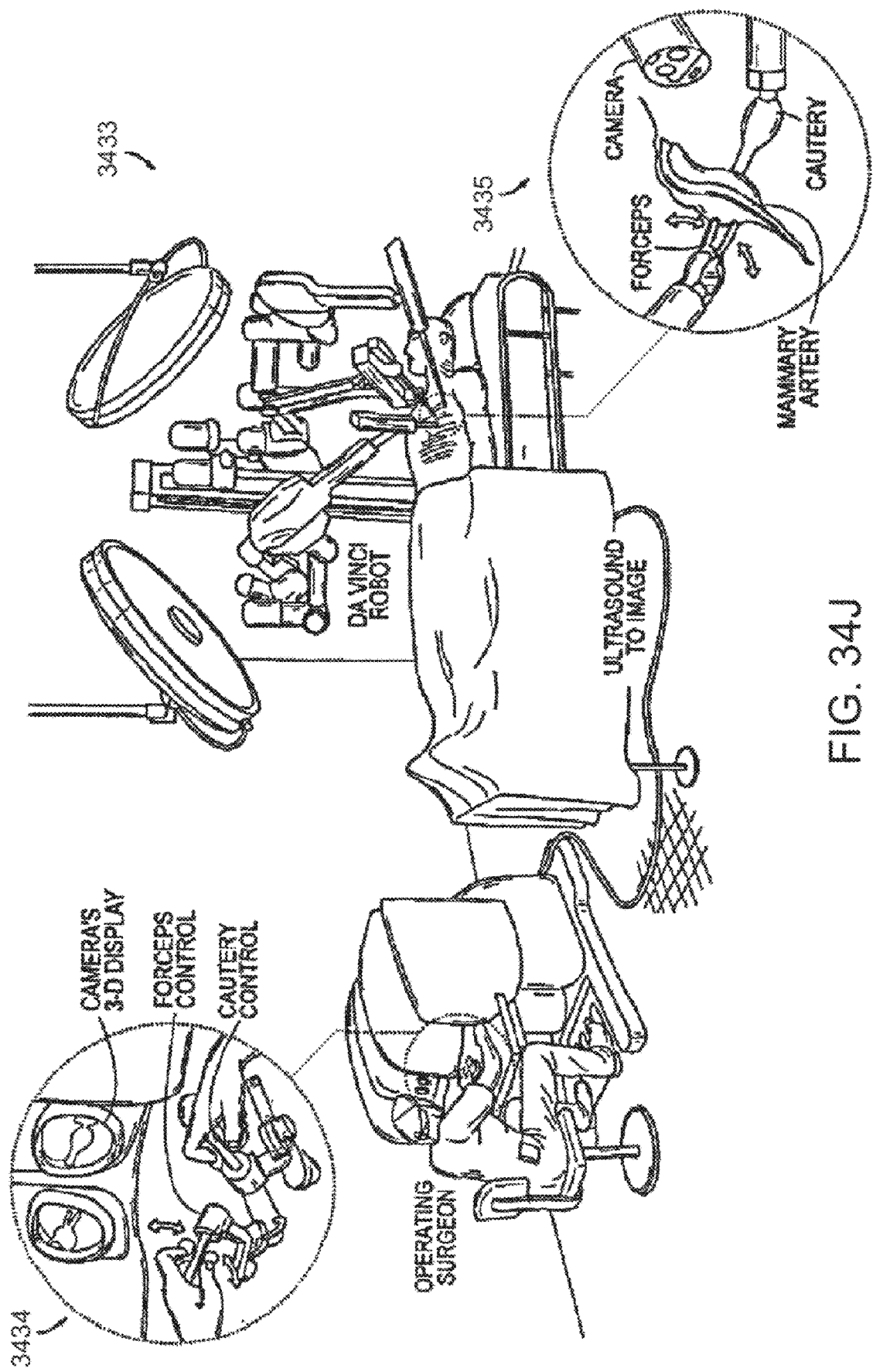
FIG. 34J is a schematic diagram illustrating a robotic imaging and surgical system integrating the ultrasound system in accordance with a preferred embodiment of the present invention.

FIG. 34J is a schematic diagram illustrating a robotic imaging and surgical system 3433 integrating the ultrasound system in accordance with a preferred embodiment of the present invention. The system ensures appropriate vessel harvesting. The operating surgeon uses the ultrasound system to visualize the forceps and cautery controls 3434. The surgeon is seated across the room from the patient and peers into a monitor and manipulates the robot with controls such as, for example, joystick-like hand controls. The robotic arms slip through the small, for example, nickel-size incisions between the ribs. A camera, forceps and a cautery 3435 are used to free up the mammary artery and attach it to the heart. The smaller incisions due to ultrasonic image guided surgery results in lower trauma to patients, less postoperative pain, less patient morbidity and shorter recovery times.

Further, image-guided surgery benefits from the provision of real-time RF data output in accordance with preferred embodiments of the system. In contrast to raw RF data, processed data includes data compression processing which masks differences between bone and tissue. RF data emphasizes the reflectivity and thus the differences between bone and tissue. Thus, the output data from the beamformer can be formatted and provided to enhance surgical imaging. This is enabling for surgeries such as, for example, hip and pelvic replacements.

In addition, computer enhanced image guided surgery further benefits a patient as it combines the dexterity of open surgery with low patient trauma.

In another preferred embodiment, an ultrasound system can be used for pacemaker placement surgery and monitoring. A three-dimensional ultrasound can be integrated into the systems for providing direct access to digital data via a shared memory.

Figure 34K:
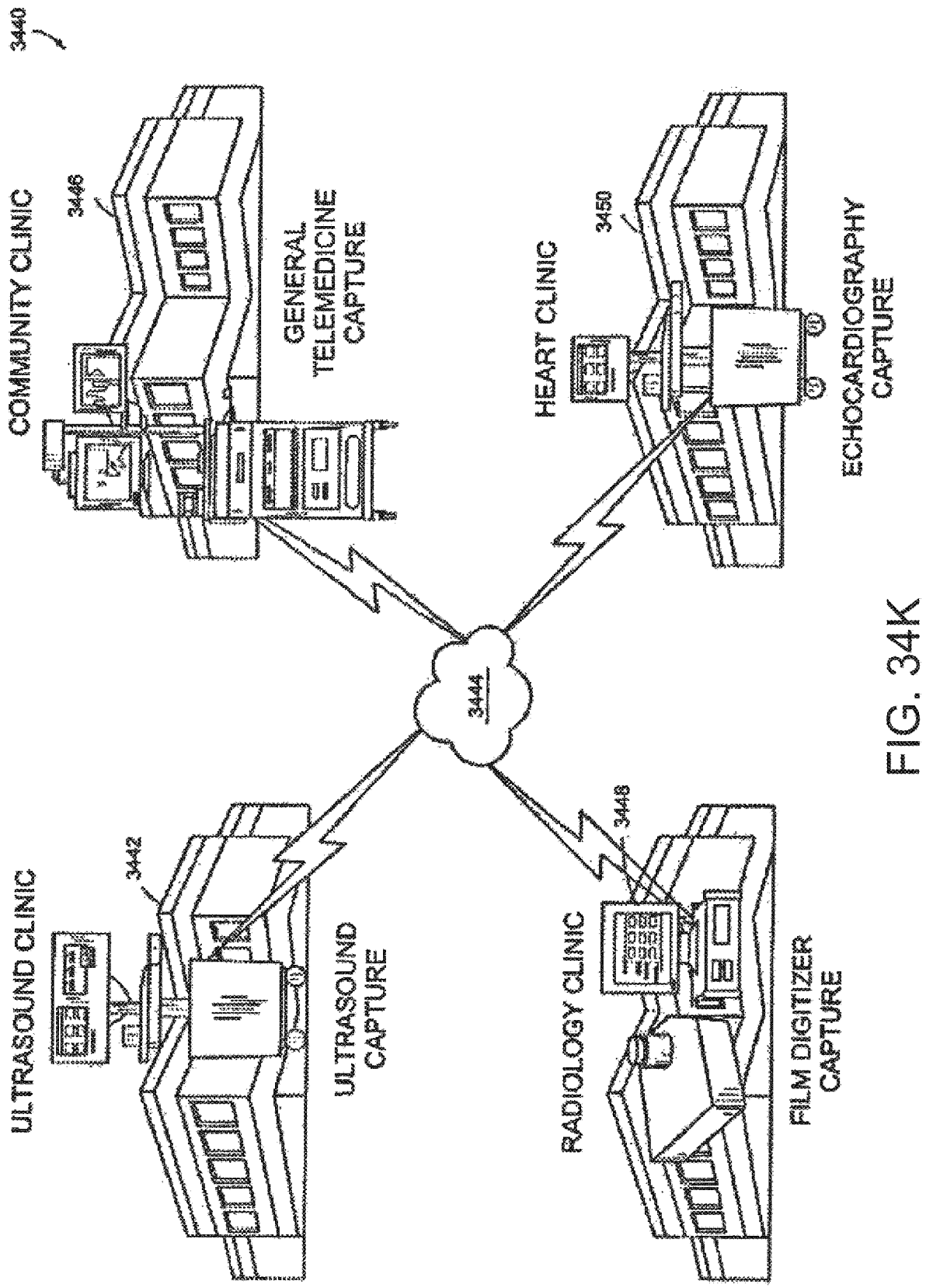
FIG. 34K is a schematic diagram illustrating an imaging and telemedicine system integrating the ultrasound system in accordance with a preferred embodiment of the present invention.

FIG. 34K is a schematic diagram illustrating an imaging and telemedicine system 3440 integrating the ultrasound system in accordance with a preferred embodiment of the present invention. Preferred embodiments of the system output the real-time RF digital data or the front-end data. The system may include an ultrasound clinic 3442 performing ultrasound capture, a community clinic 3446 performing general telemedicine capture, a radiology clinic 3448 performing film digitizer capture and a heart clinic 3450 performing echocardiography capture, that communicate over network 3444.

Figure 35:
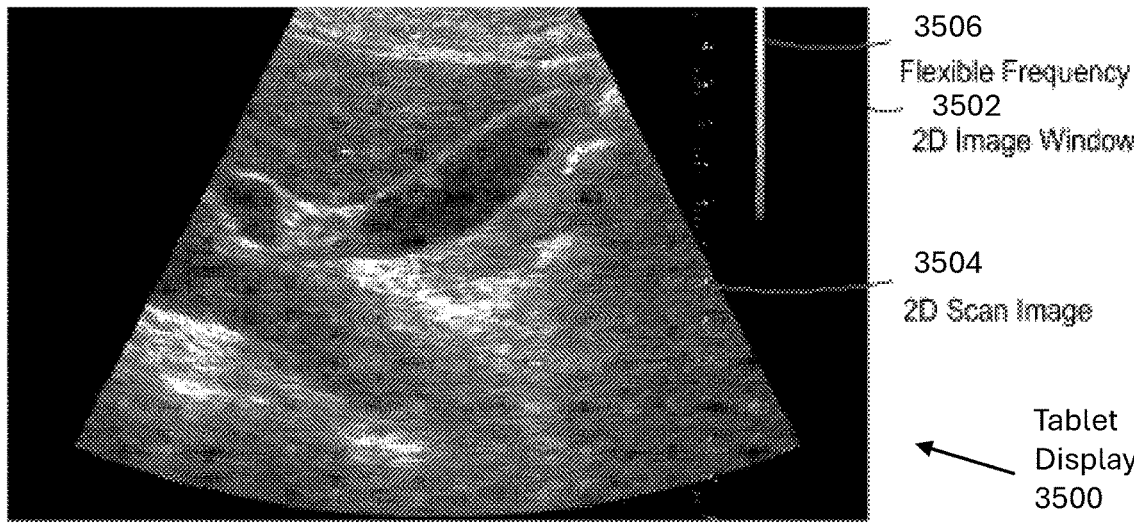
FIG. 35 illustrates a 2D imaging mode of operation with a modular ultrasound imaging system in accordance with the invention.

FIG. 35 illustrates a 2D imaging mode of operation with a modular ultrasound imaging system in accordance with the invention. The touch screen of tablet 3500 may display images obtained by 2-dimensional transducer probe using a 256 digital beamformer channels. The 2-dimensional image window 3502 depicts a 2-dimensional image scan 3504. The 2-dimensional image may be obtained using flexible frequency scans 3506, wherein the control parameters are represented on the tablet.

Figure 36:
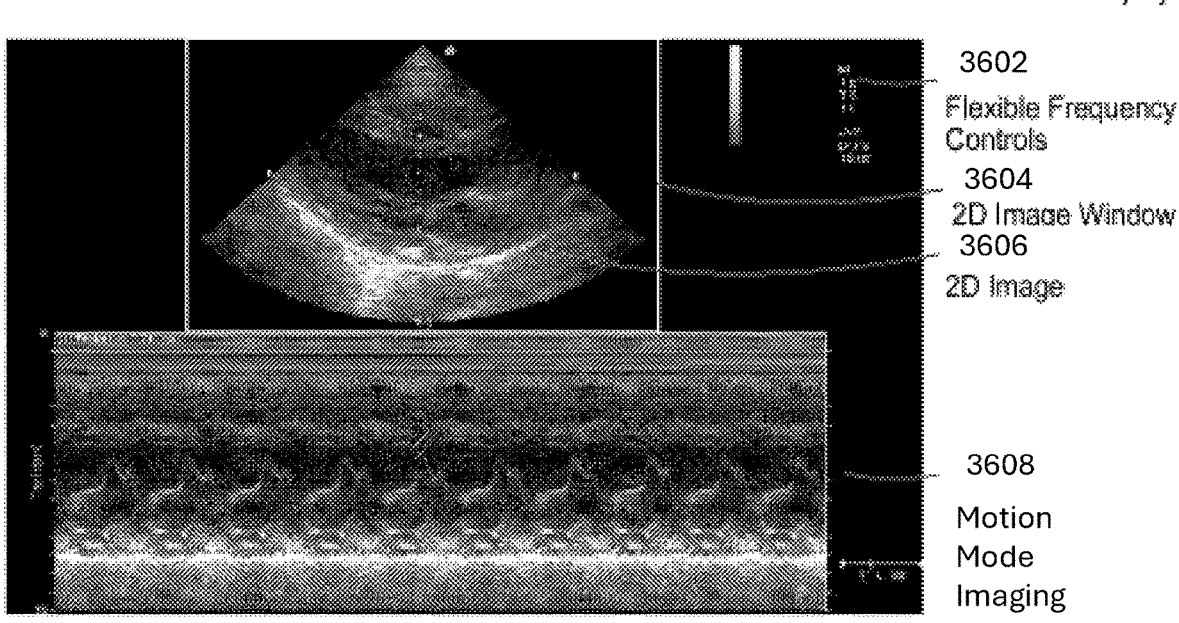
FIG. 36 illustrates a motion mode of operation with a modular ultrasound imaging system in accordance with the invention.

FIG. 36 illustrates a motion mode of operation with a modular ultrasound imaging system in accordance with the invention. The touch screen display of tablet 3600, may display images obtained by a motion mode of operation. The touch screen display of tablet 3600, may simultaneously display 2-dimensional 3606, and motion mode imaging 3608. The touch screen display of tablet 3600, may display a 2-dimensional image window 3604, with a 2-dimensional image 3606. Flexible frequency controls 3602 displayed with the graphical user interface can be used to adjust the frequency from 2 MHz to 12 MHz.

Figures 37, 38:
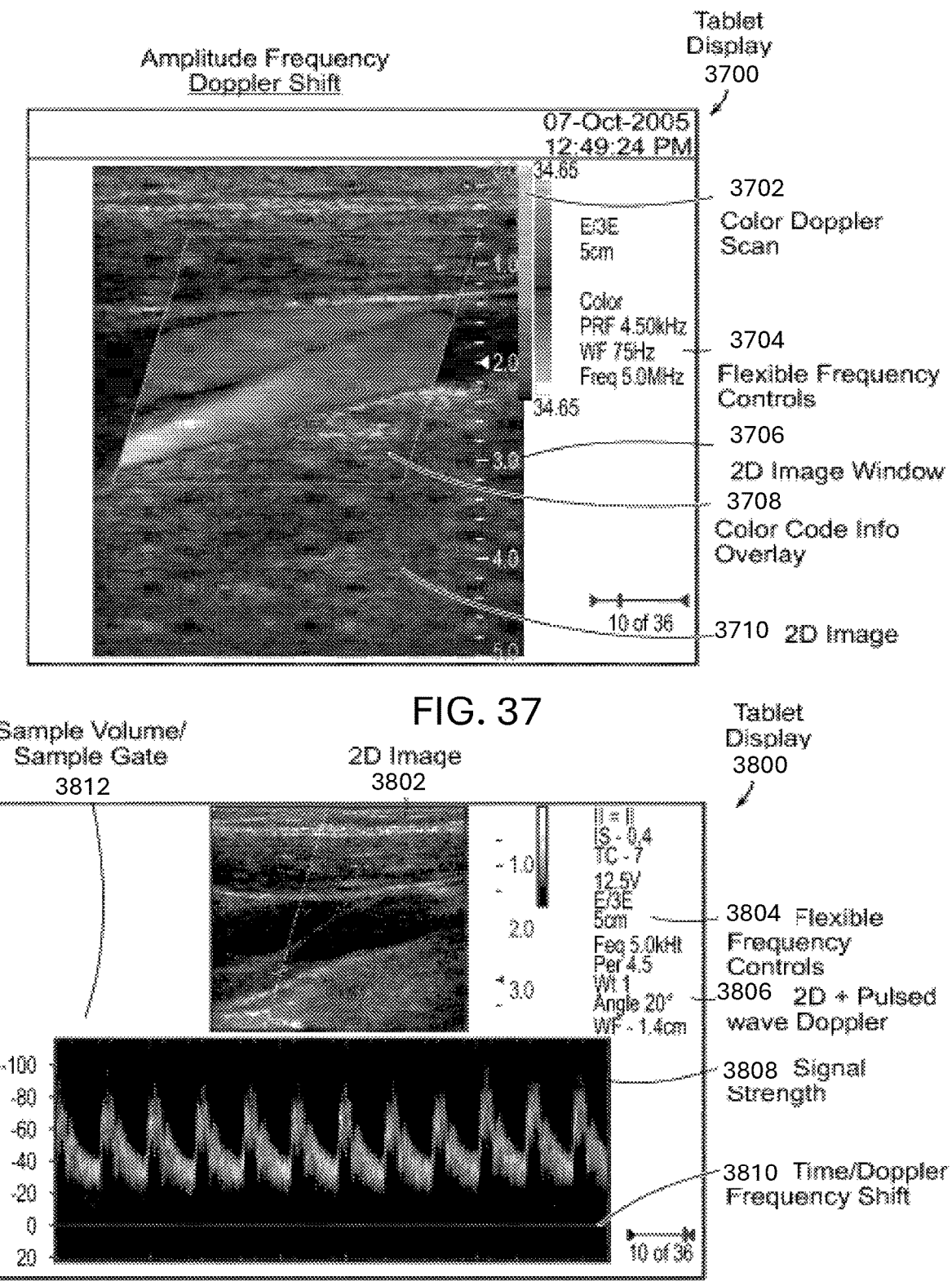
FIG. 37 illustrates a color Doppler mode of operation with a modular ultrasound imaging system in accordance with the invention.
FIG. 38 illustrates a pulsed-wave Doppler mode of operation with a modular ultrasound imaging system in accordance with the invention.

FIG. 37 illustrates a color Doppler mode of operation with a modular ultrasound imaging system in accordance with the invention. The touch screen display of tablet 3700 displays images obtained by color Doppler mode of operation. A 2-dimensional image window 3706 is used as the base display. The color coded information 3708, is overlaid on the 2-dimensional image 3710. Ultrasound-based imaging of red blood cells are derived from the received echo of the transmitted signal. The primary characteristics of the echo signal are the frequency and the amplitude. Amplitude depends on the amount of moving blood within the volume sampled by the ultrasound beam. A high frame rate or high resolution can be adjusted with the display to control the quality of the scan. Higher frequencies may be generated by rapid flow and can be displayed in lighter colors, while lower frequencies are displayed in darker colors. Flexible frequency controls 3704, and color Doppler scan information 3702, may be displayed on the tablet display 3700.

FIG. 38 illustrates a pulsed wave Doppler mode of operation with a modular ultrasound imaging system in accordance with the invention. The touch screen display of tablet 3800, may display images obtained by pulsed wave Doppler mode of operation. Pulsed wave Doppler scans produce a series of pulses used to analyse the motion of blood flow in a small region along a desired ultrasound cursor called the sample volume or sample gate 3812. The tablet display 3800 may depict a 2-dimensional image 3802, wherein the sample volume/sample gate 3812 is overlaid. The tablet display 3800 may use a mixed mode of operation 3806 to depict a 2-dimensional image 3802 and a time/Doppler frequency shift 3810. The time/Doppler frequency shift 3810 can be converted into velocity and flow if an appropriate angle between the beam and blood flow is known. Shades of gray in the time/Doppler frequency shift 3810 may represent the strength of signal 3808. The thickness of the spectral signal may be indicative of laminar or turbulent flow. The tablet display 3800 can depict adjustable frequency controls 3804.

Figure 39:
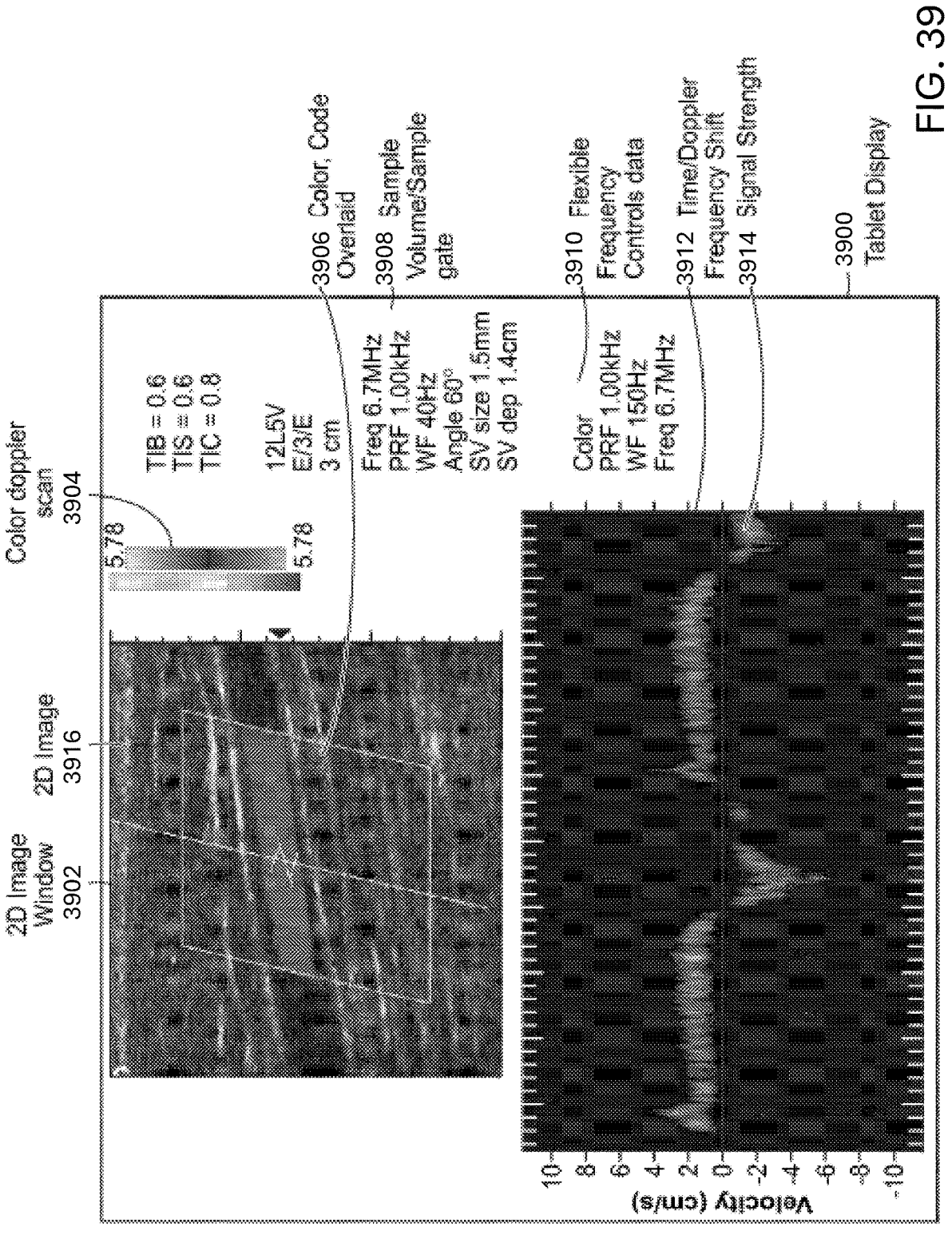
FIG. 39 illustrates a Triplex scan mode of operation with a modular ultrasound imaging system in accordance with the invention.

FIG. 39 illustrates a triplex scan mode of operation with a modular ultrasound imaging system in accordance with the invention. The tablet display 3900 may include a 2-dimensional window 3902, capable of displaying 2-dimensional images alone or in combination with the color Doppler or directional Doppler features. The touch screen display of tablet 3900, may display images obtained by color Doppler mode of operation. A 2-dimensional image window 3902 is used as the base display. The color coded information 3904 is overlaid 3906 on the 2-dimensional image 3916. The pulsed wave Doppler feature may be used alone or in combination with 2-dimensional imaging or the color Doppler imaging. The tablet display 3900 may include a pulsed wave Doppler scan represented by a sample volume/sample gate 3908 overlaid over 2 dimensional image 3916 or the color code overlaid 3906, either alone or in combination. The tablet display 3900 may depict a split screen representing the time/Doppler frequency shift 3912. The time/Doppler frequency shift 3912 can be converted into velocity and flow if an appropriate angle between the insolating beam and blood flow is known. Shades of gray in the time/Doppler frequency shift 3912 may represent the strength of signal 3914. The thickness of the spectral signal may be indicative of laminar or turbulent flow. The tablet display 3900 also may depict flexible frequency controls 3910.

Figure 40:
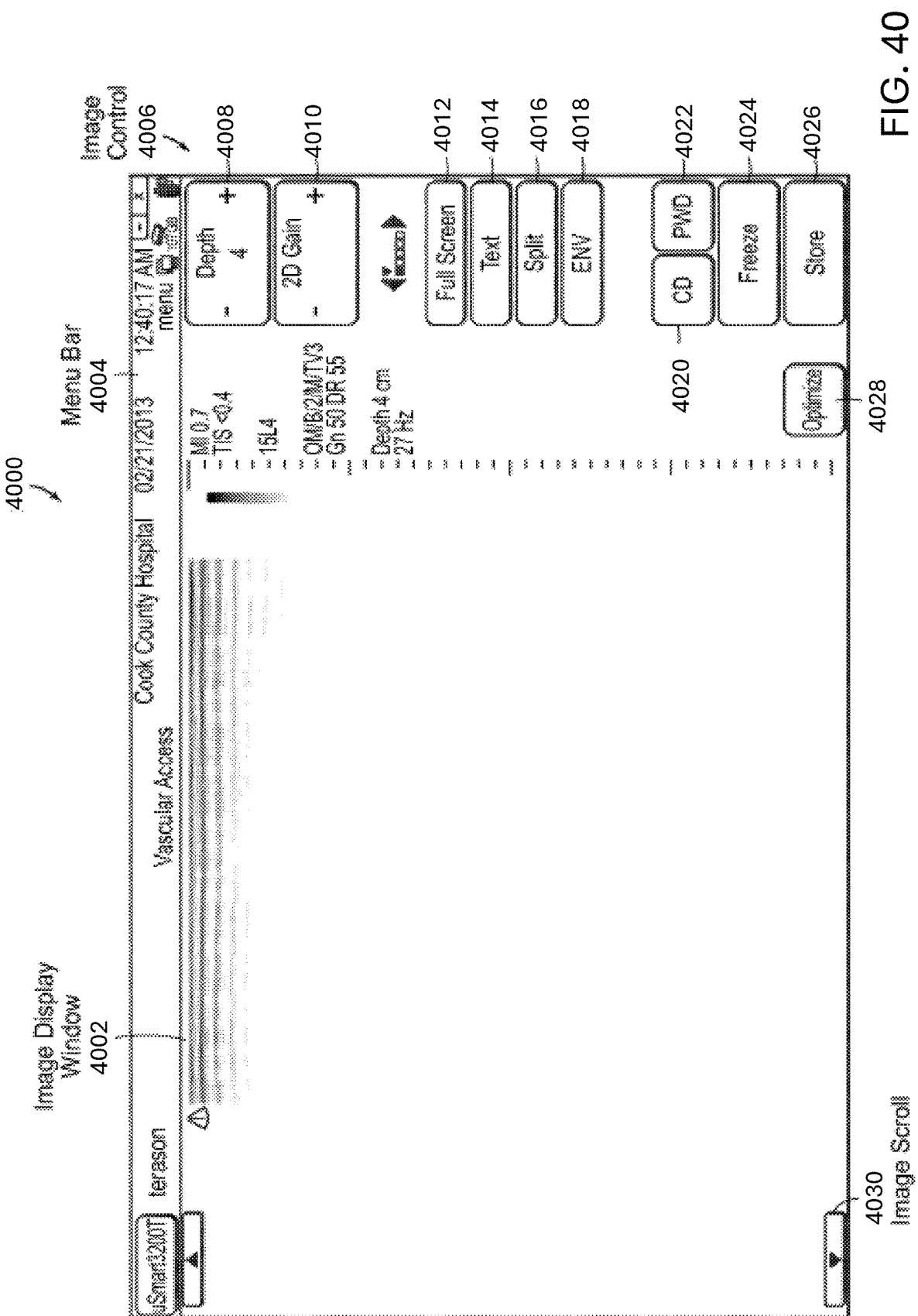
FIG. 40 illustrates a GUI Home Screen interface for a user mode of operation with a modular ultrasound imaging system in accordance with the invention.

FIG. 40 illustrates a GUI home screen interface 4000 for a user mode of operation with a modular ultrasound imaging system in accordance with the invention. The screen interface 4000 for a user mode of operation may be displayed when the ultrasound system is started. To assist a user in navigating the GUI home screen 4000, the home screen may be considered as including three exemplary work areas: a menu bar 4004, an image display window 4002, and an image control bar 4006. Additional GUI components may be provided on the main GUI home screen 4000, to enable a user to close, resize and exit the GUI home screen and/or windows in the GUI home screen.

The menu bar 4004 enables users to select ultrasound data, images and/or video for display in the image display window 4002. The menu bar may include components for selecting one or more files in a patient folder directly and an image folder directory.

The image control bar 4006 includes touch controls that may be operated by touch and touch gestures applied by the user directly to the surface of the display. Exemplary touch controls may include, but are not limited to a depth control touch controls 4008, a 2-dimensional gain touch control 4010, a full screen touch control 4012, a text touch control 4014, a split screen touch control 4016, a ENV touch control 4018, a CD touch control 4020, a PWD touch control 4022, a freeze touch control 4024, a store touch control 4026, and a optimize touch control 4028. The image display window may also include an image scroll control 4030. As noted above, cine/time-series image clip scrolling control is provided by embodiments and operational modes and/or functions related thereto may be controlled by specific single point/multipoint gestures on the surface of the touch screen display.

Figure 41:
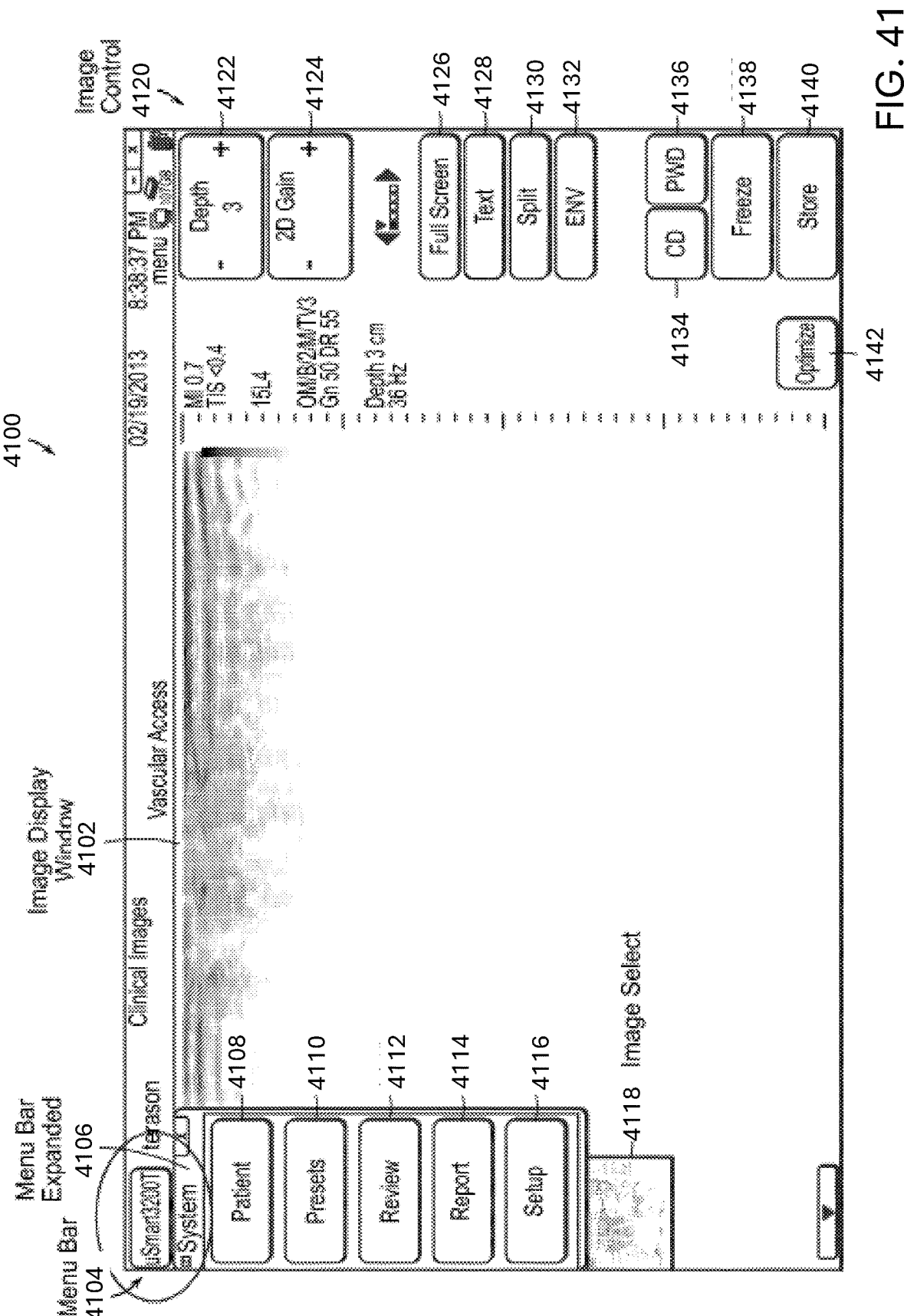
FIG. 41 illustrates a GUI Menu Screen Interface for a user mode of operation with a modular ultrasound imaging system in accordance with the invention.

FIG. 41 illustrates a GUI menu screen interface 4100 for a user mode of operation with a modular ultrasound imaging system in accordance with the invention. The screen interface 4100 for a user mode of operation may be displayed when the menu selection mode is triggered from the menu bar 4104 thereby initiating ultrasound system. To assist a user in navigating the GUI home screen 3100, the home screen may be considered as including three exemplary work areas: a menu bar 4104, an image display window 4102, and an image control bar 4120. Additional GUI components may be provided on the main GUI menu screen 4100 to, for example enable a user to close, resize and exit the GUI menu screen and/or windows in the GUI menu screen.

The menu bar 4104 enables users to select ultra sound data, images and/or video for display in the image display window 4102. The menu bar 4104 may include touch control components for selecting one or more files in a patient folder directory and an image folder directory. Depicted in an expanded format, the menu bar may include exemplary touch control such as, a patient touch control

4108, a pre-sets touch control 4110, a review touch control 4112, a report touch control 4114, and a setup touch control 4116.

The image control bar 4120 includes touch controls that may be operated by touch and touch gestures applied by the user directly to the surface of the display. Exemplary touch controls may include, but are not limited to a depth control touch controls 4122, a 2-dimensional gain touch control 4124, a full screen touch control 4126, a text touch control 4128, a split screen touch control 4130, a needle visualization ENV touch control 4132, a CD touch control 4134, a PWD touch control 4136, a freeze touch control 4138, a store touch control 4140, and a optimize touch control 4142.

Figure 42:
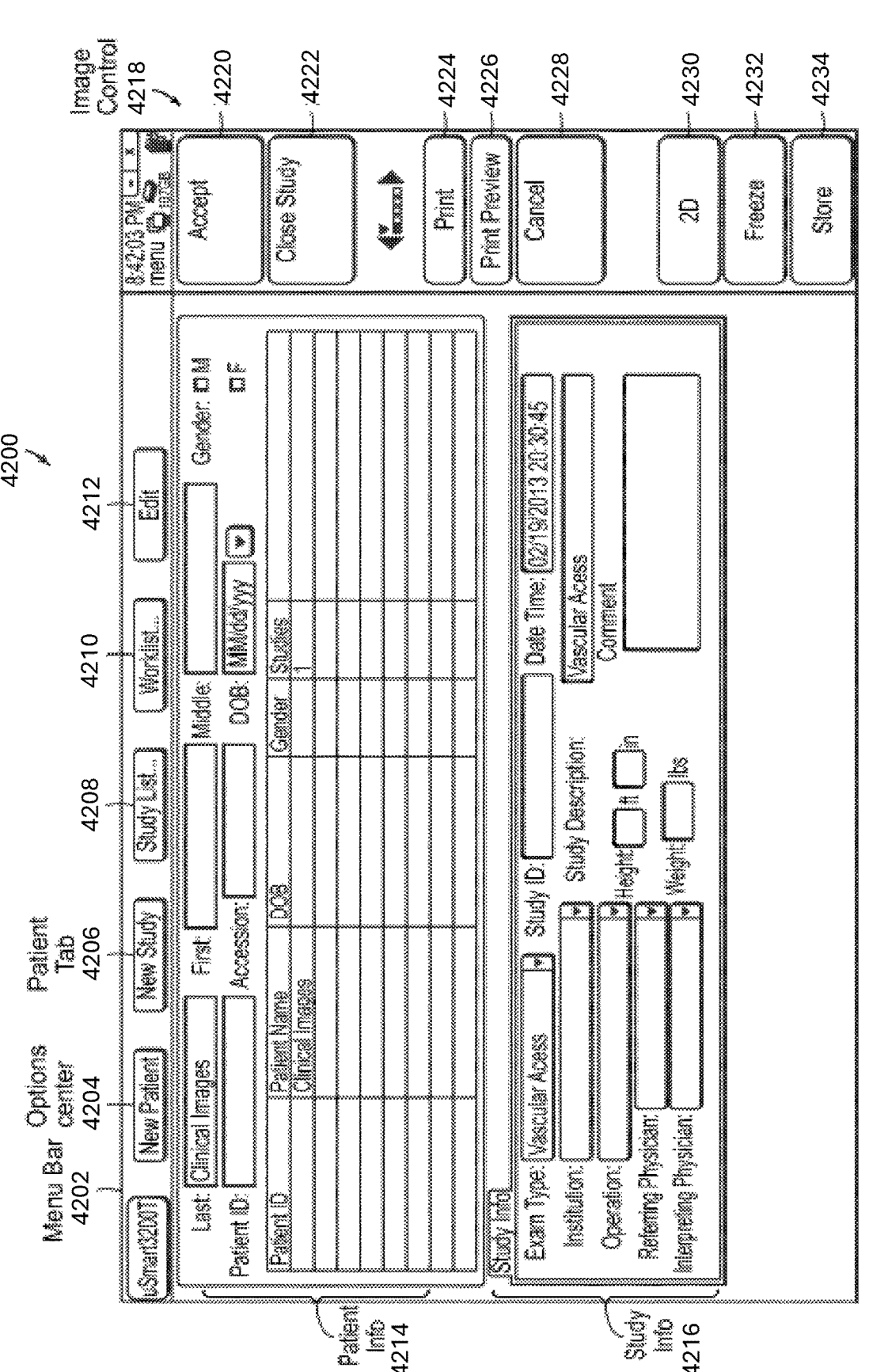
FIG. 42 illustrates a GUI Patient Data Screen Interface for a user mode of operation with a modular ultrasound imaging system in accordance with the invention.

FIG. 42 illustrates a GUI patient data screen interface 4200, for a user mode of operation, with a modular ultrasound imaging system in accordance with the invention. The screen interface for a user mode of operation 4200 may be displayed when the patient selection mode is triggered from the menu bar 4202, when the ultrasound system is started. To assist a user in navigating the GUI patient data screen 4200, the patient data screen may be considered as including five exemplary work areas: a new patient touch screen control 4204, a new study touch screen control 4206, a study list touch screen control 4208, a work list touch screen control 4210, and a edit touch screen control 4212. Within each touch screen control, further information entry fields are available 4214, 4216. For example, patient information section 4214, and study information section 4216, may be used to record data.

Within the patient data screen 4200, the image control bar 4218, includes touch controls that may be operated by touch and touch gestures applied by the user directly to the surface of the display. Exemplary touch controls may include, but are not limited to accept study touch control 4220, close study touch control 4222, print touch control 4224, print preview touch control 4226, cancel touch control 4228, a 2-dimensional touch control 4230, freeze touch control 4232, and a store touch control 4234.

Figure 43:
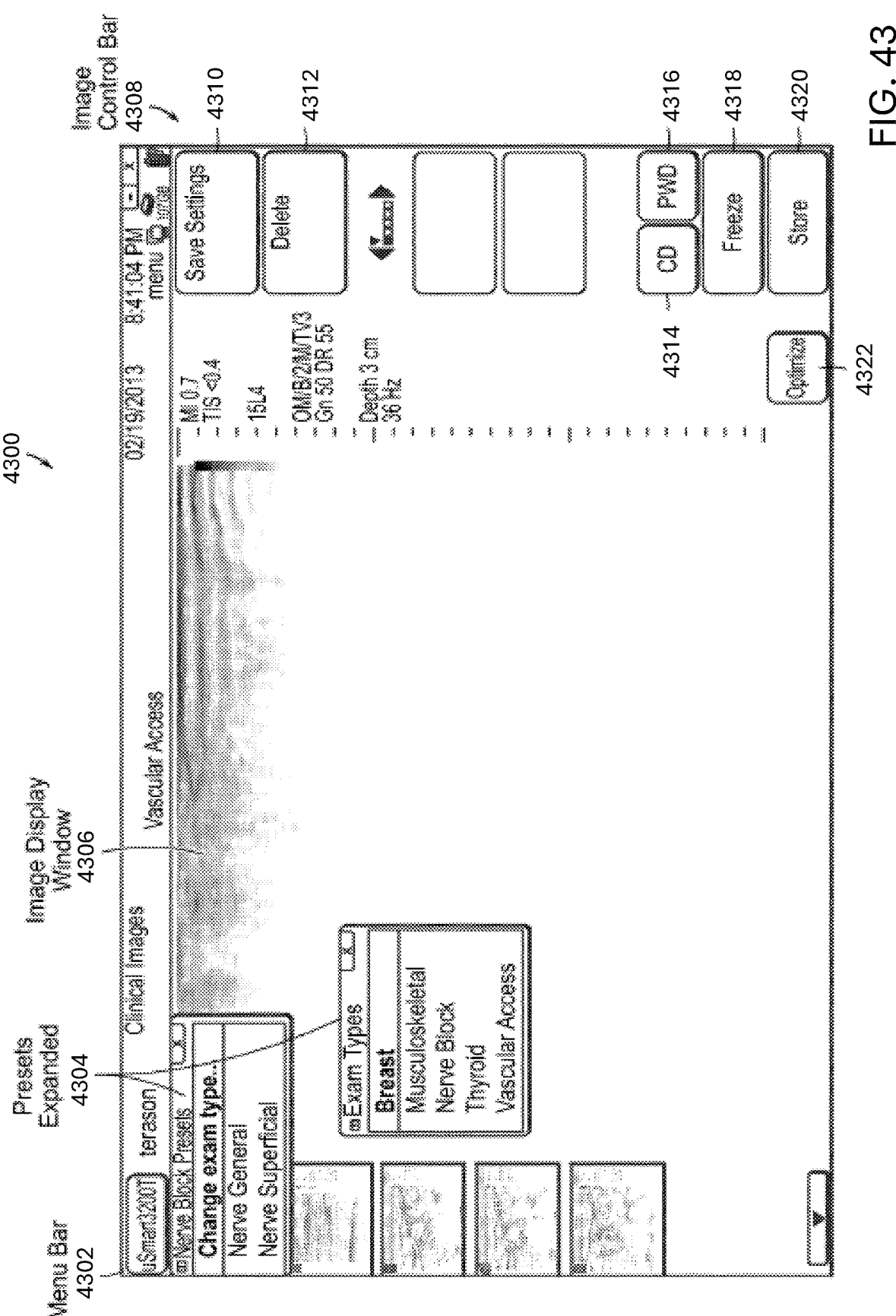
FIG. 43 illustrates a GUI Pre-sets Screen Interface for a user mode of operation with a modular ultrasound imaging system in accordance with the invention.

FIG. 43 illustrates a GUI patient data screen interface 4300, for a user mode of operation, with a modular ultrasound imaging system in accordance with the invention. The screen interface for a user mode of operation 4300 may be displayed when the pre-sets selection mode 4304 is triggered from the menu bar 4302 when the ultrasound system is started.

Within the pre-sets screen 4300, the image control bar 4308, includes touch controls that may be operated by touch and touch gestures applied by the user directly to the surface of the display. Exemplary touch controls may include, but are not limited to a save settings touch control 4310, a delete touch control 4312, CD touch control 4314, PWD touch control 4316, a freeze touch control 4318, a store touch control 4320, and a optimize touch control 4322.

Figure 44:
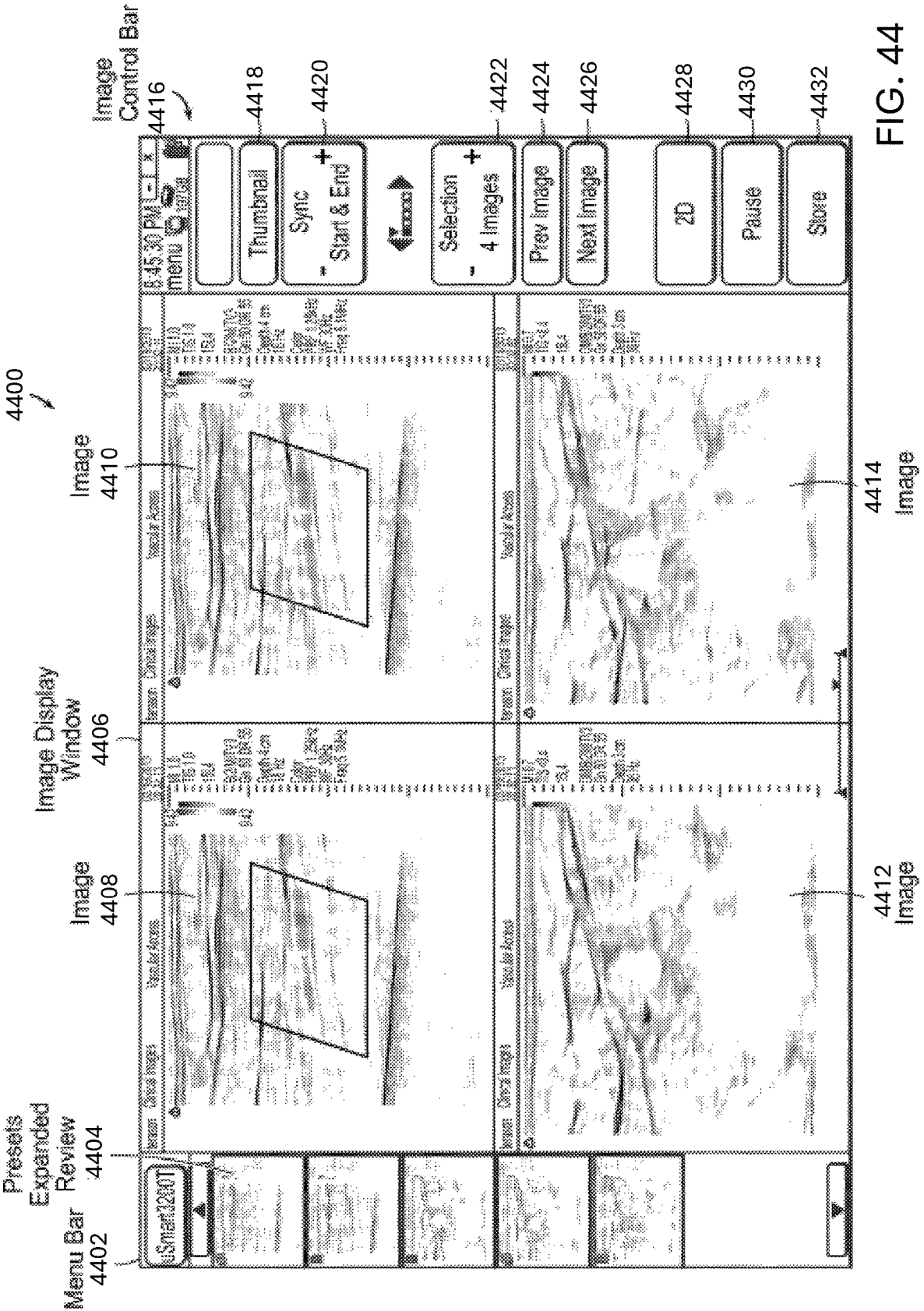
FIG. 44 illustrates a GUI Review Screen Interface for a user mode of operation with a modular ultrasound imaging system in accordance with the invention.

FIG. 44 illustrates a GUI review screen interface 4400 for a user mode of operation, with a modular ultrasound imaging system in accordance with the invention. The screen interface for a user mode of operation 4400 may be displayed when the pre-sets expanded review 4404, selection mode, is triggered from the menu bar 4402, when the ultrasound system is started.

Within the review screen 4400, the image control bar 4416, includes touch controls that may be operated by touch and touch gestures applied by the user directly to the surface of the display. Exemplary touch controls may include, but are not limited to a thumbnail settings touch control 4418, sync touch control 4420, selection touch control 4422, a previous image touch control 4424, a next image touch control 4426, a 2-dimensional image touch control 4428, a pause image touch control 4430, and a store image touch control 4432.

An image display window 4406, may allow the user to review images in a plurality of formats. Image display window 4406, may allow a user to view images 4408, 4410, 4412, 4414, in combination or subset or allow any image, to be viewed individually. The image display window 4406 may be configured to display up to four images 4408, 4410, 4412, 4414, to be viewed simultaneously.

Figure 45:
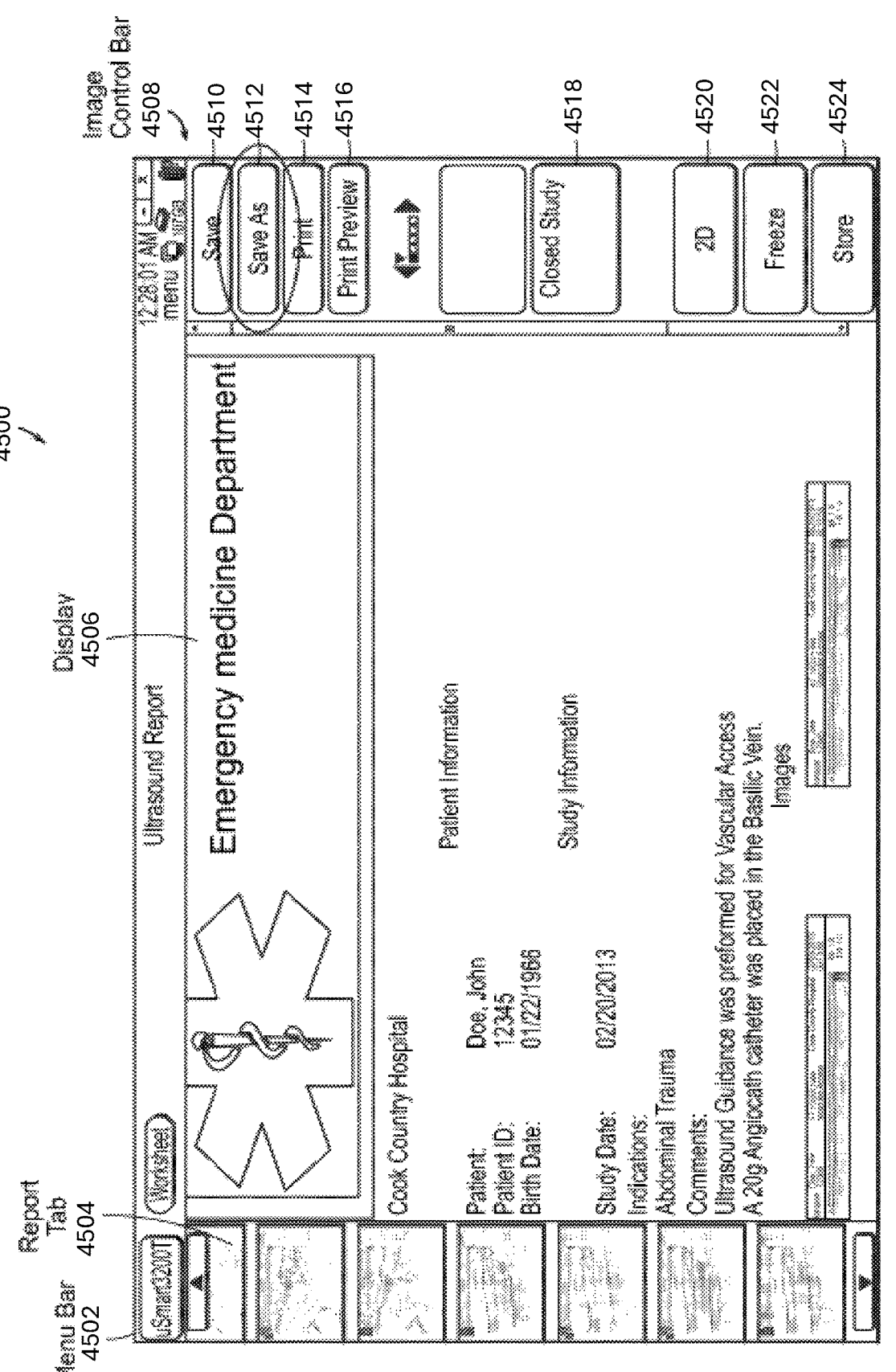
FIG. 45 illustrates a GUI Report Screen Interface for a user mode of operation with a modular ultrasound imaging system in accordance with the invention.

FIG. 45 illustrates a GUI Report Screen Interface 4500 for a user mode of operation with a modular ultrasound imaging system in accordance with the invention. The screen interface 4500 for a user mode of operation may be displayed when the report expanded review 4504, is triggered from the menu bar 4502, when the ultrasound system is started. The display screen 4506 contains the ultrasound report information 4526. The user may use the worksheet section within the ultrasound report 4526, to enter in comments, patient information and study information.

Within the report screen 4500, the image control bar 4508, includes touch controls that may be operated by touch and touch gestures applied by the user directly to the surface of the display. Exemplary touch controls may include, but are not limited to a save touch control 4510, a save as touch control 4512, a print touch control 4514, a print preview touch control 4516, a close study touch control 4518, a 2-dimensional image touch control 4520, a freeze image touch control 4522, and a store image touch control 4524.

Figure 46A:
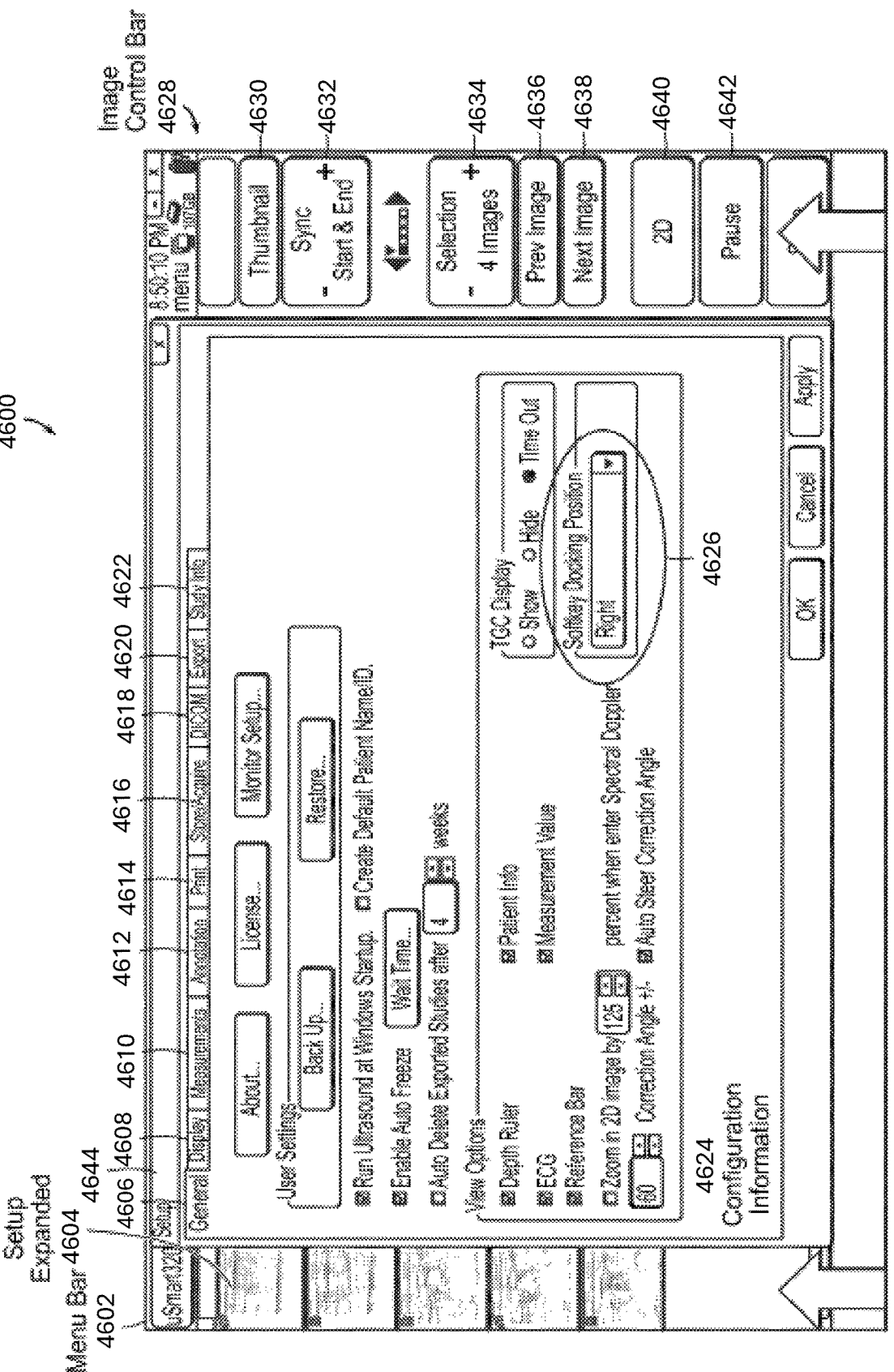
FIGS. 46A-46C illustrate a GUI Setup Display Screen Interface for a user mode of operation with a modular ultrasound imaging system in accordance with the invention.

FIG. 46A illustrates a GUI Setup Screen Interface for a user mode of operation with a modular ultrasound imaging system in accordance with the invention. The screen interface for a user mode of operation 4600 may be displayed when the report expanded review 4604, is triggered from the menu bar 4602, when the ultrasound system is started.

Figure 46B:
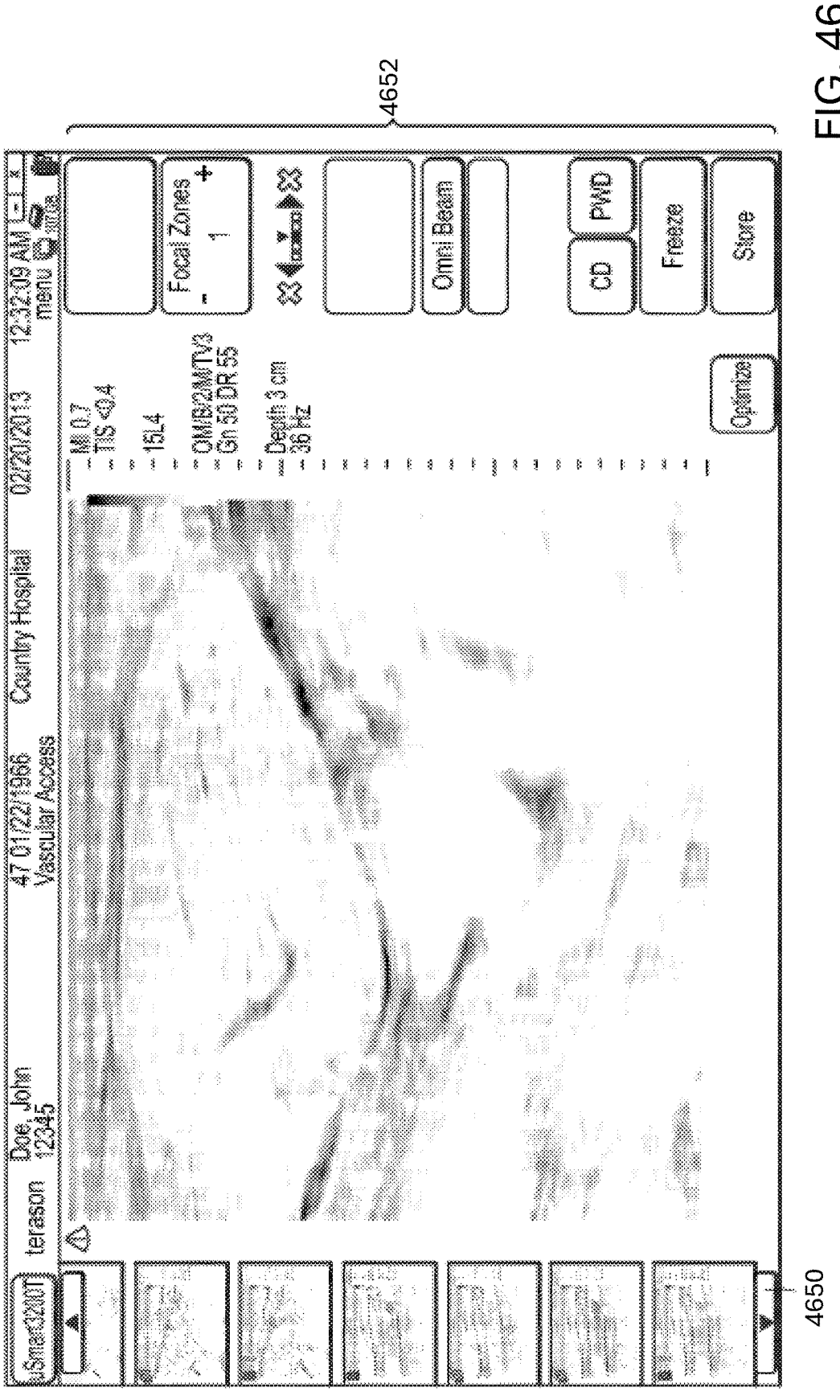
Figure 46C:
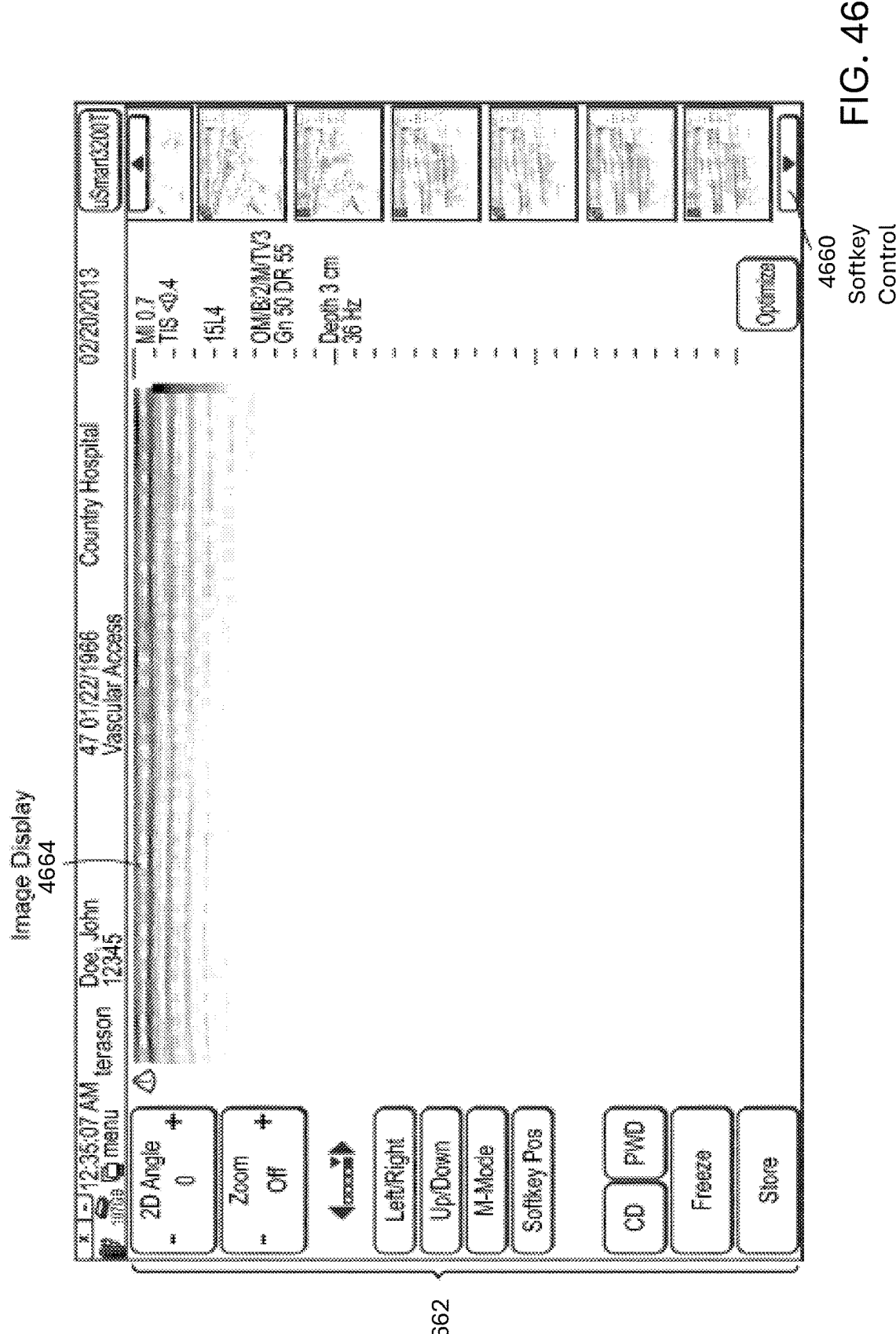

Within the setup expanded screen 4604, the setup control bar 4644, includes touch controls that may be operated by touch and touch gestures, applied by the user directly to the surface of the display. Exemplary touch controls may include, but are not limited to a general touch control 4606, a display touch control 4608, a measurements touch control 4610, annotation touch control 4612, a print touch control 4614, a store/acquire touch control 4616, a DICOM touch control 4618, a export touch control 4620, and a study info image touch control 4622. The touch controls may contain display screens that allow the user to enter configuration information. For example, the general touch control 4606 contains a configuration screen 4624, wherein the user may enter configuration information. Additionally, the general touch control 4606 contains a section allowing user configuration of the soft key docking position 4626. FIG. 46B depicts the soft key controls 4652, with a right side alignment. The figure further illustrates that activation of the soft key control arrow 4650, will change the key alignment to the opposite side, in this case, left side alignment. FIG. 46C depicts left side alignment of the soft key controls 4662; the user may activate an orientation change by using the soft key control arrow 4660 to change the position to right side alignment.

Within the review screen 4600, the image control bar 4628, includes touch controls that may be operated by touch and touch gestures applied by the user directly to the surface of the display. Exemplary touch controls may include but are not limited to, a thumbnail settings touch control 4630, sync touch control 4632, selection touch control 4634, a previous image touch control 4636, a next image touch control 4638, a 2-dimensional image touch control 4640, and a pause image touch control 4642.

Figure 47:
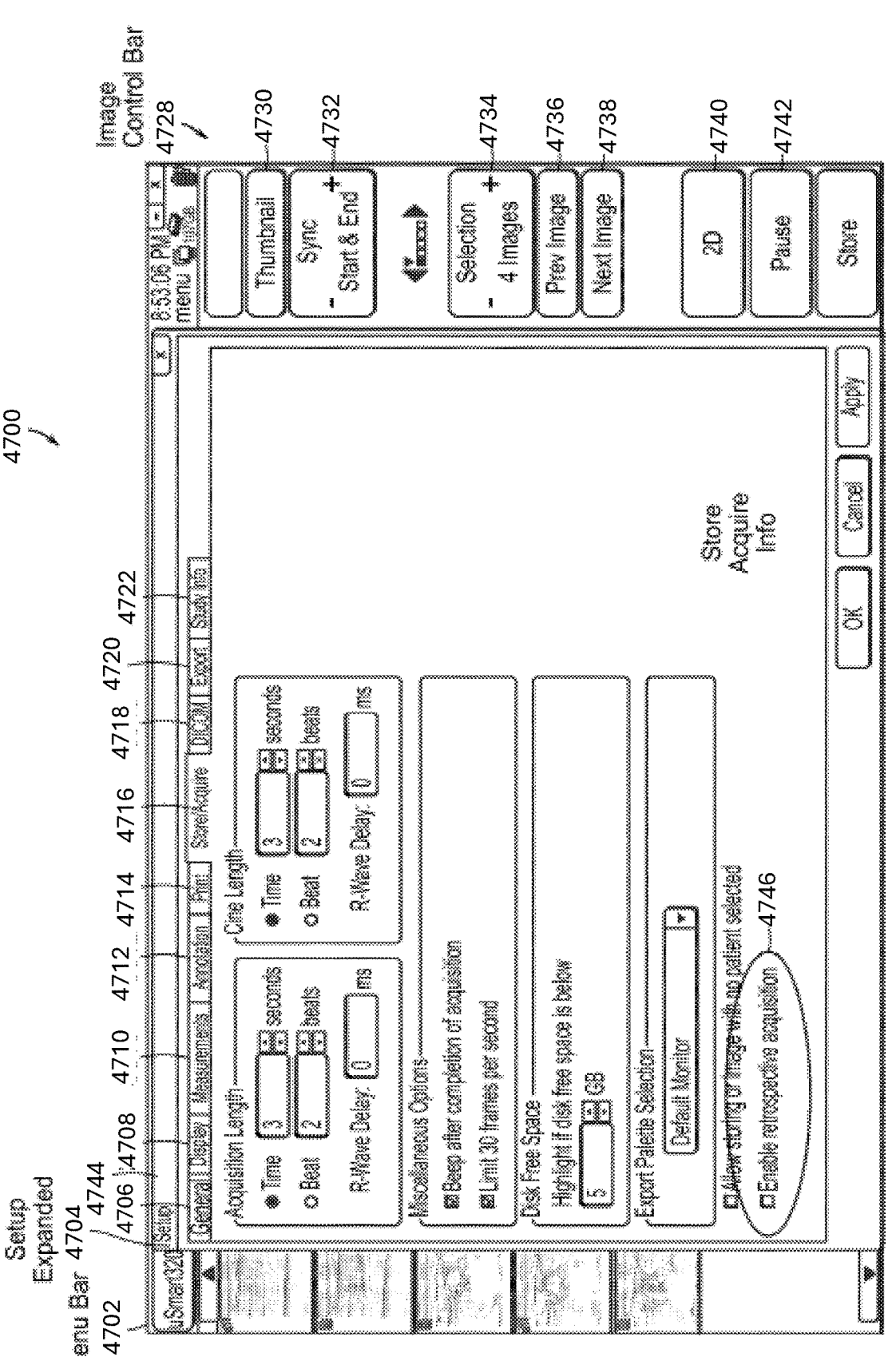
FIG. 47 illustrates a GUI Setup Store/Acquire Screen Interface for a user mode of operation with a modular ultrasound imaging system in accordance with the invention.

FIG. 47 illustrates a GUI Setup Screen Interface 4700 for a user mode of operation with a modular ultrasound imaging system in accordance with the invention. The screen interface 4700 for a user mode of operation 4700 may be displayed when the setup expanded screen 4704 is triggered from the menu bar 4702 when the ultrasound system is started.

Within the setup expanded screen 4704, the setup control bar 4744, includes touch controls that may be operated by touch and touch gestures applied by the user directly to the surface of the display. Exemplary touch controls may include, but are not limited to, a general touch control 4706, a display touch control 4708, a measurements touch control 4710, annotation touch control 4712, a print touch control 4714, a store/acquire touch control 4716, a DICOM touch control 4718, an export touch control 4720, and a study info image touch control 4722. The touch controls may contain display screens that allow the user to enter store/acquire information. For example, the store/acquire touch control 4716, contains a configuration screen 4702, wherein the user may enter configuration information. Additionally, the store/ acquire touch control 4716, contains a section allowing user enablement of retrospective acquisition. When the user enables the store function, the system is defaulted to store prospective cine loops. If the user enables the enable retrospective capture, the store function may collect the cine loop retrospectively.

Within the setup screen 4700, the image control bar 4728, includes touch controls that may be operated by touch and touch gestures applied by the user directly to the surface of the display. Exemplary touch controls may include, but are not limited to a thumbnail settings touch control 4730, sync touch control 4732, selection touch control 4734, a previous image touch control 4736, a next image touch control 4738, a 2-dimensional image touch control 4740, and a pause image touch control 4742.

A preferred embodiment of the microminiaturized PC enabled ultrasound imaging system runs on an industry standard PC and Windows® 2000 operating system (OS). It is therefore network ready which makes it ideal for telemedicine solutions while being cost efficient. It provides open architecture support embedded and thus integrated with third party applications. The preferred embodiment includes an enhanced Application Programming Interface (API), common interface, export support for third party applications, such as, but not limited to, for example, radiation therapy planning, image guided surgery, integrated solutions, for example, calculations, three-dimensional and reporting packages. The API provides a set of software interrupts, calls, and data formats that application programs use to initiate contact with network services, mainframe communication programs, telephone equipment or program-to-program communications. Software based feature enhancements reduce hardware obsolescence and provide efficient upgrades.

Further, the preferred embodiment includes system-on-chip integrated circuits (ICs) which run on PCs and have a large channel count, large dynamic range, high image quality, full feature sets, broad diagnostic coverage, minimal supply chain requirements, simplified design for easy testing and high reliability, and very low maintenance costs.

As previously described herein, the preferred embodiment includes a PC-based design which is intuitive, has a simple graphical user interface, is easy to use and train with, which leverages PC industry know-how, robust electronics, high quality displays and low manufacturing costs. It also provides support of software controlled communications with other applications, which are embedded applications that allows patient data, scanner image, Current Procedural Terminology (CPT) code management, which is a numeric coding system by which physicians record their procedures and services, physician's plan and outcome assessment reports, all on an integrated PC. The reforms to the health care system have been applying pressure to lower costs, highlight the need for first visit/in-field diagnosis, data storage and retrieval solutions which when combined with technology innovations such as, for example, data storage and retrieval based on the Digital Imaging and Communications in Medicine (DICOM) standard, broadband and Picture Archiving and Communications Systems (PACS) drives, changes in patient record storage and retrieval and transmission, innovations in lower cost/handheld devices for ultrasound data acquisition, all which enable the preferred embodiment of the present invention. The DICOM standard aids the distribution and viewing of medical images such as, for example, ultrasound, Magnetic Resonance Images (Mills), and CT scans. Broadband is a wide area network term that refers to a transmission facility providing bandwidth greater than 45 Mbps. Broadband systems are generally fiber optic in nature.

A preferred embodiment of the present invention provides image acquisition and end-user application, for example, radiation therapy, surgery, angiography, all applications executed on the same platform. This provides low cost, user friendly controls through a common software interface. The ultrasound system has scalable user interfaces for advanced users and has an intuitive Windows® based PC interface. A preferred embodiment of the ultrasound system also provides an enhanced diagnostic ability due to the features of one-stop image capture, analysis, storage, retrieval and transmittal capability for the data and images. A high image quality is provided by a 128 channel bandwidth. Besides ease of use, the ultrasound system also provides patient access at any time, any location and using any tool. Point of care imaging is provided with a 10 ounce probe in accordance with a preferred embodiment of the present invention. The data storage and retrieval abilities are based on the DICOM standard and are compatible with off-the-shelf third party analytical and patient record systems. The ultrasound system in accordance with a preferred embodiment also provides immediate image transfer ability using, but not limited to, for example, electronic mail, LAN/WAN, DICOM and Digital Imaging Network—Picture Archiving and Communications Systems (DINPACs). The choices to display the images captured include, but are not limited to, a desktop computer, a laptop computer, wearable personal computers and handheld devices such as personal digital assistants.

As described hereinbefore, the ultrasound systems of the present invention are used in minimally invasive surgery and robotic surgery methods including biopsy procedures, catheter introduction for diagnostic and therapeutic angiography, fetal imaging, cardiac imaging, vascular imaging, imaging during endoscopic procedures, imaging for telemedicine applications and imaging for veterinary applications, radiation therapy, and cryotherapy, without limitation. The embodiments use computer-based tracking systems and CT and MR images to pinpoint the precise location of the target areas. Alternative preferred embodiments of ultrasound systems can at lower cost and using smaller footprint devices provide images just prior, during, and just after the procedure. Preferred embodiments overcome the need of requiring a separate ultrasound appliance to be wheeled into the procedure room and a method to move images from the ultrasound to the device that is tracking position and registering targets against previously captured CT and MR images. A preferred embodiment of the ultrasound system provides a fully integrated solution, since it can run its' ultrasound application on the same platform as any third party application that is processing the images. The system includes a streaming video interface, an interface between a third party application and the system's ultrasound application. A key component of this system allows the two applications to run on the same computer platform (using the same operating system (OS)) such as, for example, Windows®-based platform, other platforms such as Linux can also be used and thus provide a seamless integration of the two applications. The details of the software interface to move images from the system's ultrasound application to another application are described herein below.

Preferred embodiments include control and data transfer methods that allow a third party Windows®-based application to control, for example, a portable Windows®-based ultrasound system by running the ultrasound application as a background task, sending control commands to the ultrasound application and receiving images (data) in return. Further, the embodiment configures a portable ultrasound Windows®-based application as a server of live ultrasound image frames supplying another Windows® based application that acts as a client. This client application receives these ultrasound image frames and processes them further. In addition, an alternate embodiment configures the portable ultrasound Windows®-based application as a server, interacting with a third party client application via two communication mechanisms, for example a component object model (COM) automation interface used by third party, hereinafter referred to interchangeably as external or a client to startup and control the portable ultrasound Windows®-based application and a high-speed shared memory interface to deliver live ultrasound images.

A preferred embodiment includes and configures a shared memory interface to act as a streaming video interface between a portable Windows®-based Ultrasound application and another third party Windows®-based application. This streaming video interface is designed to provide ultrasound images to a third party client in real-time.

A preferred embodiment allows the third party Windows®-based application to control the flow rate of images from the portable ultrasound Windows®-based application through the shared memory interface within the same PC platform and the amount of memory required to implement this interface. These controls consist of a way to set the number of image buffers, the size of each buffer and the rate of image transfer. This flow rate control can be set for zero data loss thus ensuring that every frame is delivered to the third party Windows®-based application from the ultrasound system, or minimum latency thus delivering the latest frame generated by ultrasound system to the third party Windows®-based application first.

A preferred embodiment formats the ultrasound image frame such that probe, spatial, and temporal information can be interpreted by the third party Windows®-based application as it retrieves the images (generated by the portable ultrasound Windows®-based application) from the shared memory interface. The actual image data passed between the server (i.e. portable ultrasound application) and the client application (third party Windows®-based application) is a Microsoft device independent bitmap (DIB) with 8 bit pixels and a 256 entry color table. The image frame also contains a header that provides the following additional information, for example, but not limited to, Probe Type, Probe Serial Number, Frame Sequence Number, Frame Rate, Frame Timestamp, Frame Trigger Timestamp, Image Width (in pixels), Image Height (in pixels), Pixel Size (in X and Y), Pixel Origin (x, y location of the first pixel in image relative to the Transducer Head, and Direction (spatial direction along or across each line of the image).

Further, the preferred embodiment controls the shared memory interface used to transfer ultrasound images between a Windows®-based portable ultrasound system and a third party Windows®-based system through the use of ActiveX controls. The Windows®-based portable ultrasound application contains an ActiveX control that transfers a frame into the shared memory and sends out a Windows® Event (that includes a pointer to the frame just written) to the third party Windows®-ased application. This third party application has a similar ActiveX control that receives this Event and pulls the image frame out of shared memory.

The graphical user interface includes one or more control programs, each of which is preferably a self-contained, for example, client-side script. The control programs are independently configured for, among other functions, generating graphical or text-based user controls in the user interface, for generating a display area in the user interface as directed by the user controls, or for displaying the processed streaming media. The control programs can be implemented as ActiveX controls, as Java applets, or as any other self-contained and/or self-executing application, or portion thereof, operable within a media gateway container environment and controllable through the web page.

Ultrasonic content can be displayed within a frame in the graphical user interface. In an embodiment, the program generates an instance of an ActiveX control. ActiveX refers to a set of object-oriented programming technologies and tools provided by Microsoft® Corporation of Redmond, Washington. The core part of the ActiveX technology is the component object model (COM). A program run in accordance with the ActiveX environment is known as "component," a self-sufficient program that can be run anywhere in the network, as long as the program is supported. This component is commonly known as an "ActiveX control." Thus, an ActiveX control is a component program object that can be re-used by many application programs within a computer or among computers in a network, regardless of the programming language with which it was created. An ActiveX control runs in what is known as a container, which is an application program utilizing the COM program interfaces.

One advantage of using a component is that it can be re-used by many applications, which are known as "component containers." Another advantage is that an ActiveX control can be created using one of several well-known languages or development tools, including C++, Visual Basic, or PowerBuilder, or with scripting tools such as VBScript. ActiveX controls can be downloaded as small executable programs, or as self-executable code for Web pages animation, for example. Similar to ActiveX controls, and suitable for the client-side scripts, are applets. An applet is typically a self-contained, self-executing computer program written in Java™, a web-based, object-oriented programming language promulgated by SUN Microsystems Corporation of Sunnyvale, Calif.

The control programs can be stored and accessed locally at the client system, or downloaded from the network. Downloading is typically done by encapsulating a control program in one or more markup language-based files. The control programs can also be used for any commonly-needed task by an application program running in one of several operating system environments. Windows®, Linux and Macintosh are examples of operating system environments that can be used in preferred embodiments.

A preferred embodiment of the Ultrasound Imaging System has specific software architecture for the image streaming capabilities. This Ultrasound Imaging System is an application that controls the Ultrasound Probe of a preferred embodiment to obtain and display visual images for medical purposes. The Imaging System has its own graphical user interface. This interface has reach in features and is conveniently organized to provide maximum flexibility working with the separate images as well as streams of images. Some of the possible medical applications require developing of graphical user interfaces with significantly different features. This involves integration of the Imaging System into other more complicated medical systems. The preferred embodiment allows exporting imaging data in a highly effective and convenient fashion for original equipment manufacturers (OEMs) to have direct access to imaging data.

The quality of the Image Streaming solution in accordance with a preferred embodiment is measured by the following criteria such as, data transfer performance. Imaging data consumes a significant amount of memory and processor power. Large numbers of separate image frames are required to produce live medical video patient examination. It becomes very important to minimize data coping operations in a process of transferring data from one process generating video data to a process consuming video data. The second criteria includes industry standard imaging format. Since applications consuming video imaging data are intended to be developed by third party companies data can be represented in industry standard formats. A third criteria is convenience. Imaging data may be presented by means of a programming interface that is convenient to use and does not require additional learning.

Further, the criteria includes scalability and extendibility. A streaming data architecture may be easily extendable to accommodate new data types. It may provide a basic framework for future multiplication of video streams targeting more than one data receiving process.

The image streaming architecture of the preferred embodiment provides methods of data transportation between two processes. The image streaming architecture defines operational parameters regulating data transferring process, and describes the mechanism of transferring parameters between processes. One of the methods to transfer operational parameters from a third party client application to the imaging system of a preferred embodiment is by usingan existing COM interface.

In a preferred embodiment, the image transferring architecture intensively uses the object-oriented programming methodology and inter-processing capabilities of the Microsoft Windows® operating system. The object-oriented methodology provides a necessary foundation allowing an architectural solution that satisfies the necessary requirements. It also lays a groundwork for future enhancements and extensions making modification relatively simple and backward compatible.

Video imaging data represents complicated data structures with mutual interferences between different data elements. It also permits and often requires different interpretation of the same data elements. The preferred embodiment of the following image transferring architecture includes a shared memory for physical data exchange. For example, Windows® shared memory is a fast and economical way to exchange data between processes. Further, the shared memory can be subdivided into separate sections of a fixed size in certain embodiments. Each section can then be at a minimum a controllable unit. In addition, the imaging data can be abstracted as objects. Each frame of the imaging data can be represented by a separate object. The objects can then be mapped to the sections of the shared memory.

Preferred embodiments can include the locking-unlocking of a section object. The programming API notification mechanism used is an event-driven mechanism. Event-driven mechanisms are implementation based on C++ pure-virtual functions.

In a preferred embodiment, the image transferring architecture consists of three layers: an application programming interface (API) layer, a programming interface implementation and shared memory access layer, and a physical shared memory layer. The application programming interface layer provides two different C++ class library interfaces to applications on a client and server side. All the associated sequence of instructions that belongs to the application itself is part of this layer as well. Application derived classes and their implementation are the key elements of application programming interface layer. The server which is the imaging data provider side uses, for example, Object Transmitter class and related derived and base classes. The client which is the imaging data consumer side uses an Object Factory class, for example, and related derived and base classes.

The programming interface implementation layer provides two different Dynamic Link Libraries (DLLs) implementing classes for the applications. This layer maps objects of the classes associated with the application to an internal implementation of objects accessing the shared memory physical system object. This layer allows the hiding of all implementation specific member variables and functions from the scope of the application. Thus, the application programming interface layers become uncluttered, easy to understand and use. The server side application can use, for example, Object-Xmitter.DLL, while the client side application can use, for example, ObjectFactory.DLL.

The physical shared memory layer represents the operating system object implementing shared memory functionality. It also describes the structure of the shared memory, it's segmentation, and memory controlling blocks.

With respect to the organization of the shared memory since shared memory is intended to be used for interprocess communications the operating system specifies a unique name at the time of it's creation. In order to manage the shared memory, other interprocess communications (IPC) system objects are required. They need to have unique names as well. To simplify a unique name generation process only one base is required. All other names are derived from the base one by an implementation code. Thus, the application programming interface requires the specification of only one base name for the logical shared memory object. The same unique name can be used by both the server side of the application and the client side of the application.

The server side of the application is responsible for the creation of shared memory creation. In a process of creation, it has to specify not only unique name of the shared memory but other configuration parameters. These parameters include, but are not limited to, segments count which specifies the number of segments to be allocated, segment size and operational flags. There are three such flags in a preferred embodiment. The first one specifies the segment submission and retrieval order. It can be one of, Last In First Out (LIFO), First In First Out (FIFO), or Last In Out (LIO).

LIO is a modification of the usual LIFO in such a way that whenever at the time when a new frame arrives, if it finds frames that were ready for retrieval, but yet not locked for retrieval, they are erased. The second flag specifies shared memory implementation behavior under a condition when a new segment allocation is requested but there is no segment available. Typically it may happen when receiving application process data slower than submitting the application. This flag may allow deleting one of the previously allocated segments. If it does not allow deleting one of the previously allocated segments, it reports an exceptional condition back to the application. Using this flag application may automatically select overwriting of data in a shared memory or it may control the data overwrite process itself. The third flag can be used only when the second one allows overwriting segments in a shared memory. It specifies how to select a segment to be overwritten. By default, shared memory implementation deletes the youngest or the most recently submitted data segment. Alternatively, the oldest segment can be selected for overwrite process.

Figure 48:
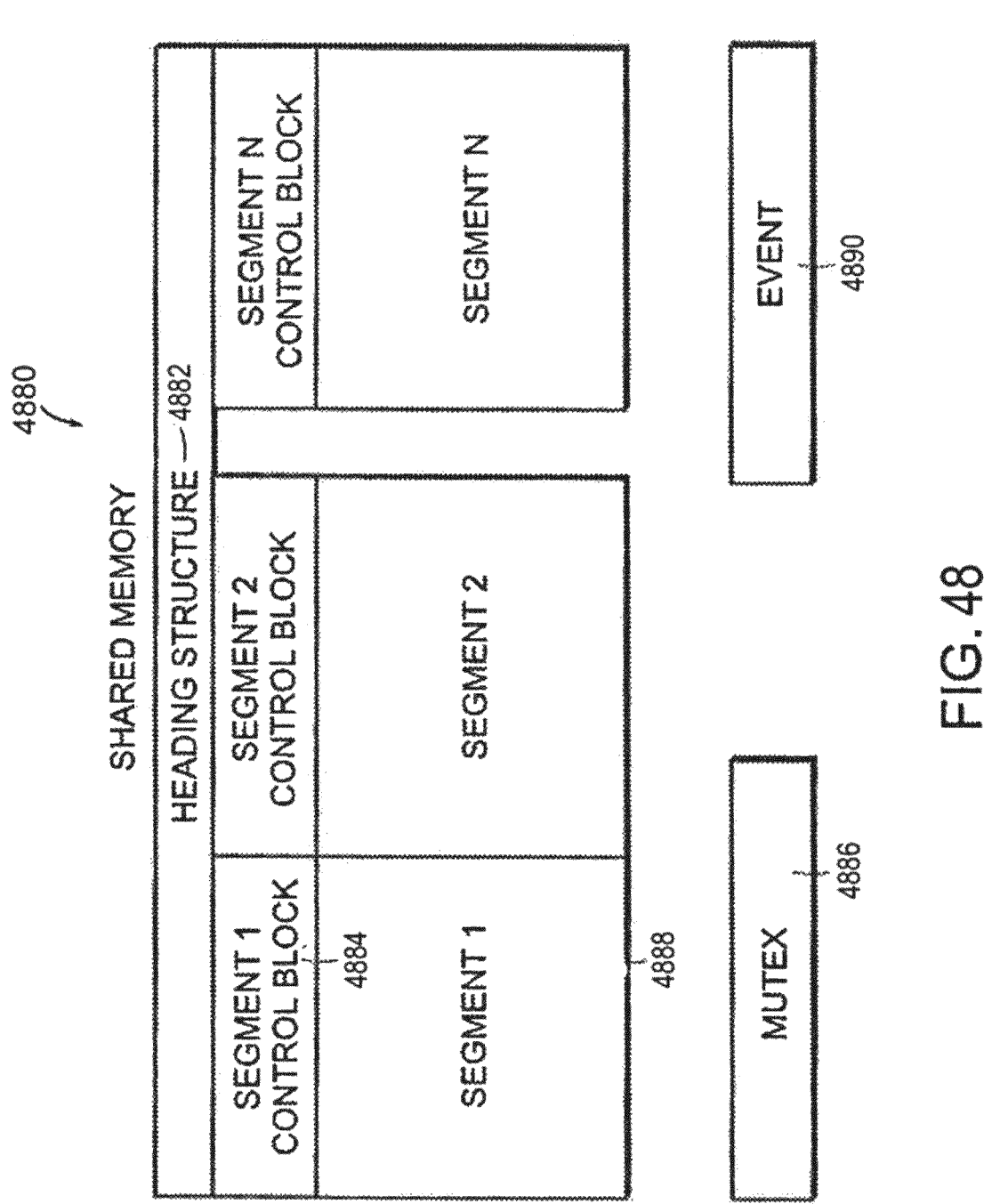
FIG. 48 is a block diagram illustrating the structure of the physical shared memory in accordance with a preferred embodiment of the present invention.

At the time of the creation of the shared memory it's physical layout is initialized. Since the operating system does not allow address calculation in a physical shared memory data pointers are not used within shared memory. All addressing within the shared memory controlling blocks and segments is implemented in terms of relative offsets from the Virtual Origin (VO). With the offset zero from the VO, the shared memory heading structure is allocated. It contains all the parameters listed herein above. FIG. 48 is a block diagram illustrating the structure of the physical shared memory 4880.

Immediately after the allocation of the shared memory heading structure 4882 follows the creation of array of headers 4884 for every memory segment. The memory segment header contains the occupied size of the segment, unique tag of the class of the object mapped to the segment, and the segment state. Each segment can be in one of four states: unused where the segment is available for allocation, locked for write where the segment is mapped to an object of a specific class and currently is being formed, written, wherein the segment is mapped to an object of a specific class and available for retrieval, and locked for read, wherein the segment is mapped to an object of a specific class and currently is in a process on data retrieval. Since every segment has its own state it is possible for the application to lock more than one segment for object forming and object retrieval. This allows the system to have flexible multithreaded architecture on both the server and client sides of the application. Further, the ability to have more than one segment in a "written" state provides a "buffering" mechanism nullifying or minimizing performance difference of the applications on the server and client sides.

The last element in a physical shared memory layout contains memory segments 4888. The logical shared memory besides physical shared memory contains a physical system mutex 4886 and system event 4890. The physical mutex 4886 provides mutual exclusive access to physical shared memory. The physical event is of a manual control type. It stays at the level "high" all the time when at least one of the segments has a "written" state. It goes to the level "low" only when there is no single segment in a "written" state. This mechanism allows to retrieve "written" objects from the shared memory without passing control to an operating system within the same time-slice allocation for the thread.

In a preferred embodiment, the object transmitting programming interface consists of three classes: namely, AObjectXmitter, USFrame, and BModeFrame. The AObjectXmitter class allows the initiation of an object transferring service specifying desired operational parameters. Once the AObjectXmitter class object is instantiated the initialized objects of USFrame and BModeFrame classes can be created. The USFrame class constructor requires a reference to an object of the AObjectXmitter class. The first action that has to be accomplished upon instantiation of the USFrame object is to establish association of the object with one of the segments in the shared memory 4924 (see FIG. 49). The function Allocate( ) maps an object to an unused shared memory segment and locks this segment for the current object usage. At the time of mapping an object a bitmap size may be provided by an application. The provided size represents only the size required for bitmap data not including the memory size required for other data elements of the object.

The BModeFrame class is a class derived from the USFrame class. It inherits all the methods and functionality that the base class has. The only additional functionality provided by BModeFrame class is additional methods allowing to provide information related specifically to the BMode operation.

After the USFrame or BModeFrame class object has been instantiated and mapped to the shared memory segment the application can fill all desired data elements of the object. It is not necessary to provide a value for every data element. At the time when an object is being mapped to the shared memory segment, all data elements of the object are being initialized with default values. The only data elements that are not initialized upon mapping are bitmap data elements. When the server side of the application has provided all desired data elements it can hand over the object to the client side of the application by calling a method, for example, Submit( ).

The USFrame or BModeFrame object can be reused by means of subsequent remapping and resubmitting. Alternatively, it can be deleted and a new one can be created when it is appropriate for an application. Since object instantiation does not require any interprocess-communication mechanisms, it is as simple as memory allocation for an ordinary variable.

There are at least two advantages of the architecture of the preferred embodiment. Since the ObjectXmitter class does have knowledge about the USFrame or BModeFrame class, it is very easy to introduce additional similar classes or directly or indirectly derived from the USFrame class. This allows the production of future versions of the Object Transmitting Programming Interface without requiring any modifications to the code or sequence of instructions that was developed for existing embodiments. Further, Object Transmitting Programming Interface classes do not have any member variables. This provides two more benefits of the interface. The first one is that these classes are COM object interface oriented and can be directly used for the COM object interface specification and implementation. The second benefit is that these classes effectively hide all implementation specific details making the interface very clear, easy to understand and use.

The Object Transmitting Programming Interface is implemented by the ObjectXmitter.DLL 4910. For every object created by the application there is a mirroring implementation object being created by the code residing in the ObjectXmitter.DLL. Since every programming interface class has a corresponding mirroring class in implementation modifications are facilitated and extend currently to specified image types. This can be accomplished by the creation of the corresponding mirroring classes in the implementation DLL. Implementation objects are responsible for handling of the shared memory and the mapping of programming interface objects. An embodiment of the present invention includes the DLL allowing instantiation of only one ObjectXmitter class object using only one communication channel with the one client application. Object Transmitting implementation transmits not only object data but provides additional information describing the object type transferred.

The Object Factory Programming Interface consists of three classes: AObjectFactory, USFrame, and BModeFrame. The class AObjectFactory contains three pure virtual member functions. This makes this class an abstract class that cannot be instantiated by an application. It is required from the application to define its own class derived from the AObjectFactory class. There is no need to define any "special" class derived from the AObjectFactory class. Since the application intends to process images that would be received, the chances that it will have a class processing images are very high. An image processing class can very well be derived from AObjectFactory class.

The class derived from an AObjectFactory class has to define and implement only pure virtual functions such as, for example, OnFrameOverrun( ) OnUSFrame( ) and OnBModeFrame( ) For instance, a derived class can be defined as follows:

```
Class ImageProcessor: public AObjectFactory {
public:
ImageProcessor(void);
~ImageProcessor(void);
virtual unsigned long OnFrameOverrun(void);
virtual unsigned long OnBModeFrame(const BModeFrame * frame);
virtual unsigned long OnUSFrame(const USFrame * frame);
};
```

Upon instantiation of an object of the class ImageProcessor base class member function Open( ) can be called. This function provides a shared memory name that matches to the shared memory name being used by the server side of application. Function Open( ) connects the client application to the server application via a specified shared memory.

At any moment after opening the shared memory, the application can expect a call on a virtual function OnFrameOverrun( ) OnUSFrame( ) and OnBModeFrame( ) Every invocation of OnUSFrame( ) function carries as an argument an object of USFrame class type. Every invocation of OnBModeFrame( ) function carries as an argument an object of BModeFrame class type. There is no need for an application to instantiate an object of USFrame or BModeFrame class. USFrame and BModeFrame objects are "given" to an application by underlying implementation on an AObjectFactory class.

The only action that application needs to accomplish is to process received frame and to release the "given" object. The application does not attempt to delete a frame object, as deletion is done by an underlying implementation. Member function Release( ) of USFrame object is called only when all data processing is done by the application and USFrame object or object of the derived class is no longer needed by the application.

Once the application has received an object of a class USFrame or BModeFrame it can retrieve imaging data and process them appropriately. The application needs to be aware that it does processing of the frame object data in a separate thread and make sure that processing function is written using a thread-safe programming technique. Since any of the pure virtual functions are being called within a separate thread created by the implementation DLL none of the subsequent calls are possible before virtual function returns control back to the calling thread. This means that as long as the application has not returned control to the implementation created thread any new frames cannot be received by the application. Meanwhile the server side of the application can continue to submit extra frames. This eventually causes the shared memory to overflow and prevents any new frame transmission.

All the time when the application processes frame data it keeps shared memory resources locked from subsequent remapping. The more frames not released by the application the less shared memory segments are available for Object Transmitting Interface on the server side of the application. If framing objects are not being released with an appropriate speed ratio eventually all memory segments of the shared memory are locked by the client application. At that time the image transmitting application stops sending new frames or overwrites frames that are not locked yet by the receiving application. If all the segments were locked by the receiving application the transmitting application does not even have an option to overwrite existing frames.

The function OnFrameOverrun( ) is called when the Frame Overrun is raised by the servicing application. This condition is raised any time when the servicing application makes an attempt to submit a new frame and there is not any available shared segments to map an object to. This condition can be cleared only by the client side of application by means of calling function ResetFrameOverrun( ) If this function is not called by the client application the Frame Overrun condition is raised and OnFrameOverrun( ) pure virtual function is called again.

The Object Factory Interface has the same advantages that were outlined herein above in describing the Object Transmitting Interface. In addition to these advantages, it implements an event-driven programming method that minimizes programming effort and maximizes execution performance. At the same time there are functions such as, for example, USFrames( ) BModeFrames( ) GetUSFrame( ) and GetBModeFrame( ) These functions can be used to implement less efficient "polling" programming methods.

The Object Factory Programming Interface is implemented by the ObjectFactory.DLL 4918. This DLL retrieves an object class type information as well as object related data from the shared memory. It creates an object of the type that is used by the transmitter. The Object factory implementation maps newly created objects to the corresponding data 4928. Object factory implementation has a separate thread that fires a newly generated and mapped object via a pure virtual function event. The application "owns" this object for the duration of processing and by calling Release( ) function indicates that the object is no longer needed by the application. The factory implementation releases resources allocated for the object locally as well as shared memory resources.

Figure 49:
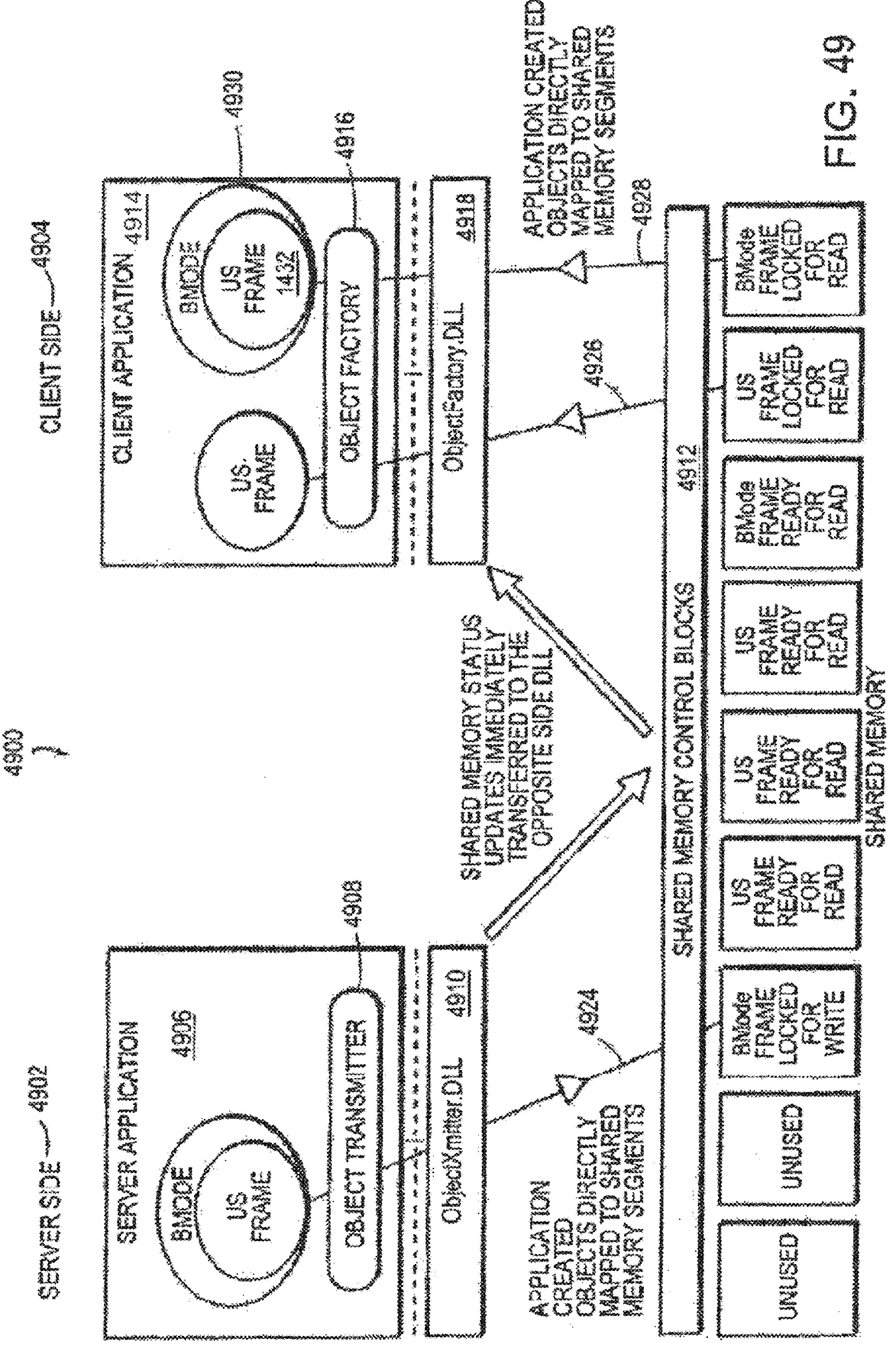
FIG. 49 is a schematic block diagram of the processing flow between the server side, the client side and the shared memory control in accordance with a preferred embodiment of the present invention.

The processing flow described herein above is pictorially represented in the block diagram FIG. 49. Preferred embodiments, include the ease of code maintenance and feature enhancement for the image transferring mechanism. The Object Transmitter 4908 and Object Factory 4916 Interfaces as well as their implementations allow such modifications to be made at a relatively low development cost. With respect to object modification, the shared memory implementation is completely independent from the transferred data types. Thus, any type modification does not require making any changes to the underlying code controlling shared memory. Since transferred data is encapsulated within classes of a particular type the only action that is needed to modify transferring an object is to modify the corresponding class defining such object. Since objects represent a class derivation tree any modification of the base class causes appropriate change of every object of the derived classes. Such modifications of the object types do not affect application code not related to modified object classes.

The new types of objects can be introduced by deriving a new class from one of the existing classes. A newly derived class can be derived from the appropriate level of the base classes. An alternative way to create a new object type is by the creation of a new base class. This method may have the advantage in the case when a newly defined class differs from existing ones significantly.

With respect to multiple Object Transferring Channels, alternate preferred embodiments, can support more than one AObjectXmitter class object and more than one corresponding communication channel. It also can be extended in such a way that it allows communication channels transmitting objects in opposite directions. This allows the application to distribute imaging data to more than one client application. It can accept incoming communication controlling image creation and probe operation.

Further, wireless and remote image streaming channels can be accommodated in preferred embodiments. A same Object Transmitting Programming Interface can be implemented to transfer images not via the shared memory 4912 but via the high-speed wireless communication network such as, for example, ISO 802.11a. It also can be used to transfer images across a wired Ethernet connection. Remote and wireless image streaming assumes that the recipient computing system can differ in performance. This makes the selection of a model of the recipient's device one of the important factors for the successful implementation.

The streamed imaging included in preferred embodiments thus utilizes a shared-memory 4912 client-server architecture that provides high bandwidth with low overhead.

The Ultrasound Imaging System software application of a preferred embodiment is used as a server of live ultrasound image frames by a client application 4914. This client-server relationship is supported by two communications mechanisms as described hereinabove. A COM automation interface is used by the client application 4914 to start-up and control the ultrasound imaging system application. A high-speed shared-memory interface delivers live ultrasound images with probe identification, spatial and temporal information from the server application 4906 to the client application 4914.

Complexities of the shared-memory implementation are encapsulated for the client application in a simple ActiveX COM API (TTFrameReceiver). The shared-memory communications 4926 have flexible parameters that are specified by the client application 4914. Queue order, number of buffers, buffer size and overwrite permission are all specified by the client when opening the image-frame stream. The queue order mode can be specified as First-In-First-Out (FIFO), Last-In-First-Out (LIFO) and Last-In-Out (LIO). In general, the FIFO mode is preferred when zero data loss is more important than minimum latency. The LIO mode delivers only the most recent image frames and is preferred when minimum latency is more important than data loss. The LIFO mode can be used when minimum latency and minimum data loss are both important. However, in the LIFO mode, frames might not always be delivered in sequential order and a more complicated client application is required to sort them after they are received. Overwrite permission, when all of the shared-memory buffers are full, is specified as not allowed, overwrite oldest and overwrite newest.

Each image frame contains a single ultrasound image, probe identification information, pixel spatial information and temporal information. The image format is a standard Microsoft device independent bitmap (DIB) with 8-bit pixels and a 256-entry color table.

The TTFrameReceiver ActiveX control provides two schemes for receiving frames. The first scheme is event driven. A COM event, FrameReady, is fired when a frame has been received. Following the FrameReady event, the image and associated data can be read using the data access methods of the interface. After image and other data have been copied, the client releases the frame by calling the ReleaseFrame method. The next FrameReady event does not occur until after the previous frame is released. In another embodiment, the client can poll for the next available frame using the WaitForFrame method.

In a preferred embodiment, both the client application and the server application are executed on the same computer. The computer can be running the Microsoft® Windows® 2000/XP operating system, for example, without limitation. The client application (USAutoView) can be developed using Microsoft® Visual C++ 6.0 and MFC. The source code can be-compiled, for example, in Visual Studio 6.0. The server side COM Automation interface and the TTFrameReceiver ActiveX control may be compatible with other MS Windows® software development environments and languages.

In an embodiment of the present invention, the name of the server side COM automation interface (ProgfD) is, for example, "Ultrasound.Document" and the interface is registered on the computer the first time the application is run. The dispatch interface can be imported into a client application from a type library.

In a preferred embodiment, automation interface is extended to support frame streaming with the addition of different methods such as void OpenFrameStream (BSTR*queueName, short numBuffers, long bufferSize, BSTR*queueOrder, short overwritepermission). The Opens frame stream transmitter on the server side 4902; opens the shared-memory interface to the client application 4914, queueNam,e is a unique name of the shared-memory "file" and is the same name that is used when opening the receiver, numBuffers is the number of buffers in the shared-memory queue, bufferSize is the size of each buffer in the shared-memory queue in bytes wherein the buffer size is 5120 bytes larger than the largest image that can be transmitted, queueOrder "LIO", "FIFO", or "LIFO", overwritePermission is 0 for overwrite not allowed, 1 for overwrite oldest, or 2 for overwrite newest. Note, OpenFrameStream must be called before opening the TTFrameReceiver control.

The next additional methods include void CloseFrameStream( ) which closes the frame stream transmitter on the server side 4902, void StartTransmitting( ) which tells the server side to start transmitting ultrasound frames, void StopTransmitting( ) which tells the server side to stop transmitting ultrasound frames, and short GetFrameStreamStatus( ) which gets the status of the frame stream transmitter. It is important to check that the stream transmitter is open before opening the TTFrameReceiver. The COM automation interface is non-blocking and the OpenFrameStream call cannot occur at the instant it is called from the client application 4914.

In a preferred embodiment, the TTFrameReceiver ActiveX Control is the client application's interface to the live ultrasound frame stream. Frame Stream Control Methods include boolean Open (BSTR name), which opens the frame stream receiver. The frame stream receiver cannot be opened until after the frame stream transmitter on the server has been opened. It also includes boolean Close( ) which closes the frame stream receiver, long WaitForFrame (long timeoutms), which wait for a frame to be ready or until end of timeout period, and boolean ReleaseFrame( ) which release the current image frame. The current frame can be released as soon as all of the desired data has been copied. The next frame cannot be received until the current frame is released. The return values of the other data access functions are not valid after the current frame is released until the next FrameReady event.

Data Access Methods in a preferred embodiment for the image includes long GetPtrBitmapinfo( ) which gets a pointer to the header (with color table) of the DIB that contain the image. The ultrasound image is stored as a standard Microsoft device independent bitmap (DIB). BITMAPINFO and BITMAPINFOHEADER structures can be cast to the returned pointer as needed. Memory for the BITMAPINFO structure is allocated in shared-memory and may not be de-allocated; instead, ReleaseFrame( ) can be called to return the memory to the shared-memory mechanism. Further methods include long GetPtrBitmapBits( ) which gets a pointer to the image pixels. The returned pointer can be cast as needed for use with the Microsoft DIB API. Memory for the bitmap pixels is allocated in shared-memory and may not be de-allocated; instead, ReleaseFrame( ) is called to return the memory to the shared-memory mechanism.

The methods related to probe identification include short GetProbeType( ) which gets the defined ultrasound probe type.being used, BSTR GetProbeType( ) which gets the defined probe name, long GetProbeSN( ) which gets the serial number of the probe being used.

With respect to temporal information, the methods include short GetSequenceNum( ) which gets the sequence number of the current frame. The sequence number is derived from an 8-bit counter and thus repeats every 256 frames. It is useful for determining gaps in the frame sequence and for re-ordering frames received when using the LIFO buffer order mode. Further, double GetRate( ) gets the frame rate when combined with the sequence number, provides precise relative timing for the received frames, BSTR GetTimestamp( ) which gets a timestamp for the current frame which provides an absolute time for the current frame that may be useful when synchronizing to external events. The resolution is approximately milliseconds. Timestamps can be averaged and used in conjunction with rate and sequence number to achieve higher precision. Lastly, with respect to temporal information, the methods include BSTR GetTriggerTimestamp( ) which gets a timestamp for the start of ultrasound scanning wherein the ultrasound probe is stopped when "freezing" the image. The trigger timestamp is recorded when live imaging is resumed.

Spatial Information in preferred embodiments has the following methods, short GetXPixels( ) which get the width of the image in pixels; short GetYPixels( ) which gets the height of the image in pixels; double GetXPixelSize( ) which gets the size of each pixel in the x-direction, (x-direction is defined to be horizontal and parallel to each image line); and double GetYPixelSize( ) which gets the size of each pixel in the y-direction. The y-direction is defined to be vertical and perpendicular to each image line. Further, double GetXOrigin( ) which get the x-location of the first pixel in the image relative to the transducer head and double GetYOrigin( ) which gets the x-location of the first pixel in the image relative to the transducer head. The positive y-direction is defined to be away from the transducer head into the patient. Another method includes short GetXDirection( ) which gets the spatial direction along each line of the image. The positive x-direction is defined to be away from the probe marker. The short GetYDirection( ) gets the spatial direction across each line of the image. The positive y-direction is defined to be away from the transducer head into the patient.

The spatial position of any pixel in the image relative to the transducer head can easily be calculated as follows:

$$PX=OX+NX*SX*DX$$

$$PY=OY+NY*SY*DY$$

wherein,
P=the position of the pixel relative to the transducer head,
O=the origin,
N=the index of the pixel in the image,
S=the pixel size,
D=the direction of the pixel.

Further, events in a preferred embodiment, void FrameReady( ) is used when a frame is ready and data can be read. The handler copies data from the data access methods and then calls ReleaseFrame( ) It is recommended that any kind of indefinite processing, for example, function that invokes message loops be avoided in the handler. Further, void FrameOverrun( ) is used when the server is unable to send a frame or a frame has to be overwritten in the buffers because the buffers are full. This only applies to the FIFO and LIFO modes, since the LIO automatically releases old buffers. This event is useful for determining whether the client application is reading frames quickly enough and whether the number of buffers allocated is sufficient for the latency of the client.

In a preferred embodiment, USAutoView is a sample client application that automates the server side and displays live ultrasound image frames. It has functions to demonstrate starting and stopping the server side, hiding and showing the server side, toggling between showing and not showing graphics on the image, freezing and resuming the ultrasound acquisition, loading a preset exam, changing the designated patient size, changing the image size, spatial information, and inverting the image.

Figure 50:
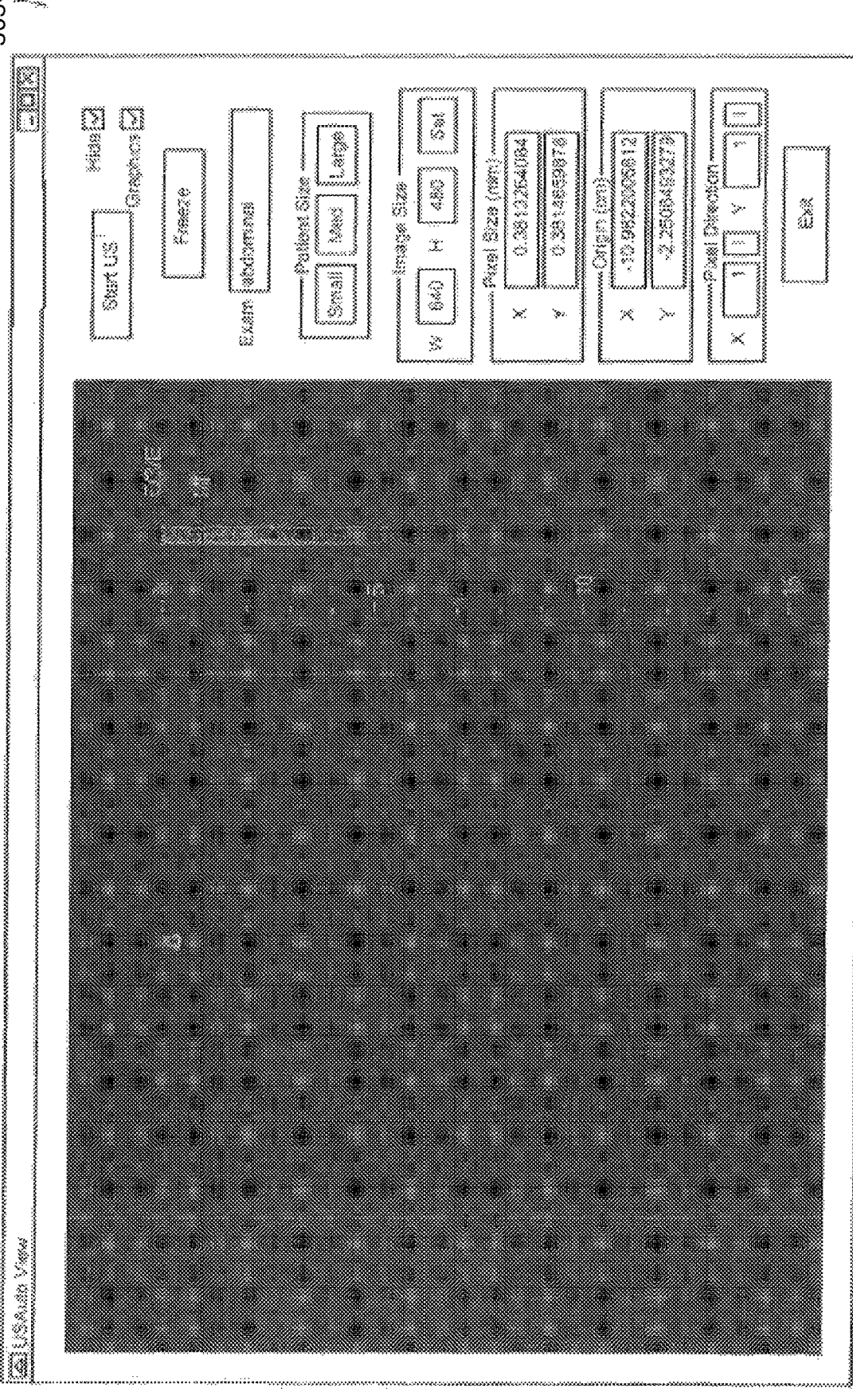
FIG. 50 is a view of a graphical user interface of the Autoview user interface in accordance with a preferred embodiment of the present invention.

FIG. 50 is a view of a graphical user interface used for a USAutoView UI 5050 in accordance with a preferred embodiment of the present invention. The USAutoView program is a Windows® dialog application with three ActiveX components. TTFrameReceiver which supplies ActiveX interface to receive ultrasound frames, TTAutomate which encapsulates automation of the server side and TTSimplelmageWnd which is the image display window. CUSAutoViewDlg is the main dialog. It manages the automation of the server side through the TTAutomate control, receiving ultrasound frames through TTFrameReceiver and image display through TTSimplelrnageWnd. The OnStartUS( ) method of CUSAutoViewDlg calls the TTAutomate and TTFrameReceiver methods needed to start or stop automation and data transmission from the server side.

The method OnFramReady( ) handles the FrameReady event from TTFrameReciever. It copies the desired data from TTFrameReceiver and then releases the frame with TTFrameReceiver's ReleaseFrame( ) method. It avoids any functions that perform indeterminate processing, such as functions that invoke message loops.

TTAutomate is an ActiveX control that encapsulates automation functions for the server side. The native COM Automation interface of the server side is non-blocking and requires waiting with GetStatusFlags to coordinate functions. TTAutomate wraps each function in the required wait loops. The wait loops allow Windows® messages to be processed so that the client application's user interface thread does not become blocked while waiting. Although automation methods in TTAutomate cannot return until the function has been completed, other Windows® messages are still processed before the function is completed. It is recommended to prevent multiple concurrent calls from message handlers to TTAutomate methods, as coordination with the server side is generally non-reentrant. Source code for this control is included in the USAutoView workspace. It may be reused or modified as desired.

TTSimplelmageWnd is an ActiveX control that provides a display window for device independent bitmaps (DIB's). The two properties of the display interface are long DIBitmapInfo and long DIBits. DIBitmapInfo corresponds to a pointer to a block of memory that contains the BITMAP-INFO structure for the DIB. DIBits corresponds to a pointer to a block of memory that contains the image pixels. To load a new image, the DIBitmapInfo is set to the pointer to the bitmap info of the DIB. Then DIBits is set to the pointer to the bitmap bits. When DIBits is set, the pointer that was set for DIBitmapInfo is expected to still be valid and both the bitmap info and bitmap bits are copied internally for display on the screen. Both DIBitmapInfo and DIBits are set to zero to clear the image. Source code for this control is included in the USAutoView workspace. It may be reused or modified as desired.

The preferred embodiments of the present invention include a plurality of probe types. For example, the probes include, but are not limited to, a convex-linear transducer array operating between, 2-4 MHz, a phased-linear transducer array operating between 2-4 MHz, a convex-linear endocavity transducer array operating between 4-8 MHz, a linear transducer array operating between 4-8 MHz and a linear transducer array operating between 5-10 MHz.

Preferred embodiments of the portable ultrasound system of the present invention provide high resolution images such as the following during an examination: B-mode, M-mode, Color Doppler (CD), Pulsed Wave Doppler (PWD), Directional Power Doppler (DirPwr) and Power Doppler (PWR). Once the system software is installed the probe device is connected into a desktop or laptop. The probe can be an industry standard transducer connected to a 28 oz. case that contains the system's beamforming hardware. If the probe is connected to a laptop, then a 4-pin FireWire cable is connected to a IEEE 1394 serial connection located on a built-in MediaBay. However, if the probe is connected to a desktop, the computer may not be equipped with a Media-Bay. One can connect the probe using an External DC Module (EDCM) connector. Before connecting the probe, one needs to make sure that the FireWire is connected on both the right and left sides of the computer.

In an embodiment, the EDCM is designed to accept a 6-pin IEEE 1394 (also referred to as FireWire) cable at one end and a Lemo connector from the probe at the other end. The EDCM accepts an input DC voltage from +10 to +40 Volts. Further, the system, in an embodiment, can be connected to a host computer with IEEE 1394. The 6-pin IEEE 1394 input to the EDCM can originate from any IEEE 1394 equipped host computer running, for example, the Windows® 2000 operating system. An external IEEE 1394 hub may also be necessary to provide the requisite DC voltage to the EDCM. In a host computer equipped with IEEE 1394, there are one of two types of IEEE 1394 connectors; a 4-pin or a 6-pin. The 6-pin connector is most often found in PC-based workstations that use internal PCI-bus cards. Typically, the 6-pin connector provides the necessary DC voltage to the EDCM. A 6-pin-male to 6-pin-male IEEE 1394 cable is used to connect the host computer to the EDCM.

The 4-pin connector is found in laptop computers that do not contain a MediaBay in accordance with a preferred embodiment or provide a DC voltage output. When using this connector type, an external IEEE-1394 hub can be used to power the EDCM and the probe.

When power is not provided from the host computer, an external IEEE-1394 hub can be used between the host computer and the EDCM. The hub derives its power from a wall outlet and is connected using a medical-grade power supply that conforms to the IEC 60601-1 electrical safety standard.

To connect the hub to the host computer, a 4-pin-male to 6-pin-male or 6-pin-male to 6-pin-male IEEE cable is required. The appropriate connector (4-pin or 6-pin) is inserted into the host computer and the 6-pin connector into the hub. The hub is then connected to the EDCM using a 6-pin-male to 6-pin-male IEEE 1394 cable. An IEEE 1394 hub is only necessary when the host computer cannot supply at least +10 to +40 DC volts and 10 watts power to the EDCM. If the host computer can supply adequate voltage and power, a 6-pin-male to 6-pin-male IEEE 1394 cable can be used to connect the computer directly to the EDCM.

Figure 51:
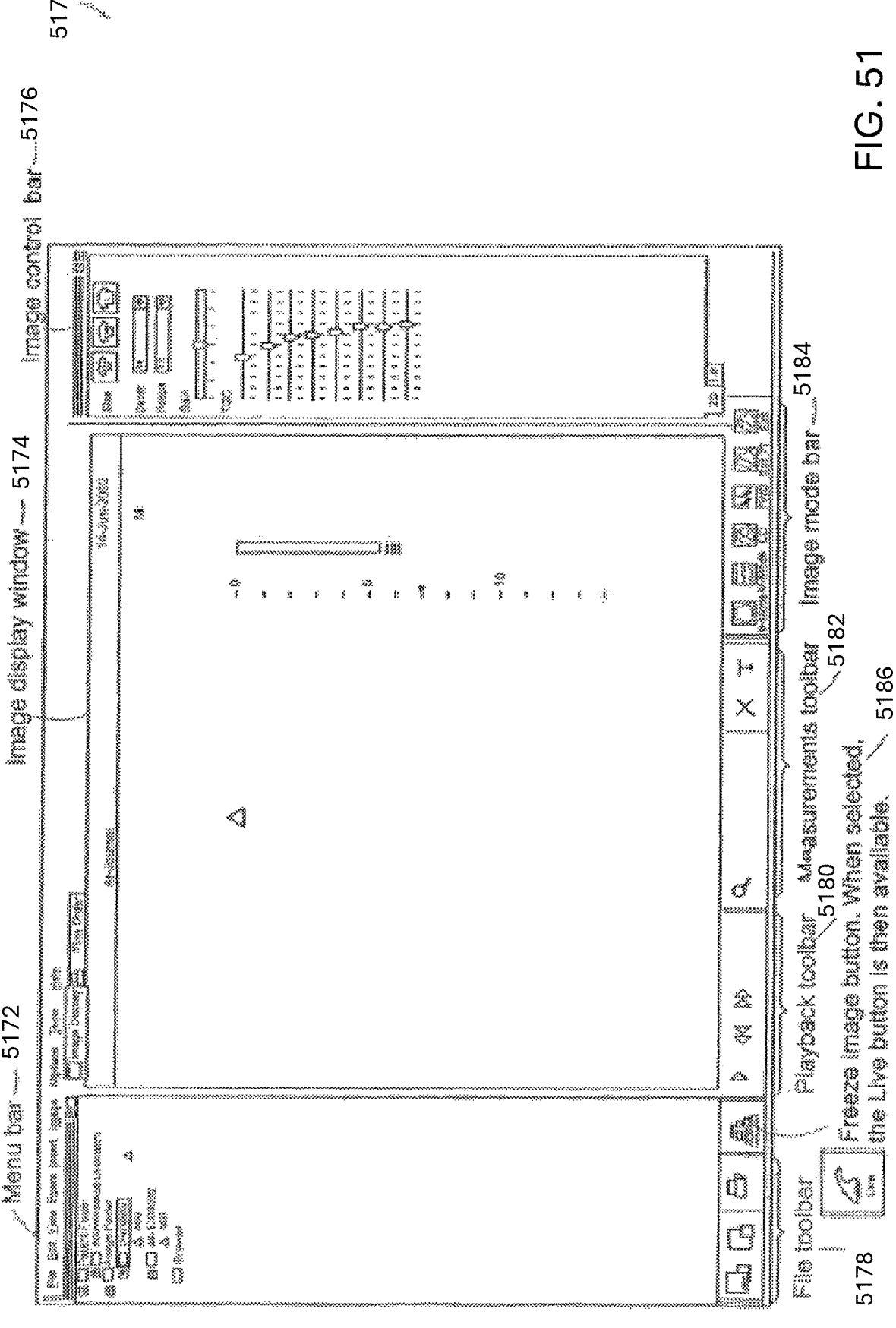
FIG. 51 illustrates a view of a main screen display of a graphical user interface in accordance with a preferred embodiment of the present invention.

FIG. 51 illustrates a view of a main screen display of a graphical user interface in accordance with a preferred embodiment of the present invention. When the user starts the system in accordance with the present invention the main screen 5170 displays. To help the user navigate, the main screen can be considered as four separate work areas that provide information to help one perform tasks. These include a menu bar 5172, an image display window 5174, an image control bar 5176, and tool bars 5180 and 5182. Main screen 5170 may also include image mode bar 5184 and freeze image button 5186.

In order to resize windows and regions the user can click the small buttons in the upper right of the window to close, resize, and exit the program. A user interface or button closes the window but leaves the program running (minimizing the window). A system button appears at the bottom of the screen, in the area called the taskbar. By clicking the system button in the taskbar the window re-opens. Another interface button enlarges the window to fill the entire screen (called maximizing), however, when the window is at its largest, the frame rates may decrease. Another interface button returns the window to the size that it was before being enlarged. The system program can be closed by another interface button.

Figures 52A, 52B:
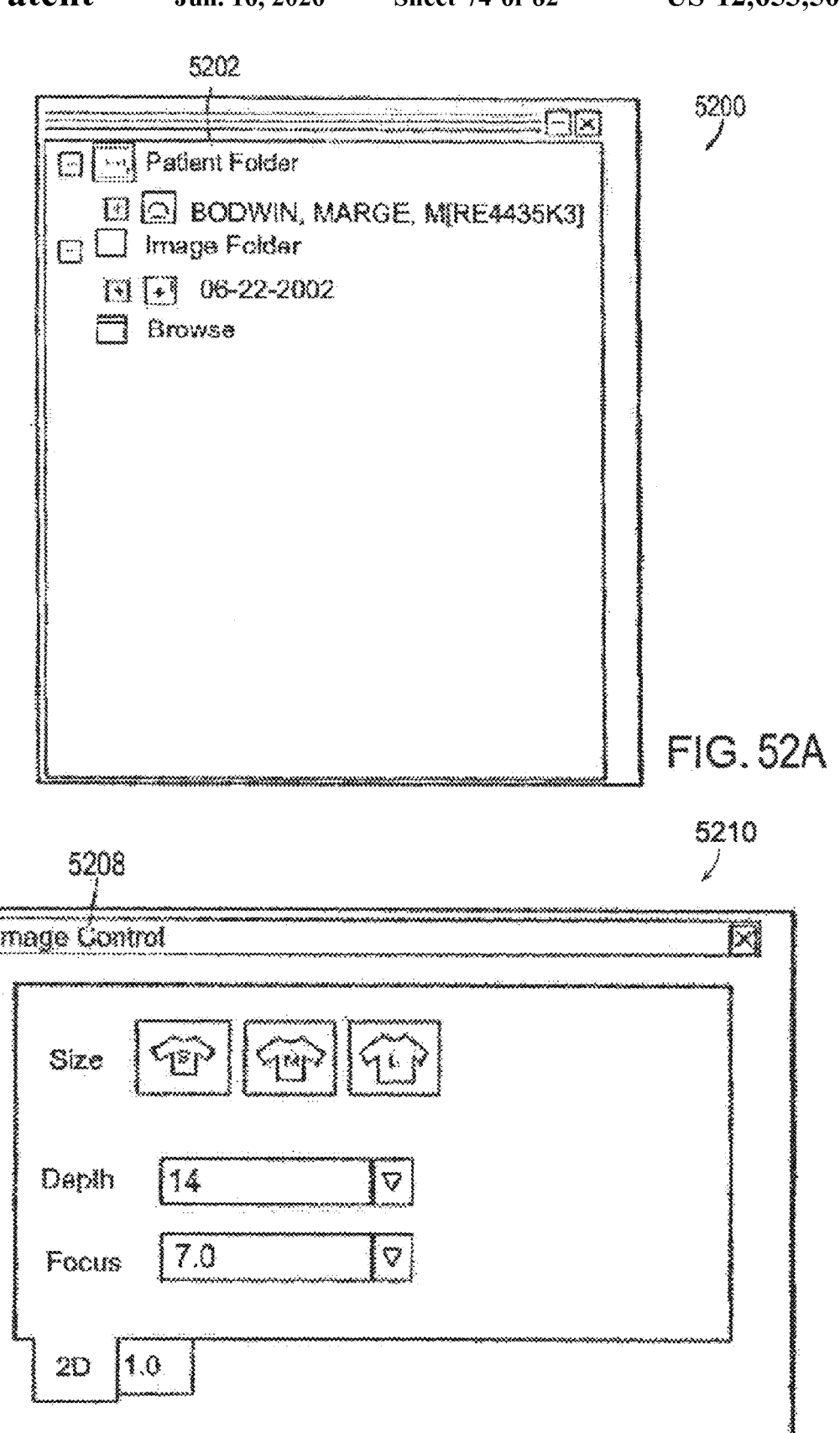
Figure 52C:
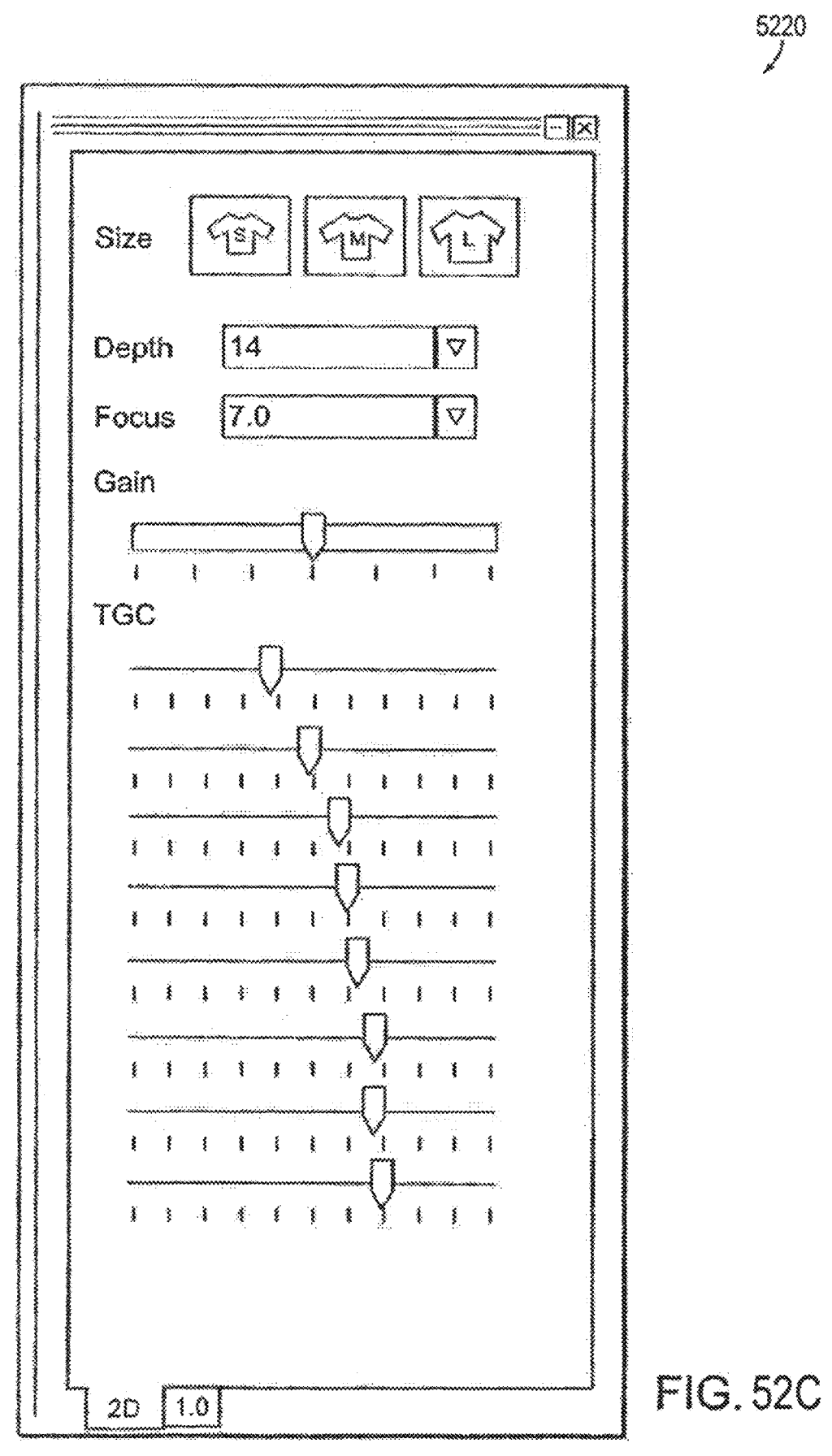

The user can increase or decrease the width of each region of the application to meet one's needs. For example, to make the Explorer window more narrow, the cursor is placed at either end of the region and by clicking and dragging the new desired size is obtained. One can re-position the size and location of each region so that they become floating windows. To create floating windows, the user simply clicks one's mouse on the double-edged border of the specific region and drags it until it appears as a floating window. To restore the floating window back to original form, one double-clicks in the window. These functionalities are depicted in FIGS. 52A-52C which are views in a graphical user interface 5200, 5210, 5220 in accordance with a preferred embodiment of the present invention.

Figure 53A:
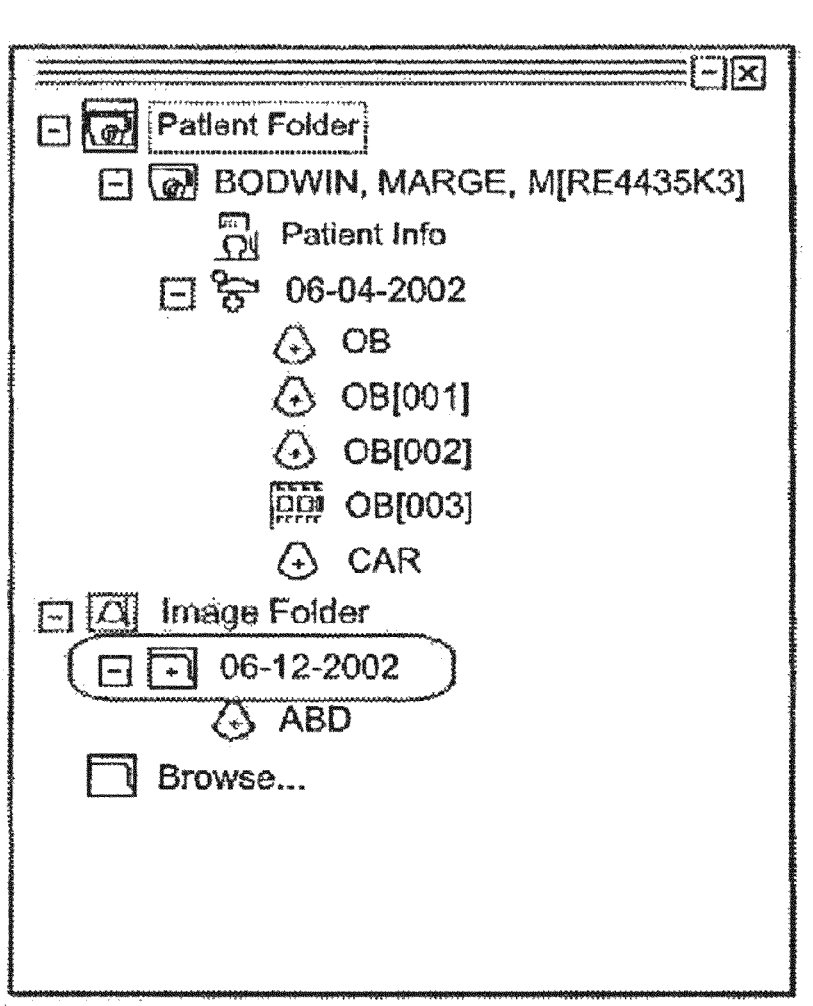
FIGS. 53A and 53B are views of a graphical user interface illustrating a patient folder and an image folder directory in accordance with a preferred embodiment of the present invention.
Figure 53B:
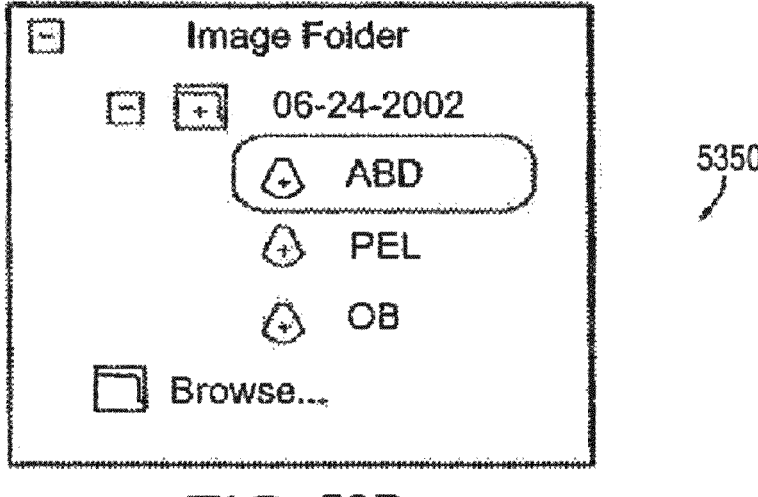

The Explorer window provides the nested level file directory 5202 for all patient folders the user creates images that are created and saved. The folder directory structure includes the following, but is not limited to, patient folder, and an image folder. The patient folder directory is where patient information files are stored along with any associated images. The image folder directory contains images by date and exam type. The images in this directory are not associated with a patient and are created without patient information. FIGS. 53A-53B illustrate the patient folder 5340 and image folder 5350 in accordance with a preferred embodiment of the present invention. The menu bar at the top of the screen provides nine options one can use to perform basic tasks. To access a menu option simply click the menu name to display the drop-down menu options. The user can also access any menu by using its shortcut key combination.

The Image display window provides two tabs: Image Display and Patient Information. The user clicks on the Image Display tab to view the ultrasound image. The image is displayed in the window according to the control settings that are defined. Once the image is saved, when the user retrieves it again, the category, date and time of the image is also shown in the Image Display window. The Patient Info tab is used to enter new patient information which is later stored in a patient folder. The user can access this tab to also make modifications and updates to the patient information.

Figure 54A:
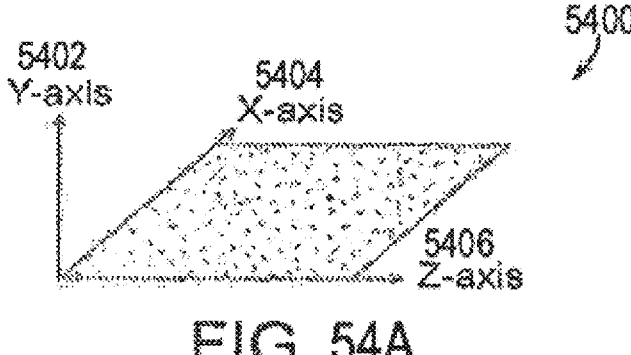
FIGS. 54A-54C illustrate XY bi-plane probe comprising a two one-dimensional, ID multi-element arrays in accordance with a preferred embodiment of the invention.
Figure 54B:
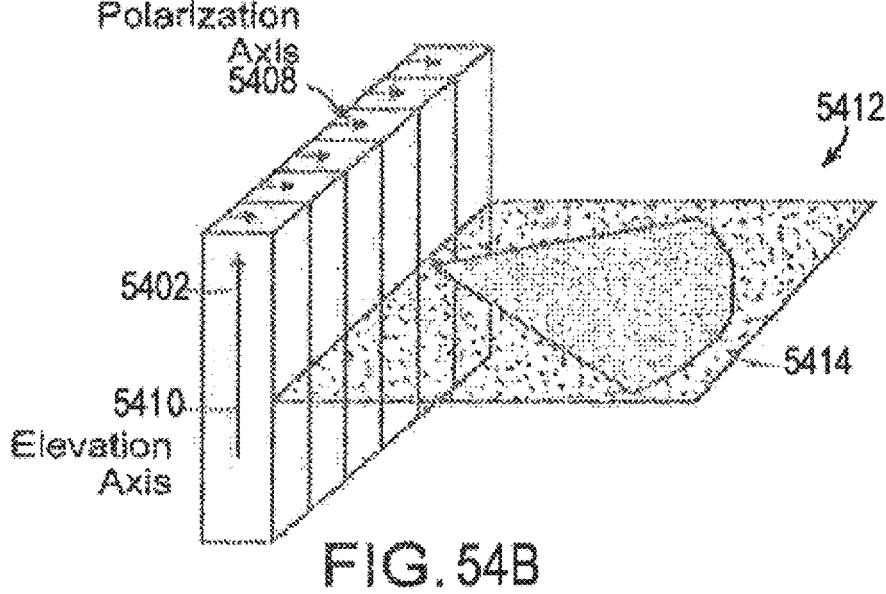

FIGS. 54A and 54B illustrate an XY bi-plane probe consisting of two one dimensional, multi-element arrays. The arrays may be constructed where one array is on top of the other with a polarization axis of each array being aligned in the same direction. The elevation axis may be at a right angle or orthogonal to one another. Illustrated by FIG. 54A, the array orientation is represented by arrangement 5400. The polarization axis 5408 of both arrays are pointed in the direction of the z-axis 5406. The elevation axis of the bottom array is pointed in y-direction 5402, and the elevation axis of the top array is in the x-direction 5404.

Figure 54C:
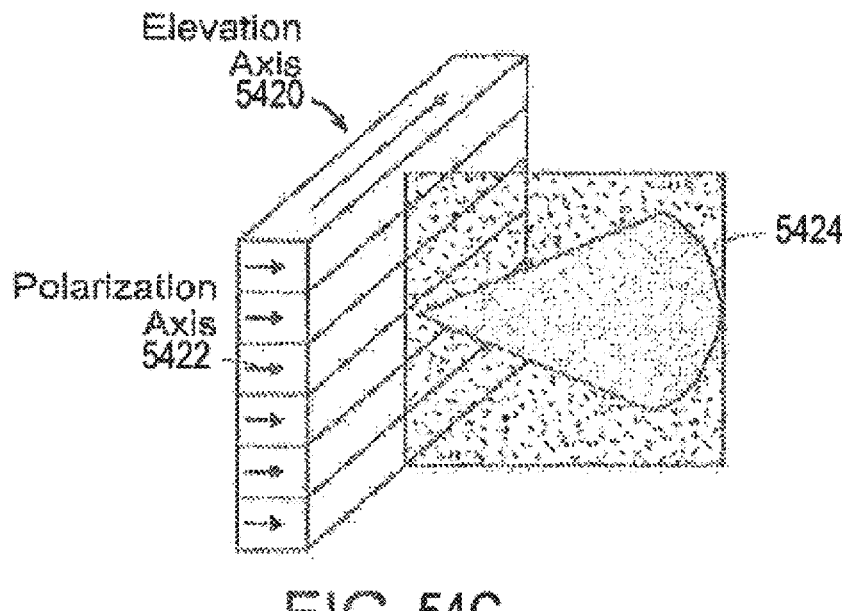

Further illustrated by FIG. 54B, a one dimensional multi-element array forms an image as depicted in arrangement 5412. A one-dimensional array with an elevation axis 5410 in a y-direction 5402 forms the ultrasound image 5414 on the x-axis 5404, z-axis 5406, plane. A one-dimensional array with the elevation axis 5410 in the x-direction 5404 forms the ultra sound image 5414 on the y-axis 5402, z-axis 5406. A one dimensional transducer array with elevation axis 5410 along a y-axis 5402 and polarization axis 5408 along a z-axis 5406 will result in an ultrasound image 5414 formed along the x 5404, z 5406 plane. An alternate embodiment illustrated by FIG. 54C depicts a one-dimensional transducer array with an elevation axis 5420 in an x-axis direction 5404, and a polarization axis 5422, in the z-axis 5406, direction. The ultrasound image 5424 is formed on the y 5402, z 5406 plane.

Figure 55:
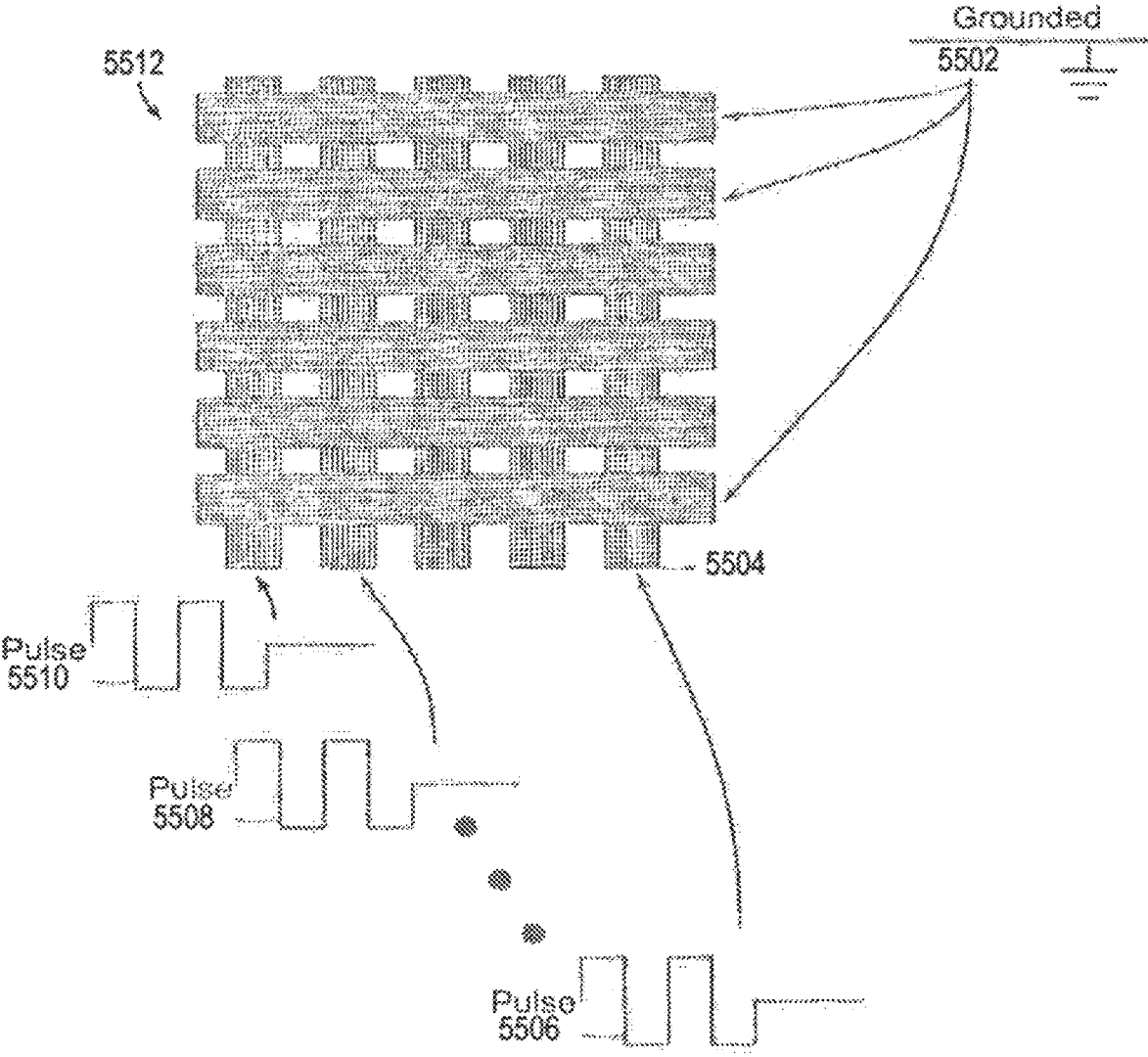
FIG. 55 illustrates the operation of a bi-plane image forming xy-probe.

FIG. 55 illustrates the operation of a bi-plane image forming xy-probe. FIG. 55 illustrates an array 5512 that has a high voltage applied for forming images. High voltage driving pulses 5506, 5508, 5510, may be applied to the bottom array 5504, with a y-axis elevation. This application may result in generation of transmission pulses for forming the line one of the received image on the XZ plane, while keeping the elements of the top array 5502 at a grounded level.

Figure 56:
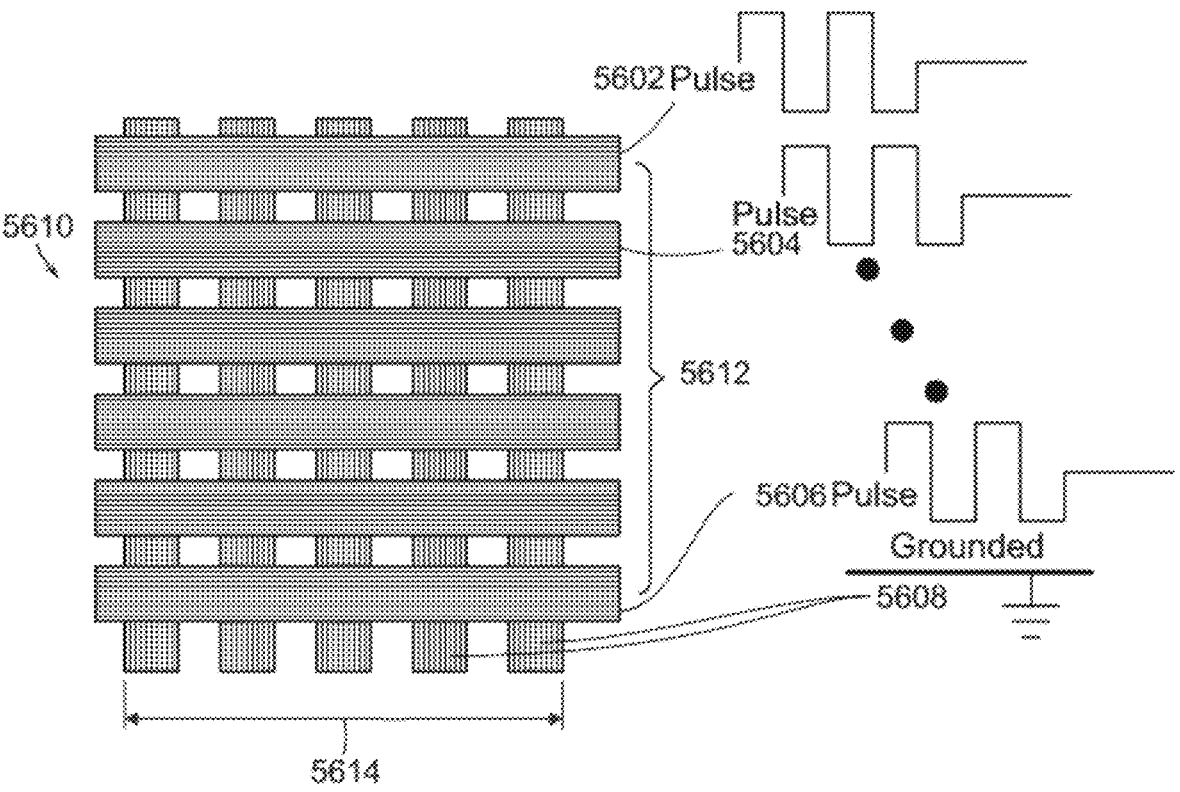
FIG. 56 illustrates the operation of a bi-plane image forming xy-probe.

FIG. 56 illustrates the operation of a bi-plane image forming xy-probe. FIG. 56 illustrates a array 5610, that has a high voltage applied to it for forming images. A high voltage pulse 5602, 5604, 5606, may be applied to the top array 5612, with elevation in the x-axis, generating transmission pulses for forming the line one of the received image on the yz-plane, while keeping the elements of the bottom array 5614, grounded 5608.

Figure 57:
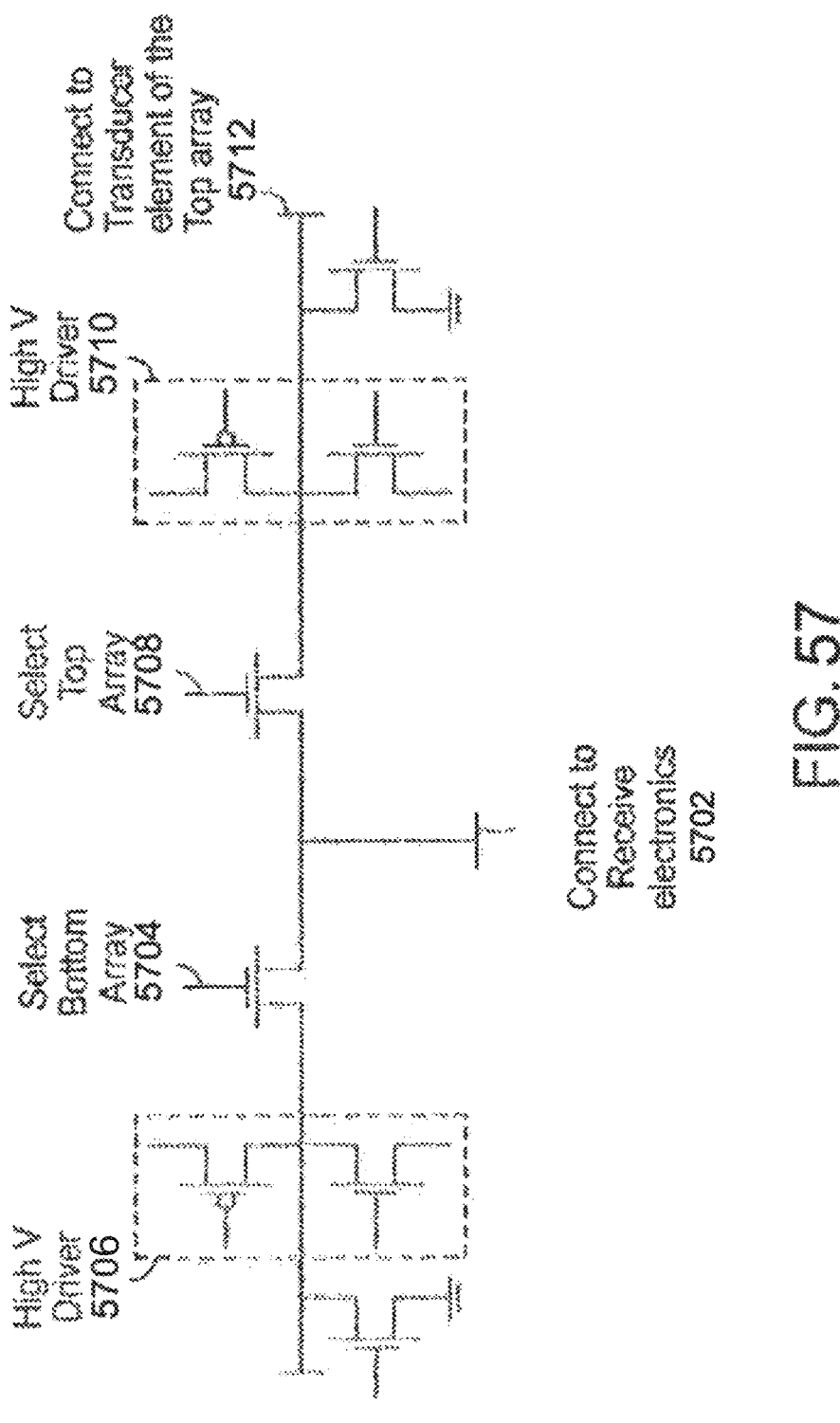
FIG. 57 illustrates a high voltage driver circuit for a bi-plane image forming xy-probe.

FIG. 57 illustrates the circuit requirements of a bi-plane image forming xy-probe. The receive beamforming requirements are depicted for a bi-plane probe. A connection to receive the electronics 5702, is made. Then elements from the select bottom array 5704, and select top array 5708, are connected to share one connection to receive electronics 5702, channel. A two to one mux circuit can be integrated on the high voltage driver 5706, 5710. The two-to one mux circuit can be integrated into high voltage driver 5706, 5710. One receive beam is formed for each transmit beam. The bi-plane system requires a total of 256 transmit beams for which 128 transmit beams are used for forming a XZ-plane image and the other 128 transmit beams are used for forming a YZ-plane image. A multiple-received beam forming technique can be used to improve the frame rate. An ultrasound system with dual received beam capabilities for each transmit beam two received beams can be formed. The bi-plane probe only needs a total of 128 transmit beams for forming the two orthogonal plane images, in which 64 transmit beams are used to form a XZ-plane image with the other 64 transmit beams for the YZ-plane image. Similarly, for an ultrasound system with a quad beam capability, the probe requires 64 transmit beams to form two orthogonal-plane images.

Figures 58A, 58B:
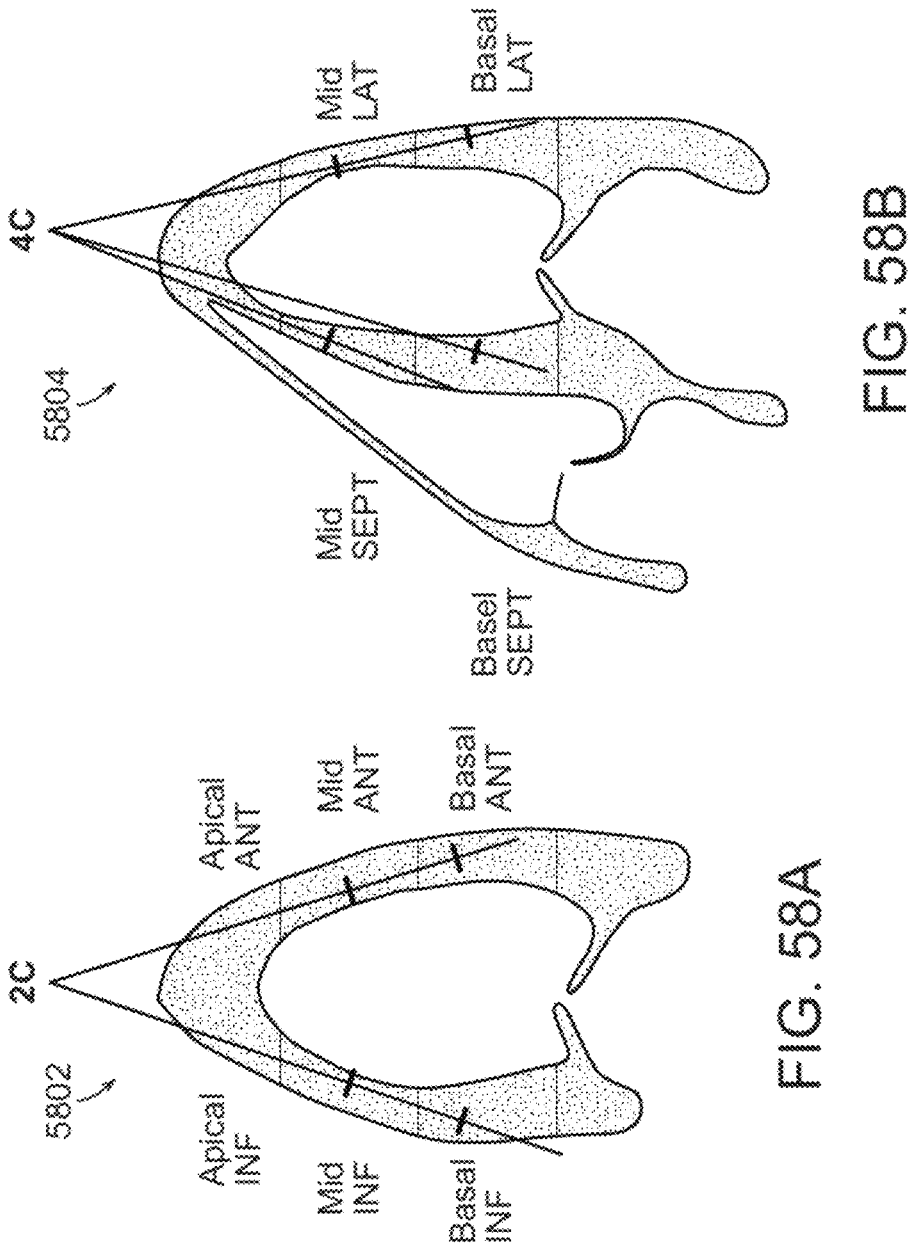
FIGS. 58A-58B illustrate simultaneous bi-plane evaluation of left ventricular condition.

FIGS. 58A-58B illustrate an application for simultaneous bi-plane evaluation. The ability to measure the LV mechanical dyssynchrony with echocardiograph can help indentify patients that are more likely to benefit from Cardiac Resynchronization Therapy. LV parameters needed to be quantified are Ts-(lateral-septal), Ts-SD, Ts-peak, etc. The Ts-(lateral-septal) can be measured on a 2D apical 4-chamber view Echo image, while the Ts-SD, Ts-peak (medial), Ts-onset (medial), Ts-peak (basal), Ts-onset (basal) can be obtained on two separated parasternal short-axis views with 6 segments at the level of mitral valve and at the papillary muscle level respectively—total 12 segments. FIG. 58A-58B depicts an xy-probe providing apical four chamber 5804, and apicial two chamber 5802 images, to be viewed simultaneously.

Figure 59A:
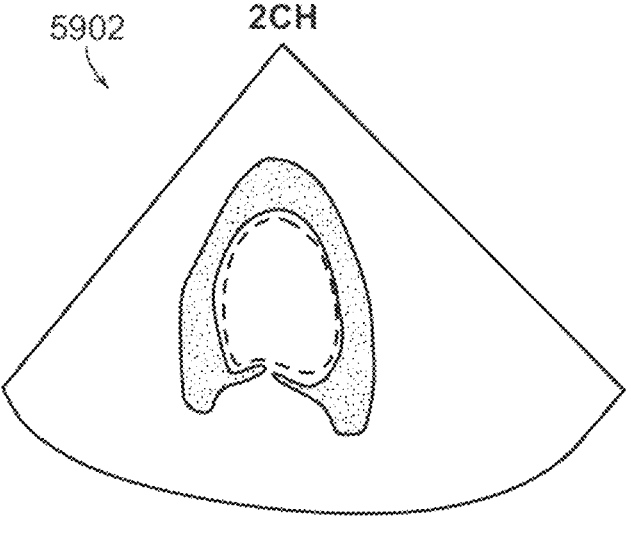
FIGS. 59A-59B illustrate ejection fraction probe measurement techniques in accordance with preferred embodiments of the invention.
Figure 59B:
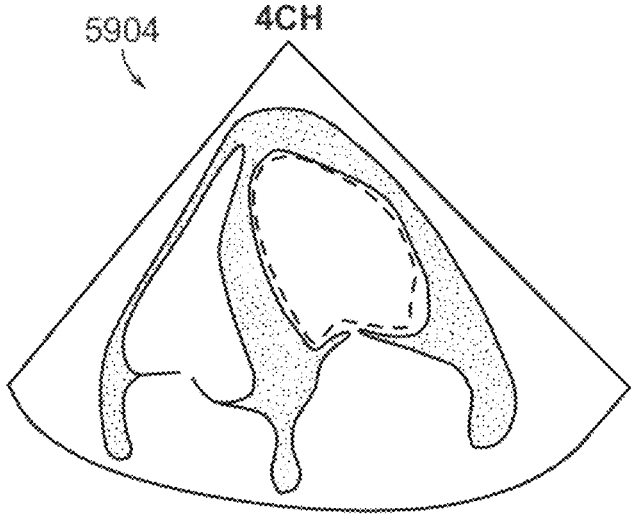

FIGS. 59A-59B illustrate ejection fraction probe measurement techniques. The bi-plane-probe provides for EF measurement, as visualization of two orthogonal planes ensure on-axis views are obtained. Auto-border detection algorithm, provides quantitative Echo results to select implant responders and guide the AV delay parameter setting. As depicted in FIGS. 59A and 59B, the XY probe acquires real-time simultaneous images from two orthogonal planes and the images 5902, 5904 are displayed on a split screen. A manual contour tracing or automatic boarder tracing technique can be used to trace the endocardial boarder at both end-systole and end-diastolic time from which the EF is calculated. The LV areas in the apical 2CH 5902, and 4CH 5904, views, A1 and A2 respectively, are measured at the end of diastole and the end of systole. The LVEDV, left ventricular end-diastolic volume, and LVESV, left ventricular the end-systole volume, are calculated using the formula:

$$V = \frac{8}{3\pi} \frac{A_1 A_2}{L}.$$

And the ejection fraction is calculated by $$EF = \frac{LVEDV - LVESD}{LVEDV}.$$

It is noted that the operations described herein are purely exemplary, and imply no particular order. Further, the operations can be used in any sequence, when appropriate, and/or can be partially used. Exemplary flowcharts are provided herein for illustrative purposes and are non-limiting examples of methods. One of ordinary skill in the art will recognize that exemplary methods may include more or fewer steps than those illustrated in the exemplary flowcharts, and that the steps in the exemplary flowcharts may be performed in a different order than shown.

In describing exemplary embodiments, specific terminology is used for the sake of clarity. For purposes of description, each specific term is intended to at least include all technical and functional equivalents that operate in a similar manner to accomplish a similar purpose. Additionally, in some instances where a particular exemplary embodiment includes a plurality of system elements or method steps, those elements or steps may be replaced with a single element or step. Likewise, a single element or step may be replaced with a plurality of elements or steps that serve the same purpose. Further, where parameters for various properties are specified herein for exemplary embodiments, those parameters may be adjusted up or down by $\frac{1}{20}$th, $\frac{1}{10}$th, $\frac{1}{5}$th, $\frac{1}{3}$rd, $\frac{1}{2}$, etc., or by rounded-off approximations thereof, unless otherwise specified.

With the above illustrative embodiments in mind, it should be understood that such embodiments can employ various computer-implemented operations involving data transferred or stored in computer systems. Such operations are those requiring physical manipulation of physical quantities. Typically, though not necessarily, such quantities take the form of electrical, magnetic, and/or optical signals capable of being stored, transferred, combined, compared, and/or otherwise manipulated.

Further, any of the operations described herein that form part of the illustrative embodiments are useful machine operations. The illustrative embodiments also relate to a device or an apparatus for performing such operations. The apparatus can be specially constructed for the required purpose, or can incorporate a general-purpose computer selectively activated or configured by a computer program stored in the computer. In particular, various general-purpose machines employing one or more processors coupled to one or more computer readable media can be used with computer programs written in accordance with the teachings disclosed herein, or it may be more convenient to construct a more specialized apparatus to perform the required operations.

The foregoing description has been directed to particular illustrative embodiments of this disclosure. It will be apparent, however, that other variations and modifications may be made to the described embodiments, with the attainment of some or all of their associated advantages. Moreover, the procedures, processes, and/or modules described herein may be implemented in hardware, software, embodied as a computer-readable medium having program instructions, firmware, or a combination thereof. For example, one or more of the functions described herein may be performed by a processor executing program instructions out of a memory or other storage device.

It will be appreciated by those skilled in the art that modifications to and variations of the above-described systems and methods may be made without departing from the inventive concepts disclosed herein. Accordingly, the disclosure should not be viewed as limited except as by the scope and spirit of the appended claims.

We claim:

1. An ultrasonic diagnostic and measurement system, comprising:

a cart mounted battery powered tablet computing device, the cart equipped with a multiport probe connector;

a transducer probe within a handheld probe housing that includes a transducer array having at least 64 transducer elements that transmits and receives ultrasound signals to and from a region of a patient in response to transmit and receive circuitry, and a beamformer integrated circuit connected to an ultrasound control circuit within the handheld probe housing, wherein the ultrasound control circuit receives digital signals to actuate an ultrasound imaging operation, the transducer probe configured to communicate with the cart mounted battery powered tablet computing device by wireless communication; and wherein the transducer probe is further configured to communicate with a handheld-operable tablet display computing device, a computing device-executable set of instructions executable on the handheld-operable tablet display computing device that communicates with the ultrasound control circuit to control an operation of the beamformer integrated circuit within the handheld probe housing, the handheld-operable tablet display computing device including a tablet display, at least a processing circuit communicatively coupled to the ultrasound control circuit to control an ultrasound imaging procedure conducted with the transducer probe; and wherein the computing device-executable set of instructions are further executable on the cart mounted battery powered tablet computing device that communicates with the ultrasound control circuit to control an operation of the beamformer integrated circuit within the handheld probe housing, the cart mounted battery powered tablet computing device including at least one processor communicatively coupled to the ultrasound control circuit, and a touch screen display configured to operate the transducer probe for an ultrasound imaging procedure in response to a touch input, the set of instructions, when executed on at least one of the handheld-operable tablet display computing device and the cart mounted battery powered tablet computing device include the steps of:

generating a display of an ultrasound image of the region of the patient in an image display area on at least one of the touch screen display and the tablet display, the ultrasound image based on ultrasound image signals processed by the beamformer integrated circuit, and operating a user interface on at least one of the touch screen display that are each configured to actuate a menu window wherein ultrasound image data, patient data and a plurality of imaging modes are touch actuated using inputs that specify a subset of touch controls to be implemented for a selected imaging mode and wherein at least one touch actuated menu window is configured to provide selection of one of a plurality of examination types from a preset selection window on at least one of the touch screen display and the tablet display wherein different examination types have a plurality of different previously programmed preset imaging parameters for each of the different examination types, the touch screen display and tablet display being further configured to accept:

a first gesture input that initiates an imaging procedure performed with the transducer array based on a selected preset examination type from the preset selection window; and a second gesture input to alter an operation of the ultrasound control circuit to select an imaging depth for the transducer array, wherein an image of a region of interest at the selected depth is generated and displayed in the image display area for the selected preset examination type.

2. The system of claim 1, wherein the first gesture input corresponds to a moving touch gesture on a virtual window within the image display area of the touch screen display.

3. The system of claim 1, wherein the transducer array comprises a bi-plane transducer array.

4. The system of claim 1, wherein the set of instructions when executed responds to a further gesture input that includes a double tap gesture against the touch screen display to generate display of a first cursor inside a region of a virtual window.

5. The system of claim 1 further comprising a tablet housing of the tablet display computing device encloses a display touch controller connected to the at least one processor that controls operation of the touch screen display, the touch screen controller operating and expanded preset selection window.

6. The system of claim 1 wherein the handheld probe housing further encloses a transmit driver circuit for at least 128 transducer elements in the transducer array and a power supply.

7. The system of claim 1, wherein the handheld probe housing further encloses a memory.

8. The system of claim 1, wherein the second gesture input corresponds to a drag gesture on the touch screen display.

9. The system of claim 1, wherein the set of instructions when executed receives a third gesture input from the touchscreen display substantially simultaneously with a fourth gesture input.

10. The system of claim 1 wherein the transducer array is connected to the ultrasound beamformer integrated circuit such that a transmit beam direction is altered with a moving gesture to steer the transmit beam direction.

11. The system of claim 1, wherein the set of instructions when executed performs at least one measurement on an ultrasound image based at least in part on a first cursor at a first location.

12. The system of claim 11, wherein the set of instructions when executed generates a display of a second cursor at a second location inside the region of a virtual window within the image display area of the touch screen display in response to a second further input from the touch screen display such that at least one measurement for the ultrasound image is based at least in part on the respective locations of the first cursor and the second cursor inside the region of the virtual window.

13. The system of claim 12, wherein the set of instructions when executed responds to a further input from the touch screen display connecting a line on the touch screen display extending from the first cursor across at least a portion of the ultrasound image to the second location inside the region of the virtual window.

14. The system of claim 1, wherein the transducer probe to the cart mounted battery powered tablet computing device with a cable, or wherein the transducer probe communicates image data using a wireless transmission protocol.

15. The system of claim 1 wherein the handheld-operable tablet display computing device that has a volume of less than 2500 cubic centimeters.

16. The system of claim 1 further comprising a tablet housing of the cart mounted battery powered tablet computing device that has one or more external communication ports to communicate with the handheld-operable tablet display computing device.

17. The system of claim 1, wherein the multiport probe connector on the cart is configured to electrically connect to the cart mounted battery powered tablet computing device to a plurality of transducer arrays, wherein the transducer array selected for operation can be switched using a touch gesture on the cart mounted battery powered tablet computing device.

18. The system of claim 1 wherein one or more of the first and second gesture inputs is associated with a preset examination type selected by scrolling through the plurality of preset examination types on the touch screen display.

19. The system of claim 1 further comprising a preset threshold that is a time-associated moving gesture, or a preset threshold that is a speed-associated moving gesture, or a preset threshold that is a direction-associated moving gesture.

20. The system of claim 1 further comprising a tablet housing of the cart mounted battery powered tablet computing device that includes a battery that provides power to the at least one processor.

21. The system of claim 1 wherein the plurality of imaging modes include one or more of B mode imaging, M mode imaging, pulsed wave spectral Doppler imaging, tissue Doppler imaging (TDI), and color flow imaging.

22. The system of claim 1 wherein one of the imaging modes comprises tissue Doppler imaging having preset velocity scales.

23. The system of claim 1 wherein the ultrasound control circuit adjusts delays to be applied to transducer signals generated by the transducer array.

24. The system of claim 1 wherein the transducer array is connected to receive circuitry enclosed within the handheld probe housing, the receive circuitry being mounted on a circuit board with the ultrasound beamformer circuit.

25. The system of claim 1 wherein the beamformer integrated circuit comprises an application specific integrated circuit that processes at least 16 transducer channels from the transducer array.

26. The system of claim 1 further comprising vertically stacked integrated circuits including the beamformer integrated circuit.

27. The system of claim 1 wherein the transducer array includes a plurality of transducers along an x axis and a further plurality of transducers along a y axis.

28. The system of claim 1 wherein a battery for the cart mounted battery powered tablet computing device includes a battery mounted on the cart.

29. An ultrasonic diagnostic and measurement system, comprising:

a cart mounted battery powered tablet computing device, the cart equipped with a multiport probe connector connected to a clock generation complex programmable logic device (CPLD) for clocking operation of an ultrasound scan using a transducer array;

a transducer probe within a handheld probe housing that includes the transducer array that includes a plurality of transducer elements that transmits and receives ultrasound signals to and from a region of a patient in response to operation of transmit and receive circuitry, and beamformer processing circuitry including an ultrasound control circuit enclosed within the handheld probe housing, wherein the ultrasound control circuit receives signals to actuate an ultrasound imaging operation of the transducer probe, the transducer probe is configured to communicate with the cart mounted battery powered tablet computing device by wireless communication and also configured to communicate with a handheld-operable ultrasound tablet display device, and a computing device-executable set of instructions executable on at least one of the cart mounted battery powered tablet computing device and the handheld-operable ultrasound tablet display device that are each configured to communicate with the ultrasound control circuit to control an operation of the beamformer processing circuitry enclosed within the handheld probe housing, the cart mounted battery powered tablet computing device and the handheld-operable ultrasound tablet display device each further respectively including at least one processor communicatively connected with the transducer probe, and a respective touch screen display configured to operate at least one transducer probe for an ultrasound imaging procedure in response to a touch control input, the set of instructions when executed:

generating a display of an ultrasound image of the region of the patient in an image display area on at least one touch screen display, the ultrasound image based on ultrasound image signals processed by the beamformer processing circuitry, and operating a user interface on the at least one touch screen display that is configured to actuate a menu window wherein ultrasound image data, patient data and a plurality of imaging modes are touch actuated inputs that specify a subset of touch controls to be implemented for a selected imaging mode and wherein at least one touch actuated menu window includes selection of one of a plurality of examination types from a preset selection window on at least one touch screen display wherein different examination types have different previously programmed preset imaging parameters, at least one touch screen display further configured to accept:

a first gesture input that initiates an imaging procedure performed with the transducer array based on a selected preset examination type from the preset selection window; and a second gesture input to alter an operation of the ultrasound control circuit to select an imaging depth for the transducer array, wherein an image of a region of interest at the selected depth is generated and displayed in the image display area for the selected preset examination type.

30. The system of claim 29, wherein the first gesture input corresponds to a moving touch gesture on a virtual window within the image display area of the at least one touch screen display.

31. The system of claim 29, wherein the transducer array comprises a bi-plane transducer array.

32. The system of claim 29 further comprising a tablet housing of the cart mounted battery powered tablet computing device that encloses a display touch controller connected to the at least one processor in the tablet housing wherein the display touch controller controls operation of the touch screen display in the tablet housing.

33. The system of claim 29 wherein the handheld probe housing further encloses a transmit driver circuit for at least 128 transducer elements in the transducer array and a power supply.

34. The system of claim 29, wherein the beamformer processing circuitry further comprises a field programmable gate array and a memory.

35. The system of claim 29, wherein the CPLD controls operation of a cable connected transducer probe.

36. The system of claim 29, wherein the transducer array is connected to the ultrasound beamformer processing circuitry such that a transmit beam direction is altered with a moving gesture to steer the transmit beam direction.

37. The system of claim 29, wherein the set of instructions when executed performs at least one measurement on an ultrasound image based at least in part on a first cursor at a first location or wherein the set of instructions when executed responds to a further input from the touch screen display connecting a line on the touch screen display extending from the first cursor across at least a portion of the ultrasound image to a second location inside the region of a virtual window.

38. The system of claim 29, wherein the handheld probe housing wirelessly communicates image data using a wireless transmission protocol.

39. The system of claim 29 wherein the plurality of imaging modes include one or more of B mode imaging, M mode imaging, pulsed wave spectral Doppler imaging, tissue Doppler imaging (TDI) having preset velocity scales, and color flow imaging.

40. An ultrasonic diagnostic and measurement system, comprising:

a cart mounted battery powered tablet computing device, the cart equipped with a multiport probe connector;

a transducer probe within a handheld probe housing that includes a transducer array having a plurality of transducer elements that transmits and receives ultrasound signals to and from a region of a patient in response to transmit and receive circuitry, and a beamformer integrated circuit connected to an ultrasound control circuit enclosed within the handheld probe housing, wherein the ultrasound control circuit receives digital signals to actuate an ultrasound imaging operation, the transducer probe configured to communicate with the cart mounted battery powered tablet computing device by wireless communication and also configured to communicate with a handheld-operable ultrasound tablet display device, and a computing device-executable set of instructions, the instructions executable on at least one of the cart mounted battery powered tablet computing device connected to the multiport probe connector and the handheld-operable ultrasound tablet display device that are each configured to be selected to communicate with the transducer probe during an ultrasound imaging procedure, wherein at least one of the cart mounted battery powered tablet computing device and the handheld-operable ultrasound tablet display device can be selected to communicate with the ultrasound control circuit to control an operation of the beamformer integrated circuit enclosed within the handheld probe housing, each of the cart mounted battery powered tablet computing device and the handheld-operable ultrasound tablet display device including, respectively, at least one processor communicatively coupled to the ultrasound control circuit, and a touch screen display configured to select at least one transducer probe for an ultrasound imaging procedure in response to a touch control input, the set of instructions when executed:

generating a display of an ultrasound image of the region of the patient in an image display area on at least one selected touch screen display, the ultrasound image based on ultrasound image signals processed by the beamformer integrated circuit, and operating a user interface on each respective touch screen display that are each configured to actuate a menu window wherein ultrasound image data, patient data and a plurality of imaging modes are touch actuated using inputs that specify a subset of touch controls to be implemented for a selected imaging mode and wherein at least one touch actuated menu window includes selection of one of a plurality of examination types from a preset selection window on the selected touch screen display wherein different examination types have different previously programmed preset imaging parameters, the selected touch screen display further configured to accept:

a first gesture input that initiates an imaging procedure performed with the transducer array based on a selected preset examination type from the preset selection window; and a second gesture input to alter an operation of the ultrasound control circuit to select an imaging depth for the transducer array, wherein an image of a region of interest at the selected depth is generated and displayed in the image display area for the selected preset examination type.

41. The system of claim 40, wherein the set of instructions when executed responds to a further gesture input that includes a double tap gesture against the selected touch screen display to generate display of a first cursor inside a region of a virtual window.

42. The system of claim 40 further comprising a tablet housing of the cart mounted battery powered tablet computing device enclosing a display touch controller connected to the at least one processor wherein the display touch controller controls operation of the touch screen display on the tablet housing.

43. The system of claim 40, wherein the hand held probe housing further encloses a memory.

44. The system of claim 40 wherein the cart mounted battery powered tablet computing device includes a tablet housing with one or more external communication ports.

* * * * *